US010508298B2

(12) United States Patent
Liu et al.

(10) Patent No.: US 10,508,298 B2
(45) Date of Patent: *Dec. 17, 2019

(54) METHODS FOR IDENTIFYING A TARGET SITE OF A CAS9 NUCLEASE

(71) Applicant: President and Fellows of Harvard College, Cambridge, MA (US)

(72) Inventors: David R. Liu, Lexington, MA (US); Vikram Pattanayak, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 449 days.

This patent is subject to a terminal disclaimer.

(21) Appl. No.: 14/874,123

(22) Filed: Oct. 2, 2015

(65) Prior Publication Data
US 2016/0090622 A1 Mar. 31, 2016

Related U.S. Application Data

(63) Continuation of application No. 14/320,370, filed on Jun. 30, 2014, now Pat. No. 9,163,284.
(Continued)

(51) Int. Cl.
*C12Q 1/68* (2018.01)
*C12Q 1/44* (2006.01)
(Continued)

(52) U.S. Cl.
CPC .............. *C12Q 1/44* (2013.01); *A61K 38/465* (2013.01); *C12N 9/22* (2013.01); *C12Q 1/6816* (2013.01);
(Continued)

(58) Field of Classification Search
CPC ........................................................ C12Q 1/68
See application file for complete search history.

(56) References Cited

U.S. PATENT DOCUMENTS 4,182,449 A 1/1980 Kozlow
4,880,635 A 11/1989 Janoff et al.
(Continued)

FOREIGN PATENT DOCUMENTS

AU 2012244264 A1 11/2012
AU 2015252023 A1 11/2015
(Continued)

OTHER PUBLICATIONS

Pattanayak et al. (Revealing off-target cleavage specificities of zinc-finger nucleases by in vitro selection, Nature Methods, vol. 8, No. 9, pp. 765-70, Aug. 11, 2011).*
(Continued)

*Primary Examiner* — Aaron A Priest
(74) *Attorney, Agent, or Firm* — Wolf, Greenfield & Sacks, P.C.

(57) ABSTRACT

Some aspects of this disclosure provide strategies, methods, and reagents for determining nuclease target site preferences and specificity of site-specific endonucleases. Some methods provided herein utilize a novel "one-cut" strategy for screening a library of concatemers comprising repeat units of candidate nuclease target sites and constant insert regions to identify library members that can been cut by a nuclease of interest via sequencing of an intact target site adjacent and identical to a cut target site.

31 Claims, 55 Drawing Sheets
Specification includes a Sequence Listing.

Related U.S. Application Data

(60) Provisional application No. 61/864,289, filed on Aug. 9, 2013.

(51) Int. Cl.
*C12N 9/22* (2006.01)
*C12Q 1/6874* (2018.01)
*C12Q 1/6816* (2018.01)
*C12Q 1/6869* (2018.01)
*A61K 38/46* (2006.01)
*C12Q 1/6883* (2018.01)

(52) U.S. Cl.
CPC ......... *C12Q 1/6869* (2013.01); *C12Q 1/6874* (2013.01); *C12Q 1/6883* (2013.01); *C12Y 301/00* (2013.01); *C12Q 2600/156* (2013.01)

(56) References Cited

U.S. PATENT DOCUMENTS

| | | |
|---|---|---|
| 4,906,477 A | 3/1990 | Kurono et al. |
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 5,139,941 A | 8/1992 | Muzyczka et al. |
| 5,449,639 A | 9/1995 | Wei et al. |
| 5,780,053 A | 7/1998 | Ashley et al. |
| 5,835,699 A | 11/1998 | Kimura |
| 5,962,313 A | 10/1999 | Podsakoff et al. |
| 6,057,153 A | 5/2000 | Shaji et al. |
| 6,453,242 B1 | 9/2002 | Eisenberg et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,163,824 B2 | 1/2007 | Cox, III et al. |
| 7,479,573 B2 | 1/2009 | Chu et al. |
| 7,794,931 B2 | 9/2010 | Breaker et al. |
| 7,919,277 B2 | 4/2011 | Russell et al. |
| 7,993,672 B2 | 8/2011 | Huang et al. |
| 8,361,725 B2 | 1/2013 | Russell et al. |
| 8,394,604 B2 | 3/2013 | Liu et al. |
| 8,546,553 B2 | 10/2013 | Terns et al. |
| 8,569,256 B2 | 10/2013 | Heyes et al. |
| 8,680,069 B2 | 3/2014 | de Fougerolles et al. |
| 8,691,750 B2 | 4/2014 | Constien et al. |
| 8,697,359 B1 | 4/2014 | Zhang |
| 8,709,466 B2 | 4/2014 | Coady et al. |
| 8,728,526 B2 | 5/2014 | Heller |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,790,664 B2 | 7/2014 | Pitard et al. |
| 8,795,965 B2 | 8/2014 | Zhang |
| 8,846,578 B2 | 9/2014 | McCray et al. |
| 8,993,233 B2 | 3/2015 | Zhang et al. |
| 8,999,641 B2 | 4/2015 | Zhang et al. |
| 9,068,179 B1 | 6/2015 | Liu et al. |
| 9,163,284 B2 | 10/2015 | Liu et al. |
| 9,228,207 B2 | 1/2016 | Liu et al. |
| 9,234,213 B2 | 1/2016 | Wu |
| 9,322,006 B2 | 4/2016 | Liu et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,388,430 B2 | 7/2016 | Liu et al. |
| 9,512,446 B1 | 12/2016 | Joung et al. |
| 9,526,724 B2 | 12/2016 | Liu et al. |
| 9,737,604 B2 | 8/2017 | Liu et al. |
| 9,816,093 B1 | 11/2017 | Donohoue et al. |
| 9,840,690 B2 | 12/2017 | Karli et al. |
| 9,840,699 B2 | 12/2017 | Liu et al. |
| 9,873,907 B2 | 1/2018 | Zeiner et al. |
| 9,879,270 B2 | 1/2018 | Hittinger et al. |
| 9,938,288 B1 | 4/2018 | Kishi et al. |
| 9,944,933 B2 | 4/2018 | Storici et al. |
| 9,982,279 B1 | 5/2018 | Gill et al. |
| 9,999,671 B2 | 6/2018 | Liu et al. |
| 10,059,940 B2 | 8/2018 | Zhong |
| 10,077,453 B2 | 9/2018 | Liu et al. |
| 10,113,163 B2 | 10/2018 | Liu et al. |
| 10,167,457 B2 | 1/2019 | Liu et al. |
| 10,227,581 B2 | 3/2019 | Liu et al. |
| 2004/0003420 A1 | 1/2004 | Kuhn et al. |
| 2004/0115184 A1 | 6/2004 | Smith et al. |
| 2005/0222030 A1 | 10/2005 | Allison et al. |
| 2006/0088864 A1 | 4/2006 | Smolke et al. |
| 2006/0104984 A1 | 5/2006 | Littlefield et al. |
| 2006/0246568 A1 | 11/2006 | Honjo et al. |
| 2007/0264692 A1 | 11/2007 | Liu et al. |
| 2008/0124725 A1 | 5/2008 | Barrangou et al. |
| 2008/0182254 A1 | 7/2008 | Hall et al. |
| 2009/0130718 A1 | 5/2009 | Short |
| 2009/0234109 A1 | 9/2009 | Han et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0316643 A1 | 12/2010 | Eckert et al. |
| 2011/0059160 A1 | 3/2011 | Essner et al. |
| 2011/0104787 A1 | 5/2011 | Church et al. |
| 2011/0189776 A1 | 8/2011 | Terns et al. |
| 2011/0217739 A1 | 9/2011 | Terns et al. |
| 2012/0129759 A1 | 5/2012 | Liu et al. |
| 2012/0141523 A1 | 6/2012 | Castado et al. |
| 2012/0244601 A1 | 9/2012 | Bertozzi et al. |
| 2012/0270273 A1 | 10/2012 | Zhang et al. |
| 2013/0117869 A1 | 5/2013 | Duchateau et al. |
| 2013/0130248 A1 | 5/2013 | Haurwitz et al. |
| 2013/0158245 A1 | 6/2013 | Russell et al. |
| 2013/0165389 A1 | 6/2013 | Schellenberger et al. |
| 2013/0309720 A1 | 11/2013 | Schultz et al. |
| 2013/0344117 A1 | 12/2013 | Mirosevich et al. |
| 2014/0004280 A1 | 1/2014 | Loomis et al. |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1 | 3/2014 | Doudna et al. |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0186843 A1 | 7/2014 | Zhang et al. |
| 2014/0186958 A1 | 7/2014 | Zhang et al. |
| 2014/0234289 A1 | 8/2014 | Liu et al. |
| 2014/0248702 A1 | 9/2014 | Cong |
| 2014/0273037 A1 | 9/2014 | Wu |
| 2014/0273226 A1 | 9/2014 | Wu |
| 2014/0273230 A1 | 9/2014 | Chen et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |

(56) References Cited

U.S. PATENT DOCUMENTS

| | | |
|---|---|---|
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0098954 A1 | 4/2015 | Hyde et al. |
| 2015/0118216 A1 | 4/2015 | Liu et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens et al. |
| 2015/0218573 A1 | 8/2015 | Loque et al. |
| 2015/0225773 A1 | 8/2015 | Farmer et al. |
| 2015/0252358 A1 | 9/2015 | Maeder et al. |
| 2015/0307889 A1 | 10/2015 | Petolino et al. |
| 2015/0315252 A1 | 11/2015 | Haugwitz et al. |
| 2016/0015682 A2 | 1/2016 | Cawthorne et al. |
| 2016/0017393 A1 | 1/2016 | Jacobson et al. |
| 2016/0017396 A1 | 1/2016 | Cann et al. |
| 2016/0032292 A1 | 2/2016 | Storici et al. |
| 2016/0032353 A1 | 2/2016 | Braman et al. |
| 2016/0046952 A1 | 2/2016 | Hittinger et al. |
| 2016/0046961 A1 | 2/2016 | Jinek et al. |
| 2016/0046962 A1 | 2/2016 | May et al. |
| 2016/0053272 A1 | 2/2016 | Wurtzel et al. |
| 2016/0053304 A1 | 2/2016 | Wurtzel et al. |
| 2016/0074535 A1 | 3/2016 | Ranganathan et al. |
| 2016/0076093 A1 | 3/2016 | Shendure et al. |
| 2016/0090603 A1 | 3/2016 | Carnes et al. |
| 2016/0115488 A1 | 4/2016 | Zhang et al. |
| 2016/0138046 A1 | 5/2016 | Wu et al. |
| 2016/0186214 A1 | 6/2016 | Brouns et al. |
| 2016/0200779 A1 | 7/2016 | Liu et al. |
| 2016/0201040 A1 | 7/2016 | Liu et al. |
| 2016/0201089 A1 | 7/2016 | Gersbach et al. |
| 2016/0206566 A1 | 7/2016 | Lu et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0244784 A1 | 8/2016 | Jacobson et al. |
| 2016/0244829 A1 | 8/2016 | Bang et al. |
| 2016/0272965 A1 | 9/2016 | Zhang et al. |
| 2016/0281072 A1 | 9/2016 | Zhang |
| 2016/0304846 A1 | 10/2016 | Liu et al. |
| 2016/0304855 A1 | 10/2016 | Stark et al. |
| 2016/0312304 A1 | 10/2016 | Sorrentino et al. |
| 2016/0333389 A1 | 11/2016 | Liu et al. |
| 2016/0340662 A1 | 11/2016 | Zhang et al. |
| 2016/0345578 A1 | 12/2016 | Barrangou et al. |
| 2016/0346360 A1 | 12/2016 | Quake et al. |
| 2016/0346361 A1 | 12/2016 | Quake et al. |
| 2016/0346362 A1 | 12/2016 | Quake et al. |
| 2016/0348074 A1 | 12/2016 | Quake et al. |
| 2016/0350476 A1 | 12/2016 | Quake et al. |
| 2016/0369262 A1 | 12/2016 | Reik et al. |
| 2017/0009242 A1 | 1/2017 | McKinley et al. |
| 2017/0014449 A1 | 1/2017 | Bangera et al. |
| 2017/0020922 A1 | 1/2017 | Wagner et al. |
| 2017/0037432 A1 | 2/2017 | Donohue et al. |
| 2017/0044520 A1 | 2/2017 | Liu et al. |
| 2017/0044592 A1 | 2/2017 | Peter et al. |
| 2017/0053729 A1 | 2/2017 | Kotani et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0073663 A1 | 3/2017 | Wang et al. |
| 2017/0073670 A1 | 3/2017 | Nishida et al. |
| 2017/0087224 A1 | 3/2017 | Quake et al. |
| 2017/0087225 A1 | 3/2017 | Quake et al. |
| 2017/0088587 A1 | 3/2017 | Quake et al. |
| 2017/0088828 A1 | 3/2017 | Quake et al. |
| 2017/0107536 A1 | 4/2017 | Zhang et al. |
| 2017/0107560 A1 | 4/2017 | Peter et al. |
| 2017/0114367 A1 | 4/2017 | Chen et al. |
| 2017/0121693 A1 | 5/2017 | Liu et al. |
| 2017/0145394 A1 | 5/2017 | Yeo et al. |
| 2017/0145405 A1 | 5/2017 | Tang et al. |
| 2017/0145438 A1 | 5/2017 | Kantor |
| 2017/0152528 A1 | 6/2017 | Zhang |
| 2017/0152787 A1 | 6/2017 | Kubo et al. |
| 2017/0159033 A1 | 6/2017 | Kamtekar et al. |
| 2017/0166928 A1 | 6/2017 | Vyas et al. |
| 2017/0175104 A1 | 6/2017 | Doudna et al. |
| 2017/0175142 A1 | 6/2017 | Zhang et al. |
| 2017/0191047 A1 | 7/2017 | Terns et al. |
| 2017/0191078 A1 | 7/2017 | Zhang et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0226522 A1 | 8/2017 | Hu et al. |
| 2017/0233703 A1 | 8/2017 | Xie et al. |
| 2017/0233756 A1 | 8/2017 | Begemann et al. |
| 2017/0247671 A1 | 8/2017 | Yung et al. |
| 2017/0247703 A1 | 8/2017 | Sloan et al. |
| 2017/0268022 A1 | 9/2017 | Liu et al. |
| 2017/0283797 A1 | 10/2017 | Robb et al. |
| 2017/0314016 A1 | 11/2017 | Kim et al. |
| 2017/0362635 A1 | 12/2017 | Chamberlain et al. |
| 2018/0064077 A1 | 3/2018 | Dunham et al. |
| 2018/0066258 A1 | 3/2018 | Powell |
| 2018/0068062 A1 | 3/2018 | Zhang et al. |
| 2018/0073012 A1 | 3/2018 | Liu et al. |
| 2018/0100147 A1 | 4/2018 | Yates et al. |
| 2018/0105867 A1 | 4/2018 | Xiao et al. |
| 2018/0119118 A1 | 5/2018 | Lu et al. |
| 2018/0127780 A1 | 5/2018 | Liu et al. |
| 2018/0155720 A1 | 6/2018 | Donohoue et al. |
| 2018/0163213 A1 | 6/2018 | Aneja et al. |
| 2018/0170984 A1 | 6/2018 | Harris et al. |
| 2018/0179503 A1 | 6/2018 | Maianti et al. |
| 2018/0179547 A1 | 6/2018 | Zhang et al. |
| 2018/0201921 A1 | 7/2018 | Malcolm |
| 2018/0230464 A1 | 8/2018 | Zhong |
| 2018/0230471 A1 | 8/2018 | Storici et al. |
| 2018/0236081 A1 | 8/2018 | Liu et al. |
| 2018/0237787 A1 | 8/2018 | Maianti et al. |
| 2018/0245066 A1 | 8/2018 | Yao et al. |
| 2018/0265864 A1 | 9/2018 | Li et al. |
| 2018/0273939 A1 | 9/2018 | Yu et al. |
| 2018/0282722 A1 | 10/2018 | Jakimo et al. |
| 2018/0305688 A1 | 10/2018 | Zhong |
| 2018/0305704 A1 | 10/2018 | Zhang |
| 2018/0312825 A1 | 11/2018 | Liu et al. |
| 2018/0312828 A1 | 11/2018 | Liu et al. |
| 2018/0312835 A1 | 11/2018 | Yao et al. |
| 2018/0327756 A1 | 11/2018 | Zhang et al. |
| 2019/0093099 A1 | 3/2019 | Liu et al. |

FOREIGN PATENT DOCUMENTS

| | | |
|---|---|---|
| AU | 2015101792 | 1/2016 |
| BR | 112015013786 A2 | 7/2017 |
| CA | 2894668 A1 | 6/2014 |

(56) References Cited

FOREIGN PATENT DOCUMENTS

| | | | |
|---|---|---|---|
| CA | 2894681 A1 | 6/2014 | |
| CA | 2894684 A1 | 6/2014 | |
| CA | 2 852 293 A1 | 11/2015 | |
| CN | 1069962 A | 3/1993 | |
| CN | 103224947 A | 7/2013 | |
| CN | 103233028 A | 8/2013 | |
| CN | 103388006 A | 11/2013 | |
| CN | 103614415 A | 3/2014 | |
| CN | 103642836 A | 3/2014 | |
| CN | 103668472 A | 3/2014 | |
| CN | 103820441 A | 5/2014 | |
| CN | 103820454 A | 5/2014 | |
| CN | 103911376 A | 7/2014 | |
| CN | 103923911 A | 7/2014 | |
| CN | 103981211 A | 8/2014 | |
| CN | 103981212 A | 8/2014 | |
| CN | 104004778 A | 8/2014 | |
| CN | 104004782 A | 8/2014 | |
| CN | 104017821 A | 9/2014 | |
| CN | 104109687 A | 10/2014 | |
| CN | 104178461 A | 12/2014 | |
| CN | 104480144 A | 1/2015 | |
| CN | 104342457 | 2/2015 | |
| CN | 104450774 A | 3/2015 | |
| CN | 104498493 A | 4/2015 | |
| CN | 104504304 A | 4/2015 | |
| CN | 104531704 A | 4/2015 | |
| CN | 104531705 A | 4/2015 | |
| CN | 104560864 A | 4/2015 | |
| CN | 104561095 A | 4/2015 | |
| CN | 104593418 A | 5/2015 | |
| CN | 104593422 A | 5/2015 | |
| CN | 104611370 A | 5/2015 | |
| CN | 104651392 A | 5/2015 | |
| CN | 104651398 A | 5/2015 | |
| CN | 104651399 A | 5/2015 | |
| CN | 104651401 A | 5/2015 | |
| CN | 104673816 A | 6/2015 | |
| CN | 104725626 A | 6/2015 | |
| CN | 104726449 A | 6/2015 | |
| CN | 104726494 A | 6/2015 | |
| CN | 104745626 A | 7/2015 | |
| CN | 104762321 A | 7/2015 | |
| CN | 104805078 A | 7/2015 | |
| CN | 104805099 A | 7/2015 | |
| CN | 104805118 A | 7/2015 | |
| CN | 104846010 A | 8/2015 | |
| CN | 104894068 A | 9/2015 | |
| CN | 104894075 A | 9/2015 | |
| CN | 104928321 A | 9/2015 | |
| CN | 104404036 A | 11/2015 | |
| CN | 105039339 A | 11/2015 | |
| CN | 105039399 A | 11/2015 | |
| CN | 105063061 A | 11/2015 | |
| CN | 105087620 A | 11/2015 | |
| CN | 105112422 A | 12/2015 | |
| CN | 105112445 A | 12/2015 | |
| CN | 105112519 A | 12/2015 | |
| CN | 105121648 A | 12/2015 | |
| CN | 105132427 A | 12/2015 | |
| CN | 105132451 A | 12/2015 | |
| CN | 105177038 A | 12/2015 | |
| CN | 105177126 A | 12/2015 | |
| CN | 105210981 A | 1/2016 | |
| CN | 105219799 A | 1/2016 | |
| CN | 105238806 A | 1/2016 | |
| CN | 105255937 A | 1/2016 | |
| CN | 105274144 A | 1/2016 | |
| CN | 105296518 A | 2/2016 | |
| CN | 105296537 A | 2/2016 | |
| CN | 105316324 A | 2/2016 | |
| CN | 105316327 A | 2/2016 | |
| CN | 105316337 A | 2/2016 | |
| CN | 105331607 A | 2/2016 | |
| CN | 105331608 A | 2/2016 | |
| CN | 105331609 A | 2/2016 | |
| CN | 105331627 A | 2/2016 | |
| CN | 105400773 A | 3/2016 | |
| CN | 105400779 A | 3/2016 | |
| CN | 105400810 A | 3/2016 | |
| CN | 105441451 A | 3/2016 | |
| CN | 105462968 A | 4/2016 | |
| CN | 105463003 A | 4/2016 | |
| CN | 105463027 A | 4/2016 | |
| CN | 105492608 A | 4/2016 | |
| CN | 105492609 A | 4/2016 | |
| CN | 105505976 A | 4/2016 | |
| CN | 105505979 A | 4/2016 | |
| CN | 105518134 A | 4/2016 | |
| CN | 105518135 A | 4/2016 | |
| CN | 105518137 A | 4/2016 | |
| CN | 105518138 A | 4/2016 | |
| CN | 105518139 A | 4/2016 | |
| CN | 105518140 A | 4/2016 | |
| CN | 105543228 A | 5/2016 | |
| CN | 105543266 A | 5/2016 | |
| CN | 105543270 A | 5/2016 | |
| CN | 105567688 A | 5/2016 | |
| CN | 105567689 A | 5/2016 | |
| CN | 105567734 A | 5/2016 | |
| CN | 105567735 A | 5/2016 | |
| CN | 105567738 A | 5/2016 | |
| CN | 105593367 A | 5/2016 | |
| CN | 105594664 A | 5/2016 | |
| CN | 105602987 A | 5/2016 | |
| CN | 105624146 A | 6/2016 | |
| CN | 105624187 A | 6/2016 | |
| CN | 105646719 A | 6/2016 | |
| CN | 105647922 A | 6/2016 | |
| CN | 105647962 A | 6/2016 | |
| CN | 105647968 A | 6/2016 | |
| CN | 105647969 A | 6/2016 | |
| CN | 105671070 A | 6/2016 | |
| CN | 105671083 A | 6/2016 | |
| CN | 105695485 A | 6/2016 | |
| CN | 105779448 A | 7/2016 | |
| CN | 105779449 A | 7/2016 | |
| CN | 105802980 A | 7/2016 | |
| CN | 105821039 A | 8/2016 | |
| CN | 105821040 A | 8/2016 | |
| CN | 105821049 A | 8/2016 | |
| CN | 105821072 A | 8/2016 | |
| CN | 105821075 A | 8/2016 | |
| CN | 105821116 A | 8/2016 | |
| CN | 105838733 A | 8/2016 | |
| CN | 105861547 A | 8/2016 | |
| CN | 105861552 A | 8/2016 | |
| CN | 105861554 A | 8/2016 | |
| CN | 105886498 A | 8/2016 | |
| CN | 105886534 A | 8/2016 | |
| CN | 105886616 A | 8/2016 | |
| CN | 105907758 A | 8/2016 | |
| CN | 105907785 A | 8/2016 | |
| CN | 105925608 A | 9/2016 | |
| CN | 105950560 A | 9/2016 | |
| CN | 105950626 A | 9/2016 | |
| CN | 105950633 A | 9/2016 | |
| CN | 105950639 A | 9/2016 | |
| CN | 105985985 A | 10/2016 | |
| CN | 106011104 A | 10/2016 | |
| CN | 106011104 A | 10/2016 | |
| CN | 106011150 A | 10/2016 | |
| CN | 106011167 A | 10/2016 | |
| CN | 106011171 A | 10/2016 | |
| CN | 106032540 A | 10/2016 | |
| CN | 106047803 A | 10/2016 | |
| CN | 106047877 A | 10/2016 | |
| CN | 106047930 A | 10/2016 | |
| CN | 106086008 A | 11/2016 | |
| CN | 106086028 A | 11/2016 | |
| CN | 106086061 A | 11/2016 | |
| CN | 106086062 A | 11/2016 | |
| CN | 106109417 A | 11/2016 | |
| CN | 106119275 A | 11/2016 | |

(56) References Cited

FOREIGN PATENT DOCUMENTS

| | | | |
|---|---|---|---|
| CN | 106119283 | A | 11/2016 |
| CN | 106148286 | A | 11/2016 |
| CN | 106148370 | A | 11/2016 |
| CN | 106148416 | A | 11/2016 |
| CN | 106167525 | A | 11/2016 |
| CN | 106167808 | A | 11/2016 |
| CN | 106167810 | A | 11/2016 |
| CN | 106167821 | A | 11/2016 |
| CN | 106172238 | A | 12/2016 |
| CN | 106190903 | A | 12/2016 |
| CN | 106191057 | A | 12/2016 |
| CN | 106191061 | A | 12/2016 |
| CN | 106191062 | A | 12/2016 |
| CN | 106191064 | A | 12/2016 |
| CN | 106191071 | A | 12/2016 |
| CN | 106191099 | A | 12/2016 |
| CN | 106191107 | A | 12/2016 |
| CN | 106191113 | A | 12/2016 |
| CN | 106191114 | A | 12/2016 |
| CN | 106191116 | A | 12/2016 |
| CN | 106191124 | A | 12/2016 |
| CN | 106222177 | A | 12/2016 |
| CN | 106222193 | A | 12/2016 |
| CN | 106222203 | A | 12/2016 |
| CN | 106244555 | A | 12/2016 |
| CN | 106244591 | A | 12/2016 |
| CN | 106244609 | A | 12/2016 |
| CN | 106282241 | A | 1/2017 |
| CN | 106318934 | A | 1/2017 |
| CN | 106318973 | A | 1/2017 |
| CN | 106350540 | A | 1/2017 |
| CN | 106367435 | A | 2/2017 |
| CN | 106399306 | A | 2/2017 |
| CN | 106399311 | A | 2/2017 |
| CN | 106399360 | A | 2/2017 |
| CN | 106399367 | A | 2/2017 |
| CN | 106399375 | A | 2/2017 |
| CN | 106399377 | A | 2/2017 |
| CN | 106434651 | A | 2/2017 |
| CN | 106434663 | A | 2/2017 |
| CN | 106434688 | A | 2/2017 |
| CN | 106434737 | A | 2/2017 |
| CN | 106434748 | A | 2/2017 |
| CN | 106434752 | A | 2/2017 |
| CN | 106434782 | A | 2/2017 |
| CN | 106446600 | A | 2/2017 |
| CN | 106479985 | A | 3/2017 |
| CN | 106480027 | A | 3/2017 |
| CN | 106480036 | A | 3/2017 |
| CN | 106480067 | A | 3/2017 |
| CN | 106480080 | A | 3/2017 |
| CN | 106480083 | A | 3/2017 |
| CN | 106480097 | A | 3/2017 |
| CN | 106544351 | A | 3/2017 |
| CN | 106544353 | A | 3/2017 |
| CN | 106544357 | A | 3/2017 |
| CN | 106554969 | A | 3/2017 |
| CN | 106566838 | A | 4/2017 |
| CN | 106701763 | | 5/2017 |
| CN | 106701808 | | 5/2017 |
| CN | 106701818 | | 5/2017 |
| CN | 106701823 | | 5/2017 |
| CN | 106701830 | | 5/2017 |
| CN | 106754912 | A | 5/2017 |
| CN | 106755026 | A | 5/2017 |
| CN | 106755077 | A | 5/2017 |
| CN | 106755088 | A | 5/2017 |
| CN | 106755091 | A | 5/2017 |
| CN | 106755097 | A | 5/2017 |
| CN | 106755424 | A | 5/2017 |
| CN | 106801056 | A | 6/2017 |
| CN | 106834323 | A | 6/2017 |
| CN | 106834341 | A | 6/2017 |
| CN | 106834347 | A | 6/2017 |
| CN | 106845151 | A | 6/2017 |
| CN | 106868008 | A | 6/2017 |
| CN | 106868031 | A | 6/2017 |
| CN | 106906240 | A | 6/2017 |
| CN | 106906242 | A | 6/2017 |
| CN | 106916820 | A | 7/2017 |
| CN | 106916852 | A | 7/2017 |
| CN | 106939303 | A | 7/2017 |
| CN | 106947750 | A | 7/2017 |
| CN | 106947780 | A | 7/2017 |
| CN | 106957830 | A | 7/2017 |
| CN | 106957831 | A | 7/2017 |
| CN | 106957844 | A | 7/2017 |
| CN | 106957855 | A | 7/2017 |
| CN | 106957858 | A | 7/2017 |
| CN | 106967697 | A | 7/2017 |
| CN | 106967726 | A | 7/2017 |
| CN | 106978428 | A | 7/2017 |
| CN | 106987570 | A | 7/2017 |
| CN | 106987757 | A | 7/2017 |
| CN | 107012164 | A | 8/2017 |
| CN | 107012174 | A | 8/2017 |
| CN | 107012213 | A | 8/2017 |
| CN | 107012250 | A | 8/2017 |
| CN | 107022562 | A | 8/2017 |
| CN | 107034188 | A | 8/2017 |
| CN | 107034218 | A | 8/2017 |
| CN | 107034229 | A | 8/2017 |
| CN | 107043775 | A | 8/2017 |
| CN | 107043779 | A | 8/2017 |
| CN | 107043787 | A | 8/2017 |
| CN | 107043787 | A | 8/2017 |
| CN | 107058320 | A | 8/2017 |
| CN | 107058328 | A | 8/2017 |
| CN | 107058358 | A | 8/2017 |
| CN | 107058372 | A | 8/2017 |
| CN | 107083392 | A | 8/2017 |
| CN | 107099533 | A | 8/2017 |
| CN | 107099850 | A | 8/2017 |
| CN | 107119053 | A | 9/2017 |
| CN | 107119071 | A | 9/2017 |
| CN | 107129999 | A | 9/2017 |
| CN | 107130000 | A | 9/2017 |
| CN | 107142272 | A | 9/2017 |
| CN | 107142282 | A | 9/2017 |
| CN | 107177591 | A | 9/2017 |
| CN | 107177595 | A | 9/2017 |
| CN | 107177631 | A | 9/2017 |
| CN | 107190006 | A | 9/2017 |
| CN | 107190008 | A | 9/2017 |
| CN | 107217042 | A | 9/2017 |
| CN | 107217075 | A | 9/2017 |
| CN | 107227307 | A | 10/2017 |
| CN | 107227352 | A | 10/2017 |
| CN | 107236737 | A | 10/2017 |
| CN | 107236739 | A | 10/2017 |
| CN | 107236741 | A | 10/2017 |
| CN | 107245502 | A | 10/2017 |
| CN | 107254485 | A | 10/2017 |
| CN | 107266541 | A | 10/2017 |
| CN | 107267515 | A | 10/2017 |
| CN | 107287245 | A | 10/2017 |
| CN | 107298701 | A | 10/2017 |
| CN | 107299114 | A | 10/2017 |
| CN | 107304435 | A | 10/2017 |
| CN | 107312785 | A | 11/2017 |
| CN | 107312793 | A | 11/2017 |
| CN | 107312795 | A | 11/2017 |
| CN | 107312798 | A | 11/2017 |
| CN | 107326042 | A | 11/2017 |
| CN | 107326046 | A | 11/2017 |
| CN | 107354156 | A | 11/2017 |
| CN | 107354173 | A | 11/2017 |
| CN | 107356793 | A | 11/2017 |
| CN | 107362372 | A | 11/2017 |
| CN | 107365786 | A | 11/2017 |
| CN | 107365804 | A | 11/2017 |
| CN | 107384894 | A | 11/2017 |
| CN | 107384922 | A | 11/2017 |
| CN | 107384926 | A | 11/2017 |

(56) References Cited

FOREIGN PATENT DOCUMENTS

| | | |
|---|---|---|
| CN | 107400677 A | 11/2017 |
| CN | 107418974 A | 12/2017 |
| CN | 107435051 A | 12/2017 |
| CN | 107435069 A | 12/2017 |
| CN | 107446922 A | 12/2017 |
| CN | 107446923 A | 12/2017 |
| CN | 107446924 A | 12/2017 |
| CN | 107446932 A | 12/2017 |
| CN | 107446951 A | 12/2017 |
| CN | 107446954 A | 12/2017 |
| CN | 107460196 A | 12/2017 |
| CN | 107460196 A | 12/2017 |
| CN | 107474129 A | 12/2017 |
| CN | 107475300 A | 12/2017 |
| CN | 107488649 A | 12/2017 |
| CN | 107502608 A | 12/2017 |
| CN | 107502618 A | 12/2017 |
| CN | 107513531 A | 12/2017 |
| CN | 107519492 A | 12/2017 |
| CN | 107523567 A | 12/2017 |
| CN | 107523583 A | 12/2017 |
| CN | 107541525 A | 1/2018 |
| CN | 107557373 A | 1/2018 |
| CN | 107557378 A | 1/2018 |
| CN | 107557381 A | 1/2018 |
| CN | 107557390 A | 1/2018 |
| CN | 107557393 A | 1/2018 |
| CN | 107557394 A | 1/2018 |
| CN | 107557455 A | 1/2018 |
| CN | 107574179 | 1/2018 |
| CN | 107586777 | 1/2018 |
| CN | 107586779 | 1/2018 |
| CN | 107604003 | 1/2018 |
| CN | 107619829 A | 1/2018 |
| CN | 107619829 A | 1/2018 |
| CN | 107619837 A | 1/2018 |
| CN | 107630006 A | 1/2018 |
| CN | 107630041 A | 1/2018 |
| CN | 107630042 A | 1/2018 |
| CN | 107630043 A | 1/2018 |
| CN | 107641631 A | 1/2018 |
| CN | 107653256 A | 2/2018 |
| CN | 107686848 A | 2/2018 |
| CN | 206970581 | 2/2018 |
| CN | 107760652 A | 3/2018 |
| CN | 107760663 A | 3/2018 |
| CN | 107760684 A | 3/2018 |
| CN | 107760715 A | 3/2018 |
| CN | 107784200 A | 3/2018 |
| CN | 107794272 A | 3/2018 |
| CN | 107794276 A | 3/2018 |
| CN | 107815463 A | 3/2018 |
| CN | 107828738 A | 3/2018 |
| CN | 107828794 A | 3/2018 |
| CN | 107828826 A | 3/2018 |
| CN | 107828874 A | 3/2018 |
| CN | 107858346 A | 3/2018 |
| CN | 107858373 A | 3/2018 |
| CN | 107880132 A | 4/2018 |
| CN | 107881184 A | 4/2018 |
| CN | 107893074 A | 4/2018 |
| CN | 107893075 A | 4/2018 |
| CN | 107893076 A | 4/2018 |
| CN | 107893080 A | 4/2018 |
| CN | 107893086 A | 4/2018 |
| CN | 107904261 A | 4/2018 |
| CN | 107937427 A | 4/2018 |
| CN | 107937432 A | 4/2018 |
| CN | 107937501 A | 4/2018 |
| CN | 107974466 A | 5/2018 |
| CN | 107988229 A | 5/2018 |
| CN | 107988246 A | 5/2018 |
| CN | 107988256 A | 5/2018 |
| CN | 107988268 A | 5/2018 |
| CN | 108018316 A | 5/2018 |
| CN | 108034656 A | 5/2018 |
| CN | 108048466 A | 5/2018 |
| CN | 108102940 A | 6/2018 |
| CN | 108103092 A | 6/2018 |
| CN | 108103098 A | 6/2018 |
| CN | 108103586 A | 6/2018 |
| CN | 108148835 A | 6/2018 |
| CN | 108148837 A | 6/2018 |
| CN | 108148873 A | 6/2018 |
| CN | 108192956 A | 6/2018 |
| CN | 108251423 A | 7/2018 |
| CN | 108251451 A | 7/2018 |
| CN | 108251452 A | 7/2018 |
| CN | 108342480 A | 7/2018 |
| CN | 108359691 A | 8/2018 |
| CN | 108359712 A | 8/2018 |
| CN | 108384784 A | 8/2018 |
| CN | 108396027 A | 8/2018 |
| CN | 108410877 A | 8/2018 |
| CN | 108410906 A | 8/2018 |
| CN | 108410907 A | 8/2018 |
| CN | 108410911 A | 8/2018 |
| CN | 108424931 A | 8/2018 |
| CN | 108441519 A | 8/2018 |
| CN | 108441520 A | 8/2018 |
| CN | 108486108 A | 9/2018 |
| CN | 108486111 A | 9/2018 |
| CN | 108486145 A | 9/2018 |
| CN | 108486146 A | 9/2018 |
| CN | 108486154 A | 9/2018 |
| CN | 108486159 A | 9/2018 |
| CN | 108486234 A | 9/2018 |
| CN | 108504657 A | 9/2018 |
| CN | 108504685 A | 9/2018 |
| CN | 108504693 A | 9/2018 |
| CN | 108546712 A | 9/2018 |
| CN | 108546717 A | 9/2018 |
| CN | 108546718 A | 9/2018 |
| CN | 108559730 A | 9/2018 |
| CN | 108559732 A | 9/2018 |
| CN | 108559745 A | 9/2018 |
| CN | 108559760 A | 9/2018 |
| CN | 108570479 A | 9/2018 |
| CN | 108588071 A | 9/2018 |
| CN | 108588123 A | 9/2018 |
| CN | 108588128 A | 9/2018 |
| CN | 108588182 A | 9/2018 |
| CN | 108610399 A | 10/2018 |
| CN | 108611364 A | 10/2018 |
| CN | 108624622 A | 10/2018 |
| CN | 108642053 A | 10/2018 |
| CN | 108642055 A | 10/2018 |
| CN | 108642077 A | 10/2018 |
| CN | 108642078 A | 10/2018 |
| CN | 108642090 A | 10/2018 |
| CN | 108690844 A | 10/2018 |
| CN | 108707604 A | 10/2018 |
| CN | 108707620 A | 10/2018 |
| CN | 108707621 A | 10/2018 |
| CN | 108707628 A | 10/2018 |
| CN | 108707629 A | 10/2018 |
| CN | 108715850 A | 10/2018 |
| CN | 108728476 A | 11/2018 |
| CN | 108728486 A | 11/2018 |
| CN | 108753772 A | 11/2018 |
| CN | 108753783 A | 11/2018 |
| CN | 108753813 A | 11/2018 |
| CN | 108753817 A | 11/2018 |
| CN | 108753832 A | 11/2018 |
| CN | 108753835 A | 11/2018 |
| CN | 108753836 A | 11/2018 |
| CN | 108795902 A | 11/2018 |
| CN | 108822217 A | 11/2018 |
| CN | 108823248 A | 11/2018 |
| CN | 108823249 A | 11/2018 |
| CN | 108823291 A | 11/2018 |
| CN | 108841845 A | 11/2018 |
| CN | 108853133 A | 11/2018 |
| CN | 108866093 A | 11/2018 |

(56) References Cited

FOREIGN PATENT DOCUMENTS

| | | | |
|---|---|---|---|
| CN | 108893529 A | 11/2018 | |
| CN | 108913664 A | 11/2018 | |
| CN | 108913691 A | 11/2018 | |
| CN | 108913714 A | 11/2018 | |
| CN | 108913717 A | 11/2018 | |
| CN | 208034188 U | 11/2018 | |
| EP | 2 604 255 A1 | 6/2013 | |
| EP | 2840140 A1 | 2/2015 | |
| EP | 2 966 170 A1 | 1/2016 | |
| EP | 3 009 511 A2 | 4/2016 | |
| EP | 3031921 A1 | 6/2016 | |
| EP | 3045537 A1 | 7/2016 | |
| EP | 3144390 A1 | 3/2017 | |
| EP | 3199632 A1 | 8/2017 | |
| EP | 3216867 A1 | 9/2017 | |
| EP | 3252160 A1 | 12/2017 | |
| GB | 2 528 177 A | 1/2016 | |
| GB | 2 531 454 A1 | 4/2016 | |
| GB | 2542653 A | 3/2017 | |
| HK | 1208045 A1 | 2/2016 | |
| JP | 2007-501626 A | 2/2007 | |
| JP | 2008-515405 A | 5/2008 | |
| JP | 2010-539929 A | 12/2010 | |
| JP | 2011-081011 A | 4/2011 | |
| JP | 2011-523353 A | 8/2011 | |
| JP | 2012-525146 A | 10/2012 | |
| JP | 2012-531909 A | 12/2012 | |
| KR | 101584933 B1 | 1/2016 | |
| KR | 20160133380 A | 11/2016 | |
| KR | 20170037025 A | 4/2017 | |
| KR | 20170037028 A | 4/2017 | |
| KR | 101748575 B1 | 6/2017 | |
| KR | 2018-0022465 A | 3/2018 | |
| RU | 2016104674 A | 8/2017 | |
| RU | 2634395 C1 | 10/2017 | |
| RU | 2652899 C1 | 5/2018 | |
| SG | 10201707569 | 10/2017 | |
| SG | 10201710486 | 1/2018 | |
| SG | 10201710487 | 1/2018 | |
| SG | 10201710488 | 1/2018 | |
| TW | 1608100 B | 12/2017 | |
| TW | 2018-29773 A | 8/2018 | |
| WO | WO 2001/036452 A2 | 5/2001 | |
| WO | WO 2001/038547 A2 | 5/2001 | |
| WO | WO-2002/059296 A2 | 8/2002 | |
| WO | WO 2002/068676 A2 | 9/2002 | |
| WO | WO 2002/103028 A2 | 12/2002 | |
| WO | WO 2004/007684 A2 | 1/2004 | |
| WO | WO 2005/014791 A2 | 2/2005 | |
| WO | WO 2006/002547 A1 | 1/2006 | |
| WO | WO 2006/042112 A2 | 4/2006 | |
| WO | WO 2007/025097 A2 | 3/2007 | |
| WO | WO 2007/136815 A2 | 11/2007 | |
| WO | WO 2007/143574 A1 | 12/2007 | |
| WO | WO 2008/108989 A2 | 9/2008 | |
| WO | WO 2010/054108 A2 | 11/2008 | |
| WO | WO 2009/134808 A2 | 11/2009 | |
| WO | WO 2010/011961 A2 | 1/2010 | |
| WO | WO 2010/054154 A2 | 5/2010 | |
| WO | WO 2010/068289 A2 | 6/2010 | |
| WO | WO 2010/075424 A2 | 7/2010 | |
| WO | WO 2010/102257 A2 | 9/2010 | |
| WO | WO 2010/129019 A2 | 11/2010 | |
| WO | WO 2010/129023 A2 | 11/2010 | |
| WO | WO 2010/144150 A2 | 12/2010 | |
| WO | WO 2011/002503 A1 | 1/2011 | |
| WO | WO 2011/017293 A2 | 2/2011 | |
| WO | WO 2011/053868 A1 | 5/2011 | |
| WO | WO 2011/053982 A2 | 5/2011 | |
| WO | WO 2011/075627 A1 | 6/2011 | |
| WO | WO 2011/091311 A2 | 7/2011 | |
| WO | WO 2011/109031 A1 | 9/2011 | |
| WO | WO 2011/143124 A2 | 11/2011 | |
| WO | WO 2012/054726 A1 | 4/2012 | |
| WO | WO 2012/065043 A2 | 5/2012 | |
| WO | WO 2012/125445 A2 | 9/2012 | |
| WO | WO 2012/138927 A2 | 10/2012 | |
| WO | WO 2012/149470 A1 | 11/2012 | |
| WO | WO 2012/158985 A2 | 11/2012 | |
| WO | WO 2012/158986 A2 | 11/2012 | |
| WO | WO 2012/164565 A1 | 12/2012 | |
| WO | WO 2013/012674 A1 | 1/2013 | |
| WO | WO 2013/013105 A2 | 1/2013 | |
| WO | WO 2013/047844 A1 | 4/2013 | |
| WO | WO 2013/066438 A2 | 5/2013 | |
| WO | WO-2013066438 A2 * | 5/2013 | ............... C12N 9/22 |
| WO | WO 2013/098244 A1 | 7/2013 | |
| WO | WO 2013/119602 A1 | 8/2013 | |
| WO | WO 2013/126794 A1 | 8/2013 | |
| WO | WO 2013/130824 A1 | 9/2013 | |
| WO | WO 2013/141680 A1 | 9/2013 | |
| WO | WO 2013/142378 A9 | 9/2013 | |
| WO | WO 2013/142578 A2 | 9/2013 | |
| WO | WO 2013/160230 A1 | 10/2013 | |
| WO | WO 2013/166315 A1 | 11/2013 | |
| WO | WO 2013/169398 A2 | 11/2013 | |
| WO | WO 2013/169802 A1 | 11/2013 | |
| WO | WO 2013/176772 A2 | 11/2013 | |
| WO | WO 2013/176915 A1 | 11/2013 | |
| WO | WO 2013/176916 A1 | 11/2013 | |
| WO | WO 2013/181440 A1 | 12/2013 | |
| WO | WO 2013/186754 A2 | 12/2013 | |
| WO | WO 2013/188037 A2 | 12/2013 | |
| WO | WO 2013/188522 A2 | 12/2013 | |
| WO | WO 2013/188638 A2 | 12/2013 | |
| WO | WO 2013/192278 A1 | 12/2013 | |
| WO | WO 2014/005042 A2 | 1/2014 | |
| WO | WO 2014/011237 A1 | 1/2014 | |
| WO | WO 2014/011901 A2 | 1/2014 | |
| WO | WO 2014/018423 A2 | 1/2014 | |
| WO | WO 2014/020608 A1 | 2/2014 | |
| WO | WO 2014/022120 A1 | 2/2014 | |
| WO | WO 2014/022702 A2 | 2/2014 | |
| WO | WO 2014/036219 A2 | 3/2014 | |
| WO | WO 2014/039513 A2 | 3/2014 | |
| WO | WO 2014/039523 A1 | 3/2014 | |
| WO | WO 2014/039684 A1 | 3/2014 | |
| WO | WO 2014/039692 A2 | 3/2014 | |
| WO | WO 2014/039702 A2 | 3/2014 | |
| WO | WO 2014/039872 A1 | 3/2014 | |
| WO | WO 2014/039970 A1 | 3/2014 | |
| WO | WO 2014/041327 A1 | 3/2014 | |
| WO | WO 2014/043143 A1 | 3/2014 | |
| WO | WO 2014/047103 A2 | 3/2014 | |
| WO | WO 2014/059173 A2 | 4/2014 | |
| WO | WO 2014/059255 A1 | 4/2014 | |
| WO | WO 2014/065596 A1 | 5/2014 | |
| WO | WO 2014/066505 A1 | 5/2014 | |
| WO | WO 2014/068346 A2 | 5/2014 | |
| WO | WO 2014/070887 A1 | 5/2014 | |
| WO | WO 2014/071006 A1 | 5/2014 | |
| WO | WO 2014/071219 A1 | 5/2014 | |
| WO | WO 2014/071235 A1 | 5/2014 | |
| WO | WO 2014/072941 A1 | 5/2014 | |
| WO | WO 2014/081729 A1 | 5/2014 | |
| WO | WO 2014/081730 A1 | 5/2014 | |
| WO | WO 2014/081855 A1 | 5/2014 | |
| WO | WO-2014/082644 A1 | 6/2014 | |
| WO | WO 2014/085261 A1 | 6/2014 | |
| WO | WO 2014/085593 A1 | 6/2014 | |
| WO | WO 2014/085830 A2 | 6/2014 | |
| WO | WO 2014/089212 A1 | 6/2014 | |
| WO | WO 2014/089290 A1 | 6/2014 | |
| WO | WO 2014/089348 A1 | 6/2014 | |
| WO | WO 2014/089513 A1 | 6/2014 | |
| WO | WO 2014/089533 A2 | 6/2014 | |
| WO | WO 2014/089541 A2 | 6/2014 | |
| WO | WO 2014/093479 A1 | 6/2014 | |
| WO | WO 2014/093595 A1 | 6/2014 | |
| WO | WO 2014/093622 A2 | 6/2014 | |
| WO | WO 2014/093635 A1 | 6/2014 | |
| WO | WO 2014/093655 A2 | 6/2014 | |
| WO | WO 2014/093661 A2 | 6/2014 | |
| WO | WO 2014/093694 A1 | 6/2014 | |

(56) References Cited

FOREIGN PATENT DOCUMENTS

| | | |
|---|---|---|
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/093736 A1 | 6/2014 |
| WO | WO 2014/093768 A1 | 6/2014 |
| WO | WO 2014/093852 A1 | 6/2014 |
| WO | WO 2014/096972 A2 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/110006 A1 | 7/2014 |
| WO | WO 2014/110552 A1 | 7/2014 |
| WO | WO 2014/113493 A1 | 7/2014 |
| WO | WO 2014/123967 A2 | 8/2014 |
| WO | WO 2014/124226 A1 | 8/2014 |
| WO | WO 2014/125668 A1 | 8/2014 |
| WO | WO 2014/127287 A1 | 8/2014 |
| WO | WO 2014/128324 A1 | 8/2014 |
| WO | WO 2014/128659 A1 | 8/2014 |
| WO | WO 2014/130706 A1 | 8/2014 |
| WO | WO 2014/130955 A1 | 8/2014 |
| WO | WO 2014/131833 A1 | 9/2014 |
| WO | WO 2014/138379 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/144951 A1 | 9/2014 |
| WO | WO 2014/145599 A2 | 9/2014 |
| WO | WO 2014/145736 A2 | 9/2014 |
| WO | WO 2014/150624 A1 | 9/2014 |
| WO | WO 2014/152432 A2 | 9/2014 |
| WO | WO 2014/153118 A1 | 9/2014 |
| WO | WO 2014/153470 A2 | 9/2014 |
| WO | WO 2014/161821 A1 | 10/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165707 A2 | 10/2014 |
| WO | WO 2014/165825 A2 | 10/2014 |
| WO | WO 2014/172458 A1 | 10/2014 |
| WO | WO 2014/172470 A | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A | 12/2014 |
| WO | WO 2014/191527 A1 | 12/2014 |
| WO | WO 2014/193583 A2 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2014/207043 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006437 A1 | 1/2015 |
| WO | WO 2015/006498 A2 | 1/2015 |
| WO | WO 2015/006747 A2 | 1/2015 |
| WO | WO 2015/007194 A1 | 1/2015 |
| WO | WO 2015/010114 A1 | 1/2015 |
| WO | WO 2015/011483 A1 | 1/2015 |
| WO | WO-2015/013583 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/024986 A1 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/028969 A2 | 3/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/032494 A2 | 3/2015 |
| WO | WO 2015/033293 A1 | 3/2015 |
| WO | WO 2015/034872 A2 | 3/2015 |
| WO | WO 2015/034885 A1 | 3/2015 |
| WO | WO 2015/035136 A2 | 3/2015 |
| WO | WO 2015/035139 A2 | 3/2015 |
| WO | WO 2015/035162 A2 | 3/2015 |
| WO | WO 2015/040075 A1 | 3/2015 |
| WO | WO 2015/040402 A1 | 3/2015 |
| WO | WO 2015/042585 A1 | 3/2015 |
| WO | WO 2015/048577 A2 | 4/2015 |
| WO | WO 2015/048690 A1 | 4/2015 |
| WO | WO 2015/048707 A2 | 4/2015 |
| WO | WO 2015/048801 A2 | 4/2015 |
| WO | WO 2015/049897 A1 | 4/2015 |
| WO | WO 2015/051191 A1 | 4/2015 |
| WO | WO 2015/052133 A1 | 4/2015 |
| WO | WO 2015/052231 A2 | 4/2015 |
| WO | WO 2015/052335 A1 | 4/2015 |
| WO | WO 2015/053995 A1 | 4/2015 |
| WO | WO 2015/054253 A1 | 4/2015 |
| WO | WO 2015/054315 A1 | 4/2015 |
| WO | WO 2015/057671 A1 | 4/2015 |
| WO | WO 2015/057834 A1 | 4/2015 |
| WO | WO 2015/057852 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO 2015/066634 A2 | 5/2015 |
| WO | WO 2015/066636 A2 | 5/2015 |
| WO | WO 2015/066637 A1 | 5/2015 |
| WO | WO 2015/066638 A2 | 5/2015 |
| WO | WO-2015/066643 A1 | 5/2015 |
| WO | WO 2015/069682 A2 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A1 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO 2015/075175 A1 | 5/2015 |
| WO | WO 2015/075195 A1 | 5/2015 |
| WO | WO 2015/075557 A2 | 5/2015 |

(56) References Cited

FOREIGN PATENT DOCUMENTS

| | | |
|---|---|---|
| WO | WO 2015/077058 A2 | 5/2015 |
| WO | WO 2015/077290 A2 | 5/2015 |
| WO | WO 2015/077318 A1 | 5/2015 |
| WO | WO 2015/079056 A1 | 6/2015 |
| WO | WO 2015/079057 A2 | 6/2015 |
| WO | WO 2015/086795 A2 | 6/2015 |
| WO | WO 2015/086798 A1 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/089486 A1 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO 2015/103057 A1 | 7/2015 |
| WO | WO 2015/103153 A1 | 7/2015 |
| WO | WO 2015/105928 A1 | 7/2015 |
| WO | WO 2015/108993 A1 | 7/2015 |
| WO | WO 2015/109752 A1 | 7/2015 |
| WO | WO 2015/110474 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO 2015/114365 A1 | 8/2015 |
| WO | WO 2015/115903 A1 | 8/2015 |
| WO | WO 2015/116686 A1 | 8/2015 |
| WO | WO 2015/116969 A2 | 8/2015 |
| WO | WO 2015/117021 A1 | 8/2015 |
| WO | WO 2015/117041 A1 | 8/2015 |
| WO | WO 2015/117081 A2 | 8/2015 |
| WO | WO 2015/118156 A1 | 8/2015 |
| WO | WO 2015/119941 A2 | 8/2015 |
| WO | WO 2015/121454 A1 | 8/2015 |
| WO | WO 2015/122967 A1 | 8/2015 |
| WO | WO 2015/123339 A1 | 8/2015 |
| WO | WO 2015/124715 A1 | 8/2015 |
| WO | WO 2015/124718 A1 | 8/2015 |
| WO | WO 2015/126927 A2 | 8/2015 |
| WO | WO 2015/127428 A1 | 8/2015 |
| WO | WO 2015/127439 A1 | 8/2015 |
| WO | WO 2015/129686 A1 | 9/2015 |
| WO | WO 2015/131101 A1 | 9/2015 |
| WO | WO 2015/133554 A1 | 9/2015 |
| WO | WO 2015/134812 A1 | 9/2015 |
| WO | WO 2015/136001 A1 | 9/2015 |
| WO | WO 2015/138510 A1 | 9/2015 |
| WO | WO 2015/138739 A2 | 9/2015 |
| WO | WO 2015/138855 A1 | 9/2015 |
| WO | WO 2015/138870 A2 | 9/2015 |
| WO | WO 2015/139008 A1 | 9/2015 |
| WO | WO 2015/139139 A1 | 9/2015 |
| WO | WO 2015/143046 A2 | 9/2015 |
| WO | WO 2015/143177 A1 | 9/2015 |
| WO | WO 2015/145417 A1 | 10/2015 |
| WO | WO 2015/148431 A1 | 10/2015 |
| WO | WO 2015/148670 A1 | 10/2015 |
| WO | WO 2015/148680 A1 | 10/2015 |
| WO | WO 2015/148761 A1 | 10/2015 |
| WO | WO 2015/148860 A1 | 10/2015 |
| WO | WO 2015/148863 A2 | 10/2015 |
| WO | WO 2015/153760 A2 | 10/2015 |
| WO | WO 2015/153780 A1 | 10/2015 |
| WO | WO 2015/153789 A1 | 10/2015 |
| WO | WO 2015/153791 A1 | 10/2015 |
| WO | WO 2015/153889 A2 | 10/2015 |
| WO | WO 2015/153940 A1 | 10/2015 |
| WO | WO 2015/155341 A1 | 10/2015 |
| WO | WO 2015/155686 A2 | 10/2015 |
| WO | WO 2015/157070 A2 | 10/2015 |
| WO | WO 2015/157534 A1 | 10/2015 |
| WO | WO 2015/159068 A1 | 10/2015 |
| WO | WO 2015/159086 A1 | 10/2015 |
| WO | WO 2015/159087 A1 | 10/2015 |
| WO | WO 2015/160683 A1 | 10/2015 |
| WO | WO 2015/161276 A2 | 10/2015 |
| WO | WO 2015/163733 A1 | 10/2015 |
| WO | WO 2015/164740 A1 | 10/2015 |
| WO | WO 2015/164748 A1 | 10/2015 |
| WO | WO 2015/165274 A1 | 11/2015 |
| WO | WO 2015/165275 A1 | 11/2015 |
| WO | WO 2015/165276 A1 | 11/2015 |
| WO | WO 2015/166272 A2 | 11/2015 |
| WO | WO 2015/167766 A1 | 11/2015 |
| WO | WO 2015/167956 A1 | 11/2015 |
| WO | WO 2015/168125 A1 | 11/2015 |
| WO | WO 2015/168158 A1 | 11/2015 |
| WO | WO 2015/168404 A1 | 11/2015 |
| WO | WO 2015/168547 A2 | 11/2015 |
| WO | WO 2015/168800 A1 | 11/2015 |
| WO | WO 2015/171603 A1 | 11/2015 |
| WO | WO 2015/171894 A1 | 11/2015 |
| WO | WO 2015/171932 A1 | 11/2015 |
| WO | WO 2015/172128 A1 | 11/2015 |
| WO | WO 2015/173436 A1 | 11/2015 |
| WO | WO 2015/175642 A2 | 11/2015 |
| WO | WO 2015/179540 A1 | 11/2015 |
| WO | WO 2015/183025 A1 | 12/2015 |
| WO | WO 2015/183026 A1 | 12/2015 |
| WO | WO 2015/183885 A1 | 12/2015 |
| WO | WO 2015/184259 A1 | 12/2015 |
| WO | WO 2015/184262 A1 | 12/2015 |
| WO | WO 2015/184268 A1 | 12/2015 |
| WO | WO 2015/188056 A1 | 12/2015 |
| WO | WO 2015/188065 A1 | 12/2015 |
| WO | WO 2015/188094 A1 | 12/2015 |
| WO | WO 2015/188109 A1 | 12/2015 |
| WO | WO 2015/188132 A1 | 12/2015 |
| WO | WO 2015/188135 A1 | 12/2015 |
| WO | WO 2015/188191 A1 | 12/2015 |
| WO | WO 2015/189693 A1 | 12/2015 |
| WO | WO 2015/191693 A2 | 12/2015 |
| WO | WO 2015/191899 A1 | 12/2015 |
| WO | WO 2015/191911 A2 | 12/2015 |
| WO | WO 2015/193858 A1 | 12/2015 |
| WO | WO 2015/195547 A1 | 12/2015 |
| WO | WO 2015/195621 A1 | 12/2015 |
| WO | WO 2015/195798 A1 | 12/2015 |
| WO | WO 2015/198020 A1 | 12/2015 |
| WO | WO 2015/200334 A1 | 12/2015 |
| WO | WO 2015/200378 A1 | 12/2015 |
| WO | WO 2015/200555 A2 | 12/2015 |
| WO | WO 2015/200805 A2 | 12/2015 |
| WO | WO 2016/001978 A1 | 1/2016 |
| WO | WO 2016/004010 A1 | 1/2016 |
| WO | WO 2016/007347 A1 | 1/2016 |
| WO | WO 2016/007604 A1 | 1/2016 |
| WO | WO 2016/007948 A1 | 1/2016 |
| WO | WO 2016/011080 A2 | 1/2016 |
| WO | WO 2016/011210 A2 | 1/2016 |
| WO | WO 2016/011428 A1 | 1/2016 |
| WO | WO 2016/012544 A2 | 1/2016 |
| WO | WO 2016/012552 A1 | 1/2016 |
| WO | WO 2016/014409 A1 | 1/2016 |
| WO | WO 2016/014565 A2 | 1/2016 |
| WO | WO 2016/014794 A1 | 1/2016 |
| WO | WO 2016/014837 A1 | 1/2016 |
| WO | WO 2016/016119 A1 | 2/2016 |
| WO | WO 2016/016358 A1 | 2/2016 |
| WO | WO 2016/019144 A2 | 2/2016 |
| WO | WO 2016/020399 A1 | 2/2016 |
| WO | WO 2016/021972 A1 | 2/2016 |
| WO | WO 2016/021973 A1 | 2/2016 |
| WO | WO 2016/022363 A2 | 2/2016 |
| WO | WO 2016/022866 A1 | 2/2016 |

(56) References Cited

FOREIGN PATENT DOCUMENTS

| | | |
|---|---|---|
| WO | WO 2016/022931 A1 | 2/2016 |
| WO | WO 2016/025131 A1 | 2/2016 |
| WO | WO 2016/025469 A1 | 2/2016 |
| WO | WO 2016/025759 A1 | 2/2016 |
| WO | WO 2016/026444 A1 | 2/2016 |
| WO | WO 2016/028682 A1 | 2/2016 |
| WO | WO 2016/028843 A1 | 2/2016 |
| WO | WO 2016/028887 A1 | 2/2016 |
| WO | WO 2016/033088 A1 | 3/2016 |
| WO | WO 2016/033230 A1 | 3/2016 |
| WO | WO 2016/033246 A1 | 3/2016 |
| WO | WO 2016/033298 A1 | 3/2016 |
| WO | WO 2016/035044 A1 | 3/2016 |
| WO | WO 2016/036754 A1 | 3/2016 |
| WO | WO 2016/037157 A2 | 3/2016 |
| WO | WO 2016/040030 A1 | 3/2016 |
| WO | WO 2016/040594 A1 | 3/2016 |
| WO | WO 2016/044182 A1 | 3/2016 |
| WO | WO 2016/044416 A1 | 3/2016 |
| WO | WO 2016/046635 A1 | 3/2016 |
| WO | WO 2016/049024 A2 | 3/2016 |
| WO | WO 2016/049163 A2 | 3/2016 |
| WO | WO 2016/049230 A1 | 3/2016 |
| WO | WO 2016/049251 A1 | 3/2016 |
| WO | WO 2016/049258 A2 | 3/2016 |
| WO | WO 2016/053397 A2 | 4/2016 |
| WO | WO 2016/054326 A1 | 4/2016 |
| WO | WO 2016/057061 A2 | 4/2016 |
| WO | WO 2016/057821 A2 | 4/2016 |
| WO | WO 2016/057835 A2 | 4/2016 |
| WO | WO 2016/057850 A2 | 4/2016 |
| WO | WO 2016/057951 A2 | 4/2016 |
| WO | WO 2016/057961 A2 | 4/2016 |
| WO | WO 2016/061073 A1 | 4/2016 |
| WO | WO 2016/061374 A1 | 4/2016 |
| WO | WO 2016/061481 A1 | 4/2016 |
| WO | WO 2016/061523 A1 | 4/2016 |
| WO | WO-2016/064894 A2 | 4/2016 |
| WO | WO 2016/069282 A1 | 5/2016 |
| WO | WO 2016/069283 A1 | 5/2016 |
| WO | WO 2016/069591 A2 | 5/2016 |
| WO | WO 2016/069910 A1 | 5/2016 |
| WO | WO 2016/069912 A1 | 5/2016 |
| WO | WO 2016/070037 A2 | 5/2016 |
| WO | WO 2016/070070 A1 | 5/2016 |
| WO | WO 2016/070129 A1 | 5/2016 |
| WO | WO 2016/072399 A1 | 5/2016 |
| WO | WO 2016/072936 A1 | 5/2016 |
| WO | WO 2016/073433 A1 | 5/2016 |
| WO | WO 2016/073559 A1 | 5/2016 |
| WO | WO 2016/073990 A2 | 5/2016 |
| WO | WO 2016/075662 A2 | 5/2016 |
| WO | WO-2016/076672 A1 | 5/2016 |
| WO | WO 2016/077273 A1 | 5/2016 |
| WO | WO 2016/077350 A1 | 5/2016 |
| WO | WO 2016/080097 A1 | 5/2016 |
| WO | WO-2016/080795 A1 | 5/2016 |
| WO | WO 2016/081923 A2 | 5/2016 |
| WO | WO 2016/081924 A1 | 5/2016 |
| WO | WO 2016/082135 A1 | 6/2016 |
| WO | WO 2016/083811 A1 | 6/2016 |
| WO | WO 2016/084084 A1 | 6/2016 |
| WO | WO 2016/084088 A1 | 6/2016 |
| WO | WO 2016/086177 A2 | 6/2016 |
| WO | WO 2016/089433 A1 | 6/2016 |
| WO | WO 2016/089866 A1 | 6/2016 |
| WO | WO 2016/089883 A1 | 6/2016 |
| WO | WO 2016/090385 A1 | 6/2016 |
| WO | WO-2016/094679 A1 | 6/2016 |
| WO | WO 2016/094845 A2 | 6/2016 |
| WO | WO 2016/094867 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/094888 A1 | 6/2016 |
| WO | WO 2016/097212 A1 | 6/2016 |
| WO | WO 2016/097231 A2 | 6/2016 |
| WO | WO 2016/097751 A1 | 6/2016 |
| WO | WO 2016/099887 A1 | 6/2016 |
| WO | WO 2016/100272 A1 | 6/2016 |
| WO | WO 2016/100389 A1 | 6/2016 |
| WO | WO 2016/100568 A1 | 6/2016 |
| WO | WO 2016/100571 A1 | 6/2016 |
| WO | WO 2016/100951 A2 | 6/2016 |
| WO | WO 2016/100955 A2 | 6/2016 |
| WO | WO 2016/100974 A1 | 6/2016 |
| WO | WO 2016/103233 A2 | 6/2016 |
| WO | WO 2016/104716 A1 | 6/2016 |
| WO | WO 2016/106236 A1 | 6/2016 |
| WO | WO-2016/106239 A1 | 6/2016 |
| WO | WO 2016/106244 A1 | 6/2016 |
| WO | WO 2016/106338 A2 | 6/2016 |
| WO | WO 2016/108926 A1 | 7/2016 |
| WO | WO 2016/109255 A1 | 7/2016 |
| WO | WO 2016/109840 A2 | 7/2016 |
| WO | WO 2016/110214 A1 | 7/2016 |
| WO | WO 2016/110453 A1 | 7/2016 |
| WO | WO 2016/110511 A1 | 7/2016 |
| WO | WO 2016/110512 A1 | 7/2016 |
| WO | WO-2016/111546 A2 | 7/2016 |
| WO | WO-2016/112242 A1 | 7/2016 |
| WO | WO 2016/112351 A1 | 7/2016 |
| WO | WO 2016/112963 A1 | 7/2016 |
| WO | WO 2016/114972 A1 | 7/2016 |
| WO | WO 2016/115179 A1 | 7/2016 |
| WO | WO 2016/115326 A1 | 7/2016 |
| WO | WO 2016/115355 A1 | 7/2016 |
| WO | WO 2016/116032 A1 | 7/2016 |
| WO | WO 2016/120480 A1 | 8/2016 |
| WO | WO 2016/123071 A1 | 8/2016 |
| WO | WO 2016/123230 A1 | 8/2016 |
| WO | WO 2016/123243 A1 | 8/2016 |
| WO | WO 2016/123578 A1 | 8/2016 |
| WO | WO 2016/126747 A1 | 8/2016 |
| WO | WO 2016/130600 A2 | 8/2016 |
| WO | WO 2016/130697 A1 | 8/2016 |
| WO | WO-2016/131009 A1 | 8/2016 |
| WO | WO 2016/132122 A1 | 8/2016 |
| WO | WO-2016/133165 A1 | 8/2016 |
| WO | WO 2016/135507 A1 | 9/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/137774 A1 | 9/2016 |
| WO | WO 2016/137949 A1 | 9/2016 |
| WO | WO 2016/141224 A1 | 9/2016 |
| WO | WO 2016/141893 A1 | 9/2016 |
| WO | WO 2016/142719 A1 | 9/2016 |
| WO | WO 2016/145150 A2 | 9/2016 |
| WO | WO 2016/148994 A1 | 9/2016 |
| WO | WO 2016/149484 A2 | 9/2016 |
| WO | WO 2016/149547 A1 | 9/2016 |
| WO | WO 2016/150336 A1 | 9/2016 |
| WO | WO 2016/150855 A1 | 9/2016 |
| WO | WO 2016/154016 A2 | 9/2016 |
| WO | WO 2016/154579 A2 | 9/2016 |
| WO | WO 2016/154596 A1 | 9/2016 |
| WO | WO 2016/155482 A1 | 10/2016 |
| WO | WO 2016/161004 A1 | 10/2016 |
| WO | WO 2016/161207 A1 | 10/2016 |
| WO | WO 2016/161260 A1 | 10/2016 |
| WO | WO 2016/161380 A1 | 10/2016 |
| WO | WO-2016/161446 A1 | 10/2016 |
| WO | WO 2016/164356 A1 | 10/2016 |
| WO | WO 2016/164797 A1 | 10/2016 |
| WO | WO 2016/166340 A1 | 10/2016 |
| WO | WO-2016/167300 A1 | 10/2016 |
| WO | WO 2016/170484 A1 | 10/2016 |
| WO | WO 2016/172359 A2 | 10/2016 |
| WO | WO 2016/172727 A1 | 10/2016 |
| WO | WO 2016/174056 A1 | 11/2016 |
| WO | WO 2016/174151 A1 | 11/2016 |
| WO | WO 2016/174250 A1 | 11/2016 |
| WO | WO 2016/176191 A1 | 11/2016 |

(56) References Cited

FOREIGN PATENT DOCUMENTS

| | | |
|---|---|---|
| WO | WO 2016/176404 A1 | 11/2016 |
| WO | WO 2016/176690 A2 | 11/2016 |
| WO | WO 2016/177682 A1 | 11/2016 |
| WO | WO 2016/178207 A1 | 11/2016 |
| WO | WO 2016/179038 A1 | 11/2016 |
| WO | WO 2016/179112 A1 | 11/2016 |
| WO | WO 2016/181357 A1 | 11/2016 |
| WO | WO 2016/182893 A1 | 11/2016 |
| WO | WO 2016/182917 A1 | 11/2016 |
| WO | WO 2016/182959 A1 | 11/2016 |
| WO | WO 2016/183236 A1 | 11/2016 |
| WO | WO 2016/183298 A2 | 11/2016 |
| WO | WO 2016/183345 A1 | 11/2016 |
| WO | WO 2016/183402 A2 | 11/2016 |
| WO | WO 2016/183438 A1 | 11/2016 |
| WO | WO 2016/183448 A1 | 11/2016 |
| WO | WO 2016/184955 A2 | 11/2016 |
| WO | WO 2016/184989 A1 | 11/2016 |
| WO | WO 2016/185411 A1 | 11/2016 |
| WO | WO 2016/186745 A1 | 11/2016 |
| WO | WO 2016/186772 A2 | 11/2016 |
| WO | WO 2016/186946 A1 | 11/2016 |
| WO | WO 2016/186953 A1 | 11/2016 |
| WO | WO 2016/187717 A1 | 12/2016 |
| WO | WO 2016/187904 A1 | 12/2016 |
| WO | WO 2016/191684 A1 | 12/2016 |
| WO | WO 2016/191869 A1 | 12/2016 |
| WO | WO 2016/196273 A1 | 12/2016 |
| WO | WO 2016/196282 A1 | 12/2016 |
| WO | WO 2016/196308 A1 | 12/2016 |
| WO | WO-2016/196361 A1 | 12/2016 |
| WO | WO 2016/196499 A1 | 12/2016 |
| WO | WO 2016/196539 A2 | 12/2016 |
| WO | WO 2016/196655 A1 | 12/2016 |
| WO | WO 2016/196805 A1 | 12/2016 |
| WO | WO 2016/196887 A1 | 12/2016 |
| WO | WO 2016/197132 A1 | 12/2016 |
| WO | WO 2016/197133 A1 | 12/2016 |
| WO | WO 2016/197354 A1 | 12/2016 |
| WO | WO 2016/197355 A1 | 12/2016 |
| WO | WO 2016/197356 A1 | 12/2016 |
| WO | WO 2016/197357 A1 | 12/2016 |
| WO | WO 2016/197358 A1 | 12/2016 |
| WO | WO 2016/197359 A1 | 12/2016 |
| WO | WO 2016/197360 A1 | 12/2016 |
| WO | WO 2016/197361 A1 | 12/2016 |
| WO | WO 2016/197362 A1 | 12/2016 |
| WO | WO 2016/198361 A1 | 12/2016 |
| WO | WO 2016/198500 A1 | 12/2016 |
| WO | WO 2016/200263 A1 | 12/2016 |
| WO | WO 2016/201047 A1 | 12/2016 |
| WO | WO 2016/201138 A1 | 12/2016 |
| WO | WO 2016/201152 A1 | 12/2016 |
| WO | WO 2016/201153 A1 | 12/2016 |
| WO | WO 2016/201155 A1 | 12/2016 |
| WO | WO 2016/205276 A1 | 12/2016 |
| WO | WO 2016/205613 A1 | 12/2016 |
| WO | WO 2016/205623 A1 | 12/2016 |
| WO | WO 2016/205680 A1 | 12/2016 |
| WO | WO 2016/205688 A2 | 12/2016 |
| WO | WO 2016/205703 A1 | 12/2016 |
| WO | WO 2016/205711 A1 | 12/2016 |
| WO | WO 2016/205728 A1 | 12/2016 |
| WO | WO 2016/205745 A2 | 12/2016 |
| WO | WO 2016/205749 A1 | 12/2016 |
| WO | WO 2016/205759 A2 | 12/2016 |
| WO | WO 2016/205764 A2 | 12/2016 |
| WO | WO 2017/001572 A1 | 1/2017 |
| WO | WO 2017/001988 A1 | 1/2017 |
| WO | WO 2017/004261 A1 | 1/2017 |
| WO | WO 2017/004279 A2 | 1/2017 |
| WO | WO 2017/004616 A1 | 1/2017 |
| WO | WO 2017/005807 A1 | 1/2017 |
| WO | WO 2017/009399 A1 | 1/2017 |
| WO | WO-2017/010556 A1 | 1/2017 |
| WO | WO 2017/011519 A1 | 1/2017 |
| WO | WO 2017/011721 A1 | 1/2017 |
| WO | WO 2017/011804 A1 | 1/2017 |
| WO | WO 2017/015015 A1 | 1/2017 |
| WO | WO 2017/015101 A1 | 1/2017 |
| WO | WO 2017/015567 A1 | 1/2017 |
| WO | WO 2017/015637 A1 | 1/2017 |
| WO | WO 2017/017016 A1 | 2/2017 |
| WO | WO 2017/019867 A1 | 2/2017 |
| WO | WO 2017/019895 A1 | 2/2017 |
| WO | WO 2017/023803 A1 | 2/2017 |
| WO | WO 2017/023974 A1 | 2/2017 |
| WO | WO 2017/024047 A1 | 2/2017 |
| WO | WO 2017/024319 A1 | 2/2017 |
| WO | WO 2017/024343 A1 | 2/2017 |
| WO | WO-2017/024602 A1 | 2/2017 |
| WO | WO 2017/025323 A1 | 2/2017 |
| WO | WO 2017/027423 A1 | 2/2017 |
| WO | WO 2017/028768 A1 | 2/2017 |
| WO | WO 2017/029664 A1 | 2/2017 |
| WO | WO 2017/031360 A1 | 2/2017 |
| WO | WO 2017/031483 A1 | 2/2017 |
| WO | WO 2017/035416 A2 | 3/2017 |
| WO | WO 2017/040348 A1 | 3/2017 |
| WO | WO 2017/040511 A1 | 3/2017 |
| WO | WO 2017/040709 A1 | 3/2017 |
| WO | WO 2017/040786 A1 | 3/2017 |
| WO | WO 2017/040793 A1 | 3/2017 |
| WO | WO 2017/040813 A2 | 3/2017 |
| WO | WO-2017/043573 A1 | 3/2017 |
| WO | WO-2017/043656 A1 | 3/2017 |
| WO | WO 2017/044419 A1 | 3/2017 |
| WO | WO 2017/044776 A1 | 3/2017 |
| WO | WO 2017/044857 A2 | 3/2017 |
| WO | WO 2017/049129 A2 | 3/2017 |
| WO | WO 2017/050963 A1 | 3/2017 |
| WO | WO 2017/053312 A1 | 3/2017 |
| WO | WO 2017/053431 A2 | 3/2017 |
| WO | WO 2017/053713 A1 | 3/2017 |
| WO | WO 2017/053729 A1 | 3/2017 |
| WO | WO 2017/053753 A1 | 3/2017 |
| WO | WO 2017/053762 A1 | 3/2017 |
| WO | WO 2017/053879 A1 | 3/2017 |
| WO | WO 2017/054721 A1 | 4/2017 |
| WO | WO 2017/058658 A2 | 4/2017 |
| WO | WO 2017/059241 A1 | 4/2017 |
| WO | WO 2017/062605 A1 | 4/2017 |
| WO | WO 2017/062723 A1 | 4/2017 |
| WO | WO 2017/062754 A1 | 4/2017 |
| WO | WO 2017/062855 A1 | 4/2017 |
| WO | WO 2017/062886 A1 | 4/2017 |
| WO | WO 2017/062983 A1 | 4/2017 |
| WO | WO 2017/064439 A1 | 4/2017 |
| WO | WO 2017/064546 A1 | 4/2017 |
| WO | WO 2017/064566 A2 | 4/2017 |
| WO | WO 2017/066175 A1 | 4/2017 |
| WO | WO 2017/066497 A2 | 4/2017 |
| WO | WO 2017/066588 A2 | 4/2017 |
| WO | WO 2017/066707 A1 | 4/2017 |
| WO | WO 2017/068077 A1 | 4/2017 |
| WO | WO 2017/068377 A1 | 4/2017 |
| WO | WO 2017/069829 A1 | 4/2017 |
| WO | WO 2017/070029 A1 | 4/2017 |
| WO | WO 2017/070032 A1 | 4/2017 |
| WO | WO 2017/070169 A1 | 4/2017 |
| WO | WO 2017/070284 A1 | 4/2017 |
| WO | WO 2017/070598 A1 | 4/2017 |
| WO | WO 2017/070605 A1 | 4/2017 |
| WO | WO 2017/070632 A2 | 4/2017 |
| WO | WO 2017/070633 A2 | 4/2017 |
| WO | WO 2017/072590 A1 | 5/2017 |
| WO | WO 2017/074526 A1 | 5/2017 |
| WO | WO 2017/074962 A1 | 5/2017 |
| WO | WO 2017/075261 A1 | 5/2017 |
| WO | WO 2017/075335 A1 | 5/2017 |
| WO | WO 2017/075475 A1 | 5/2017 |
| WO | WO 2017/077135 A1 | 5/2017 |
| WO | WO 2017/077329 A2 | 5/2017 |
| WO | WO 2017/078751 A1 | 5/2017 |

(56) References Cited

FOREIGN PATENT DOCUMENTS

| | | |
|---|---|---|
| WO | WO 2017/079400 A1 | 5/2017 |
| WO | WO 2017/079428 A1 | 5/2017 |
| WO | WO 2017/079673 A1 | 5/2017 |
| WO | WO 2017/079724 A1 | 5/2017 |
| WO | WO 2017/081097 A1 | 5/2017 |
| WO | WO 2017/081288 A1 | 5/2017 |
| WO | WO 2017/083368 A1 | 5/2017 |
| WO | WO 2017/083722 A1 | 5/2017 |
| WO | WO 2017/083766 A1 | 5/2017 |
| WO | WO 2017/087395 A1 | 5/2017 |
| WO | WO 2017/090724 A1 | 6/2017 |
| WO | WO 2017/091510 A1 | 6/2017 |
| WO | WO 2017/091630 A1 | 6/2017 |
| WO | WO 2017/092201 A1 | 6/2017 |
| WO | WO 2017/093370 A1 | 6/2017 |
| WO | WO 2017/095111 A1 | 6/2017 |
| WO | WO 2017/096041 A1 | 6/2017 |
| WO | WO 2017/096237 A1 | 6/2017 |
| WO | WO 2017/100158 A1 | 6/2017 |
| WO | WO 2017/100431 A2 | 6/2017 |
| WO | WO 2017/104404 A1 | 6/2017 |
| WO | WO 2017/105251 A1 | 6/2017 |
| WO | WO 2017/105350 A1 | 6/2017 |
| WO | WO 2017/105991 A1 | 6/2017 |
| WO | WO 2017/106414 A1 | 6/2017 |
| WO | WO 2017/106528 A2 | 6/2017 |
| WO | WO 2017/106537 A2 | 6/2017 |
| WO | WO 2017/106569 A1 | 6/2017 |
| WO | WO 2017/106616 A1 | 6/2017 |
| WO | WO 2017/106657 A1 | 6/2017 |
| WO | WO 2017/106767 A1 | 6/2017 |
| WO | WO-2017/109134 A1 | 6/2017 |
| WO | WO 2017/109757 A1 | 6/2017 |
| WO | WO 2017/112620 A1 | 6/2017 |
| WO | WO 2017/115268 A1 | 7/2017 |
| WO | WO 2017/117395 A1 | 7/2017 |
| WO | WO 2017/118598 A1 | 7/2017 |
| WO | WO 2017/118720 A1 | 7/2017 |
| WO | WO 2017/123609 A1 | 7/2017 |
| WO | WO 2017/123910 A1 | 7/2017 |
| WO | WO 2017/124086 A1 | 7/2017 |
| WO | WO 2017/124100 A1 | 7/2017 |
| WO | WO 2017/124652 A1 | 7/2017 |
| WO | WO 2017/126987 A1 | 7/2017 |
| WO | WO 2017/127807 A1 | 7/2017 |
| WO | WO 2017/131237 A1 | 8/2017 |
| WO | WO 2017/132112 A1 | 8/2017 |
| WO | WO 2017/136520 A1 | 8/2017 |
| WO | WO 2017/136629 A1 | 8/2017 |
| WO | WO 2017/136794 A1 | 8/2017 |
| WO | WO 2017/139264 A1 | 8/2017 |
| WO | WO 2017/139505 A2 | 8/2017 |
| WO | WO-2017/141173 A2 | 8/2017 |
| WO | WO 2017/142835 A1 | 8/2017 |
| WO | WO 2017/142999 A2 | 8/2017 |
| WO | WO 2017/143042 A2 | 8/2017 |
| WO | WO-2017/147278 A1 | 8/2017 |
| WO | WO-2017/147432 A1 | 8/2017 |
| WO | WO-2017/147446 A1 | 8/2017 |
| WO | WO-2017/147555 A1 | 8/2017 |
| WO | WO-2017/151444 A1 | 9/2017 |
| WO | WO-2017/152015 A1 | 9/2017 |
| WO | WO 2017/155717 A1 | 9/2017 |
| WO | WO-2017/157422 A1 | 9/2017 |
| WO | WO-2017/158153 A1 | 9/2017 |
| WO | WO-2017/160689 A1 | 9/2017 |
| WO | WO-2017/160752 A1 | 9/2017 |
| WO | WO-2017/160890 A1 | 9/2017 |
| WO | WO-2017/161068 A1 | 9/2017 |
| WO | WO-2017/165826 A1 | 9/2017 |
| WO | WO-2017/165862 A1 | 9/2017 |
| WO | WO-2017/172644 A2 | 10/2017 |
| WO | WO-2017/172645 A2 | 10/2017 |
| WO | WO-2017/172860 A1 | 10/2017 |
| WO | WO-2017/172860 A2 | 10/2017 |
| WO | WO-2017/173004 A1 | 10/2017 |
| WO | WO-2017/173054 A1 | 10/2017 |
| WO | WO-2017/173092 A1 | 10/2017 |
| WO | WO-2017/174329 A1 | 10/2017 |
| WO | WO-2017/176529 A1 | 10/2017 |
| WO | WO 2017/176806 A1 | 10/2017 |
| WO | WO-2017/178590 A1 | 10/2017 |
| WO | WO-2017/180694 A1 | 10/2017 |
| WO | WO-2017/180711 A1 | 10/2017 |
| WO | WO-2017/180915 A2 | 10/2017 |
| WO | WO-2017/180926 A1 | 10/2017 |
| WO | WO-2017/181107 A2 | 10/2017 |
| WO | WO-2017/181735 A2 | 10/2017 |
| WO | WO-2017/182468 A1 | 10/2017 |
| WO | WO-2017/184334 A1 | 10/2017 |
| WO | WO-2017/184768 A1 | 10/2017 |
| WO | WO-2017/184786 A1 | 10/2017 |
| WO | WO-2017/186550 A1 | 11/2017 |
| WO | WO-2017/189308 A1 | 11/2017 |
| WO | WO-2017/189336 A1 | 11/2017 |
| WO | WO-2017/190257 A1 | 11/2017 |
| WO | WO-2017/190664 A1 | 11/2017 |
| WO | WO-2017/191210 A1 | 11/2017 |
| WO | WO-2017/192172 A1 | 11/2017 |
| WO | WO-2017/192512 A2 | 11/2017 |
| WO | WO-2017/192544 A1 | 11/2017 |
| WO | WO-2017/192573 A1 | 11/2017 |
| WO | WO-2017/193029 A2 | 11/2017 |
| WO | WO-2017/193053 A1 | 11/2017 |
| WO | WO-2017/196768 A1 | 11/2017 |
| WO | WO-2017/197038 A1 | 11/2017 |
| WO | WO-2017/197238 A1 | 11/2017 |
| WO | WO-2017/197301 A1 | 11/2017 |
| WO | WO 2017/201476 A1 | 11/2017 |
| WO | WO-2017/205290 A1 | 11/2017 |
| WO | WO-2017/205423 A1 | 11/2017 |
| WO | WO-2017/207589 A1 | 12/2017 |
| WO | WO-2017/208247 A1 | 12/2017 |
| WO | WO-2017/209809 A1 | 12/2017 |
| WO | WO-2017/213896 A1 | 12/2017 |
| WO | WO-2017/213898 A2 | 12/2017 |
| WO | WO-2017/214460 A1 | 12/2017 |
| WO | WO-2017/216392 A1 | 12/2017 |
| WO | WO-2017/216771 A2 | 12/2017 |
| WO | WO 2017/218185 A1 | 12/2017 |
| WO | WO-2017/219027 A1 | 12/2017 |
| WO | WO-2017/219033 A1 | 12/2017 |
| WO | WO-2017/220751 A1 | 12/2017 |
| WO | WO-2017/222370 A1 | 12/2017 |
| WO | WO-2017/222773 A1 | 12/2017 |
| WO | WO-2017/222834 A1 | 12/2017 |
| WO | WO-2017/223107 A1 | 12/2017 |
| WO | WO-2017/223330 A1 | 12/2017 |
| WO | WO-2018/000657 A1 | 1/2018 |
| WO | WO-2018/002719 A1 | 1/2018 |
| WO | WO-2018/005117 A1 | 1/2018 |
| WO | WO-2018/005289 A2 | 1/2018 |
| WO | WO-2018/005691 A1 | 1/2018 |
| WO | WO-2018/005782 A1 | 1/2018 |
| WO | WO-2018/005873 A1 | 1/2018 |
| WO | WO 2018/06693 A1 | 1/2018 |
| WO | WO-2018/009520 A1 | 1/2018 |
| WO | WO-2018/009562 A1 | 1/2018 |
| WO | WO-2018/009822 A1 | 1/2018 |
| WO | WO-2018/013821 A1 | 1/2018 |
| WO | WO-2018/013990 A1 | 1/2018 |
| WO | WO-2018/014384 A1 | 1/2018 |
| WO | WO-2018/015444 A1 | 1/2018 |
| WO | WO-2018/015936 A2 | 1/2018 |
| WO | WO-2018/017754 A1 | 1/2018 |
| WO | WO-2018/018979 A1 | 2/2018 |
| WO | WO-2018/020248 A1 | 2/2018 |
| WO | WO-2018/022480 A1 | 2/2018 |
| WO | WO-2018/022634 A1 | 2/2018 |
| WO | WO-2018/025206 A1 | 2/2018 |
| WO | WO-2018/026723 A1 | 2/2018 |
| WO | WO-2018/026976 A1 | 2/2018 |
| WO | WO-2018/027078 A1 | 2/2018 |
| WO | WO 2018/030608 A1 | 2/2018 |

(56) References Cited

FOREIGN PATENT DOCUMENTS

| | | |
|---|---|---|
| WO | WO-2018/031683 A1 | 2/2018 |
| WO | WO-2018/035250 A1 | 2/2018 |
| WO | WO-2018/035300 A1 | 2/2018 |
| WO | WO-2018/035423 A1 | 2/2018 |
| WO | WO-2018/035503 A1 | 2/2018 |
| WO | WO-2018/039145 A1 | 3/2018 |
| WO | WO-2018/039438 A1 | 3/2018 |
| WO | WO-2018/039440 A1 | 3/2018 |
| WO | WO-2018/039448 A1 | 3/2018 |
| WO | WO-2018/045630 A1 | 3/2018 |
| WO | WO-2018/048827 A1 | 3/2018 |
| WO | WO-2018/049168 A1 | 3/2018 |
| WO | WO-2018/051347 A1 | 3/2018 |
| WO | WO-2018/058064 A1 | 3/2018 |
| WO | WO-2018/062866 A2 | 4/2018 |
| WO | WO-2018/064352 A1 | 4/2018 |
| WO | WO-2018/064371 A1 | 4/2018 |
| WO | WO-2018/064516 A1 | 4/2018 |
| WO | WO-2018/067546 A1 | 4/2018 |
| WO | WO-2018/067846 A1 | 4/2018 |
| WO | WO-2018/068053 A2 | 4/2018 |
| WO | WO-2018/069474 A1 | 4/2018 |
| WO | WO-2018/071623 A2 | 4/2018 |
| WO | WO-2018/071663 A1 | 4/2018 |
| WO | WO-2018/071868 A1 | 4/2018 |
| WO | WO-2018/071892 A1 | 4/2018 |
| WO | WO-2018/074979 | 4/2018 |
| WO | WO-2018/079134 A1 | 5/2018 |
| WO | WO-2018/080573 A1 | 5/2018 |
| WO | WO-2018/081504 A1 | 5/2018 |
| WO | WO-2018/081535 A2 | 5/2018 |
| WO | WO-2018/081728 A1 | 5/2018 |
| WO | WO-2018/083128 A2 | 5/2018 |
| WO | WO 2018/083606 A1 | 5/2018 |
| WO | WO-2018/085288 A1 | 5/2018 |
| WO | WO-2018/086623 A1 | 5/2018 |
| WO | WO-2018/093990 A1 | 5/2018 |
| WO | WO 2018/098383 A1 | 5/2018 |
| WO | WO 2018/098480 A1 | 5/2018 |
| WO | WO 2018/098587 A1 | 6/2018 |
| WO | WO 2018/099256 A1 | 6/2018 |
| WO | WO 2018/103686 A1 | 6/2018 |
| WO | WO 2018/106268 A1 | 6/2018 |
| WO | WO 2018/107028 A1 | 6/2018 |
| WO | WO 2018/107103 A1 | 6/2018 |
| WO | WO 2018/107129 A1 | 6/2018 |
| WO | WO 2018-108272 A1 | 6/2018 |
| WO | WO 2018/109101 A1 | 6/2018 |
| WO | WO 2018/111946 A1 | 6/2018 |
| WO | WO 2018/111947 A1 | 6/2018 |
| WO | WO 2018/112336 A1 | 6/2018 |
| WO | WO 2018/112446 A2 | 6/2018 |
| WO | WO 2018/119354 A1 | 6/2018 |
| WO | WO 2018/119359 A1 | 6/2018 |
| WO | WO 2018/130830 A1 | 7/2018 |
| WO | WO 2018/135838 A1 | 7/2018 |
| WO | WO 2018/136396 A2 | 7/2018 |
| WO | WO 2018/138385 A1 | 8/2018 |
| WO | WO 2018/148246 A1 | 8/2018 |
| WO | WO 2018/148256 A1 | 8/2018 |
| WO | WO 2018/148647 A2 | 8/2018 |
| WO | WO 2018/149418 A1 | 8/2018 |
| WO | WO 2018/149888 A1 | 8/2018 |
| WO | WO 2018/152418 A1 | 8/2018 |
| WO | WO 2018/154380 A1 | 8/2018 |
| WO | WO 2018/154387 A1 | 8/2018 |
| WO | WO 2018/154412 A1 | 8/2018 |
| WO | WO 2018/154413 A1 | 8/2018 |
| WO | WO 2018/154418 A1 | 8/2018 |
| WO | WO 2018/154439 A1 | 8/2018 |
| WO | WO 2018/154459 A1 | 8/2018 |
| WO | WO 2018/154462 A2 | 8/2018 |
| WO | WO 2018/156372 A1 | 8/2018 |
| WO | WO 2018/161009 A1 | 9/2018 |
| WO | WO 2018/165504 A1 | 9/2018 |
| WO | WO 2018/165629 A1 | 9/2018 |
| WO | WO 2018/170015 A1 | 9/2018 |
| WO | WO 2018/170340 A1 | 9/2018 |
| WO | WO 2018/175502 A2 | 9/2018 |
| WO | WO 2018/177351 A1 | 10/2018 |
| WO | WO 2018/179578 A1 | 10/2018 |
| WO | WO 2018/183403 A1 | 10/2018 |
| WO | WO 2018/195545 A2 | 10/2018 |
| WO | WO 2018/195555 A1 | 10/2018 |
| WO | WO 2018/197020 A1 | 11/2018 |
| WO | WO 2018/197495 A1 | 11/2018 |
| WO | WO 2018/202800 A1 | 11/2018 |
| WO | WO 2018/204493 A1 | 11/2018 |
| WO | WO 2018/208755 A1 | 11/2018 |
| WO | WO 2018/208998 A1 | 11/2018 |
| WO | WO 2018/209158 A2 | 11/2018 |
| WO | WO 2018/209320 A1 | 11/2018 |
| WO | WO 2018/213708 A1 | 11/2018 |
| WO | WO 2018/213726 A1 | 11/2018 |
| WO | WO 2018/213771 A1 | 11/2018 |
| WO | WO 2018/213791 A1 | 11/2018 |
| WO | WO 2018/217852 A1 | 11/2018 |
| WO | WO 2018/217981 A1 | 11/2018 |
| WO | WO 2018/218166 A1 | 11/2018 |
| WO | WO 2018/218188 A2 | 11/2018 |
| WO | WO 2018/218206 A1 | 11/2018 |

OTHER PUBLICATIONS

Jinek et al. (A Programmable Dual-RNA—Guided DNA Endonuclease in Adaptive Bacterial Immunity, Science, vol. 337 No. 6096 pp. 816-821, Jun. 28, 2012).*
Carroll (A CRISPR Approach to Gene Targeting, Mol Ther. Sep. 2012;20(9):1658-60).*
Barrangou (RNA-mediated programmable DNA cleavage, Nature Biotechnology 30, 836-838, Sep. 10, 2012).*
Cong et al. (Multiplex Genome Engineering Using CRISPR/Cas Systems, Science, vol. 339 No. 6121 pp. 819-823, Jan. 3, 2013).*
Mali et al. (RNA-Guided Human Genome Engineering via Cas9, Science, vol. 339, No. 6121 pp. 823-826, Jan. 3, 2013).*
International Preliminary Report on Patentability for PCT/US2014/052231, dated Mar. 3, 2016.
International Preliminary Report on patentability for PCT/US2014/050283, dated Feb. 18, 2016.
International Preliminary Report on Patentability for PCT/US2014/054247, dated Mar. 17, 2016.
International Preliminary Report on Patentability for PCT/US2014/054291, dated Mar. 17, 2016.
International Preliminary Report on Patentability or PCT/US2014/054252, dated Mar. 17, 2016.
International Preliminary Report on Patentability for PCT/US2014/070038, dated Jun. 23, 2016.
International Search Report and Written Opinion for PCT/US2015/042770, dated Feb. 23, 2016.
International Preliminary Report on Patentability for PCT/US2015/042770, dated Dec. 19, 2016.
International Search Report and Written Opinion for PCT/US2015/058479, dated Feb. 11, 2016.
International Preliminary Report on Patentability for PCT/US2015/058479, dated May 11, 2017.
Invitation to Pay Additional Fees for PCT/US2016/058344, dated Mar. 1, 2017.
International Search Report and Written Opinion for PCT/US2016/058344, dated Apr. 20, 2017.
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA1-ugi pH1-gRNA(HPRT), 2017, Akihiko Kondo.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Barnes et al., Repair and genetic consequences of endogenous DNA base damage in mammalian cells. Annu Rev Genet. 2004;38:445-76.

(56) References Cited

OTHER PUBLICATIONS

Beale et al., Comparison of the differential context-dependence of DNA deamination by APOBEC enzymes: correlation with mutation spectra in vivo. J Mol Biol. Mar. 26, 2004;337(3):585-96.

Begley, Scientists unveil the 'most clever CRISPR gadget' so far. STAT, Apr. 20, 2016. https://www.statnews.com/2016/04/20/clever-crispr-advance-unveiled/.

Birling et al., Site-specific recombinases for manipulation of the mouse genome. Methods Mol Biol. 2009;561:245-63. doi: 10.1007/978-1-60327-019-9_16.

Bitinaite et al., FokI dimerization is required for DNA cleavage. Proc Natl Acad Sci U S A. Sep. 1, 1998;95(18):10570-5.

Borman, Improved route to single-base genome editing. Chemical & Engineering News, Apr. 25, 2016;94(17)p5. http://cen.acs.org/articles/94/i17/Improved-route-single-base-genome.html.

Britt et al., Re-engineering plant gene targeting. Trends Plant Sci. Feb. 2003;8(2):90-5.

Brusse et al., Spinocerebellar ataxia associated with a mutation in the fibroblast growth factor 14 gene (SCA27): A new phenotype. Mov Disord. Mar. 2006;21(3):396-401.

Buchholz et al., Alteration of Cre recombinase site specificity by substrate-linked protein evolution. Nat Biotechnol. Nov. 2001;19(11):1047-52.

Bulow et al., Multienzyme systems obtained by gene fusion. Trends Biotechnol. Jul. 1991;9(7):226-31.

Caldecott et al., Single-strand break repair and genetic disease. Nat Rev Genet. Aug. 2008;9(8):619-31. doi: 10.1038/nrg2380.

Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/Atvbaha.117.309881. Epub Jul. 27, 2015.

Chavez et al., Highly efficient Cas9-mediated transcriptional programming. Nat Methods. Apr. 2015;12(4):326-8. doi: 10.1038/nmeth.3312. Epub Mar. 2, 2015.

Chavez et al., Precise Cas9 targeting enables genomic mutation prevention. doi: https://doi.org/10.1101/058974. [Preprint].

Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.

Chichili et al., Linkers in the structural biology of protein-protein interactions. Protein Science. 2013;22:153-67.

Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.

Chu et al., Increasing the efficiency of homology-directed repair for CRISPR-Cas9-induced precise gene editing in mammalian cells. Nat Biotech. Feb. 13, 2015;33:543-8.

Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.

Cox et al., Therapeutic genome editing: prospects and challenges. Nat Med. Feb. 2015;21(2):121-31. doi: 10.1038/nm.3793.

Cunningham et al., Ensembl 2015. Nucleic Acids Res. Jan. 2015;43(Database issue):D662-9. doi: 10.1093/nar/gku1010. Epub Oct. 28, 2014.

Davis et al., Small molecule-triggered Cas9 protein with improved genome-editing specificity. Nat Chem Biol. May 2015;11(5):316-8. doi: 10.1038/nchembio.1793. Epub Apr. 6, 2015.

Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.

Doudna et al., Genome editing. The new frontier of genome engineering with CRISPR-Cas9. Science. Nov. 28, 2014;346(6213):1258096. doi: 10.1126/science.1258096.

Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.

Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.

Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.

Freshney, Culture of Animal Cells. A Manual of Basic Technique. Alan R. Liss, Inc. New York. 1983;4.

Fung et al., Repair at single targeted DNA double-strand breaks in pluripotent and differentiated human cells. PLoS One. 2011;6(5):e20514. doi: 10.1371/journal.pone.0020514. Epub May 25, 2011.

Gaj et al., A comprehensive approach to zinc-finger recombinase customization enables genomic targeting in human cells. Nucleic Acids Res. Feb. 6, 2013;41(6):3937-46.

Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.

Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.

Gao et al., DNA-guided genome editing using the *Natronobacterium gregoryi* Argonaute. Nat Biotechnol. Jul. 2016;34(7):768-73. doi: 10.1038/nbt.3547. Epub May 2, 2016.

Gardlik et al., Vectors and delivery systems in gene therapy. Med Sci Monit. Apr. 2005;11(4):RA110-21. Epub Mar. 24, 2005.

Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.

Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.

Gonzalez et al., an iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.

Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.

Harris et al., RNA editing enzyme APOBEC1 and some of its homologs can act as DNA mutators. Mol Cell. Nov. 2002;10(5):1247-53.

Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.

Hilton et al., Enabling functional genomics with genome engineering. Genome Res. Oct. 2015;25(10):1442-55. doi: 10.1101/gr.190124.115.

Hondares et al., Peroxisome Proliferator-activated Receptor a (PPARα) Induces PPARγ Coactivator 1α (PGC-1α) Gene Expression and Contributes to Thermogenic Activation of Brown Fat. J Biol Chem Oct. 2011; 286(50):43112-22. doi: 10.1074/jbc.M111.252775.

Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.

Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.

Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.

Kellendonk et al., Regulation of Cre recombinase activity by the synthetic steroid RU 486. Nucleic Acids Res. Apr. 15, 1996;24(8):1404-11.

Kim et al., Genome-wide target specificities of CRISPR RNA-guided programmable deaminases. Nat Biotechnol. May 2017;35(5):475-480. doi: 10.1038/nbt.3852. Epub Apr. 10, 2017.

(56) References Cited

OTHER PUBLICATIONS

Kim et al., Highly efficient RNA-guided base editing in mouse embryos. Nat Biotechnol. May 2017;35(5):435-437. doi: 10.1038/nbt.3816. Epub Feb. 27, 2017.

Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.

Kim et al., The role of apolipoprotein E in Alzheimer's disease. Neuron. Aug. 13, 2009;63(3):287-303. doi:10.1016/j.neuron.2009.06.026.

Kim et al., Transcriptional repression by zinc finger peptides. Exploring the potential for applications in gene therapy. J Biol Chem. Nov. 21, 1997;272(47):29795-800.

Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.

Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.

Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.

Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.

Klippel et al., Isolation and characterization of unusual gin mutants. EMBO J. Dec. 1, 1988;7(12):3983-9.

Klippel et al., The DNA invertase Gin of phage Mu: formation of a covalent complex with DNA via a phosphoserine at amino acid position 9. EMBO J. Apr. 1988;7(4):1229-37.

Komor et al., Programmable editing of a target base in genomic DNA without double-stranded DNA cleavage. Nature. Apr. 20, 2016;533(7603):420-4. doi: 10.1038/nature17946.

Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.

Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.

Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.

Ledford, Gene-editing hack yields pinpoint precision. Nature, Apr. 20, 2016. http://www.nature.com/news/gene-editing-hack-yields-pinpoint-precision-1.19773.

Lee et al., A chimeric thyroid hormone receptor constitutively bound to DNA requires retinoid X receptor for hormone-dependent transcriptional activation in yeast. Mol Endocrinol. Sep. 1994;8(9):1245-52.

Lee et al., Recognition of liposomes by cells: in vitro binding and endocytosis mediated by specific lipid headgroups and surface charge density. Biochim Biophys Acta. Jan. 31, 1992;1103(2):185-97.

Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.

Li et al., Highly efficient and precise base editing in discarded human tripronuclear embryos. Protein Cell. Aug. 19, 2017. doi: 10.1007/s13238-017-0458-7. [Epub ahead of print].

Lin et al., Enhanced homology-directed human genome engineering by controlled timing of CRISPR/Cas9 delivery. Elife. Dec. 15, 2014;3:e04766. doi: 10.7554/eLife.04766.

Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.

Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2013.

Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.

Ma et al., Targeted AID-mediated mutagenesis (TAM) enables efficient genomic diversification in mammalian cells. Nature Methods. Oct. 2016;13:1029-35. doi:10.1038/nmeth.4027.

Marioni et al., DNA methylation age of blood predicts all-cause mortality in later life. Genome Biol. Jan. 30, 2015;16:25. doi: 10.1186/s13059-015-0584-6.

Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.

Mercer et al., Chimeric Tale recombinases with programmable DNA sequence specificity. Nucleic Acids Res. Nov. 2012;40(21):11163-72. doi: 10.1093/nar/gks875. Epub Sep. 26, 2012.

Minoche et al., Evaluation of genomic high-throughput sequencing data generated on Illumina HiSeq and genome analyzer systems. Genome Biol. Nov. 8, 2011;12(11):R112. doi: 10.1186/gb-2011-12-11-r112.

Mol et al., Crystal structure of human uracil-DNA glycosylase in complex with a protein inhibitor: protein mimicry of DNA. Cell. Sep. 8, 1995;82(5):701-8.

Nishida et al., Targeted nucleotide editing using hybrid prokaryotic and vertebrate adaptive immune systems. Science. Sep. 16, 2016;353(6305). pii: aaf8729. doi: 10.1126/science.aaf8729. Epub Aug. 4, 2016.

Offord, Advances in Genome Editing. The Scientist, Apr. 20, 2016. http://www.the-scientist.com/?articles.view/articleNo/45903/title/Advances-in-Genome-Editing/.

Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.

Petolino et al., Editing Plant Genomes: a new era of crop improvement. Plant Biotechnol J. Feb. 2016;14(2):435-6. doi: 10.1111/pbi.12542.

Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.

Pluciennik et al., PCNA function in the activation and strand direction of MutLα endonuclease in mismatch repair. Proc Natl Acad Sci U S A. Sep. 14, 2010;107(37):16066-71. doi: 10.1073/pnas.1010662107. Epub Aug. 16, 2010.

Prorocic et al., Zinc-finger recombinase activities in vitro. Nucleic Acids Res. Nov. 2011;39(21):9316-28. doi: 10.1093/nar/gkr652. Epub Aug. 17, 2011.

Prykhozhij et al., CRISPR multitargeter: a web tool to find common and unique CRISPR single guide RNA targets in a set of similar sequences. PLoS One. Mar. 5, 2010;10(3):e0119372. doi: 10.1371/journal.pone.0119372. eCollection 2015.

Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.

Ran et al., Genome engineering using the CRISPR-Cas9 system. Nat Protoc. Nov. 2013;8(11):2281-308. doi: 10.1038/nprot.2013.143. Epub Oct. 24, 2013.

Ran et al., In vivo genome editing using *Staphylococcus aureus* Cas9. Nature. Apr. 9, 2015;520(7546):186-91. doi: 10.1038/nature14299. Epub Apr. 1, 2015.

Rath et al., Fidelity of end joining in mammalian episomes and the impact of Metnase on joint processing. BMC Mol Biol. Mar. 22, 2014;15:6. doi: 10.1186/1471-2199-15-6.

Rebuzzini et al., New mammalian cellular systems to study mutations introduced at the break site by non-homologous end-joining. DNA Repair (Amst). May 2, 2005;4(5):546-55.

(56) References Cited

OTHER PUBLICATIONS

Rees et al., Improving the DNA specificity and applicability of base editing through protein engineering and protein delivery. Nat Commun. Jun. 6, 2017;8:15790. doi: 10.1038/ncomms15790.

Richardson et al., Enhancing homology-directed genome editing by catalytically active and inactive Crispr-Cas9 using asymmetric donor DNA. Nat Biotechnol. Mar. 2016;34(3):339-44. doi: 10.1038/nbt.3481. Epub Jan. 20, 2016.

Rong et al., Homologous recombination in human embryonic stem cells using CRISPR/Cas9 nickase and a long DNA donor template. Protein Cell. Apr. 2014;5(4):258-60. doi: 10.1007/s13238014-0032-5.

Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.

Sadelain et al., Safe harbours for the integration of new DNA in the human genome. Nat Rev Cancer. Dec. 1, 2011;12(1):51-8. doi: 10.1038/nrc3179.

Sanjana et al., A transcription activator-like effector toolbox for genome engineering. Nat Protoc. Jan. 5, 2012;7(1):171-92. doi: 10.1038/nprot.2011.431.

Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.

Sclimenti et al., Directed evolution of a recombinase for improved genomic integration at a native human sequence. Nucleic Acids Res. Dec. 15, 2001;29(24):5044-51.

Seripa et al., The missing ApoE allele. Ann Hum Genet. Jul. 2007;71(Pt 4):496-500. Epub Jan. 22, 2007.

Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.

Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.

Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.

Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.

Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.

Simonelli et al., Base excision repair intermediates are mutagenic in mammalian cells. Nucleic Acids Res. Aug. 2, 2005;33(14):4404-11. Print 2005.

Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.

Sjoblom et al., the consensus coding sequences of human breast and colorectal cancers. Science. Oct. 13, 2006;314(5797):268-74. Epub Sep. 7, 2006.

Slaymaker et al., Rationally engineered Cas9 nucleases with improved specificity. Science. Jan. 1, 2016;351(6268):84-8. doi: 10.1126/science.aad5227. Epub Dec. 1, 2015.

Smith et al., Expression of a dominant negative retinoic acid receptor γ in Xenopus embryos leads to partial resistance to retinoic acid. Roux Arch Dev Biol. Mar. 1994;203(5):254-265. doi: 10.1007/BF00360521.

Stenglein et al., APOBEC3 proteins mediate the clearance of foreign Dna from human cells. Nat Struct Mol Biol. Feb. 2010;17(2):222-9. doi: 10.1038/nsmb.1744. Epub Jan. 10, 2010.

Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.

Swarts et al., Argonaute of the archaeon *Pyrococcus furiosus* is a DNA-guided nuclease that targets cognate DNA. Nucleic Acids Res. May 26, 2015;43(10):5120-9. doi: 10.1093/nar/gkv415. Epub Apr. 29, 2015.

Swarts et al., DNA-guided DNA interference by a prokaryotic Argonaute. Nature. Mar. 13, 2014;507(7491):258-61. doi: 10.1038/nature12971. Epub Feb. 16, 2014.

Swarts et al., The evolutionary journey of Argonaute proteins. Nat Struct Mol Biol. Sep. 2014;21(9):743-53. doi: 10.1038/nsmb.2879.

Tagalakis et al., Lack of RNA-DNA oligonucleotide (chimeraplast) mutagenic activity in mouse embryos. Mol Reprod Dev. Jun. 2005;71(2):140-4.

Thyagarajan et al., Mammalian genomes contain active recombinase recognition sites. Gene. Feb. 22, 2000;244(1-2):47-54.

Thyagarajan et al., Site-specific genomic integration in mammalian cells mediated by phage phiC31 integrase. Mol Cell Biol. Jun. 2001;21(12):3926-34.

Tirumalai et al., Recognition of core-type DNA sites by lambda integrase. J Mol Biol. Jun. 12, 1998;279(3):513-27.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.

Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.

Turan et al., Recombinase-mediated cassette exchange (RMCE): traditional concepts and current challenges. J Mol Biol. Mar. 25, 2011;407(2):193-221. doi: 10.1016/j jmb.2011.01.004. Epub Jan. 15, 2011.

Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.

Wang et al., Efficient delivery of genome-editing proteins using bioreducible lipid nanoparticles. Proc Natl Acad Sci U S A. Feb. 29, 2016. pii: 201520244. [Epub ahead of print].

Wang et al., Nucleation, propagation and cleavage of target RNAs in Ago silencing complexes. Nature. Oct. 8, 2009;461(7265):754-61. doi: 10.1038/nature08434.

Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.

Warren et al., A chimeric Cre recombinase with regulated directionality. Proc Natl Acad Sci U S A. Nov. 25, 2008;105(47):18278-83. doi: 10.1073/pnas.0809949105. Epub Nov. 14, 2008.

Warren et al., Mutations in the amino-terminal domain of lambda-integrase have differential effects on integrative and excisive recombination. Mol Microbiol. Feb. 2005;55(4):1104-12.

Wijnker et al., Managing meiotic recombination in plant breeding. Trends Plant Sci. Dec. 2008;13(12):640-6. doi: 10.1016/j.tplants.2008.09.004. Epub Oct. 22, 2008.

Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.

Xu et al., Sequence determinants of improved CRISPR sgRNA design. Genome Res. Aug. 2015;25(8):1147-57. doi: 10.1101/gr.191452.115. Epub Jun. 10, 2015.

Yang et al., Genome editing with targeted deaminases. BioRxiv. Preprint. First posted online Jul. 28, 2016.

Yuen et al., Control of transcription factor activity and osteoblast differentiation in mammalian cells using an evolved small-molecule-dependent intein. J Am Chem Soc. Jul. 12, 2006;128(27):8939-46.

Zetsche et al., A split-Cas9 architecture for inducible genome editing and transcription modulation. Nat Biotechnol. Feb. 2015;33(2):139-42. doi: 10.1038/nbt.3149.

(56) References Cited

OTHER PUBLICATIONS

Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zhang et al., Comparison of non-canonical PAMs for CRISPR/Cas9-mediated DNA cleavage in human cells. Sci Rep. Jun. 2014;4:5405.
Zhang et al., Programmable base editing of zebrafish genome using a modified CRISPR-Cas9 system. Nat Commun. Jul. 25, 2017;8(1):118. doi: 10.1038/s41467-017-00175-6.
Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.
Zuris et al., Cationic lipid-mediated delivery of proteins enables efficient protein-based genome editing in vitro and in vivo. Nat Biotechnol. 2015;33:73-80.
Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.
Chew et al., A multifunctional AAV-CRISPR-Cas9 and its host response. Nat Methods. Oct. 2016;13(10):868-74. doi: 10.1038/nmeth.3993. Epub Sep. 5, 2016.
Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Hower et al., Shape-based peak identification for ChIP-Seq. BMC Bioinformatics. Jan. 12, 2011;12:15. doi: 10.1186/1471-2105-12-15.
International Search Report and Written Opinion for PCT/US2017/045381, dated Oct. 26, 2017.
International Search Report and Written Opinion for PCT/US2017/046144, dated Oct. 10, 2017.
International Search Report and Written Opinion for PCT/US2017/48390, dated Jan. 9, 2018.
Invitation to Pay Additional Fees for PCT/US2017/056671, dated Dec. 21, 2017.
Invitation to Pay Additional Fees for PCT/US2017/48390, dated Nov. 7, 2017.
Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.
Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).
Shah et al., Inteins: nature's gift to protein chemists. Chem Sci. 2014;5(1):446-461.
Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.
Wang et al., Recombinase technology: applications and possibilities. Plant Cell Rep. Mar. 2011;30(3):267-85. doi: 10.1007/s00299-010-0938-1. Epub Oct. 24, 2010.
Yang et al., Engineering and optimising deaminase fusions for genome editing. Nat Commun. Nov. 2, 2016;7:13330. doi: 10.1038/ncomms13330.
Yuan et al., Tetrameric structure of a serine integrase catalytic domain. Structure. Aug. 6, 2006;16(8):1275-86. doi: 10.1016/j.str.2008.04.018.
Zheng et al., DNA editing in DNA/RNA hybrids by adenosine deaminases that act on RNA. Nucleic Acids Res. Apr. 7, 2017;45(6):3369-3377. doi: 10.1093/nar/gkx050.
U.S. Appl. No. 61/716,256, Jinek et al., filed Oct. 19, 2012.
U.S. Appl. No. 61/717,324, Cho et al., filed Oct. 23, 2012.
U.S. Appl. No. 61/734,256, Chen et al., filed Dec. 6, 2012.
U.S. Appl. No. 61/758,624, Chen et al., filed Jan. 30, 2013.
U.S. Appl. No. 61/761,046, Knight et al., filed Feb. 5, 2013.
U.S. Appl. No. 61/794,422, Knight et al., filed Mar. 15, 2013.
U.S. Appl. No. 61/803,599, Kim et al., filed Mar. 20, 2013.
U.S. Appl. No. 61/837,481, Cho et al., filed Jun. 20, 2013.
International Search Report and Written Opinion for PCT/US2012/047778, dated May 30, 2013.
International Preliminary Report on Patentability for PCT/US2012/047778, dated Feb. 6, 2014.
Partial Supplementary European Search Report for Application No. EP 12845790.0, dated Mar. 18, 2015.
Supplementary European Search Report for Application No. EP 12845790.0, dated Oct. 12, 2015.
International Search Report and Written Opinion for PCT/US2014/052231, dated Dec. 4, 2014.
International Search Report and Written Opinion for PCT/US2014/052231, dated Jan. 30, 2015 (Corrected Version).
International Search Report and Written Opinion for PCT/US2014/050283, dated Nov. 6, 2014.
International Search Report and Written Opinion for PCT/US2014/054247, dated Mar. 27, 2015.
Invitation to Pay Additional Fees for PCT/US2014/054291, dated Dec. 18, 2014.
International Search Report and Written Opinion for PCT/US2014/054291, dated Mar. 27, 2015.
International Search Report and Written Opinion for PCT/US2014/054252, dated Mar. 5, 2015.
International Search Report and Written Opinion for PCT/US2014/070038, dated Apr. 14, 2015.
International Search Report for PCT/US2013/032589, dated Jul. 26, 2013.
No Author Listed, EMBL Accession No. Q99ZW2. Nov. 2012. 2 pages.
No Author Listed, Invitrogen Lipofectamine™ 2000 product sheets, 2002. 2 pages.
No Author Listed, Invitrogen Lipofectamine™ 2000 product sheets, 2005. 3 pages.
No Author Listed, Invitrogen Lipofectamine™ LTX product sheets, 2011. 4 pages.
No Author Listed, Thermo Fisher Scientific—How Cationic Lipid Mediated Transfection Works, retrieved from the internet Aug. 27, 2015. 2 pages.
NCBI Reference Sequence: NM_002427.3. Wu et al., May 3, 2014. 5 pages.
Genbank Submission; NIH/NCBI, Accession No. J04623. Kita et al., Apr. 26, 1993. 2 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NP_472073.1. Glaser et al., Jun. 27, 2013. 2 pages.
Genbank Submission; NIH/NCBI, Accession No. P42212. Prasher et al., Mar. 19, 2014. 7 pages.
Genbank Submission; NIH/NCBI, Accession No. YP_002342100.1. Bernardini et al., Jun. 10, 2013. 2 pages.

(56) References Cited

OTHER PUBLICATIONS

Genbank Submission; NIH/NCBI, Accession No. YP_002344900.1. Gundogdu et al., Mar. 19, 2014. 2 pages.
Genbank Submission; NIH/NCBI, Accession No. YP_820832.1. Makarova et al., Aug. 27, 2013. 2 pages.
UniProt Submission; UniProt, Accession No. P01011. Last modified Jun. 11, 2014, version 2. 15 pages.
UniProt Submission; UniProt, Accession No. P01011. Last modified Sep. 18, 2013, version 2. 15 pages.
UniProt Submission; UniProt, Accession No. P04264. Last modified Jun. 11, 2014, version 6. 15 pages.
Uniprot Submission; UniProt, Accession No. P04275. Last modified Jul. 9, 2014, version 107. 29 pages.
Akopian et al., Chimeric recombinases with designed DNA sequence recognition. Proc Natl Acad Sci U S A. Jul. 22, 2003;100(15):8688-91. Epub Jul. 1, 2003.
Alexandrov et al., Signatures of mutational processes in human cancer. Nature. Aug. 22, 2013;500(7463):415-21. doi: 10.1038/nature12477. Epub Aug. 14, 2013.
Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Bedell et al., In vivo genome editing using a high-efficiency TALEN system. Nature. Nov. 1, 2012;491(7422):114-8. Doi: 10.1038/nature11537. Epub Sep. 23, 2012.
Beumer et al., Efficient gene targeting in *Drosophila* with zinc-finger nucleases. Genetics. Apr. 2006;172(4):2391-403. Epub Feb. 1, 2006.
Bibikova et al., Stimulation of homologous recombination through targeted cleavage by chimeric nucleases. Mol Cell Biol. Jan. 2001;21(1):289-97.
Bibikova et al., Targeted chromosomal cleavage and mutagenesis in *Drosophila* using zinc-finger nucleases. Genetics. Jul. 2002;161(3):1169-75.
Boch et al., Breaking the code of DNA binding specificity of Tal-type III effectors. Science. Dec. 11, 2009;326(5959):1509-12. Doi: 10.1126/science.1178811.
Boch, TALEs of genome targeting. Nat Biotechnol. Feb. 2011;29(2):135-6. Doi: 10.1038/nbt.1767.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Branden and Tooze, Introduction to Protein Structure. 1999; 2nd edition. Garland Science Publisher: 3-12.
Brown et al., Serine recombinases as tools for genome engineering. Methods. Apr. 2011;53(4):372-9. doi: 10.1016/j.ymeth.2010.12.031. Epub Dec. 30, 2010.
Bulyk et al., Exploring the DNA-binding specificities of zinc fingers with DNA microarrays. Proc Natl Acad Sci U S A. Jun. 19, 2001;98(13):7158-63. Epub Jun. 12, 2001.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cameron, Recent advances in transgenic technology. Mol Biotechnol. Jun. 1997;7(3):253-65.
Caron et al., Intracellular delivery of a Tat-eGFP fusion protein into muscle cells. Mol Ther. Mar. 2001;3(3):310-8.
Carroll et al., Gene targeting in *Drosophila* and *Caenorhabditis elegans* with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Charpentier et al., Biotechnology: Rewriting a genome. Nature. Mar. 7, 2013;495(7439):50-1. doi: 10.1038/495050a.
Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Christian et al, Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2010;186(2):757-61. Doi: 10.1534/genetics.110.120717. Epub Jul. 26, 2010.
Chung-Il et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cong et al., Comprehensive interrogation of natural TALE DNA-binding modules and transcriptional repressor domains. Nat Commun. Jul. 24, 2012;3:968. doi: 10.1038/ncomms1962.
Cong et al., Multiplex genome engineering using CRISPR/Cas systems. Science. Feb. 15, 2013;339(6121):819-23. doi: 10.1126/science.1231143. Epub Jan. 3, 2013.
Cornu et al., DNA-binding specificity is a major determinant of the activity and toxicity of zinc-finger nucleases. Mol Ther. Feb. 2008;16(2):352-8. Epub Nov. 20, 2007.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
Cradick et al., ZFN-site searches genomes for zinc finger nuclease target sites and off-target sites. BMC Bioinformatics. May 13, 2011;12:152. doi: 10.1186/1471-2105-12-152.
Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.
Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.
Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.
De Souza, Primer: genome editing with engineered nucleases. Nat Methods. Jan. 2012;9(1):27.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.
Doyon et al., Enhancing zinc-finger-nuclease activity with improved obligate heterodimeric architectures. Nat Methods. Jan. 2011;8(1):74-9. Doi: 10.1038/nmeth.1539. Epub Dec. 5, 2010.
Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.
Esvelt et al., Genome-scale engineering for systems and synthetic biology. Mol Syst Biol. 2013;9:641. doi: 10.1038/msb.2012.66.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.

(56) References Cited

OTHER PUBLICATIONS

Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fuchs et al., Polyarginine as a multifunctional fusion tag. Protein Sci. Jun. 2005;14(6):1538-44.
Gabriel et al., An unbiased genome-wide analysis of zinc-finger nuclease specificity. Nat Biotechnol. Aug. 7, 2011;29(9):816-23. doi: 10.1038/nbt.1948.
Gaj et al., Structure-guided reprogramming of serine recombinase DNA sequence specificity. Proc Natl Acad Sci U S A. Jan. 11, 2011;108(2):498-503. doi: 10.1073/pnas.1014214108. Epub Dec. 27, 2010.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gao et al., Crystal structure of a TALE protein reveals an extended N-terminal DNA binding region. Cell Res. Dec. 2012;22(12):1716-20. doi: 10.1038/cr.2012.156. Epub Nov. 13, 2012.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Gordley et al., Evolution of programmable zinc finger-recombinases with activity in human cells. J Mol Biol. Mar. 30, 2007;367(3):802-13. Epub Jan. 12, 2007.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Guo et al., Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Guo et al., Protein tolerance to random amino acid change. Proc Natl Acad Sci U S A. Jun. 22, 2004;101(25):9205-10. Epub Jun. 14, 2004.
Guo et al., Structure of Cre recombinase complexed with DNA in a site-specific recombination synapse. Nature. Sep. 4, 1997;389(6646):40-6.
Gupta et al., Zinc finger protein-dependent and -independent contributions to the in vivo off-target activity of zinc finger nucleases. Nucleic Acids Res. Jan. 2011;39(1):381-92. doi: 10.1093/nar/gkq787. Epub Sep. 14, 2010.
Hale et al., RNA-guided Rna cleavage by a CRISPR RNA-Cas protein complex. Cell. Nov. 25, 2009;139(5):945-56. doi: 10.1016/j.cell.2009.07.040.
Händel et al., Expanding or restricting the target site repertoire of zinc-finger nucleases: the inter-domain linker as a major determinant of target site selectivity. Mol Ther. Jan. 2009;17(1):104-11. doi: 10.1038/mt.2008.233. Epub Nov. 11, 2008.
Hartung et al., Cre mutants with altered DNA binding properties. J Biol Chem. Sep. 4, 1998;273(36):22884-91.

Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Hill et al., Functional analysis of conserved histidines in ADP-glucose pyrophosphorylase from *Escherichia coli*.Biochem Biophys Res Commun. Mar. 17, 1998;244(2):573-7.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Hockemeyer et al., Genetic engineering of human pluripotent cells using TALE nucleases. Nat Biotechnol. Jul. 7, 2011;29(8):731-4. doi: 10.1038/nbt.1927.
Horvath et al., CRISPR/Cas, the immune system of bacteria and archaea. Science. Jan. 8, 2010;327(5962):167-70. doi: 10.1126/science.1179555.
Houdebine, The methods to generate transgenic animals and to control transgene expression. J Biotechnol. Sep. 25, 2002;98(2-3):145-60.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Huang et al., Heritable gene targeting in zebrafish using customized TALENs. Nat Biotechnol. Aug. 5, 2011;29(8):699-700. doi: 10.1038/nbt.1939.
Humbert et al., Targeted gene therapies: tools, applications, optimization. Crit Rev Biochem Mol Biol. May-Jun. 2012;47(3):264-81. doi: 10.3109/10409238.2012.658112.
Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Jamieson et al., Drug discovery with engineered zinc-finger proteins. Nat Rev Drug Discov. May 2003;2(5):361-8.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Jinek et al., Structures of Cas9 endonucleases reveal RNA-mediated conformational activation. Science. Mar. 14, 2014;343(6176):1247997. doi: 10.1126/science.1247997. Epub Feb. 6, 2014.
Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Joung et al.,TALENs: a widely applicable technology for targeted genome editing. Nat Rev Mol Cell Biol. Jan. 2013;14(1):49-55. doi: 10.1038/nrm3486. Epub Nov. 21, 2012.
Kaiser et al., Gene therapy. Putting the fingers on gene repair. Science. Dec. 23, 2005;310(5756):1894-6.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Kappel et al., Regulating gene expression in transgenic animals. Curr Opin Biotechnol. Oct. 1992;3(5):548-53.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.
Kilbride et al., Determinants of product topology in a hybrid Cre-Tn3 resolvase site-specific recombination system. J Mol Biol. Jan. 13, 2006;355(2):185-95. Epub Nov. 9, 2005.
Kim et al., A library of TAL effector nucleases spanning the human genome. Nat Biotechnol. Mar. 2013;31(3):251-8. Doi: 10.1038/nbt.2517. Epub Feb. 17, 2013.

(56) References Cited

OTHER PUBLICATIONS

Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., Hybrid restriction enzymes: zinc finger fusions to Fok I cleavage domain. Proc Natl Acad Sci U S A. Feb. 6, 1996;93(3):1156-60.
Kim et al., TALENs and ZFNs are associated with different mutationsignatures. Nat Methods. Mar. 2013;10(3):185. doi: 10.1038/nmeth.2364. Epub Feb. 10, 2013.
Kim et al., Targeted genome editing in human cells with zinc finger nucleases constructed via modular assembly. Genome Res. Jul. 2009;19(7):1279-88. doi: 10.1101/gr.089417.108. Epub May. 21, 2009.
Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.
Klug et al., Zinc fingers: a novel protein fold for nucleic acid recognition. Cold Spring Harb Symp Quant Biol. 1987;52:473-82.
Krishna et al., Structural classification of zinc fingers: survey and summary. Nucleic Acids Res. Jan. 15, 2003;31(2):532-50.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lazar et al., Transforming growth factor alpha: mutation of aspartic acid 47 and leucine 48 results in different biological activities. Mol Cell Biol. Mar. 1988;8(3):1247-52.
Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Li et al., Current approaches for engineering proteins with diverse biological properties. Adv Exp Med Biol. 2007;620:18-33.
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li et al., TAL nucleases (TALNs): hybrid proteins composed of Tal effectors and FokI DNA-cleavage domain. Nucleic Acids Res. Jan. 2011;39(1):359-72. doi: 10.1093/nar/gkq704. Epub Aug. 10, 2010.
Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Liu et al., Design of polydactyl zinc-finger proteins for unique addressing within complex genomes. Proc Natl Acad Sci U S A. May 27, 1997;94(11):5525-30.
Liu et al., Fast Colorimetric Sensing of Adenosine and Cocaine Based on a General Sensor Design Involving Aptamers and Nanoparticles. Angew Chem. 2006;118(1):96-100.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Lundberg et al., Delivery of short interfering RNA using endosomolytic cell-penetrating peptides. Faseb J. Sep. 2007;21(11):2664-71. Epub Apr. 26, 2007.
Maeder et al., CRISPR RNA-guided activation of endogenous human genes. Nat Methods. Oct. 2013;10(10):977-9. doi: 10.1038/nmeth.2598. Epub Jul. 25, 2013.
Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.
Maeder et al., Robust, synergistic regulation of human gene expression using TALE activators. Nat Methods. Mar. 2013;10(3):243-5. doi: 10.1038/nmeth.2366. Epub Feb. 10, 2013.
Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.
Mak et al., The crystal structure of TAL effector PthXo1 bound to its DNA target. Science. Feb. 10, 2012;335(6069):716-9. doi: 10.1126/science.1216211. Epub Jan. 5, 2012.
Mali et al., Cas9 as a versatile tool for engineeringbiology. Nat Methods. Oct. 2013;10(10):957-63. doi: 10.1038/nmeth.2649.
Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.
Mali et al., RNA-guided human genome engineering via Cas9. Science. Feb. 15, 2013;339(6121):823-6. doi: 10.1126/science.1232033. Epub Jan. 3, 2013.
Mani et al., Design, engineering, and characterization of zinc finger nucleases. Biochem Biophys Res Commun. Sep. 23, 2005;335(2):447-57.
Meckler et al., Quantitative analysis of TALE-DNA interactions suggests polarity effects. Nucleic Acids Res. Apr. 2013;41(7):4118-28. doi: 10.1093/nar/gkt085. Epub Feb. 13, 2013.
Meng et al., Profiling the DNA-binding specificities of engineered Cys2His2 zinc finger domains using a rapid cell-based method. Nucleic Acids Res. 2007;35(11):e81. Epub May 30, 2007.
Meng et al., Targeted gene inactivation in zebrafish using engineered zinc-finger nucleases. Nat Biotechnol. Jun. 2008;26(6):695-701. doi: 10.1038/nbt1398. Epub May 25, 2008.
Miller et al., A TALE nuclease architecture for efficient genome editing. Nat Biotechnol. Feb. 2011;29(2):143-8. doi:10.1038/nbt.1755. Epub Dec. 22, 2010.
Miller et al., An improved zinc-finger nuclease architecture for highly specific genome editing. Nat Biotechnol. Jul. 2007;25(7):778-85. Epub Jul. 1, 2007.
Moore et al., Improved somatic mutagenesis in zebrafish using transcription activator-like effector nucleases (TALENs). PLoS One. 2012;7(5):e37877. Doi: 10.1371/journal.pone.0037877. Epub May 24, 2012.
Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.
Moscou et al., A simple cipher governs DNA recognition by TAL effectors. Science. Dec. 11, 2009;326(5959):1501. doi: 10.1126/science.1178817.
Mullins et al., Transgenesis in nonmurine species. Hypertension. Oct. 1993;22(4):630-3.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Mussolino et al., Tale nucleases: tailored genome engineering made easy. Curr Opin Biotechnol. Oct. 2012;23(5):644-50. doi: 10.1016/j.copbio.2012.01.013. Epub Feb. 17, 2012.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
Osborn et al., Talen-based gene correction for epidermolysis bullosa. Mol Ther. Jun. 2013;21(6):1151-9. doi: 10.1038/mt.2013.56. Epub Apr. 2, 2013.

(56) References Cited

OTHER PUBLICATIONS

Pabo et al., Design and selection of novel Cys2His2 zinc finger proteins. Annu Rev Biochem. 2001;70:313-40.

Pan et al., Biological and biomedical applications of engineered nucleases. Mol Biotechnol. Sep. 2013;55(1):54-62. doi: 10.1007/s12033-012-9613-9.

Pattanayak et al., Determining the specificities of TALENs, Cas9, and other genome-editing enzymes. Methods Enzymol. 2014;546:47-78. doi: 10.1016/B978-0-12-801185-0.00003-9.

Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.

Pattanayak et al., Revealing off-target cleavage specificities of zinc-finger nucleases by in vitro selection. Nat Methods. Aug. 7, 2011;8(9):765-70. doi: 10.1038/nmeth.1670.

Pavletich et al., Zinc finger-DNA recognition: crystal structure of a Zif268-DNA complex at 2.1 A. Science. May 10, 1991;252(5007):809-17.

Pennisi et al., The tale of the TALEs. Science. Dec. 14, 2012;338(6113):1408-11. doi: 10.1126/science.338.6113.1408.

Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.

Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.

Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.

Petek et al., Frequent endonuclease cleavage at off-target locations in vivo. Mol Ther. May 2010;18(5):983-6. Doi: 10.1038/mt.2010.35. Epub Mar. 9, 2010.

Phillips, The challenge of gene therapy and DNA delivery. J Pharm Pharmacol. Sep. 2001;53(9):1169-74.

Porteus, Design and testing of zinc finger nucleases for use in mammalian cells. Methods Mol Biol. 2008;435:47-61. doi: 10.1007/978-1-59745-232-8_4.

Proudfoot et al., Zinc finger recombinases with adaptable DNA sequence specificity. PLoS One. Apr. 29, 2011;6(4):e19537. doi: 10.1371/journal.pone.0019537.

Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.

Qi et al., Repurposing CRISPR as an RNA-guided platform for sequence-specific control of gene expression. Cell. Feb. 28, 2013;152(5):1173-83. doi: 10.1016/j.cell.2013.02.022.

Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.

Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.

Ramirez et al., Unexpected failure rates for modular assembly of engineered zinc fingers. Nat Methods. May 2008;5(5):374-5. Doi: 10.1038/nmeth0508-374.

Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.

Reyon et al., Flash assembly of TALENs for high-throughput genome editing. Nat Biotechnol. May 2012;30(5):460-5. doi: 10.1038/nbt.2170.

Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.

Samal et al., Cationic polymers and their therapeutic potential. Chem Soc Rev. Nov. 7, 2012;41(21):7147-94. doi: 10.1039/c2cs35094g. Epub Aug. 10, 2012.

Sander et al., CRISPR-Cas systems for editing, regulating and targeting genomes. Nat Biotechnol. Apr. 2014;32(4):347-55. doi: 10.1038/nbt.2842. Epub Mar. 2, 2014.

Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.

Sander et al., Targeted gene disruption in somatic zebrafish cells using engineered TALENs. Nat Biotechnol. Aug. 5, 2011;29(8):697-8. doi: 10.1038/nbt.1934.

Sang, Prospects for transgenesis in the chick. Mech Dev. Sep. 2004;121(9):1179-86.

Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.

Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

Schriefer et al., Low pressure DNA shearing: a method for random DNA sequence analysis. Nucleic Acids Res. Dec. 25, 1990;18(24):7455-6.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Schwartz et al., Post-translational enzyme activation in an animal via optimized conditional protein splicing. Nat Chem Biol. Jan. 2007;3(1):50-4. Epub Nov. 26, 2006.

Schwarze et al., In vivo protein transduction: delivery of a biologically active protein into the mouse. Science. Sep. 3, 1999;285(5433):1569-72.

Segal et al., Evaluation of a modular strategy for the construction of novel polydactyl zinc finger DNA-binding proteins. Biochemistry. Feb. 25, 2003;42(7):2137-48.

Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.

Sells et al., Delivery of protein into cells using polycationic liposomes. Biotechniques. Jul. 1995;19(1):72-6, 78.

Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Serganov et al., Structural basis for discriminative regulation of gene expression by adenine-and guanine-sensing mRNAs. Chem Biol. Dec. 2004;11(12):1729-41.

Sheridan, First CRISPR-Cas patent opens race to stake out intellectual property. Nat Biotechnol. 2014;32(7):599-601.

Shimizu et al., Adding fingers to an engineered zinc finger nuclease can reduce activity. Biochemistry. Jun. 7, 2011;50(22):5033-41. doi: 10.1021/bi200393g. Epub May 11, 2011.

Siebert et al., An improved PCR method for walking in uncloned genomic DNA. Nucleic Acids Res. Mar. 25, 1995;23(6):1087-8.

Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.

Szczepek et al., Structure-based redesign of the dimerization interface reduces the toxicity of zinc-finger nucleases. Nat Biotechnol. Jul. 2007;25(7):786-93. Epub Jul. 1, 2007.

Tebas et al., Gene editing of CCR5 in autologous CD4 T cells of persons infected with HIV. N Engl J Med. Mar. 6, 2014;370(10):901-10. doi: 10.1056/NEJMoa1300662.

Thorpe et al., Functional correction of episomal mutations with short DNA fragments and RNA-DNA oligonucleotides. J Gene Med. Mar.-Apr. 2002;4(2):195-204.

(56) References Cited

OTHER PUBLICATIONS

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Urnov et al., Genome editing with engineered zinc finger nucleases. Nat Rev Genet. Sep. 2010;11(9):636-46. doi: 10.1038/nrg2842.
Urnov et al., Highly efficient endogenous human gene correction using designed zinc-finger nucleases. Nature. Jun. 2, 2005;435(7042):646-51. Epub Apr. 3, 2005.
Van Duyne et al., Teaching Cre to follow directions. Proc Natl Acad Sci U S A. Jan. 6, 2009;106(1):4-5. doi: 10.1073/pnas.0811624106. Epub Dec. 31, 2008.
Vanamee et al., FokI requires two specific DNA sites for cleavage. J Mol Biol. May 25, 2001;309(1):69-78.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wah et al., Structure of FokI has implications for DNA cleavage. Proc Natl Acad Sci U S A. Sep. 1, 1998 ;95(18):10564-9.
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Weber et al., Assembly of designer TAL effectors by Golden Gate cloning. PLoS One. 2011;6(5):e19722. doi:10.1371/journal.pone.0019722. Epub May 19, 2011.
Wiedenheft et al., RNA-guided genetic silencing systems in bacteria and archaea. Nature. Feb. 15, 2012;482(7385):331-8. doi: 10.1038/nature10886. Review.
Wolfe et al., Analysis of zinc fingers optimized via phage display: evaluating the utility of a recognition code. J Mol Biol. Feb. 5, 1999;285(5):1917-34.
Wood et al., Targeted genome editing across species using ZFNs and TALENs. Science. Jul. 15, 2011;333(6040):307. doi: 10.1126/science.1207773. Epub Jun. 23, 2011.
Wu et al., Correction of a genetic disease in mouse via use of CRISPR-Cas9. Cell Stem Cell. Dec. 5, 2013;13(6):659-62. doi: 10.1016/j.stem.2013.10.016.
Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Zhang et al., Conditional gene manipulation: Cre-ating a new biological era. J Zhejiang Univ Sci B. Jul. 2012;13(7):511-24. doi: 10.1631/jzus.B1200042. Review.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
Abudayyeh et al., C2c2 is a single-component programmable RNA-guided RNA-targeting Crispr effector. Science Aug. 2016;353(6299):aaf5573. DOI: 10.1126/science.aaf5573.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.
Bolotin et al., Clustered regularly interspaced short palindrome repeats (CRISPRs) have spacers of extrachromosomal origin. Microbiology. Aug. 2005;151(Pt 8):2551-61.
Brouns et al., Small CRISPR RNAs guide antiviral defense in prokaryotes. Science. Aug. 15, 2008;321(5891):960-4. doi: 10.1126/science.1159689.
Buchwald et al., Long-term, continuous intravenous heparin administration by an implantable infusion pump in ambulatory patients with recurrent venous thrombosis. Surgery. Oct. 1980;88(4):507-16.
Burstein et al., New CRISPR-Cas systems from uncultivated microbes. Nature Feb. 2017;542(7640):237-240.
Covino et al., The CCL2/CCR2 Axis in the Pathogenesis of HIV-1 Infection: A New Cellular Target for Therapy? Current Drug Targets Dec. 2016;17(1):76-110. DOI: 10.2174/1389450117011512171101917.
Dicarlo et al., Genome engineering in *Saccharomyces cerevisiae* using CRISPR-Cas systems. Nucleic Acids Research Apr. 2013;41(7):4336-43.
Ding et al., Permanent alteration of PCSK9 with in vivo CRISPR-Cas9 genome editing. Circ Res. Aug. 15, 2014;115(5):488-92. doi: 10.1161/Circresaha.115.304351. Epub Jun. 10, 2014.
During et al., Controlled release of dopamine from a polymeric brain implant: in vivo characterization. Ann Neurol. Apr. 1989;25(4):351-6.
East-Seletsky et al., Two distinct RNase activities of CRISPR-C2c2 enable guide-RNA processing and RNA detection. Nature Oct. 2016;538(7624):270-3.
Ferretti et al., Complete genome sequence of an M1 strain of *Streptococcus pyogenes*. Proc Natl Acad Sci U S A. Apr. 10, 2001;98(8):4658-63.
Fukui et al., DNA Mismatch Repair in Eukaryotes and Bacteria. J Nucleic Acids. Jul. 27, 2010;2010. pii: 260512. doi: 10.4061/2010/260512.
Garneau et al., The CRISPR/Cas bacterial immune system cleaves bacteriophage and plasmid DNA. Nature. Nov. 4, 2010;468(7320):67-71. doi: 10.1038/nature09523.
Heller et al., Replisome assembly and the direct restart of stalled replication forks. Nat Rev Mol Cell Biol. Dec. 2006;7(12):932-43. Epub Nov. 8, 2006.
Howard et al., Intracerebral drug delivery in rats with lesion-induced memory deficits. J Neurosurg. Jul. 1989;71(1):105-12.
Ishino et al., Nucleotide sequence of the iap gene, responsible for alkaline phosphatase isozyme conversion in *Escherichia coli*, and identification of the gene product. J Bacteriol. Dec. 1987;169(12):5429-33.
Jansen et al., Identification of genes that are associated with DNA repeats in prokaryotes. Mol Microbiol. Mar. 2002;43(6):1565-75.
Kaya et al., A bacterial Argonaute with noncanonical guide RNA specificity. Proc. Natl. Acad. Sci. USA Apr. 2016;113(15):4057-62.
Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.
Kunz et al., DNA Repair in mammalian cells: Mismatched repair: variations on a theme. Cell Mol Life Sci. Mar. 2009;66(6):1021-38. doi: 10.1007/s00018-009-8739-9.
Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.
Langer et al., New methods of drug delivery. Science. Sep. 28, 1990;249(4976):1527-33.

(56) References Cited

OTHER PUBLICATIONS

Lau et al., Molecular basis for discriminating between normal and damaged bases by the human alkyladenine glycosylase, AAG. Proc Natl Acad Sci U S A. Dec. 5, 2000;97(25):13573-8.

Lee et al., Failure to detect DNA-guided genome editing using Natronobacterium gregoryi Argonaute. Nat Biotechnol. Nov. 28, 2016;35(1):17-18. doi: 10.1038/nbt.3753.

Levy et al., Inhibition of calcification of bioprosthetic heart valves by local controlled-release diphosphonate. Science. Apr. 12, 1985;228(4696):190-2.

Lieber et al., Mechanism and regulation of human non-homologous DNA end-joining. Nat Rev Mol Cell Biol. Sep. 2003;4(9):712-20.

Liu et al., C2c1-sgRNA Complex Structure Reveals RNA-Guided DNA Cleavage Mechanism. Molecular Cell Jan. 2017;65(2):310-22.

Liu et al., Distance determination by GIY-YIG intron endonucleases: discrimination between repression and cleavage functions. Nucleic Acids Res. Mar. 31, 2006;34(6):1755-64. Print 2006.

Losey et al., Crystal structure of *Staphylococcus sureus* tRNA adenosine deaminase tadA in complex with RNA. Nature Struct. Mol. Biol. Feb. 2006;13(2):153-9.

Lyons et al., Efficient Recognition of an Unpaired Lesion by a DNA Repair Glycosylase. J. Am. Chem. Soc., 2009;131(49):17742-3. DOI: 10.1021/ja908378y.

Makarova et al., Prokaryotic homologs of Argonaute proteins are predicted to function as key components of a novel system of defense against mobile genetic elements. Biology Direct 2009;4:29.

Makarova et al., An updated evolutionary classification of CRISPR-Cas systems. Nat Rev Microbiol. Nov. 2015;13(11):722-36. doi: 10.1038/nrmicro3569. Epub Sep. 28, 2015.

Makarova et al., Evolution and classification of the CRISPR-Cas systems. Nat Rev Microbiol. Jun. 2011;9(6):467-77. doi: 10.1038/nrmicro2577. Epub May 9, 2011.

Marraffini et al., CRISPR interference limits horizontal gene transfer in *Staphylococci* by targeting DNA. Science. Dec. 19, 2008;322(5909):1843-5. doi: 10.1126/science.1165771.

Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.

Mojica et al., Intervening sequences of regularly spaced prokaryotic repeats derive from foreign genetic elements. J Mol Evol. Feb. 2005;60(2):174-82.

Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.

Prashant et al., CAS9 transcriptional activators for target specificity screening and paired nickases for cooperative genome engineering. Nature Biotechnology 2013;31(9):833-8.

Ray et al., Homologous recombination: ends as the means. Trends Plant Sci. Oct. 2002;7(10):435-40.

Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.

Saudek et al., A preliminary trial of the programmable implantable medication system for insulin delivery. N Engl J Med. Aug. 31, 1989;321(9):574-9.

Sefton et al., Implantable pumps. Crit Rev Biomed Eng. 1987;14(3):201-40.

Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.

Shmakov et al., Discovery and Functional Characterization of Diverse Class 2 CRISPR Cas Systems. Molecular Cell Nov. 2015;60(3):385-97.

Stephens et al., The landscape of cancer genes and mutational processes in breast cancer. Nature Jun. 2012;486:400-404. doi:10.1038/nature11017.

Vagner et al., Efficiency of homologous DNA recombination varies along the Bacillus subtilis chromosome. J Bacteriol. Sep. 1988;170(9):3978-82.

Wang et al., CRISPR-Cas9 Targeting of PCSK9 in Human Hepatocytes In Vivo-Brief Report. Arterioscler Thromb Vasc Biol. May 2016;36(5):783-6. doi: 10.1161/ATVBAHA.116.307227. Epub Mar. 3, 2016.

Wolf et al., tadA, an essential tRNA-specific adenosine deaminase from *Escherichia coli*. EMBO J. Jul. 15, 2002;21(14):3841-51.

Yamano et al., Crystal Structure of Cpf1 in Complex with Guide RNA and Target DNA. Cell May 2016;165(4)949-62.

Yang et al., PAM-dependent Target DNA Recognition and Cleavage by C2C1 CRISPR-Cas endonuclease. Cell Dec. 2016;167(7):1814-28.

Zhang et al., Stabilized plasmid-lipid particles for regional gene therapy: formulation and transfection properties. Gene Ther. Aug. 1999;6(8):1438-47.

Aihara et al., A conformational switch controls the DNA cleavage activity of lambda integrase. Mol Cell. 2003 Jul;12(1):187-98.

Ames et al., A eubacterial riboswitch class that senses the coenzyme tetrahydrofolate. Chem Biol. Jul. 30, 2010;17(7):681-5. doi: 10.1016/j.chembiol.2010.05.020.

Batey et al., Structure of a natural guanine-responsive riboswitch complexed with the metabolite hypoxanthine. Nature. Nov. 18, 2004;432(7015):411-5.

Briner et al., Guide RNA functional modules direct Cas9 activity and orthogonality. Mol Cell. Oct. 23, 2014;56(2):333-339. doi: 10.1016/j.molcel.2014.09.019.

Buskirk et al., Directed evolution of ligand dependence: small-molecule-activated protein splicing. Proc Natl Acad Sci U S A. Jul. 20, 2004;101(29):10505-10. Epub Jul. 9, 2004.

Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.

Cobb et al., Directed evolution as a powerful synthetic biology tool. Methods. Mar. 15, 2013;60(1):81-90. doi: 10.1016/j.ymeth.2012.03.009. Epub Mar. 23, 2012.

Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012 Review.

Davis et al., DNA double strand break repair via non-homologous end-joining. Transl Cancer Res. Jun. 2013;2(3):130-143.

Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.

Doench et al., Optimized sgRNA design to maximize activity and minimize off-target effects of CRISPR-Cas9. Nat Biotechnol. Feb. 2016;34(2):184-191. doi: 10.1038/nbt.3437.

Edwards et al., Crystal structures of the thi-box riboswitch bound to thiamine pyrophosphate analogs reveal adaptive RNA-small molecule recognition. Structure. Sep. 2006;14(9):1459-68.

Endo et al., Toward establishing an efficient and versatile gene targeting system in higher plants. Biocatalysis and Agricultural Biotechnology 2014;3,(1):2-6.

Extended European Search Report for EP 15830407.1, dated Mar. 2, 2018.

Fang et al., Synthetic Studies Towards Halichondrins: Synthesis of the Left Halves of Norhalichondrins and Homohalichondrins. Tetrahedron Letters 1992;33(12):1557-1560.

Ferry et al., Rational design of inducible CRISPR guide RNAs for de novo assembly of transcriptional programs. Nat Commun. Mar. 3, 2017;8:14633. doi: 10.1038/ncomms14633.

Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.

Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.

Hickford et al., Antitumour polyether macrolides: four new halichondrins from the New Zealand deep-water marine sponge Lissodendoryx sp. Bioorg Med Chem. Mar. 15, 2009;17(6):2199-203. doi: 10.1016/j.bmc.2008.10.093. Epub Nov. 19, 2008.

(56) References Cited

OTHER PUBLICATIONS

Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol. 2015.12.009.

Hwang et al., Efficient In Vivo Genome Editing Using RNA-Guided Nucleases. Nat Biotechnol. Mar. 31, 2013; 31(3): 227-229. doi: 10.1038/nbt.2501. Epub Jan. 29, 2013.

International Preliminary Report on Patentability for PCT/US2016/058344, dated May 3, 2018.

International Search Report and Written Opinion for PCT/US2017/056671, dated Feb. 20, 2018.

International Search Report and Written Opinion for PCT/US2017/068105, dated Apr. 4, 2018.

International Search Report and Written Opinion for PCT/US2017/068114, dated Mar. 20, 2018.

International Search Report for PCT/US2018/021664, dated Jun. 21, 2018.

International Search Report for PCT/US2018/021878, dated Aug. 20, 2018.

International Search Report for PCT/US2018/021880, dated Jun. 20, 2018.

International Search Report for PCT/US2018/024208, dated Aug. 23, 2018.

International Search Report for PCT/US2018/025887, dated Jun. 21, 2018.

International Search Report for PCT/US2018/032460, dated Jul. 11, 2018.

Invitation to Pay Additional Fees for PCT/US2018/021878, dated Jun. 8, 2018.

Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.

Klein et al., Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb.1563.Epub Feb. 22, 2009.

Kohli et al., Local sequence targeting in the AID/APOBEC family differentially impacts retroviral restriction and antibody diversification. J Biol Chem. Dec. 24, 2010;285(52):40956-64. doi: 10.1074/jbc. M110.177402. Epub Oct. 6, 2010.

Komor et al., CRISPR-Based Technologies for the Manipulation of Eukaryotic Genomes. Cell. Jan. 12, 2017;168(1-2):20-36. doi: 10.1016/j.cell.2016.10.044.

Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.

Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.

Kwon et al., Chemical basis of glycine riboswitch cooperativity. RNA. Jan. 2008;14(1):25-34. Epub Nov. 27, 2007.

Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.

Lewis et al., Building the Class 2 CRISPR-Cas Arsenal. Mol Cell 2017;65(3):377-379.

Li et al., Base editing with a Cpf1-cytidine deaminase fusion. Nat Biotechnol. Apr. 2018;36(4):324-327. doi: 10.1038/nbt.4102. Epub Mar. 19, 2018.

Li et al., Multiplex and homologous recombination-mediated genome editing in Arabidopsis and Nicotiana benthamiana using guide RNA and Cas9. Nat Biotechnol. Aug. 31, 2013;(8):688-91. doi: 10.1038/nbt.2654.

Liang et al., Rapid and highly efficient mammalian cell engineering via Cas9 protein transfection. Send to; J Biotechnol. Aug 20, 2015;208:44-53. doi: 10.1016/j.jbiotec.2015.04.024.

Liu et al., Balancing AID and DNA repair during somatic hypermutation. Trends Immunol. Apr. 2009;30(4):173-81. doi: 10.1016/j.it. 2009.01.007.

Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.

Montange et al., Structure of the S-adenosylmethionine riboswitch regulatory mRNA element. Nature. Jun. 29, 2006;441(7097):1172-5.

Mootz et al., Conditional protein splicing: a new tool to control protein structure and function in vitro and in vivo. J Am Chem Soc. Sep. 3, 2003;125(35):10561-9.

Mootz et al., Protein splicing triggered by a small molecule. J Am Chem Soc. Aug. 7, 2002;124(31):9044-5.

Nahvi et al., Coenzyme B12 riboswitches are widespread genetic control elements in prokaryotes. Nucleic Acids Res. Jan. 2, 2004;32(1):143-50.

Neel et al., Riboswitches: Classification, function and in silico approach, International Journal of Pharma Sciences and Research. 2010;1(9):409-420.

Ni et al., Nucleic acid aptamers: clinical applications and promising new horizons. Curr Med Chem. 2011;18(27):4206-14. Review.

Pearl, Structure and function in the uracil-DNA glycosylase superfamily. Mutat Res. Aug. 30, 2000;460(3-4):165-81.

Peck et al., Directed evolution of a small-molecule-triggered intein with improved splicing properties in mammalian cells. Chem Biol. May 27, 2011;18(5):619-30. doi: 10.1016/j.chembiol.2011.02.014.

Plosky et al., CRISPR-Mediated Base Editing without DNA Double-Strand Breaks. Mol Cell. May 19, 2016;62(4):477-8. doi: 10.1016/j.molcel.2016.05.006.

Roth et al., A riboswitch selective for the queuosine precursor preQ1 contains an unusually small aptamer domain. Nat Struct Mol Biol. Apr. 2007;14(4):308-17. Epub Mar. 25, 2007.

Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.

Serganov et al., Structural basis for gene regulation by a thiamine pyrophosphate-sensing riboswitch. Nature. Jun. 29, 2006;441(7097):1167-71. Epub May 21, 2006.

Shee et al., Engineered proteins detect spontaneous DNA breakage in human and bacterial cells. Elife. Oct. 29, 2013 2:e01222. doi: 10.7554/eLife.01222.

Sudarsan et al., an mRNA structure in bacteria that controls gene expression by binding lysine. Genes Dev. Nov. 1, 2003;17(21):2688-97.

Sudarsan et al., Riboswitches in eubacteria sense the second messenger cyclic di-GMP. Science. Jul. 18, 2008;321(5887):411-3. doi: 10.1126/science.1159519.

Suess et al., A theophylline responsive riboswitch based on helix slipping controls gene expression in vivo. Nucleic Acids Res. Mar. 5, 2004;32(4):1610-4.

Tang et al., Aptazyme-embedded guide RNAs enable ligand-responsive genome editing and transcriptional activation. Nat Commun. Jun. 28, 2017;8:15939. doi: 10.1038/ncomms15939.

Tourdot et al., A general strategy to enhance immunogenicity of low-affinity HLA-A2. 1-associated peptides: implication in the identification of cryptic tumor epitopes. Eur J Immunol. Dec. 30, 2000;(12):3411-21.

Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.

Weinberg et al., The aptamer core of SAM-IV riboswitches mimics the ligand-binding site of Sam-I riboswitches. RNA. May 2008;14(5):822-8. doi: 10.1261/rna.988608. Epub Mar. 27, 2008.

Winkler et al., An mRNA structure that controls gene expression by binding FMN. Proc Natl Acad Sci U S A. Dec. 10, 2002;99(25):15908-13. Epub Nov. 27, 2002.

Winkler et al., Control of gene expression by a natural metabolite-responsive ribozyme. Nature. Mar. 18, 2004;428(6980):281-6.

(56) References Cited

OTHER PUBLICATIONS

Winkler et al., Thiamine derivatives bind messenger RNAs directly to regulate bacterial gene expression. Nature. Oct 31, 2002;419(6910):952-6. Epub Oct. 16, 2002.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamamoto et al., Virological and immunological bases for HIV-1 vaccine design. Uirusu 2007;57(2): 133-139. https://doi.org/10.2222/jsv.57.133.
Yang et al., New CRISPR-Cas systems discovered. Cell Res. Mar. 2017;27(3):313-314. doi: 10.1038/cr.2017.21. Epub Feb. 21, 2017.
Zimmermann et al., Molecular interactions and metal binding in the theophylline-binding core of an RNA aptamer. RNA. May 2000;6(5):659-67.
U.S. Appl. No. 61/838,178, filed Jun. 21, 2013, Joung et al.
Bershtein et al., Advances in laboratory evolution of enzymes. Curr Opin; Chem Biol. Apr. 2008;12(2):151-8. doi: 10.1016/j.cbpa.2008.01.027. Epub Mar. 7, 2008 Review.
Bogdanove et al., TAL effectors: customizable proteins for DNA targeting. Science. Sep. 30, 2011;333(6051):1843-6. doi: 10.1126/science.1204094.
Hida et al., Directed evolution for drug and nucleic acid; delivery. Adv Drug Deliv Rev. Dec. 22, 2007;59(15):1562-78. Epub Aug. 28, 2007;Review.
Husimi, Selection and evolution of bacteriophages in cellstat. Adv Biophys. ; 1989;25:1-43. Review.
Kakiyama et al., A peptide release system using a photo-cleavable linker in a cell array format for cell-toxicity analysis. Polymer J. Feb. 27, 2013;45:535-9.
Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.
Nelson et al., Filamentous phage DNA cloning vectors: a noninfective mutant with a nonpolar deletion in gene III. Virology. 1981; 108(2): 338-50.
Rakonjac et al., Roles of PIII in filamentous phage assembly. J Mol Biol. 1998; 282(1)25-41.
Riechmann et al.,. The C-terminal domain of TolA is the coreceptor for filamentous phage infection of E. coli.Cell. 1997; 90(2):351-60. PMID:9244308.
Smith, Filamentous fusion phage: novel expression vectors that display cloned antigens on the virion surface. Science. Jun. 14, 1985;228(4705):1315-7.
Yuan et al., Laboratory-directed protein evolution. Microbiol Mol Biol Rev. 2005; 69(3):373-92. PMID: 16148303.
Extended European Search Report for EP18199195.1, dated Feb. 12, 2019.
International Preliminary Report on Patentability for PCT/US2014/048390, dated Mar. 7, 2019.
International Preliminary Report on Patentability for PCT/US2017/046144, dated Feb. 21, 2019.
International Preliminary Report on Patentability for PCT/US2017/045381, dated Feb. 14, 2019.
International Preliminary Report on Patentability for PCT/US2017/056671, dated Apr. 25, 2019.
Office Action, dated Nov. 10, 2014, in connection with U.S. Appl. No. U.S. Appl. No. 14/320,370.
Office Action, dated Jan. 30, 2015, in connection with U.S. Appl. No. 14/320,370.
Notice of Allowance and Applicant Initiated Interview Summary, dated Jun. 10, 2015, in connection with U.S. Appl. No. 14/320,370.
Office Action, dated Dec. 4, 2014, in connection with U.S. Appl. No. 14/320,413.
Office Action, dated Apr. 1, 2015, in connection with U.S. Appl. No. 14/320,413.
Advisory Action and Applicant Initiated Interview Summary, dated Jul. 30, 2015, in connection with U.S. Appl. No. 14/320,413.
Requirement for Restriction/Election, dated Oct. 19, 2017, in connection with U.S. Appl. No. 14/911,117.
Office Action, dated Mar. 12, 2018, in connection with U.S. Appl. No. 14/911,117.
Office Action, dated Oct. 15, 2018, in connection with U.S. Appl. No. 14/911,117.
Office Action, dated May 20, 2019, in connection with U.S. Appl. No. 14/911,117.

\* cited by examiner

```
                          Non-PAM        PAM
                            end          end
                            ←            →

CLTA 1    5'---------AGTCCTCATCTCCCTCAAGCAGG----------3' SEQ ID NO: 8
V1.0      3'---------TCAGGAGTAGAGGGAGTTCGTCC----------5' SEQ ID NO: 9
                     ||||||||||||||||||||||
                5'-GAGUCCUCAUCUCCCUCAAGCGUUUUAGAGCUA G
                                  •|||||• ||||          A
                          3'-GCCUGAUCGGAAUAAAAUU CGAU   A
                             SEQ ID NO: 10         GAA  A

CLTA 2    5'---------CTCCCTCAAGCAGGCCCCGCTGG----------3' SEQ ID NO: 11
V1.0      3'---------GAGGGAGTTCGTCCGGGGCGACC----------5' SEQ ID NO: 12
                     ||||||||||||||||||||||
                5'-GCUCCCUCAAGCAGGCCCCGCGUUUUAGAGCUA G
                                  •|||||• ||||          A
                          3'-GCCUGAUCGGAAUAAAAUU CGAU   A
                             SEQ ID NO: 13         GAA  A

CLTA 3    5'---------TGTGAAGAGCTTCACTGAGTAGG----------3' SEQ ID NO: 14
V1.0      3'---------ACACTTCTCGAAGTGACTCATCC----------5' SEQ ID NO: 15
                     ||||||||||||||||||||||
                5'-GUGUGAAGAGCUUCACUGAGUGUUUUAGAGCUA G
                                  •|||||• ||||          A
                          3'-GCCUGAUCGGAAUAAAAUU CGAU   A
                             SEQ ID NO: 16         GAA  A

CLTA 4    5'---------GCAGATGTAGTGTTTCCACAGGG----------3' SEQ ID NO: 17
V1.0      3'---------CGTCTACATCACAAAGGTGTCCC----------5' SEQ ID NO: 18
                     ||||||||||||||||||||||
                5'-GGCAGAUGUAGUGUUUCCACAGUUUUAGAGCUA G
                                  •|||||• ||||          A
                          3'-GCCUGAUCGGAAUAAAAUU CGAU   A
                             SEQ ID NO: 19         GAA  A
```

FIG. 3C

```
                        Non-PAM      PAM
                         end         end
                         ←           →

CLTA 1   5'--------AGTCCTCATCTCCCTCAAGCAGG--------3' SEQ ID NO: 20
V2.1     3'--------TCAGGAGTAGAGGGAGTTCGTCC---------5' SEQ ID NO: 21
                   ||||||||||||||||||||||
         5'-GAGUCCUCAUCUCCCUCAAGCGUUUUAGAGCUAUGCU G
                                        *|||||* ||||||||  A
         3'-CUAUUGCCUGAUCGGAAUAAAAAUU CGAUACGA  A
                   SEQ ID NO: 22                 GAA

CLTA 2   5'--------CTCCCTCAAGCAGGCCCCGCTGG---------3' SEQ ID NO: 23
V2.1     3'--------GAGGGAGTTCGTCCGGGGCGACC---------5' SEQ ID NO: 24
                   ||||||||||||||||||||||
         5'-GCUCCCUCAAGCAGGCCCCGCGUUUUAGAGCUAUGCU G
                                        *|||||* ||||||||  A
         3'-CUAUUGCCUGAUCGGAAUAAAAAUU CGAUACGA  A
                   SEQ ID NO: 25                 GAA

CLTA 3   5'--------TGTGAAGAGCTTCACTGAGTAGG---------3' SEQ ID NO: 26
V2.1     3'--------ACACTTCTCGAAGTGACTCATCC---------5' SEQ ID NO: 27
                   ||||||||||||||||||||||
         5'-GUGUGAAGAGCUUCACUGAGUGUUUUAGAGCUAUGCU G
                                        *|||||* ||||||||  A
         3'-CUAUUGCCUGAUCGGAAUAAAAAUU CGAUACGA  A
                   SEQ ID NO: 28                 GAA

CLTA 4   5'--------GCAGATGTAGTGTTTCCACAGGG---------3' SEQ ID NO: 29
V2.1     3'--------CGTCTACATCACAAAGGTGTCCC--------5' SEQ ID NO: 30
                   ||||||||||||||||||||||
         5'-GGCAGAUGUAGUGUUUCCACAGUUUUAGAGCUAUGCU G
                                        *|||||* ||||||||  A
         3'-CUAUUGCCUGAUCGGAAUAAAAAUU CGAUACGA  A
                   SEQ ID NO: 31                 GAA
```

FIG. 3D

|  | sequence | In vitro selection enrichment value | % cut |
|---|---|---|---|
| SEQ ID NO: 34 CLTA4-0 | GCAGATGTAGTGTTTCCACAGGG | 7.9 | 85% |
| SEQ ID NO: 35 CLTA4-1 | GaAGATGTAGTGTTTCCACAGGG | 27.5 | 84% |
| SEQ ID NO: 36 CLTA4-2a | GaAGATGTAGTGTTTCCACtGGG | 43.9 | 79% |
| SEQ ID NO: 37 CLTA4-2b | GCAGATGgAGgGTTTCCACAGGG | 1.0 | 35% |
| SEQ ID NO: 38 CLTA4-2c | GCAGATGTAGTGTTaCCAgAGGG | 0.084 | none detected |
| SEQ ID NO: 39 CLTA4-3 | GggGATGTAGTGTTTCCACtGGG | 95.9 | 72% |

SEQUENCE LISTING

```
<160> NUMBER OF SEQ ID NOS: 410

<210> SEQ ID NO 1
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(21)
<223> OTHER INFORMATION: n is a, c, g, or t

<400> SEQUENCE: 1
agtcctcatc tccctcaagc ngg                                              23

<210> SEQ ID NO 2
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 2
atgtctcccg catgcgctca gtcctcatct ccctcaagca ggccccgc                   48

<210> SEQ ID NO 3
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 3
gcggggcctg cttgagggag atgaggactg agcgcatgcg ggagacat                   48
```

```
<210> SEQ ID NO 4
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 4
tggtgcactg aagagccacc ctgtggaaac actacatctg caatatct                48

<210> SEQ ID NO 5
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 5
agatattgca gatgtagtgt ttccacaggg tggctcttca gtgcacca                48

<210> SEQ ID NO 6
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 6
taatcctact cagtgaagct cttcacagtc attggattaa ttatgttg                48

<210> SEQ ID NO 7
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 7
caacataatt aatccaatga ctgtgaagag cttcactgag taggatta                48

<210> SEQ ID NO 8
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 8
agtcctcatc tccctcaagc agg                                           23

<210> SEQ ID NO 9
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 9
cctgcttgag ggagatgagg act                                           23

<210> SEQ ID NO 10
<211> LENGTH: 60
<212> TYPE: RNA
<213> ORGANISM: Artificial Sequence
<220> FEATURE:
<223> OTHER INFORMATION: Synthetic Oligonucleotide
```

```
<400> SEQUENCE: 10
gaguccucau cucccucaag cguuuuagag cuagaaauag cuuaaaauaa ggcuaguccg      60

<210> SEQ ID NO 11
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 11
ctccctcaag caggccccgc tgg                                             23

<210> SEQ ID NO 12
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 12
ccagcggggc ctgcttgagg gag                                             23

<210> SEQ ID NO 13
<211> LENGTH: 60
<212> TYPE: RNA
<213> ORGANISM: Artificial Sequence
<220> FEATURE:
<223> OTHER INFORMATION: Synthetic Oligonucleotide

<400> SEQUENCE: 13
gcucccucaa gcaggccccg cguuuuagag cuagaaauag cuuaaaauaa ggcuaguccg      60

<210> SEQ ID NO 14
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 14
tgtgaagagc ttcactgagt agg                                             23

<210> SEQ ID NO 15
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 15
cctactcagt gaagctcttc aca                                             23

<210> SEQ ID NO 16
<211> LENGTH: 60
<212> TYPE: RNA
<213> ORGANISM: Artificial Sequence
<220> FEATURE:
<223> OTHER INFORMATION: Synthetic Oligonucleotide

<400> SEQUENCE: 16
gugugaagag cuucacugag uguuuuagag cuagaaauag cuuaaaauaa ggcuaguccg      60

<210> SEQ ID NO 17
```

```
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 17
gcagatgtag tgtttccaca ggg                                            23

<210> SEQ ID NO 18
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 18
ccctgtggaa acactacatc tgc                                            23

<210> SEQ ID NO 19
<211> LENGTH: 60
<212> TYPE: RNA
<213> ORGANISM: Artificial Sequence
<220> FEATURE:
<223> OTHER INFORMATION: Synthetic Oligonucleotide

<400> SEQUENCE: 19
ggcagaugua guguuuccac aguuuuagag cuagaaauag cuuaaaauaa ggcuaguccg     60

<210> SEQ ID NO 20
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 20
agtcctcatc tccctcaagc agg                                            23

<210> SEQ ID NO 21
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 21
cctgcttgag ggagatgagg act                                            23

<210> SEQ ID NO 22
<211> LENGTH: 73
<212> TYPE: RNA
<213> ORGANISM: Artificial Sequence
<220> FEATURE:
<223> OTHER INFORMATION: Synthetic Oligonucleotide

<400> SEQUENCE: 22
gaguccucau cucccucaag cguuuuagag cuaugcugaa aagcauagcu uaaaauaagg     60
cuaguccguu auc                                                       73

<210> SEQ ID NO 23
<211> LENGTH: 23
<212> TYPE: DNA
<213> ORGANISM: Artificial Sequence
<220> FEATURE:
<223> OTHER INFORMATION: Synthetic Oligonucleotide
```

```
<400> SEQUENCE: 23
ctccctcaag caggccccgc tgg                                              23

<210> SEQ ID NO 24
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 24
ccagcggggc ctgcttgagg gag                                              23

<210> SEQ ID NO 25
<211> LENGTH: 73
<212> TYPE: RNA
<213> ORGANISM: Artificial Sequence
<220> FEATURE:
<223> OTHER INFORMATION: Synthetic Oligonucleotide

<400> SEQUENCE: 25
gcucccucaa gcaggccccg cguuuuagag cuaugcugaa aagcauagcu uaaaauaagg      60
cuaguccguu auc                                                         73

<210> SEQ ID NO 26
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 26
tgtgaagagc ttcactgagt agg                                              23

<210> SEQ ID NO 27
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 27
cctactcagt gaagctcttc aca                                              23

<210> SEQ ID NO 28
<211> LENGTH: 73
<212> TYPE: RNA
<213> ORGANISM: Artificial Sequence
<220> FEATURE:
<223> OTHER INFORMATION: Synthetic Oligonucleotide

<400> SEQUENCE: 28
gugugaagag cuucacugag uguuuuagag cuaugcugaa aagcauagcu uaaaauaagg      60
cuaguccguu auc                                                         73

<210> SEQ ID NO 29
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 29
```
gcagatgtag tgtttccaca ggg    23

<210> SEQ ID NO 30
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 30
ccctgtggaa acactacatc tgc    23

<210> SEQ ID NO 31
<211> LENGTH: 73
<212> TYPE: RNA
<213> ORGANISM: Artificial Sequence
<220> FEATURE:
<223> OTHER INFORMATION: Synthetic Oligonucleotide

<400> SEQUENCE: 31
ggcagaugua guguuuccac aguuuuagag cuaugcugaa aagcauagcu uaaaauaagg    60
cuaguccguu auc    73

<210> SEQ ID NO 32
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (21)..(21)
<223> OTHER INFORMATION: n is a, c, g, or t

<400> SEQUENCE: 32
ctccctcaag caggccccgc ngg    23

<210> SEQ ID NO 33
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (21)..(21)
<223> OTHER INFORMATION: n is a, c, g, or t

<400> SEQUENCE: 33
gcagatgtag tgtttccaca ngg    23

<210> SEQ ID NO 34
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 34
gcagatgtag tgtttccaca ggg    23

<210> SEQ ID NO 35
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 35
gaagatgtag tgtttccaca ggg                                          23

<210> SEQ ID NO 36
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 36
gaagatgtag tgtttccact ggg                                          23

<210> SEQ ID NO 37
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 37
gcagatggag ggtttccaca ggg                                          23

<210> SEQ ID NO 38
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 38
gcagatgtag tgttaccaga ggg                                          23

<210> SEQ ID NO 39
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 39
ggggatgtag tgtttccact ggg                                          23

<210> SEQ ID NO 40
<211> LENGTH: 4104
<212> TYPE: DNA
<213> ORGANISM: Artificial Sequence
<220> FEATURE:
<223> OTHER INFORMATION: Synthetic Oligonucleotide

<400> SEQUENCE: 40
atggataaga aatactcaat aggcttagat atcggcacaa atagcgtcgg atgggcggtg      60
atcactgatg attataaggt tccgtctaaa aagttcaagg ttctgggaaa tacagaccgc     120
cacagtatca aaaaaaatct tatagggget cttttatttg gcagtggaga gacagcggaa     180
gcgactcgtc tcaaacggac agctcgtaga aggtatacac gtcggaagaa tcgtatttgt     240
tatctacagg agatttttc aaatgagatg gcgaaagtag atgatagttt ctttcatcga     300
cttgaagagt cttttttggt ggaagaagac aagaagcatg aacgtcatcc tatttttgga     360
aatatagtag atgaagttgc ttatcatgag aaatatccaa ctatctatca tctgcgaaaa     420
aaattggcag attctactga taaagcggat ttgcgcttaa tctatttggc cttagcgcat     480

```
atgattaagt tcgtggtca tttttgatt gagggagatt taaatcctga taatagtgat    540
gtggacaaac tatttatcca gttggtacaa atctacaatc aattatttga agaaaaccct   600
attaacgcaa gtagagtaga tgctaaagcg attcttctg cacgattgag taaatcaaga    660
cgattagaaa atctcattgc tcagctcccc ggtgagaaga gaaatggctt gtttgggaat   720
ctcattgctt tgtcattggg attgaccct aattttaaat caatttttga tttggcagaa    780
gatgctaaat tacagctttc aaaagatact tacgatgatg atttagataa tttattggcg   840
caaattggag atcaatatgc tgatttgttt ttggcagcta agaatttatc agatgctatt   900
ttactttcag atatcctaag agtaaatagt gaaataacta aggctcccct atcagcttca   960
atgattaagc gctacgatga acatcatcaa gacttgactc ttttaaaagc tttagttcga  1020
caacaacttc cagaaaagta taagaaaatc ttttttgatc aatcaaaaaa cggatatgca  1080
ggttatattg atggggagc tagccaagaa gaattttata aatttatcaa accaatttta   1140
gaaaaaatgg atggtactga ggaattattg gtgaaactaa atcgtgaaga tttgctgcgc  1200
aagcaacgga cctttgacaa cggctctatt ccccatcaaa ttcacttggg tgagctgcat  1260
gctattttga aagacaaga agactttat ccattttaa aagacaatcg tgagaagatt    1320
gaaaaaatct tgacttttcg aattccttat tatgttggtc cattggcgcg tggcaatagt  1380
cgttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaaagt actaccaaaa catagtttgc tttatgagta ttttacggtt  1560
tataacgaat tgcacaaggt caaatatgtt actgagggaa tgcgaaaacc agcatttctt  1620
tcaggtgaac agaagaaagc cattgttgat ttactcttca aaacaaatcg aaaagtaacc  1680
gttaagcaat taaagaaga ttatttcaaa aaaatagaat gttttgatag tgttgaaatt   1740
tcaggagttg aagatagatt taatgcttca ttaggcgcct accatgattt gctaaaaatt  1800
attaaagata aagatttttt ggataatgaa gaaaatgaag atatcttaga ggatattgtt  1860
ttaacattga ccttatttga agatagggg atgattgagg aaagacttaa aacatatgct   1920
cacctctttg atgataaggt gatgaaacag cttaaacgtc gccgttatac tggttgggga  1980
cgtttgtctc gaaaattgat taatggtatt agggataagc aatctggcaa aacaatatta  2040
gatttttga atcagatgg ttttgccaat cgcaattta tgcagctgat ccatgatgat     2100
agtttgacat taaagaaga tattcaaaaa gcacaggtgt ctggacaagg ccatagttta  2160
catgaacaga ttgctaactt agctggcagt cctgctatta aaaaggtat tttacagact   2220
gtaaaaattg ttgatgaact ggtcaaagta atggggcata agccagaaaa tatcgttatt  2280
gaaatggcac gtgaaaatca gacaactcaa aagggccaga aaattcgcg agagcgtatg   2340
aaacgaatcg aagaaggtat caagaatta ggaagtcaga ttcttaaaga gcatcctgtt   2400
gaaaatactc aattgcaaaa tgaaaagctc tatctctatt atctacaaaa tggaagagac  2460
atgtatgtgg accaagaatt agatattaat cgtttaagtg attatgatgt cgatcacatt  2520
gttccacaaa gtttcattaa agacgattca atagacaata aggtactaac gcgttctgat  2580
aaaaatcgtg gtaaatcgga taacgttcca agtgaagaag tagtcaaaaa gatgaaaaac  2640
tattggagac aacttctaaa cgccaagtta atcactcaac gtaagtttga aatttaacg   2700
aaagctgaac gtggaggttt gagtgaactt gataaagctg gttttatcaa acgccaattg  2760
gttgaaactc gccaaatcac taagcatgtg gcacaaattt tggatagtcg catgaatact  2820
aaatacgatg aaaatgataa acttattcga gaggttaaag tgattaccct taaatctaaa  2880
```

```
ttagtttctg acttccgaaa agatttccaa ttctataaag tacgtgagat taacaattac   2940
catcatgccc atgatgcgta tctaaatgcc gtcgttggaa ctgctttgat taagaaatat   3000
ccaaaacttg aatcggagtt tgtctatggt gattataaag tttatgatgt tcgtaaaatg   3060
attgctaagt ctgagcaaga aataggcaaa gcaaccgcaa atatttctt ttactctaat    3120 atcatgaact tcttcaaaac agaaattaca cttgcaaatg gagagattcg caaacgccct   3180
ctaatcgaaa ctaatgggga aactggagaa attgtctggg ataaagggcg agattttgcc   3240
acagtgcgca agtattgtc catgccccaa gtcaatattg tcaagaaaac agaagtacag    3300
acaggcggat tctccaagga gtcaatttta ccaaaaagaa attcggacaa gcttattgct   3360
cgtaaaaaag actgggatcc aaaaaaatat ggtggttttg atagtccaac ggtagcttat   3420
tcagtcctag tggttgctaa ggtggaaaaa gggaaatcga agaagttaaa atccgttaaa   3480
gagttactag ggatcacaat tatggaaaga agttcctttg aaaaaaatcc gattgacttt   3540
ttagaagcta aaggatataa ggaagttaaa aaagacttaa tcattaaact acctaaatat   3600 agtcttttg agttagaaaa cggtcgtaaa cggatgctgg ctagtgccgg agaattacaa    3660
aaaggaaatg agctggctct gccaagcaaa tatgtgaatt ttttatattt agctagtcat   3720
tatgaaaagt tgaagggtag tccagaagat aacgaacaaa acaattgtt tgtggagcag    3780 cataagcatt atttagatga gattattgag caaatcagtg aatttctaa gcgtgttatt    3840 ttagcagatg ccaatttaga taaagttctt agtgcatata acaaacatag agacaaacca   3900
atacgtgaac aagcagaaaa tattattcat ttatttacgt tgacgaatct tggagctccc   3960
gctgctttta aatattttga tacaacaatt gatcgtaaac gatatacgtc tacaaaagaa   4020
gttttagatg ccactcttat ccatcaatcc atcactggtc tttatgaaac acgcattgat   4080
ttgagtcagc taggaggtga ctga                                          4104
```

<210> SEQ ID NO 41
<211> LENGTH: 1367
<212> TYPE: PRT
<213> ORGANISM: Artificial Sequence
<220> FEATURE:
<223> OTHER INFORMATION: Synthetic Polypeptide

<400> SEQUENCE: 41

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140
```

```
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560
```

-continued

Val Lys Gln Leu Lys Glu Asp Tyr Phe Lys Ile Glu Cys Phe Asp
             565                 570                 575

Ser Val Glu Ile Ser Gly Val Glu Asp Arg Phe Asn Ala Ser Leu Gly
         580                 585                 590

Ala Tyr His Asp Leu Leu Lys Ile Ile Lys Asp Lys Asp Phe Leu Asp
             595                 600                 605

Asn Glu Glu Asn Glu Asp Ile Leu Glu Asp Ile Val Leu Thr Leu Thr
         610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
             645                 650                 655

Thr Gly Trp Gly Arg Leu Ser Arg Lys Leu Ile Asn Gly Ile Arg Asp
             660                 665                 670

Lys Gln Ser Gly Lys Thr Ile Leu Asp Phe Leu Lys Ser Asp Gly Phe
         675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
             725                 730                 735

Ile Leu Gln Thr Val Lys Ile Val Asp Glu Leu Val Lys Val Met Gly
             740                 745                 750

His Lys Pro Glu Asn Ile Val Ile Glu Met Ala Arg Glu Asn Gln Thr
             755                 760                 765

Thr Gln Lys Gly Gln Lys Asn Ser Arg Glu Arg Met Lys Arg Ile Glu
         770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
             805                 810                 815

Asn Gly Arg Asp Met Tyr Val Asp Gln Glu Leu Asp Ile Asn Arg Leu
         820                 825                 830

Ser Asp Tyr Asp Val Asp His Ile Val Pro Gln Ser Phe Ile Lys Asp
         835                 840                 845

Asp Ser Ile Asp Asn Lys Val Leu Thr Arg Ser Asp Lys Asn Arg Gly
         850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
             885                 890                 895

Asp Asn Leu Thr Lys Ala Glu Arg Gly Gly Leu Ser Glu Leu Asp Lys
             900                 905                 910

Ala Gly Phe Ile Lys Arg Gln Leu Val Glu Thr Arg Gln Ile Thr Lys
             915                 920                 925

His Val Ala Gln Ile Leu Asp Ser Arg Met Asn Thr Lys Tyr Asp Glu
         930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
             965                 970                 975

Ile Asn Asn Tyr His His Ala His Asp Ala Tyr Leu Asn Ala Val Val

```
               980             985             990
Gly Thr Ala Leu Ile Lys Lys Tyr Pro Lys Leu Glu Ser Glu Phe Val
              995            1000            1005
Tyr Gly Asp Tyr Lys Val Tyr Asp Val Arg Lys Met Ile Ala Lys
   1010            1015            1020
Ser Glu Gln Glu Ile Gly Lys Ala Thr Ala Lys Tyr Phe Phe Tyr
   1025            1030            1035
Ser Asn Ile Met Asn Phe Phe Lys Thr Glu Ile Thr Leu Ala Asn
   1040            1045            1050
Gly Glu Ile Arg Lys Arg Pro Leu Ile Glu Thr Asn Gly Glu Thr
   1055            1060            1065
Gly Glu Ile Val Trp Asp Lys Gly Arg Asp Phe Ala Thr Val Arg
   1070            1075            1080
Lys Val Leu Ser Met Pro Gln Val Asn Ile Val Lys Lys Thr Glu
   1085            1090            1095
Val Gln Thr Gly Gly Phe Ser Lys Glu Ser Ile Leu Pro Lys Arg
   1100            1105            1110
Asn Ser Asp Lys Leu Ile Ala Arg Lys Lys Asp Trp Asp Pro Lys
   1115            1120            1125
Lys Tyr Gly Gly Phe Asp Ser Pro Thr Val Ala Tyr Ser Val Leu
   1130            1135            1140
Val Val Ala Lys Val Glu Lys Gly Lys Ser Lys Lys Leu Lys Ser
   1145            1150            1155
Val Lys Glu Leu Leu Gly Ile Thr Ile Met Glu Arg Ser Ser Phe
   1160            1165            1170
Glu Lys Asn Pro Ile Asp Phe Leu Glu Ala Lys Gly Tyr Lys Glu
   1175            1180            1185
Val Lys Lys Asp Leu Ile Ile Lys Leu Pro Lys Tyr Ser Leu Phe
   1190            1195            1200
Glu Leu Glu Asn Gly Arg Lys Arg Met Leu Ala Ser Ala Gly Glu
   1205            1210            1215
Leu Gln Lys Gly Asn Glu Leu Ala Leu Pro Ser Lys Tyr Val Asn
   1220            1225            1230
Phe Leu Tyr Leu Ala Ser His Tyr Glu Lys Leu Lys Gly Ser Pro
   1235            1240            1245
Glu Asp Asn Glu Gln Lys Gln Leu Phe Val Glu Gln His Lys His
   1250            1255            1260
Tyr Leu Asp Glu Ile Ile Glu Gln Ile Ser Glu Phe Ser Lys Arg
   1265            1270            1275
Val Ile Leu Ala Asp Ala Asn Leu Asp Lys Val Leu Ser Ala Tyr
   1280            1285            1290
Asn Lys His Arg Asp Lys Pro Ile Arg Glu Gln Ala Glu Asn Ile
   1295            1300            1305
Ile His Leu Phe Thr Leu Thr Asn Leu Gly Ala Pro Ala Ala Phe
   1310            1315            1320
Lys Tyr Phe Asp Thr Thr Ile Asp Arg Lys Arg Tyr Thr Ser Thr
   1325            1330            1335
Lys Glu Val Leu Asp Ala Thr Leu Ile His Gln Ser Ile Thr Gly
   1340            1345            1350
Leu Tyr Glu Thr Arg Ile Asp Leu Ser Gln Leu Gly Gly Asp
   1355            1360            1365

<210> SEQ ID NO 42
```

<211> LENGTH: 100
<212> TYPE: DNA
<213> ORGANISM: Artificial Sequence
<220> FEATURE:
<223> OTHER INFORMATION: Synthetic Oligonucleotide

<400> SEQUENCE: 42
aacacatggg tcgacacaaa cacaactcgg caggtacttg cagatgtagt ctttccacat    60
gggtcgacac aaacacaact cggcaggtat ctcgtatgcc                         100

<210> SEQ ID NO 43
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 43
ctcggcaggt                                                           10

<210> SEQ ID NO 44
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 44
acttgcagat gtagtctttc cacatgggtc gacacaaaca caa                      43

<210> SEQ ID NO 45
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 45
tgtgtttgtg tt                                                        12

<210> SEQ ID NO 46
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 46
agaagaagaa ga                                                        12

<210> SEQ ID NO 47
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 47
ttctctttct ct                                                        12

<210> SEQ ID NO 48
<211> LENGTH: 12
<212> TYPE: DNA
<213> ORGANISM: Artificial Sequence
<220> FEATURE:
<223> OTHER INFORMATION: Synthetic Oligonucleotide

```
<400> SEQUENCE: 48
acacaaacac aa                                                           12

<210> SEQ ID NO 49
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 49
acttgcagat gtagtctttc cacatgggtc gacacaaaca caa                         43

<210> SEQ ID NO 50
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 50
acttgcagat gtagtctttc cacatgggtc g                                      31

<210> SEQ ID NO 51
<211> LENGTH: 100
<212> TYPE: DNA
<213> ORGANISM: Artificial Sequence
<220> FEATURE:
<223> OTHER INFORMATION: Synthetic Oligonucleotide

<400> SEQUENCE: 51
aacacatggg tcgacacaaa cacaactcgg caggtacttg cagatgtagt ctttccacat       60
gggtcgacac aaacacaact cggcaggtat ctcgtatgcc                            100

<210> SEQ ID NO 52
<211> LENGTH: 162
<212> TYPE: DNA
<213> ORGANISM: Artificial Sequence
<220> FEATURE:
<223> OTHER INFORMATION: Synthetic Oligonucleotide

<400> SEQUENCE: 52
caatctcccg catgcgctca gtcctcatct ccctcaagca ggccccgctg gtgcactgaa       60
gagccaccct gtgaaacact acatctgcaa tatcttaatc ctactcagtg aagctcttca     120
cagtcattgg attaattatg ttgagttctt ttggaccaaa cc                        162

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
gctggtgcac tgaagagcca                                                   20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 54
aatatcttaa tcctactcag                                              20

<210> SEQ ID NO 55
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 55
ccctgtgaaa cactacatct gc                                           22

<210> SEQ ID NO 56
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 56
gcagatgtag tgtttcacag gg                                           22

<210> SEQ ID NO 57
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 57
gcagatgtag tgtttccaca ggg                                          23

<210> SEQ ID NO 58
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 58
gcagatgtag tgtttccaca ggg                                          23

<210> SEQ ID NO 59
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 59
acatatgtag tatttccaca ggg                                          23

<210> SEQ ID NO 60
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 60
gcatatgtag tgtttccaaa tgt                                          23

<210> SEQ ID NO 61
<211> LENGTH: 23
```

```
<212> TYPE: DNA
<213> ORGANISM: Artificial Sequence
<220> FEATURE:
<223> OTHER INFORMATION: Synthetic Oligonucleotide

<400> SEQUENCE: 61
ccagatgtag tattcccaca ggg                                             23

<210> SEQ ID NO 62
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 62 gcagtttag tgttttcaca ggg                                              23

<210> SEQ ID NO 63
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 63
gcagagttag tgtttccaca cag                                             23

<210> SEQ ID NO 64
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 64
gcagatggag ggttttcaca ggg                                             23

<210> SEQ ID NO 65
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 65
ggaaatttag tgtttccaca ggg                                             23

<210> SEQ ID NO 66
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 66
aaagaagtag tatttccaca tgg                                             23

<210> SEQ ID NO 67
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 67
```
aaagatgtag tcattccaca agg                                          23

<210> SEQ ID NO 68
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 68
aaatatgtag tctttccaca ggg                                          23

<210> SEQ ID NO 69
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 69
atagatgtag tgtttccaaa gga                                          23

<210> SEQ ID NO 70
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 70
ccagaggtag tgctcccaca ggg                                          23

<210> SEQ ID NO 71
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 71
ccagatgtga ggtttccaca agg                                          23

<210> SEQ ID NO 72
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 72
ctacatgtag tgtttccata tgg                                          23

<210> SEQ ID NO 73
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 73
tagatgaagt gcttccacat gg                                           22

<210> SEQ ID NO 74
<211> LENGTH: 23
<212> TYPE: DNA
<213> ORGANISM: Artificial Sequence

```
<220> FEATURE:
<223> OTHER INFORMATION: Synthetic Oligonucleotide

<400> SEQUENCE: 74
gaaaatggag tgtttacaca tgg                                              23

<210> SEQ ID NO 75
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 75
gcaaatgaag tgtcaccaca agg                                              23

<210> SEQ ID NO 76
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 76
gcaaatgtat tatttccact agg                                              23

<210> SEQ ID NO 77
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 77
gcagatgtag cttttgtaca tgg                                              23

<210> SEQ ID NO 78
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 78
gcagcttaag tgttttcaca tgg                                              23

<210> SEQ ID NO 79
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 79
ttacatgtag tgtttacaca cgg                                              23

<210> SEQ ID NO 80
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 80
gaagaggaag tgtttgccca ggg                                              23
```

<210> SEQ ID NO 81
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 81
gaagatgtgg agttgacaca tgg                                              23

<210> SEQ ID NO 82
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 82
gcagaagtac tgttgttaca agg                                              23

<210> SEQ ID NO 83
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 83
gcagatgtgg aattacaaca ggg                                              23

<210> SEQ ID NO 84
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 84
gcagtcatag tgtatacaca tgg                                              23

<210> SEQ ID NO 85
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 85
taagatgtag tatttccaaa agt                                              23

<210> SEQ ID NO 86
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 86
gcagctggca tttctccaca cgg                                              23

<210> SEQ ID NO 87
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 87
ggagatctga tggttctaca agg                                            23

<210> SEQ ID NO 88
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 88
taaaatgcag tgtatccata tgg                                            23

<210> SEQ ID NO 89
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 89
gccagaatag tttttcaaca agg                                            23

<210> SEQ ID NO 90
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 90
ttgtatttag agattgcaca agg                                            23

<210> SEQ ID NO 91
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 91
agtcctcatc tccctcaagc agg                                            23

<210> SEQ ID NO 92
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 92
agtcctcaac tccctcaagc agg                                            23

<210> SEQ ID NO 93
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 93
agccctcatt tccctcaagc agg                                            23

<210> SEQ ID NO 94

<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 94
actcctcatc cccctcaagc cgg            23

<210> SEQ ID NO 95
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 95
agtcatcatc tccctcaagc aga            23

<210> SEQ ID NO 96
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 96
cgtcctcctc tccccaagc agg             23

<210> SEQ ID NO 97
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 97
tgtcctcttc tccctcaagc aga            23

<210> SEQ ID NO 98
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 98
aagcttcatc tctctcaagc tgg            23

<210> SEQ ID NO 99
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 99
agtactcttt tccctcaggc tgg            23

<210> SEQ ID NO 100
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 100
agtcttaaat tccctcaagc agg                                              23

<210> SEQ ID NO 101
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 101
agtgctcatc taccagaagc tgg                                              23

<210> SEQ ID NO 102
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 102
cctcctcatc tccctgcagc agg                                              23

<210> SEQ ID NO 103
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 103
ctacatcatc tccctcaagc tgg                                              23

<210> SEQ ID NO 104
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 104
ggtcctcatc tccctaaaac aga                                              23

<210> SEQ ID NO 105
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 105
tgtcctcatc ggcctcaggc agg                                              23

<210> SEQ ID NO 106
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 106
agacaccatc tcccttgagc tgg                                              23

<210> SEQ ID NO 107
<211> LENGTH: 23
<212> TYPE: DNA

```
<213> ORGANISM: Artificial Sequence
<220> FEATURE:
<223> OTHER INFORMATION: Synthetic Oligonucleotide

<400> SEQUENCE: 107
aggcatcatc tacatcaagt tgg                                           23

<210> SEQ ID NO 108
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 108
agtaatcact tccatcaagc cgg                                           23

<210> SEQ ID NO 109
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 109
tcccctcacc tccctaaagc agg                                           23

<210> SEQ ID NO 110
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 110
tgtctttatt tccctctagc tgg                                           23

<210> SEQ ID NO 111
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 111
agtcctcatc tccctcaagc agg                                           23

<210> SEQ ID NO 112
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 112
gcagatgtag tgtttccaca ggg                                           23

<210> SEQ ID NO 113
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 113
acatatgtag tatttccaca ggg                                           23
```

<210> SEQ ID NO 114
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 114
gcatatgtag tgtttccaaa tgt                                    23

<210> SEQ ID NO 115
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 115
ccagatgtag tattcccaca ggg                                    23

<210> SEQ ID NO 116
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 116
gcagttttag tgttttcaca ggg                                    23

<210> SEQ ID NO 117
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 117
gcagagttag tgtttccaca cag                                    23

<210> SEQ ID NO 118
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 118
gcagatggag ggttttcaca ggg                                    23

<210> SEQ ID NO 119
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 119
ggaaatttag tgtttccaca ggg                                    23

<210> SEQ ID NO 120
<211> LENGTH: 23
<212> TYPE: DNA
<213> ORGANISM: Artificial Sequence
<220> FEATURE:

<223> OTHER INFORMATION: Synthetic Oligonucleotide

<400> SEQUENCE: 120
aaagaagtag tatttccaca tgg                                              23

<210> SEQ ID NO 121
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 121
aaagatgtag tcattccaca agg                                              23

<210> SEQ ID NO 122
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 122
aaatatgtag tctttccaca ggg                                              23

<210> SEQ ID NO 123
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 123
atagatgtag tgtttccaaa gga                                              23

<210> SEQ ID NO 124
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 124
ccagaggtag tgctcccaca ggg                                              23

<210> SEQ ID NO 125
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 125
ccagatgtga ggtttccaca agg                                              23

<210> SEQ ID NO 126
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 126
ctacatgtag tgtttccata tgg                                              23

```
<210> SEQ ID NO 127
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 127
ctagatgaag tgcttccaca tgg                                               23

<210> SEQ ID NO 128
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 128
gaaaatggag tgtttacaca tgg                                               23

<210> SEQ ID NO 129
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 129
gcaaatgaag tgtcaccaca agg                                               23

<210> SEQ ID NO 130
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 130
gcaaatgtat tatttccact agg                                               23

<210> SEQ ID NO 131
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 131
gcagatgtag cttttgtaca tgg                                               23

<210> SEQ ID NO 132
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 132
gcagcttaag tgttttcaca tgg                                               23

<210> SEQ ID NO 133
<211> LENGTH: 23
<212> TYPE: DNA
<213> ORGANISM: Artificial Sequence
<220> FEATURE:
<223> OTHER INFORMATION: Synthetic Oligonucleotide
```

-continued

<400> SEQUENCE: 133
ttacatgtag tgtttacaca cgg                                              23

<210> SEQ ID NO 134
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 134
gaagaggaag tgtttgccca ggg                                              23

<210> SEQ ID NO 135
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 135
gaagatgtgg agttgacaca tgg                                              23

<210> SEQ ID NO 136
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 136
gcagaagtac tgttgttaca agg                                              23

<210> SEQ ID NO 137
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 137
gcagatgtgg aattacaaca ggg                                              23

<210> SEQ ID NO 138
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 138
gcagtcatag tgtatacaca tgg                                              23

<210> SEQ ID NO 139
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 139
taagatgtag tatttccaaa agt                                              23

<210> SEQ ID NO 140
<211> LENGTH: 23

```
<212> TYPE: DNA
<213> ORGANISM: Artificial Sequence
<220> FEATURE:
<223> OTHER INFORMATION: Synthetic Oligonucleotide

<400> SEQUENCE: 140
gcagctggca tttctccaca cgg                                                 23

<210> SEQ ID NO 141
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 141
ggagatctga tggttctaca agg                                                 23

<210> SEQ ID NO 142
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 142
taaaatgcag tgtatccata tgg                                                 23

<210> SEQ ID NO 143
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 143
gccagaatag tttttcaaca agg                                                 23

<210> SEQ ID NO 144
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 144
ttgtatttag agattgcaca agg                                                 23

<210> SEQ ID NO 145
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 145
agtcctcatc tccctcaagc agg                                                 23

<210> SEQ ID NO 146
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 146
```
agtcctcaac tccctcaagc agg                                                   23

<210> SEQ ID NO 147
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 147
agccctcatt tccctcaagc agg                                                   23

<210> SEQ ID NO 148
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 148
actcctcatc ccccctcaagc cgg                                                  23

<210> SEQ ID NO 149
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 149
agtcatcatc tccctcaagc aga                                                   23

<210> SEQ ID NO 150
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 150
cgtcctcctc tcccccaagc agg                                                   23

<210> SEQ ID NO 151
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 151
tgtcctcttc tccctcaagc aga                                                   23

<210> SEQ ID NO 152
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 152
aagcttcatc tctctcaagc tgg                                                   23

<210> SEQ ID NO 153
<211> LENGTH: 23
<212> TYPE: DNA
<213> ORGANISM: Artificial Sequence

```
<220> FEATURE:
<223> OTHER INFORMATION: Synthetic Oligonucleotide

<400> SEQUENCE: 153
agtactcttt tccctcaggc tgg                                               23

<210> SEQ ID NO 154
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 154
agtcttaaat tccctcaagc agg                                               23

<210> SEQ ID NO 155
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 155
agtgctcatc taccagaagc tgg                                               23

<210> SEQ ID NO 156
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 156
cctcctcatc tccctgcagc agg                                               23

<210> SEQ ID NO 157
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 157
ctacatcatc tccctcaagc tgg                                               23

<210> SEQ ID NO 158
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 158
ggtcctcatc tccctaaaac aga                                               23

<210> SEQ ID NO 159
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 159
tgtcctcatc ggcctcaggc agg                                               23
```

<210> SEQ ID NO 160
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 160
agacaccatc tcccttgagc tgg                                           23

<210> SEQ ID NO 161
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 161
aggcatcatc tacatcaagt tgg                                           23

<210> SEQ ID NO 162
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 162
agtaatcact tccatcaagc cgg                                           23

<210> SEQ ID NO 163
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 163
tcccctcacc tccctaaagc agg                                           23

<210> SEQ ID NO 164
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 164
tgtctttatt tccctctagc tgg                                           23

<210> SEQ ID NO 165
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 165
agtcctcatc tccctcaagc agg                                           23

<210> SEQ ID NO 166
<211> LENGTH: 23
<212> TYPE: DNA
<213> ORGANISM: Artificial Sequence
<220> FEATURE:
<223> OTHER INFORMATION: Synthetic Oligonucleotide

```
<400> SEQUENCE: 166
agtcctcatc tccctcaagc agg                                              23

<210> SEQ ID NO 167
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 167
agtcctcatc tccctcaaag cagg                                             24

<210> SEQ ID NO 168
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 168
agtcctcatc tccctcagca gg                                               22

<210> SEQ ID NO 169
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 169
agtcctcatc tccctcatag cagg                                             24

<210> SEQ ID NO 170
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 170
agtcctcata gcagg                                                       15

<210> SEQ ID NO 171
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 171
agtcctcatc tagcagg                                                     17

<210> SEQ ID NO 172
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 172
agtcctcaag cagg                                                        14

<210> SEQ ID NO 173
```

```
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 173
agtcctcatc tccctcaaag gcagtgtttg ttacttgagt ttgtcagcag g      51

<210> SEQ ID NO 174
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 174
agtcctcatc tccctcatta gcagg                                   25

<210> SEQ ID NO 175
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 175
agtcctcatc tccctcaggg cttgtttaca gctcaccttt gaatttgcac aagcgtgcaa   60
gcagg                                                              65

<210> SEQ ID NO 176
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 176
agtcctcatc tccctagcag g                                       21

<210> SEQ ID NO 177
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 177
agtcctcatc cctcaagcag g                                       21

<210> SEQ ID NO 178
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 178
agtcctcatc tccctaagca gg                                      22

<210> SEQ ID NO 179
<211> LENGTH: 23
<212> TYPE: DNA
<213> ORGANISM: Artificial Sequence
<220> FEATURE:
<223> OTHER INFORMATION: Synthetic Oligonucleotide
```

```
<400> SEQUENCE: 179
agtcctcaac tccctcaagc agg                                          23

<210> SEQ ID NO 180
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 180
agtcctcaac tccctcaaag cagg                                         24

<210> SEQ ID NO 181
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 181
agtcctcaac tccctca                                                 17

<210> SEQ ID NO 182
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 182
agtcctcaac tccctcagca gg                                           22

<210> SEQ ID NO 183
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 183
agtcctcaac tccctcaaga aaggtgttga aaatcagaaa gagagaaaca agcagg      56

<210> SEQ ID NO 184
<211> LENGTH: 62
<212> TYPE: DNA
<213> ORGANISM: Artificial Sequence
<220> FEATURE:
<223> OTHER INFORMATION: Synthetic Oligonucleotide

<400> SEQUENCE: 184
agtcctcaac tccctcaatc tacggtccat tcccgtttcc actcaccttg cgccgcagca  60
gg                                                                 62

<210> SEQ ID NO 185
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 185
agtcctcaac tccctaagca gg                                           22
```

<210> SEQ ID NO 186
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 186
agtcctcaac tccctcaacc aactttaaca tcctgctggt tctgtcatta ataagttgaa    60
agcagg                                                              66

<210> SEQ ID NO 187
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 187
agtcctcaac tccctcacag caaataaaaa agttgtttat gcatattcag ataagcaaag    60
cagg                                                                64

<210> SEQ ID NO 188
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 188
agtcctcaac tcccaagcag g                                             21

<210> SEQ ID NO 189
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 189
actcctcatc ccccctcaagc cgg                                          23

<210> SEQ ID NO 190
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 190
actcctcatc ccccctcaaag ccgg                                         24

<210> SEQ ID NO 191
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 191
actcctcatc ccccctcagag ccgg                                         24

<210> SEQ ID NO 192
<211> LENGTH: 13

```
<212> TYPE: DNA
<213> ORGANISM: Artificial Sequence
<220> FEATURE:
<223> OTHER INFORMATION: Synthetic Oligonucleotide

<400> SEQUENCE: 192
actcctcagc cgg                                                           13

<210> SEQ ID NO 193
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 193
actcctcatc cccctcaaaa gccgg                                              25

<210> SEQ ID NO 194
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 194
actcctcatc cccctcagca gccgg                                              25

<210> SEQ ID NO 195
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 195
actcctcatc cccctcatag ccgg                                               24

<210> SEQ ID NO 196
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 196
actcctcatc cccctcatcc ccgg                                               24

<210> SEQ ID NO 197
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 197
actcctcatc ccagccgg                                                      18

<210> SEQ ID NO 198
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 198
```

-continued actcctcatc ccctaagcc gg                                                    22

<210> SEQ ID NO 199
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 199
actcctcatc ccctcaata gccgg                                                 25

<210> SEQ ID NO 200
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 200
actcctcacc ccctcagca gccgg                                                 25

<210> SEQ ID NO 201
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 201
gcagatgtag tgtttccaca ggg                                                  23

<210> SEQ ID NO 202
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 202
gcagatgtag tgtttcacag gg                                                   22

<210> SEQ ID NO 203
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 203
gcagatgtag tgtttcccac aggg                                                 24

<210> SEQ ID NO 204
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 204
gcagatgtag tgcacaggg                                                       19

<210> SEQ ID NO 205
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 205
gcagatgtag tgtttcccag gg                                         22

<210> SEQ ID NO 206
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 206
gcagatgtac acaggg                                                16

<210> SEQ ID NO 207
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 207
gcagatgtag tgtcacaggg                                            20

<210> SEQ ID NO 208
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 208
gcagatgtag tgttcacagg g                                          21

<210> SEQ ID NO 209
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 209
gcagatgtag tgtttccagg g                                          21

<210> SEQ ID NO 210
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 210
gcagatgtag tcacaggg                                              18

<210> SEQ ID NO 211
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 211
gcagatgtag gg                                                    12

```
<210> SEQ ID NO 212
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 212
acatatgtag tatttccaca ggg                                             23

<210> SEQ ID NO 213
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 213
acatatgtag tatttcccac aggg                                            24

<210> SEQ ID NO 214
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 214
acatatgtag tatttcacag gg                                              22

<210> SEQ ID NO 215
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 215
acatatgtag tatttccagg g                                               21

<210> SEQ ID NO 216
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 216
acatatcaca ggg                                                        13

<210> SEQ ID NO 217
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 217
acatcacagg g                                                          11

<210> SEQ ID NO 218
<211> LENGTH: 18
<212> TYPE: DNA
<213> ORGANISM: Artificial Sequence
<220> FEATURE:
<223> OTHER INFORMATION: Synthetic Oligonucleotide
```

```
<400> SEQUENCE: 218
acatatgtag tcacaggg                                                    18

<210> SEQ ID NO 219
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 219
acatatgtag tatttcc                                                     17

<210> SEQ ID NO 220
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 220
acatatgtag gg                                                          12

<210> SEQ ID NO 221
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 221
acatatgtag cacaggg                                                     17

<210> SEQ ID NO 222
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 222
ccagatgtag tattcccaca ggg                                              23

<210> SEQ ID NO 223
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 223
ccagatgtag tattccccac aggg                                             24

<210> SEQ ID NO 224
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 224
ccagatgtag tatacaggg                                                   19

<210> SEQ ID NO 225
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 225
ccagatgtag tatcacaggg                                               20

<210> SEQ ID NO 226
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 226
ccagatgtag tattcccaac acaggg                                        26

<210> SEQ ID NO 227
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 227
ccagatgtag tattcacagg g                                             21

<210> SEQ ID NO 228
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 228
ccagatgtag tattcccagg g                                             21

<210> SEQ ID NO 229
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 229
ccagatgtag tattccacag gg                                            22

<210> SEQ ID NO 230
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 230
ctagatgaag tgcttccaca tgg                                           23

<210> SEQ ID NO 231
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 231
```
ctagatgaag tgcttcccac atgg						24

<210> SEQ ID NO 232
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 232
ctagatgaag tgcttcacat gg						22

<210> SEQ ID NO 233
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 233
ctagatgaag tg						12

<210> SEQ ID NO 234
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 234
ctagatgaag tgcttccaca catgg						25

<210> SEQ ID NO 235
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 235
ctagatgaag tgcttccatg g						21

<210> SEQ ID NO 236
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 236
ctagatgaag tgcttcccat gg						22

<210> SEQ ID NO 237
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 237
taatacgact cactatagga gtcctcatct ccctcaagcg ttttagagct atgctg						56

<210> SEQ ID NO 238
<211> LENGTH: 56
<212> TYPE: DNA

```
<213> ORGANISM: Artificial Sequence
<220> FEATURE:
<223> OTHER INFORMATION: Synthetic Oligonucleotide

<400> SEQUENCE: 238
taatacgact cactataggc tccctcaagc aggccccgcg ttttagagct atgctg      56

<210> SEQ ID NO 239
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 239
taatacgact cactataggt gtgaagagct tcactgagtg ttttagagct atgctg      56

<210> SEQ ID NO 240
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 240
taatacgact cactataggg cagatgtagt gtttccacag ttttagagct atgctg      56

<210> SEQ ID NO 241
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 241
gataacggac tagccttatt taacttgct atgcttttca gcatagctct aaaac         55

<210> SEQ ID NO 242
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 242
cggactagcc ttattttaac ttgctatttc tagctctaaa acgcttgagg gagatgagga   60
ctcctatagt gagtcgtatt a                                              81

<210> SEQ ID NO 243
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 243
cggactagcc ttattttaac ttgctatttc tagctctaaa acgcggggcc tgcttgaggg   60
agcctatagt gagtcgtatt a                                              81

<210> SEQ ID NO 244
<211> LENGTH: 81
<212> TYPE: DNA
<213> ORGANISM: Artificial Sequence
<220> FEATURE:
<223> OTHER INFORMATION: Synthetic Oligonucleotide
```

<400> SEQUENCE: 244
cggactagcc ttattttaac ttgctatttc tagctctaaa acactcagtg aagctcttca    60
cacctatagt gagtcgtatt a    81

<210> SEQ ID NO 245
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 245
cggactagcc ttattttaac ttgctatttc tagctctaaa actgtggaaa cactacatct    60
gccctatagt gagtcgtatt a    81

<210> SEQ ID NO 246
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 246
taatacgact cactatagg    19

<210> SEQ ID NO 247
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(37)
<223> OTHER INFORMATION: n is a, c, g, or t

<400> SEQUENCE: 247
aacacannnn ccngcttgag ggagatgagg actnnnnacc tgccgagaac aca    53

<210> SEQ ID NO 248
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(37)
<223> OTHER INFORMATION: n is a, c, g, or t

<400> SEQUENCE: 248
tcttctnnnn ccngcggggc ctgcttgagg gagnnnnacc tgccgagtct tct                53

<210> SEQ ID NO 249
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(37)
<223> OTHER INFORMATION: n is a, c, g, or t

<400> SEQUENCE: 249
agagaannnn ccnactcagt gaagctcttc acannnnacc tgccgagaga gaa                53

<210> SEQ ID NO 250
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(37)
<223> OTHER INFORMATION: n is a, c, g, or t

<400> SEQUENCE: 250
ttgtgtnnnn ccntgtggaa acactacatc tgcnnnnacc tgccgagttg tgt                53

<210> SEQ ID NO 251
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 251
ctagcagtcc tcatctccct caagcaggc                                            29

<210> SEQ ID NO 252
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 252
agctgcctgc ttgagggaga tgaggactg                                            29

<210> SEQ ID NO 253
<211> LENGTH: 29
<212> TYPE: DNA
<213> ORGANISM: Artificial Sequence

```
<220> FEATURE:
<223> OTHER INFORMATION: Synthetic Oligonucleotide

<400> SEQUENCE: 253
ctagtctccc tcaagcaggc cccgctggt                                    29

<210> SEQ ID NO 254
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 254
agctaccagc ggggcctgct tgagggaga                                    29

<210> SEQ ID NO 255
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 255
ctagctgtga agagcttcac tgagtagga                                    29

<210> SEQ ID NO 256
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 256
agcttcctac tcagtgaagc tcttcacag                                    29

<210> SEQ ID NO 257
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 257
ctagtgcaga tgtagtgttt ccacagggt                                    29

<210> SEQ ID NO 258
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 258
agctaccctg tggaaacact acatctgca                                    29

<210> SEQ ID NO 259
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 259
gcgacacgga aatgttgaat actcat                                       26
```

```
<210> SEQ ID NO 260
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 260
ggagtcaggc aactatggat gaacg                                          25

<210> SEQ ID NO 261
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 261
actgtgaaga gcttcactga gtaggattaa gatattgcag atgtagtgtt tccacagggt    60

<210> SEQ ID NO 262
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 262
actgtgaaga gcttcactga gtaggattaa gatattgaag atgtagtgtt tccacagggt    60

<210> SEQ ID NO 263
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 263
actgtgaaga gcttcactga gtaggattaa gatattgaag atgtagtgtt tccactgggt    60

<210> SEQ ID NO 264
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 264
actgtgaaga gcttcactga gtaggattaa gatattgcag atggagggtt tccacagggt    60

<210> SEQ ID NO 265
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 265
actgtgaaga gcttcactga gtaggattaa gatattgcag atgtagtgtt accagagggt    60

<210> SEQ ID NO 266
<211> LENGTH: 60
<212> TYPE: DNA
<213> ORGANISM: Artificial Sequence
<220> FEATURE:
<223> OTHER INFORMATION: Synthetic Oligonucleotide
```

<400> SEQUENCE: 266
actgtgaaga gcttcactga gtaggattaa gatattgggg atgtagtgtt tccactgggt    60

<210> SEQ ID NO 267
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 267
tccctcaagc aggccccgct ggtgcactga agagccaccc tgtggaaaca ctacatctgc    60

<210> SEQ ID NO 268
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 268
tccctcaagc aggccccgct ggtgcactga agagccaccc tgtggaaaca ctacatcttc    60

<210> SEQ ID NO 269
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 269
tccctcaagc aggccccgct ggtgcactga agagccaccc agtggaaaca ctacatcttc    60

<210> SEQ ID NO 270
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 270
tccctcaagc aggccccgct ggtgcactga agagccaccc tgtggaaacc ctccatctgc    60

<210> SEQ ID NO 271
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 271
tccctcaagc aggccccgct ggtgcactga agagccaccc tctggtaaca ctacatctgc    60

<210> SEQ ID NO 272
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 272
tccctcaagc aggccccgct ggtgcactga agagccaccc agtggaaaca ctacatcccc    60

<210> SEQ ID NO 273

```
<211> LENGTH: 62
<212> TYPE: DNA
<213> ORGANISM: Artificial Sequence
<220> FEATURE:
<223> OTHER INFORMATION: Synthetic Oligonucleotide

<400> SEQUENCE: 273
aatgatacgg cgaccaccga gatctacact ctttccctac acgacgctct tccgatctaa      60
ca                                                                    62

<210> SEQ ID NO 274
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 274
tgttagatcg aagagcgtc gtgtagggaa agagtgtaga tctcggtgg                  49

<210> SEQ ID NO 275
<211> LENGTH: 62
<212> TYPE: DNA
<213> ORGANISM: Artificial Sequence
<220> FEATURE:
<223> OTHER INFORMATION: Synthetic Oligonucleotide

<400> SEQUENCE: 275
aatgatacgg cgaccaccga gatctacact ctttccctac acgacgctct tccgatcttt     60
ca                                                                    62

<210> SEQ ID NO 276
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 276
tgaaagatcg aagagcgtc gtgtagggaa agagtgtaga tctcggtgg                  49

<210> SEQ ID NO 277
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 277
aatgatacgg cgaccaccga gatctacact ctttccctac acgacgctct tccgatct       58

<210> SEQ ID NO 278
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 278
agatcggaag agcgtcgtgt agggaaagag tgtagatctc ggtgg                     45

<210> SEQ ID NO 279
<211> LENGTH: 15
<212> TYPE: DNA
<213> ORGANISM: Artificial Sequence
```

```
<220> FEATURE:
<223> OTHER INFORMATION: Synthetic Oligonucleotide

<400> SEQUENCE: 279
gacggcatac gagat                                              15

<210> SEQ ID NO 280
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 280
aacaatctcg tatgccgtct tctgcttg                                28

<210> SEQ ID NO 281
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 281
tcttatctcg tatgccgtct tctgcttg                                28

<210> SEQ ID NO 282
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 282
agagatctcg tatgccgtct tctgcttg                                28

<210> SEQ ID NO 283
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 283
ttgtatctcg tatgccgtct tctgcttg                                28

<210> SEQ ID NO 284
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 284
caagcagaag acggcatacg agattgtgtt ctcggcaggt                   40

<210> SEQ ID NO 285
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 285
caagcagaag acggcatacg agatagaaga ctcggcaggt                   40
```

<210> SEQ ID NO 286
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 286
caagcagaag acggcatacg agatttctct ctcggcaggt                40

<210> SEQ ID NO 287
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 287
caagcagaag acggcatacg agatacacaa ctcggcaggt                40

<210> SEQ ID NO 288
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 288
aatgatacgg cgaccaccga                                      20

<210> SEQ ID NO 289
<211> LENGTH: 82
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (59)..(62)
<223> OTHER INFORMATION: n is a, c, g, or t

<400> SEQUENCE: 289
aatgatacgg cgaccaccga gatctacact ctttccctac acgacgctct tccgatctnn    60
nnacctacct gccgagaaca ca                                             82

<210> SEQ ID NO 290
<211> LENGTH: 82
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (59)..(62)
<223> OTHER INFORMATION: n is a, c, g, or t

<400> SEQUENCE: 290
aatgatacgg cgaccaccga gatctacact ctttccctac acgacgctct tccgatctnn    60
nnacctacct gccgagtctt ct                                             82

<210> SEQ ID NO 291
<211> LENGTH: 82
<212> TYPE: DNA
<213> ORGANISM: Artificial Sequence
<220> FEATURE:
<223> OTHER INFORMATION: Synthetic Oligonucleotide

```
<220> FEATURE:
<221> NAME/KEY: misc_feature
<222> LOCATION: (59)..(62)
<223> OTHER INFORMATION: n is a, c, g, or t

<400> SEQUENCE: 291
aatgatacgg cgaccaccga gatctacact ctttccctac acgacgctct tccgatctnn    60
nnacctacct gccgagagag aa                                              82

<210> SEQ ID NO 292
<211> LENGTH: 82
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (59)..(62)
<223> OTHER INFORMATION: n is a, c, g, or t

<400> SEQUENCE: 292
aatgatacgg cgaccaccga gatctacact ctttccctac acgacgctct tccgatctnn    60
nnacctacct gccgagttgt gt                                              82

<210> SEQ ID NO 293
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 293
caagcagaag acggcatacg agat                                            24

<210> SEQ ID NO 294
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 294
acactctttc cctacacgac gctcttccga tctcaagtct agcaagcagg cca            53

<210> SEQ ID NO 295
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 295
acactctttc cctacacgac gctcttccga tctcaggcac tgagtgggaa agt            53

<210> SEQ ID NO 296
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 296
acactctttc cctacacgac gctcttccga tcttaacccc aagtcagcaa gca            53

<210> SEQ ID NO 297
```

```
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 297
acactctttc cctacacgac gctcttccga tctttgctgg tcaatacect ggc         53

<210> SEQ ID NO 298
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 298
acactctttc cctacacgac gctcttccga tcttgagtac ccctgaaatg ggc         53

<210> SEQ ID NO 299
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 299
acactctttc cctacacgac gctcttccga tcttcgctac caatcagggc ttt         53

<210> SEQ ID NO 300
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 300
acactctttc cctacacgac gctcttccga tctccattgc cacttgtttg cat         53

<210> SEQ ID NO 301
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 301
acactctttc cctacacgac gctcttccga tctcctaccc ccacaacttt gct         53

<210> SEQ ID NO 302
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 302
acactctttc cctacacgac gctcttccga tctgtgtaca tccagtgcac cca         53

<210> SEQ ID NO 303
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 303
```

```
acactctttc cctacacgac gctcttccga tcttcggaaa ggactttgaa tacttgt      57
```

<210> SEQ ID NO 304
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 304

```
acactctttc cctacacgac gctcttccga tctcggccca agacctcatt cac          53
```

<210> SEQ ID NO 305
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 305

```
acactctttc cctacacgac gctcttccga tctgtcctct ctggggcaga agt          53
```

<210> SEQ ID NO 306
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 306

```
acactctttc cctacacgac gctcttccga tctagctgag tcatgagttg tctcc        55
```

<210> SEQ ID NO 307
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 307

```
acactctttc cctacacgac gctcttccga tctctgccag cttctcacac cat          53
```

<210> SEQ ID NO 308
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 308

```
acactctttc cctacacgac gctcttccga tctctgaagg acaaaggcgg gaa          53
```

<210> SEQ ID NO 309
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 309

```
acactctttc cctacacgac gctcttccga tctaaggtgc taaaggctcc acg          53
```

<210> SEQ ID NO 310
<211> LENGTH: 53
<212> TYPE: DNA

```
<213> ORGANISM: Artificial Sequence
<220> FEATURE:
<223> OTHER INFORMATION: Synthetic Oligonucleotide

<400> SEQUENCE: 310
acactctttc cctacacgac gctcttccga tctgaccatt ggtgagccca gag          53

<210> SEQ ID NO 311
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 311
acactctttc cctacacgac gctcttccga tcttttttcg ggcaactgct cac          53

<210> SEQ ID NO 312
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 312
acactctttc cctacacgac gctcttccga tctgcaagcc ttctctcctc aga          53

<210> SEQ ID NO 313
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 313
acactctttc cctacacgac gctcttccga tctacacaaa cttccctgag accc         54

<210> SEQ ID NO 314
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 314
acactctttc cctacacgac gctcttccga tcttgagtta gccctgctgt tca          53

<210> SEQ ID NO 315
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 315
acactctttc cctacacgac gctcttccga tcttgaagag cttcactgag tagga        55

<210> SEQ ID NO 316
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 316
acactctttc cctacacgac gctcttccga tcttcccctt acagccaatt tcgt         54
```

<210> SEQ ID NO 317
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 317
acactctttc cctacacgac gctcttccga tcttgctgat gaaatgcaat taagaggt      58

<210> SEQ ID NO 318
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 318
acactctttc cctacacgac gctcttccga tctggtccct gcaagccagt atg      53

<210> SEQ ID NO 319
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 319
acactctttc cctacacgac gctcttccga tctatcaaag ccttgtatca cagtt      55

<210> SEQ ID NO 320
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 320
acactctttc cctacacgac gctcttccga tctcccaaat aatgcaggag ccaa      54

<210> SEQ ID NO 321
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 321
acactctttc cctacacgac gctcttccga tctctgcctt tagtgggaca gactt      55

<210> SEQ ID NO 322
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 322
acactctttc cctacacgac gctcttccga tctagtaacc ctagtagccc tcca      54

<210> SEQ ID NO 323
<211> LENGTH: 54
<212> TYPE: DNA
<213> ORGANISM: Artificial Sequence
<220> FEATURE:

<223> OTHER INFORMATION: Synthetic Oligonucleotide

<400> SEQUENCE: 323
acactctttc cctacacgac gctcttccga tctcattgca gtgagccgag attg     54

<210> SEQ ID NO 324
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 324
acactctttc cctacacgac gctcttccga tcttggcaaa gttcacttcc atgt     54

<210> SEQ ID NO 325
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 325
acactctttc cctacacgac gctcttccga tcttgctctg tgatgtctgc cac      53

<210> SEQ ID NO 326
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 326
acactctttc cctacacgac gctcttccga tcttgtgtag gattgtgaac cagca    55

<210> SEQ ID NO 327
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 327
acactctttc cctacacgac gctcttccga tcttcccagc ccagcatttt tct      53

<210> SEQ ID NO 328
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 328
acactctttc cctacacgac gctcttccga tctaggttgc tttgtgcaca gtc      53

<210> SEQ ID NO 329
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 329
acactctttc cctacacgac gctcttccga tctcctggct tgggatgttg gaa      53

```
<210> SEQ ID NO 330
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 330
acactctttc cctacacgac gctcttccga tctttgccca aggtcatact gct        53

<210> SEQ ID NO 331
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 331
acactctttc cctacacgac gctcttccga tctacccact aggtagccat aatcca     56

<210> SEQ ID NO 332
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 332
acactctttc cctacacgac gctcttccga tctcggtcat gtcgcttgga aga        53

<210> SEQ ID NO 333
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 333
acactctttc cctacacgac gctcttccga tctttggccc atattgcttt atgctg     56

<210> SEQ ID NO 334
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 334
acactctttc cctacacgac gctcttccga tctattaggg gttggctgca tga        53

<210> SEQ ID NO 335
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 335
acactctttc cctacacgac gctcttccga tctccaagac gtgttgcatg ctg        53

<210> SEQ ID NO 336
<211> LENGTH: 57
<212> TYPE: DNA
<213> ORGANISM: Artificial Sequence
<220> FEATURE:
<223> OTHER INFORMATION: Synthetic Oligonucleotide
```

<400> SEQUENCE: 336
acactctttc cctacacgac gctcttccga tcttgggagg tgataaattc cctaaat    57

<210> SEQ ID NO 337
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 337
acactctttc cctacacgac gctcttccga tctccagaga caaaggtggg gag    53

<210> SEQ ID NO 338
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 338
acactctttc cctacacgac gctcttccga tcttcataca gaagagcaaa gtacca    56

<210> SEQ ID NO 339
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 339
acactctttc cctacacgac gctcttccga tctcaaagag gggtatcggg agc    53

<210> SEQ ID NO 340
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 340
acactctttc cctacacgac gctcttccga tctaaatgga agaaccaagt agatgaa    57

<210> SEQ ID NO 341
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 341
acactctttc cctacacgac gctcttccga tcttttttggt tgacagatgg ccaca    55

<210> SEQ ID NO 342
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 342
acactctttc cctacacgac gctcttccga tcttcttact tgtgtgattt tagaacaa    58

<210> SEQ ID NO 343
<211> LENGTH: 53

```
<212> TYPE: DNA
<213> ORGANISM: Artificial Sequence
<220> FEATURE:
<223> OTHER INFORMATION: Synthetic Oligonucleotide

<400> SEQUENCE: 343
acactctttc cctacacgac gctcttccga tctgatggtt catgcagagg gct        53

<210> SEQ ID NO 344
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 344
acactctttc cctacacgac gctcttccga tctgctggtc tttcctgagc tgt        53

<210> SEQ ID NO 345
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 345
acactctttc cctacacgac gctcttccga tctctccatc agatacctgt accca      55

<210> SEQ ID NO 346
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 346
acactctttc cctacacgac gctcttccga tctgggaaaa cactctctct ctgct      55

<210> SEQ ID NO 347
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 347
acactctttc cctacacgac gctcttccga tctggaggcc acgacacaca ata        53

<210> SEQ ID NO 348
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 348
gtgactggag ttcagacgtg tgctcttccg atctcacagg gtggctcttc agtg       54

<210> SEQ ID NO 349
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 349
```
gtgactggag ttcagacgtg tgctcttccg atcttgcaca tgtttccaca gggt          54

<210> SEQ ID NO 350
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 350
gtgactggag ttcagacgtg tgctcttccg atctagtgtt tccaggagcg gttt          54

<210> SEQ ID NO 351
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 351
gtgactggag ttcagacgtg tgctcttccg atctaagcct caggcacaac tctg          54

<210> SEQ ID NO 352
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 352
gtgactggag ttcagacgtg tgctcttccg atcttagggg aggggcaaag aca           53

<210> SEQ ID NO 353
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 353
gtgactggag ttcagacgtg tgctcttccg atctgggaac agtggtatgc tggt          54

<210> SEQ ID NO 354
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 354
gtgactggag ttcagacgtg tgctcttccg atctagtgtg gacactgaca aggaa         55

<210> SEQ ID NO 355
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 355
gtgactggag ttcagacgtg tgctcttccg atcttcactg cctgggtgct ttag          54

<210> SEQ ID NO 356
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 356
gtgactggag ttcagacgtg tgctcttccg atcttacccc agcctccagc ttta    54

<210> SEQ ID NO 357
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 357
gtgactggag ttcagacgtg tgctcttccg atcttgacta ctggggagcg atga    54

<210> SEQ ID NO 358
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 358
gtgactggag ttcagacgtg tgctcttccg atctaggctg ttatgcagga aaggaa    56

<210> SEQ ID NO 359
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 359
gtgactggag ttcagacgtg tgctcttccg atctgcggtt gaggtggatg gaag    54

<210> SEQ ID NO 360
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 360
gtgactggag ttcagacgtg tgctcttccg atctggcagc atcccttaca tcct    54

<210> SEQ ID NO 361
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 361
gtgactggag ttcagacgtg tgctcttccg atctagaaaa agcttcccca gaaagga    57

<210> SEQ ID NO 362
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 362
gtgactggag ttcagacgtg tgctcttccg atctctgcac caacctctac gtcc    54

<210> SEQ ID NO 363
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 363
gtgactggag ttcagacgtg tgctcttccg atctctggag agggcatagt tggc        54

<210> SEQ ID NO 364
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 364
gtgactggag ttcagacgtg tgctcttccg atcttggaag gctctttgtg ggtt        54

<210> SEQ ID NO 365
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 365
gtgactggag ttcagacgtg tgctcttccg atctttccta gcgggaactg gaaa        54

<210> SEQ ID NO 366
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 366
gtgactggag ttcagacgtg tgctcttccg atctaggcta atggggtagg ggat        54

<210> SEQ ID NO 367
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 367
gtgactggag ttcagacgtg tgctcttccg atcttgtcca tgttggctga ggtg        54

<210> SEQ ID NO 368
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 368
gtgactggag ttcagacgtg tgctcttccg atctcaggcc aaccttgaca actt        54

<210> SEQ ID NO 369
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 369
gtgactggag ttcagacgtg tgctcttccg atctagcagg ccaaagatgt ctcc    54

<210> SEQ ID NO 370
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 370
gtgactggag ttcagacgtg tgctcttccg atcttctgct cttgaggtta tttgtcc    57

<210> SEQ ID NO 371
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 371
gtgactggag ttcagacgtg tgctcttccg atctgggacc aatttgctac tcatgg    56

<210> SEQ ID NO 372
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 372
gtgactggag ttcagacgtg tgctcttccg atcttggagg ctgtaaacgt cctg    54

<210> SEQ ID NO 373
<211> LENGTH: 59
<212> TYPE: DNA
<213> ORGANISM: Artificial Sequence
<220> FEATURE:
<223> OTHER INFORMATION: Synthetic Oligonucleotide

<400> SEQUENCE: 373
gtgactggag ttcagacgtg tgctcttccg atcttgctat gatttgctga attactcct    59

<210> SEQ ID NO 374
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 374
gtgactggag ttcagacgtg tgctcttccg atctgcaatt ttgcagacca ccatc    55

<210> SEQ ID NO 375
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 375
gtgactggag ttcagacgtg tgctcttccg atctggcagc ttgcaacctt cttg    54

<210> SEQ ID NO 376

```
<210> SEQ ID NO 376
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 376
gtgactggag ttcagacgtg tgctcttccg atcttcatga gagtttcccc aaca          54

<210> SEQ ID NO 377
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 377
gtgactggag ttcagacgtg tgctcttccg atctacttga gggggaaaaa gtttctta      58

<210> SEQ ID NO 378
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 378
gtgactggag ttcagacgtg tgctcttccg atcttggtcc ctgtctgtca ttgg          54

<210> SEQ ID NO 379
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 379
gtgactggag ttcagacgtg tgctcttccg atctaagcga gtgactgtct ggga          54

<210> SEQ ID NO 380
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 380
gtgactggag ttcagacgtg tgctcttccg atctcatggg tgggacacgt agtt          54

<210> SEQ ID NO 381
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 381
gtgactggag ttcagacgtg tgctcttccg atctggcttt cctggacacc ctatc         55

<210> SEQ ID NO 382
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 382
```
gtgactggag ttcagacgtg tgctcttccg atctagagcg agggagcgat gta     53

<210> SEQ ID NO 383
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 383
gtgactggag ttcagacgtg tgctcttccg atctttgtgg accactgctt agtgc     55

<210> SEQ ID NO 384
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 384
gtgactggag ttcagacgtg tgctcttccg atctcaacta ccctgaggcc acc     53

<210> SEQ ID NO 385
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 385
gtgactggag ttcagacgtg tgctcttccg atctggtcag cactcctcag cttt     54

<210> SEQ ID NO 386
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 386
gtgactggag ttcagacgtg tgctcttccg atcttggagg atgcatgcca catt     54

<210> SEQ ID NO 387
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 387
gtgactggag ttcagacgtg tgctcttccg atctcccagc tctttgacc cttc     54

<210> SEQ ID NO 388
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 388
gtgactggag ttcagacgtg tgctcttccg atctcccaca ccaggctgta agg     53

<210> SEQ ID NO 389
<211> LENGTH: 58
<212> TYPE: DNA

```
<213> ORGANISM: Artificial Sequence
<220> FEATURE:
<223> OTHER INFORMATION: Synthetic Oligonucleotide

<400> SEQUENCE: 389
gtgactggag ttcagacgtg tgctcttccg atcttagata tatgggtgtg tctgtacg        58

<210> SEQ ID NO 390
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 390
gtgactggag ttcagacgtg tgctcttccg atctttccaa agtggctgaa ccat            54

<210> SEQ ID NO 391
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 391
gtgactggag ttcagacgtg tgctcttccg atctcccaca gggctgatgt ttca            54

<210> SEQ ID NO 392
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 392
gtgactggag ttcagacgtg tgctcttccg atctttgtaa tgcaacctct gtcatgc         57

<210> SEQ ID NO 393
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 393
gtgactggag ttcagacgtg tgctcttccg atctccagct ccagcaatcc atga            54

<210> SEQ ID NO 394
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 394
gtgactggag ttcagacgtg tgctcttccg atcttttggg aaagatagcc ctgga           55

<210> SEQ ID NO 395
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 395
gtgactggag ttcagacgtg tgctcttccg atctcaatga aacagcgggg aggt            54
```

```
<210> SEQ ID NO 396
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 396
gtgactggag ttcagacgtg tgctcttccg atctacaatc acgtgtcctt cact         54

<210> SEQ ID NO 397
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 397
gtgactggag ttcagacgtg tgctcttccg atctcagatc cctcctgggc aatg         54

<210> SEQ ID NO 398
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 398
gtgactggag ttcagacgtg tgctcttccg atctgtcagg aggcaaggag gaac         54

<210> SEQ ID NO 399
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 399
gtgactggag ttcagacgtg tgctcttccg atctacttcc ttccttttga gaccaagt    58

<210> SEQ ID NO 400
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 400
gtgactggag ttcagacgtg tgctcttccg atctgcggca gattcctggt gatt         54

<210> SEQ ID NO 401
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 401
gtgactggag ttcagacgtg tgctcttccg atctggtcac catcagcaca gtca         54

<210> SEQ ID NO 402
<211> LENGTH: 56
<212> TYPE: DNA
<213> ORGANISM: Artificial Sequence
<220> FEATURE:
```

<223> OTHER INFORMATION: Synthetic Oligonucleotide

<400> SEQUENCE: 402
caagcagaag acggcatacg agatatatca gtgtgactgg agttcagacg tgtgct        56

<210> SEQ ID NO 403
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 403
caagcagaag acggcatacg agattttcac cggtgactgg agttcagacg tgtgct        56

<210> SEQ ID NO 404
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 404
caagcagaag acggcatacg agatccactc atgtgactgg agttcagacg tgtgct        56

<210> SEQ ID NO 405
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 405
caagcagaag acggcatacg agattacgta cggtgactgg agttcagacg tgtgct        56

<210> SEQ ID NO 406
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 406
caagcagaag acggcatacg agatcgaaac tcgtgactgg agttcagacg tgtgct        56

<210> SEQ ID NO 407
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 407
caagcagaag acggcatacg agatatcagt atgtgactgg agttcagacg tgtgct        56

<210> SEQ ID NO 408
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 408
aatgatacgg cgaccaccga gatctacaca ttactcgaca ctctttccct acacgac       57

```
<210> SEQ ID NO 409
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 409
aatgatacgg cgaccaccga gatctacact ccggagaaca ctctttccct acacgac        57

<210> SEQ ID NO 410
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 410
aatgatacgg cgaccaccga gatctacacc gctcattaca ctctttccct acacgac        57
```

METHODS FOR IDENTIFYING A TARGET SITE OF A CAS9 NUCLEASE

RELATED APPLICATION

This application is a continuation of and claims priority under 35 U.S.C. § 120 to U.S. application Ser. No. 14/320,370, filed Jun. 30, 2014, which claims priority under 35 U.S.C. § 119(e) to U.S. provisional patent application, U.S. Ser. No. 61/864,289, filed Aug. 9, 2013, each of which is incorporated herein by reference.

GOVERNMENT SUPPORT

This invention was made with Government support under grant numbers HR0011-11-2-0003 and N66001-12-C-4207, awarded by the Department of Defense. The Government has certain rights in the invention.

BACKGROUND OF THE INVENTION

Site-specific endonucleases theoretically allow for the targeted manipulation of a single site within a genome and are useful in the context of gene targeting as well as for therapeutic applications. In a variety of organisms, including mammals, site-specific endonucleases have been used for genome engineering by stimulating either non-homologous end joining or homologous recombination. In addition to providing powerful research tools, site-specific nucleases also have potential as gene therapy agents, and two site-specific endonucleases have recently entered clinical trials: one, CCR5-2246, targeting a human CCR-5 allele as part of an anti-HIV therapeutic approach (NCT00842634, NCT01044654, NCT01252641), and the other one, VF24684, targeting the human VEGF-A promoter as part of an anti-cancer therapeutic approach (NCT01082926).

Specific cleavage of the intended nuclease target site without or with only minimal off-target activity is a prerequisite for clinical applications of site-specific endonuclease, and also for high-efficiency genomic manipulations in basic research applications, as imperfect specificity of engineered site-specific binding domains has been linked to cellular toxicity and undesired alterations of genomic loci other than the intended target. Most nucleases available today, however, exhibit significant off-target activity, and thus may not be suitable for clinical applications. Technology for evaluating nuclease specificity and for engineering nucleases with improved specificity are therefore needed.

SUMMARY OF THE INVENTION

Some aspects of this disclosure are based on the recognition that the reported toxicity of some engineered site-specific endonucleases is based on off-target DNA cleavage, rather than on off-target binding alone. Some aspects of this disclosure provide strategies, compositions, systems, and methods to evaluate and characterize the sequence specificity of site-specific nucleases, for example, RNA-programmable endonucleases, such as Cas9 endonucleases, zinc finger nucleases (ZNFs), homing endonucleases, or transcriptional activator-like element nucleases (TALENs).

The strategies, methods, and reagents of the present disclosure represent, in some aspects, an improvement over previous methods for assaying nuclease specificity. For example, some previously reported methods for determining nuclease target site specificity profiles by screening libraries of nucleic acid molecules comprising candidate target sites relied on a "two-cut" in vitro selection method which requires indirect reconstruction of target sites from sequences of two half-sites resulting from two adjacent cuts of the nuclease of a library member nucleic acid (see e.g., PCT Application WO 2013/066438; and Pattanayak, V., Ramirez, C. L., Joung, J. K. & Liu, D. R. Revealing off-target cleavage specificities of zinc-finger nucleases by in vitro selection. *Nature methods* 8, 765-770 (2011), the entire contents of each of which are incorporated herein by reference). In contrast to such "two-cut" strategies, the methods of the present disclosure utilize an optimized "one cut" screening strategy, which allows for the identification of library members that have been cut at least once by the nuclease. As explained in more detail elsewhere herein, the "one-cut" selection strategies provided herein are compatible with single end high-throughput sequencing methods and do not require computational reconstruction of cleaved target sites from cut half-sites, thus streamlining the nuclease profiling process.

Some aspects of this disclosure provide in vitro selection methods for evaluating the cleavage specificity of endonucleases and for selecting nucleases with a desired level of specificity. Such methods are useful, for example, for characterizing an endonuclease of interest and for identifying a nuclease exhibiting a desired level of specificity, for example, for identifying a highly specific endonuclease for clinical applications.

Some aspects of this disclosure provide methods of identifying suitable nuclease target sites that are sufficiently different from any other site within a genome to achieve specific cleavage by a given nuclease without any or at least minimal off-target cleavage. Such methods are useful for identifying candidate nuclease target sites that can be cleaved with high specificity on a genomic background, for example, when choosing a target site for genomic manipulation in vitro or in vivo.

Some aspects of this disclosure provide methods of evaluating, selecting, and/or designing site-specific nucleases with enhanced specificity as compared to current nucleases. For example, provided herein are methods that are useful for selecting and/or designing site-specific nucleases with minimal off-target cleavage activity, for example, by designing variant nucleases with binding domains having decreased binding affinity, by lowering the final concentration of the nuclease, by choosing target sites that differ by at least three base pairs from their closest sequence relatives in the genome, and, in the case of RNA-programmable nucleases, by selecting a guide RNA that results in the fewest off-target sites being bound and/or cut.

Compositions and kits useful in the practice of the methods described herein are also provided.

Some aspects of this disclosure provide methods for identifying a target site of a nuclease. In some embodiments, the method comprises (a) providing a nuclease that cuts a double-stranded nucleic acid target site, wherein cutting of the target site results in cut nucleic acid strands comprising a 5' phosphate moiety; (b) contacting the nuclease of (a) with a library of candidate nucleic acid molecules, wherein each nucleic acid molecule comprises a concatemer of a sequence comprising a candidate nuclease target site and a constant insert sequence, under conditions suitable for the nuclease to cut a candidate nucleic acid molecule comprising a target site of the nuclease; and (c) identifying nuclease target sites cut by the nuclease in (b) by determining the sequence of an uncut nuclease target site on the nucleic acid strand that was cut by the nuclease in step (b). In some embodiments, the nuclease creates blunt ends. In some embodiments, the nuclease creates a 5' overhang. In some embodiments, the determining of step (c) comprises ligating a first nucleic acid adapter to the 5' end of a nucleic acid strand that was cut by the nuclease in step (b) via 5'-phosphate-dependent ligation. In some embodiments, the nucleic acid adapter is provided in double-stranded form. In some embodiments, the 5'-phosphate-dependent ligation is a blunt end ligation. In some embodiments, the method comprises filling in the 5'-overhang before ligating the first nucleic acid adapter to the nucleic acid strand that was cut by the nuclease. In some embodiments, the determining of step (c) further comprises amplifying a fragment of the concatemer cut by the nuclease that comprises an uncut target site via a PCR reaction using a PCR primer that hybridizes with the adapter and a PCR primer that hybridizes with the constant insert sequence. In some embodiments, the method further comprises enriching the amplified nucleic acid molecules for molecules comprising a single uncut target sequence. In some embodiments, the step of enriching comprises a size fractionation. In some embodiments, the determining of step (c) comprises sequencing the nucleic acid strand that was cut by the nuclease in step (b), or a copy thereof obtained via PCR. In some embodiments, the library of candidate nucleic acid molecules comprises at least $10^8$, at least $10^9$, at least $10^{10}$, at least $10^{11}$, or at least $10^{12}$ different candidate nuclease cleavage sites. In some embodiments, the nuclease is a therapeutic nuclease which cuts a specific nuclease target site in a gene associated with a disease. In some embodiments, the method further comprises determining a maximum concentration of the therapeutic nuclease at which the therapeutic nuclease cuts the specific nuclease target site, and does not cut more than 10, more than 5, more than 4, more than 3, more than 2, more than 1, or no additional nuclease target sites. In some embodiments, the method further comprises administering the therapeutic nuclease to a subject in an amount effective to generate a final concentration equal or lower than the maximum concentration. In some embodiments, the nuclease is an RNA-programmable nuclease that forms a complex with an RNA molecule, and wherein the nuclease:RNA complex specifically binds a nucleic acid sequence complementary to the sequence of the RNA molecule. In some embodiments, the RNA molecule is a single-guide RNA (sgRNA). In some embodiments, the sgRNA comprises 5-50 nucleotides, 10-30 nucleotides, 15-25 nucleotides, 18-22 nucleotides, 19-21 nucleotides, e.g., 10, 11, 12, 13, 14, 15, 16, 17, 18, 19, 20, 21, 22, 23, 24, 25, 26, 27, 28, 29, or 30 nucleotides. In some embodiments, the nuclease is a Cas9 nuclease. In some embodiments, the nuclease target site comprises a [sgRNA-complementary sequence]-[protospacer adjacent motif (PAM)] structure, and the nuclease cuts the target site within the sgRNA-complementary sequence. In some embodiments, the sgRNA-complementary sequence comprises 10, 11, 12, 13, 14, 15, 16, 17, 18, 19, 20, 21, 22, 23, 24, 25, 26, 27, 28, 29, or 30 nucleotides. In some embodiments, the nuclease comprises an unspecific nucleic acid cleavage domain. In some embodiments, the nuclease comprises a FokI cleavage domain. In some embodiments, the nuclease comprises a nucleic acid cleavage domain that cleaves a target sequence upon cleavage domain dimerization. In some embodiments, the nuclease comprises a binding domain that specifically binds a nucleic acid sequence. In some embodiments, the binding domain comprises a zinc finger. In some embodiments, the binding domain comprises at least 2, at least 3, at least 4, or at least 5 zinc fingers. In some embodiments, the nuclease is a Zinc Finger Nuclease. In some embodiments, the binding domain comprises a Transcriptional Activator-Like Element. In some embodiments, the nuclease is a Transcriptional Activator-Like Element Nuclease (TALEN). In some embodiments, the nuclease is an organic compound. In some embodiments, the nuclease comprises an enediyne functional group. In some embodiments, the nuclease is an antibiotic. In some embodiments, the compound is dynemicin, neocarzinostatin, calicheamicin, esperamicin, bleomycin, or a derivative thereof. In some embodiments, the nuclease is a homing endonuclease.

Some aspects of this disclosure provide libraries of nucleic acid molecules, in which each nucleic acid molecule comprises a concatemer of a sequence comprising a candidate nuclease target site and a constant insert sequence of 10-100 nucleotides. In some embodiments, the constant insert sequence is at least 15, at least 20, at least 25, at least 30, at least 35, at least 40, at least 45, at least 50, at least 55, at least 60, at least 65, at least 70, at least 75, at least 80, or at least 95 nucleotides long. In some embodiments, the constant insert sequence is not more than 15, not more than 20, not more than 25, not more than 30, not more than 35, not more than 40, not more than 45, not more than 50, not more than 55, not more than 60, not more than 65, not more than 70, not more than 75, not more than 80, or not more than 95 nucleotides long. In some embodiments, the candidate nuclease target sites are sites that can be cleaved by an RNA-programmable nuclease, a Zinc Finger Nuclease (ZFN), a Transcription Activator-Like Effector Nuclease (TALEN), a homing endonuclease, an organic compound nuclease, or an enediyne antibiotic (e.g., dynemicin, neocarzinostatin, calicheamicin, esperamicin, bleomycin). In some embodiments, the candidate nuclease target site can be cleaved by a Cas9 nuclease. In some embodiments, the library comprises at least $10^5$, at least $10^6$, at least $10^7$, at least $10^8$, at least $10^9$, at least $10^{10}$, at least $10^{11}$, or at least $10^{12}$ different candidate nuclease target sites. In some embodiments, the library comprises nucleic acid molecules of a molecular weight of at least 0.5 kDa, at least 1 kDa, at least 2 kDa, at least 3 kDa, at least 4 kDa, at least 5 kDa, at least 6 kDa, at least 7 kDa, at least 8 kDa, at least 9 kDa, at least 10 kDa, at least 12 kDa, or at least 15 kDa. In some embodiments, the library comprises candidate nuclease target sites that are variations of a known target site of a nuclease of interest. In some embodiments, the variations of a known nuclease target site comprise 10 or fewer, 9 or fewer, 8 or fewer, 7 or fewer, 6 or fewer, 5 or fewer, 4 or fewer, 3 or fewer, or 2 or fewer mutations as compared to a known nuclease target site. In some embodiments, the variations differ from the known target site of the nuclease of interest by more than 5%, more than 10%, more than 15%, more than 20%, more than 25%, or more than 30% on average, distributed binomially. In some embodiments, the variations differ from the known target site by no more than 10%, no more than 15%, no more than 20%, no more than 25%, nor more than 30%, no more than 40%, or no more than 50% on average, distributed binomially. In some embodiments, the nuclease of interest is a Cas9 nuclease, a zinc finger nuclease, a TALEN, a homing endonuclease, an organic compound nuclease, or an enediyne antibiotic (e.g., dynemicin, neocarzinostatin, calicheamicin, esperamicin, bleomycin). In some embodiments, the candidate nuclease target sites are Cas9 nuclease target sites that comprise a [sgRNA-complementary sequence]-[PAM] structure, wherein the sgRNA-complementary sequence comprises 10, 11, 12, 13, 14, 15, 16, 17, 18, 19, 20, 21, 22, 23, 24, 25, 26, 27, 28, 29, or 30 nucleotides.

Some aspects of this disclosure provide methods for selecting a nuclease that specifically cuts a consensus target site from a plurality of nucleases. In some embodiments, the method comprises (a) providing a plurality of candidate nucleases that cut the same consensus sequence; (b) for each of the candidate nucleases of step (a), identifying a nuclease target site cleaved by the candidate nuclease that differ from the consensus target site using a method provided herein; (c) selecting a nuclease based on the nuclease target site(s) identified in step (b). In some embodiments, the nuclease selected in step (c) is the nuclease that cleaves the consensus target site with the highest specificity. In some embodiments, the nuclease that cleaves the consensus target site with the highest specificity is the candidate nuclease that cleaves the lowest number of target sites that differ from the consensus site. In some embodiments, the candidate nuclease that cleaves the consensus target site with the highest specificity is the candidate nuclease that cleaves the lowest number of target sites that are different from the consensus site in the context of a target genome. In some embodiments, the candidate nuclease selected in step (c) is a nuclease that does not cleave any target site other than the consensus target site. In some embodiments, the candidate nuclease selected in step (c) is a nuclease that does not cleave any target site other than the consensus target site within the genome of a subject at a therapeutically effective concentration of the nuclease. In some embodiments, the method further comprises contacting a genome with the nuclease selected in step (c). In some embodiments, the genome is a vertebrate, mammalian, human, non-human primate, rodent, mouse, rat, hamster, goat, sheep, cattle, dog, cat, reptile, amphibian, fish, nematode, insect, or fly genome. In some embodiments, the genome is within a living cell. In some embodiments, the genome is within a subject. In some embodiments, the consensus target site is within an allele that is associated with a disease or disorder. In some embodiments, cleavage of the consensus target site results in treatment or prevention of a disease or disorder, e.g., amelioration or prevention of at least one sign and/or symptom of the disease or disorder. In some embodiments, cleavage of the consensus target site results in the alleviation of a sign and/or symptom of the disease or disorder. In some embodiments, cleavage of the consensus target site results in the prevention of the disease or disorder. In some embodiments, the disease is HIV/AIDS. In some embodiments, the allele is a CCR5 allele. In some embodiments, the disease is a proliferative disease. In some embodiments, the disease is cancer. In some embodiments, the allele is a VEGFA allele.

Some aspects of this disclosure provide isolated nucleases that have been selected according to a method provided herein. In some embodiments, the nuclease has been engineered to cleave a target site within a genome. In some embodiments, the nuclease is a Cas9 nuclease comprising an sgRNA that is complementary to the target site within the genome. In some embodiments, the nuclease is a Zinc Finger Nuclease (ZFN) or a Transcription Activator-Like Effector Nuclease (TALEN), a homing endonuclease, or an organic compound nuclease (e.g., an enediyne, an antibiotic nuclease, dynemicin, neocarzinostatin, calicheamicin, esperamicin, bleomycin, or a derivative thereof). In some embodiments, the nuclease has been selected based on cutting no other candidate target site, not more than one candidate target site, not more than two candidate target sites, not more than three candidate target sites, not more than four candidate target sites, not more than five candidate target sites, not more than six candidate target sites, not more than seven candidate target sites, not more than eight candidate target sites, not more than eight candidate target sites, not more than nine candidate target sites, or not more than ten candidate target sites in addition to its known nuclease target site.

Some aspects of this disclosure provide kits comprising a library of nucleic acid molecules comprising candidate nuclease target sites as provided herein. Some aspects of this disclosure provide kits comprising an isolated nuclease as provided herein. In some embodiments, the nuclease is a Cas9 nuclease. In some embodiments, the kit further comprises a nucleic acid molecule comprising a target site of the isolated nuclease. In some embodiments, the kit comprises an excipient and instructions for contacting the nuclease with the excipient to generate a composition suitable for contacting a nucleic acid with the nuclease. In some embodiments, the composition is suitable for contacting a nucleic acid within a genome. In some embodiments, the composition is suitable for contacting a nucleic acid within a cell. In some embodiments, the composition is suitable for contacting a nucleic acid within a subject. In some embodiments, the excipient is a pharmaceutically acceptable excipient.

Some aspects of this disclosure provide pharmaceutical compositions that are suitable for administration to a subject. In some embodiments, the composition comprises an isolated nuclease as provided herein. In some embodiments, the composition comprises a nucleic acid encoding such a nuclease. In some embodiments, the composition comprises a pharmaceutically acceptable excipient.

Other advantages, features, and uses of the invention will be apparent from the detailed description of certain non-limiting embodiments of the invention; the drawings, which are schematic and not intended to be drawn to scale; and the claims.

BRIEF DESCRIPTION OF THE DRAWINGS

(FIG. 1A) Cas9 complexed with a short guide RNA (sgRNA) recognizes ~20 bases of a target DNA substrate that is complementary to the sgRNA sequence and cleaves both DNA strands. The white triangles represent cleavage locations. (FIG. 1B) A modified version of our previously described in vitro selection was used to comprehensively profile Cas9 specificity. A concatemeric pre-selection DNA library in which each molecule contains one of $10^{12}$ distinct variants of a target DNA sequence (white rectangles) was generated from synthetic DNA oligonucleotides by ligation and rolling-circle amplification. This library was incubated with a Cas9:sgRNA complex of interest. Cleaved library members contain 5' phosphate groups (circles) and therefore are substrates for adapter ligation and PCR. The resulting amplicons were subjected to high-throughput DNA sequencing and computational analysis.

(FIG. 2G) Effect of Cas9:sgRNA concentration on specificity. Positional specificity changes between enzyme-limiting (200 nM DNA, 100 nM Cas9:sgRNA v2.1) and enzyme-saturating (200 nM DNA, 1000 nM Cas9:sgRNA v2.1) conditions, normalized to the maximum possible change in positional specificity, are shown for CLTA1. (FIG. 2H) Effect of sgRNA architecture on specificity. Positional specificity changes between sgRNA v1.0 and sgRNA v2.1 under enzyme-saturating conditions, normalized to the maximum possible change in positional specificity, are shown for CLTA1. See FIGS. 6-8, 25, and 26 for corresponding data for CLTA2, CLTA3, and CLTA4.

FIGS. 3A-3D. Target sites profiled in this study. (FIG. 3A) The 5' end of the sgRNA has 20 nucleotides that are complementary to the target site. The target site contains an NGG motif (PAM) adjacent to the region of RNA:DNA complementarity. (FIG. 3B) Four human clathrin gene (CLTA) target sites are shown. (FIGS. 3C, 3D) Four human clathrin gene (CLTA) target sites are shown with sgRNAs. sgRNA v1.0 is shorter than sgRNA v2.1. The PAM is shown for each site. The non-PAM end of the target site corresponds to the 5' end of the sgRNA.

(FIG. 5A) Post-selection PCR products are shown for the 12 selections performed. DNA containing 1.5 repeats were quantified for each selection and pooled in equimolar amounts before gel purification and sequencing. (FIGS. 5B-5E) Distributions of mutations are shown for pre-selection (black) and post-selection libraries (colored). The post-selection libraries are enriched for sequences with fewer mutations than the pre-selection libraries. Mutations are counted from among the 20 base pairs specified by the sgRNA and the two-base pair PAM. P-values are <0.01 for all pairwise comparisons between distributions in each panel. P-values were calculated using t-tests, assuming unequal size and unequal variance.

(FIG. 23B), CLTA3 (FIG. 23C), and CLTA4 (FIG. 24D) sgRNA v2.1. The specificity score indicates the enrichment of the PAM dinucleotide in the post-selection library relative to the pre-selection library, normalized to the maximum possible enrichment of that dinucleotide. A specificity score of +1.0 indicates that a dinucleotide is 100% enriched in the post-selection library, and a specificity score of −1.0 indicates that a dinucleotide is 100% de-enriched. GG dinucleotides were the most enriched in the post-selection libraries, and AG, GA, GC, GT, and TG show less relative de-enrichment compared to the other possible PAM dinucleotides.

DEFINITIONS

Figure 1A:
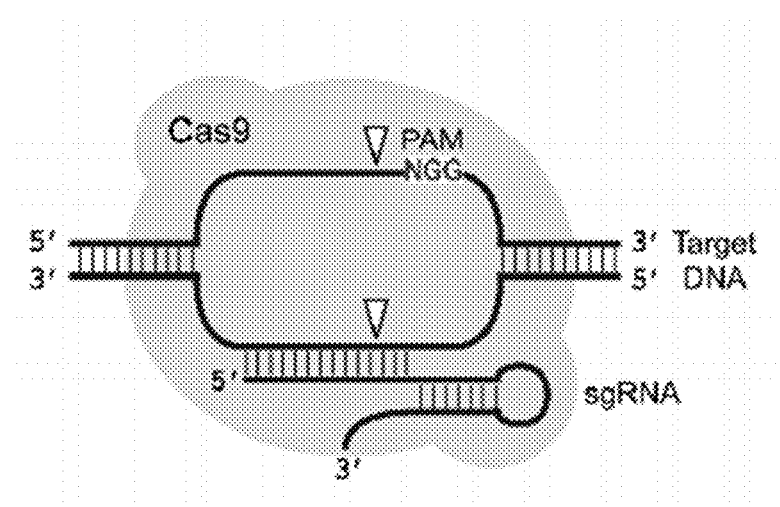
FIGS. 1A-1B. In vitro selection overview.

As used herein and in the claims, the singular forms "a," "an," and "the" include the singular and the plural reference unless the context clearly indicates otherwise. Thus, for example, a reference to "an agent" includes a single agent and a plurality of such agents.

The term "Cas9" or "Cas9 nuclease" refers to an RNA-guided nuclease comprising a Cas9 protein, or a fragment thereof. A Cas9 nuclease is also referred to sometimes as a casn 1 nuclease or a CRISPR (clustered regularly interspaced short palindromic repeat)-associated nuclease. CRISPR is an adaptive immune system that provides protection against mobile genetic elements (e.g., viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (mc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNA species. However, single guide RNAs ("sgRNA", or simply "gNRA") can be engineered so as to incorporate aspects of both the crRNA and tracrRNA into a single RNA molecule. See, e.g., Jinek M., Chylinski K., Fonfara I., Hauer M., Doudna J. A., Charpentier E. *Science* 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S.* pyogenes and S. thermophilus. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, proteins comprising Cas9 or fragments thereof proteins are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 98% identical, at least about 99% identical, at least about 99.5% identical, or at least about 99.9% to the corresponding fragment of wild type Cas9. In some embodiments, wild type Cas9 corresponds to Cas9 from Streptococcus pyogenes (NCBI Reference Sequence: NC_017053.1, SEQ ID NO:40 (nucleotide); SEQ ID NO:41 (amino acid)).

```
                                                              (SEQ ID NO: 40)
ATGGATAAGAAATACTCAATAGGCTTAGATATCGGCACAAATAGCGTCGGATGGGCGGTGATCACTGATG

ATTATAAGGTTCCGTCTAAAAAGTTCAAGGTTCTGGGAAATACAGACCGCCACAGTATCAAAAAAATCT

TATAGGGGCTCTTTTATTTGGCAGTGGAGAGACAGCGGAAGCGACTCGTCTCAAACGGACAGCTCGTAGA

AGGTATACACGTCGGAAGAATCGTATTTGTTATCTACAGGAGATTTTTTCAAATGAGATGGCGAAAGTAG

ATGATAGTTTCTTTCATCGACTTGAAGAGTCTTTTTTGGTGGAAGAAGACAAGAAGCATGAACGTCATCC

TATTTTTGGAAATATAGTAGATGAAGTTGCTTATCATGAGAAATATCCAACTATCTATCATCTGCGAAAA

AAATTGGCAGATTCTACTGATAAAGCGGATTTGCGCTTAATCTATTTGGCCTTAGCGCATATGATTAAGT

TTCGTGGTCATTTTTTGATTGAGGGAGATTTAAATCCTGATAATAGTGATGTGGACAAACTATTTATCCA

GTTGGTACAAATCTACAATCAATTATTTGAAGAAAACCCTATTAACGCAAGTAGAGTAGATGCTAAAGCG

ATTCTTTCTGCACGATTGAGTAAATCAAGACGATTAGAAAATCTCATTGCTCAGCTCCCCGGTGAGAAGA

GAAATGGCTTGTTTGGGAATCTCATTGCTTTGTCATTGGGATTGACCCCTAATTTTAAATCAAATTTTGA

TTTGGCAGAAGATGCTAAATTACAGCTTTCAAAAGATACTTACGATGATGATTTAGATAATTTATTGGCG

CAAATTGGAGATCAATATGCTGATTTGTTTTTGGCAGCTAAGAATTTATCAGATGCTATTTTACTTTCAG

ATATCCTAAGAGTAAATAGTGAAATAACTAAGGCTCCCCTATCAGCTTCAATGATTAAGCGCTACGATGA

ACATCATCAAGACTTGACTCTTTTAAAAGCTTTAGTTCGACAACAACTTCCAGAAAAGTATAAAGAAATC

TTTTTTGATCAATCAAAAAACGGATATGCAGGTTATATTGATGGGGGAGCTAGCCAAGAAGAATTTTATA

AATTTATCAAACCAATTTTAGAAAAAATGGATGGTACTGAGGAATTATTGGTGAAACTAAATCGTGAAGA

TTTGCTGCGCAAGCAACGGACCTTTGACAACGGCTCTATTCCCCATCAAATTCACTTGGGTGAGCTGCAT

GCTATTTTGAGAAGACAAGAAGACTTTTATCCATTTTTAAAAGACAATCGTGAGAAGATTGAAAAAATCT

TGACTTTTCGAATTCCTTATTATGTTGGTCCATTGGCGCGTGGCAATAGTCGTTTTGCATGGATGACTCG

GAAGTCTGAAGAAACAATTACCCCATGGAATTTTGAAGAAGTTGTCGATAAAGGTGCTTCAGCTCAATCA

TTTATTGAACGCATGACAAACTTTGATAAAAATCTTCCAAATGAAAAAGTACTACCAAAACATAGTTTGC

TTTATGAGTATTTTACGGTTTATAACGAATTGACAAAGGTCAAATATGTTACTGAGGGAATGCGAAAACC

AGCATTTCTTTCAGGTGAACAGAAGAAAGCCATTGTTGATTTACTCTTCAAAACAAATCGAAAAGTAACC

GTTAAGCAATTAAAAGAAGATTATTTCAAAAAAATAGAATGTTTTGATAGTGTTGAAATTTCAGGAGTTG

AAGATAGATTTAATGCTTCATTAGGCGCCTACCATGATTTGCTAAAAATTATTAAAGATAAAGATTTTTT

GGATAATGAAGAAAATGAAGATATCTTAGAGGATATTGTTTTAACATTGACCTTATTTGAAGATAGGGGG

ATGATTGAGGAAAGACTTAAAACATATGCTCACCTCTTTGATGATAAGGTGATGAAACAGCTTAAACGTC

GCCGTTATACTGGTTGGGGACGTTTGTCTCGAAAATTGATTAATGGTATTAGGGATAAGCAATCTGGCAA

AACAATATTAGATTTTTTGAAATCAGATGGTTTTGCCAATCGCAATTTTATGCAGCTGATCCATGATGAT

AGTTTGACATTTAAAGAAGATATTCAAAAAGCACAGGTGTCTGGACAAGGCCATAGTTTACATGAACAGA
```

-continued

```
TTGCTAACTTAGCTGGCAGTCCTGCTATTAAAAAAGGTATTTTACAGACTGTAAAAATTGTTGATGAACT

GGTCAAAGTAATGGGGCATAAGCCAGAAAATATCGTTATTGAAATGGCACGTGAAAATCAGACAACTCAA

AAGGGCCAGAAAAATTCGCGAGAGCGTATGAAACGAATCGAAGAAGGTATCAAAGAATTAGGAAGTCAGA

TTCTTAAAGAGCATCCTGTTGAAAATACTCAATTGCAAAATGAAAAGCTCTATCTCTATTATCTACAAAA

TGGAAGAGACATGTATGTGGACCAAGAATTAGATATTAATCGTTTAAGTGATTATGATGTCGATCACATT

GTTCCACAAAGTTTCATTAAAGACGATTCAATAGACAATAAGGTACTAACGCGTTCTGATAAAAATCGTG

GTAAATCGGATAACGTTCCAAGTGAAGAAGTAGTCAAAAAGATGAAAAACTATTGGAGACAACTTCTAAA

CGCCAAGTTAATCACTCAACGTAAGTTTGATAATTTAACGAAAGCTGAACGTGGAGGTTTGAGTGAACTT

GATAAAGCTGGTTTTATCAAACGCCAATTGGTTGAAACTCGCCAAATCACTAAGCATGTGGCACAAATTT

TGGATAGTCGCATGAATACTAAATACGATGAAAATGATAAACTTATTCGAGAGGTTAAAGTGATTACCTT

AAAATCTAAATTAGTTTCTGACTTCCGAAAAGATTTCCAATTCTATAAAGTACGTGAGATTAACAATTAC

CATCATGCCCATGATGCGTATCTAAATGCCGTCGTTGGAACTGCTTTGATTAAGAAATATCCAAACTTG

AATCGGAGTTTGTCTATGGTGATTATAAAGTTTATGATGTTCGTAAAATGATTGCTAAGTCTGAGCAAGA

AATAGGCAAAGCAACCGCAAAATATTTCTTTTACTCTAATATCATGAACTTCTTCAAAACAGAAATTACA

CTTGCAAATGGAGAGATTCGCAAACGCCCTCTAATCGAAACTAATGGGGAAACTGGAGAAATTGTCTGGG

ATAAAGGGCGAGATTTTGCCACAGTGCGCAAAGTATTGTCCATGCCCCAAGTCAATATTGTCAAGAAAAC

AGAAGTACAGACAGGCGGATTCTCCAAGGAGTCAATTTTACCAAAAAGAAATTCGGACAAGCTTATTGCT

CGTAAAAAAGACTGGGATCCAAAAAAATATGGTGGTTTTGATAGTCCAACGGTAGCTTATTCAGTCCTAG

TGGTTGCTAAGGTGGAAAAAGGGAAATCGAAGAAGTTAAAATCCGTTAAAGAGTTACTAGGGATCACAAT

TATGGAAAGAAGTTCCTTTGAAAAAAATCCGATTGACTTTTTAGAAGCTAAAGGATATAAGGAAGTTAAA

AAAGACTTAATCATTAAACTACCTAAATATAGTCTTTTTGAGTTAGAAAACGGTCGTAAACGGATGCTGG

CTAGTGCCGGAGAATTACAAAAAGGAAATGAGCTGGCTCTGCCAAGCAAATATGTGAATTTTTTATATTT

AGCTAGTCATTATGAAAAGTTGAAGGGTAGTCCAGAAGATAACGAACAAAAACAATTGTTTGTGGAGCAG

CATAAGCATTATTTAGATGAGATTATTGAGCAAATCAGTGAATTTTCTAAGCGTGTTATTTTAGCAGATG

CCAATTTAGATAAAGTTCTTAGTGCATATAACAAACATAGAGACAAACCAATACGTGAACAAGCAGAAAA

TATTATTCATTTATTTACGTTGACGAATCTTGGAGCTCCCGCTGCTTTTAAATATTTTGATACAACAATT

GATCGTAAACGATATACGTCTACAAAAGAAGTTTTAGATGCCACTCTTATCCATCAATCCATCACTGGTC

TTTATGAAACACGCATTGATTTGAGTCAGCTAGGAGGTGACTGA
```

(SEQ ID NO: 41)
```
MDKKYSIGLDIGTNSVGWAVITDDYKVPSKKFKVLGNTDRHSIKKNLIGALLFGSGETAEATRLKRTARR

RYTRRKNRICYLQEIFSNEMAKVDDSFFHRLEESFLVEEDKKHERHPIFGNIVDEVAYHEKYPTIYHLRK

KLADSTDKADLRLIYLALAHMIKFRGHFLIEGDLNPDNSDVDKLFIQLVQIYNQLFEENPINASRVDAKA

ILSARLSKSRRLENLIAQLPGEKRNGLFGNLIALSLGLTPNFKSNFDLAEDAKLQLSKDTYDDDLDNLLA

QIGDQYADLFLAAKNLSDAILLSDILRVNSEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNGSIPHQIHLGELH

AILRRQEDFYPFLKDNREKIEKILTFRIPYYVGPLARGNSRFAWMTRKSEETITPWNFEEVVDKGASAQS

FIERMTNFDKNLPNEKVLPKHSLLYEYFTVYNELTKVKYVTEGMRKPAFLSGEQKKAIVDLLFKTNRKVT

VKQLKEDYFKKIECFDSVEISGVEDRFNASLGAYHDLLKIIKDKDFLDNEENEDILEDIVLTLTLFEDRG

MIEERLKTYAHLFDDKVMKQLKRRRYTGWGRLSRKLINGIRDKQSGKTILDFLKSDGFANRNFMQLIHDD

SLTFKEDIQKAQVSGQGHSLHEQIANLAGSPAIKKGILQTVKIVDELVKVMGHKPENIVIEMARENQTTQ

KGQKNSRERMKRIEEGIKELGSQILKEHPVENTQLQNEKLYLYYLQNGRDMYVDQELDINRLSDYDVDHI
```

```
                                         -continued
VPQSFIKDDSIDNKVLTRSDKNRGKSDNVPSEEVVKKMKNYWRQLLNAKLITQRKFDNLTKAERGGLSEL

DKAGFIKRQLVETRQITKHVAQILDSRMNTKYDENDKLIREVKVITLKSKLVSDFRKDFQFYKVREINNY

HHAHDAYLNAVVGTALIKKYPKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQTGGFSKESILPKRNSDKLIA

RKKDWDPKKYGGFDSPTVAYSVLVVAKVEKGKSKKLKSVKELLGITIMERSSFEKNPIDFLEAKGYKEVK

KDLIIKLPKYSLFELENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGD
```

The term "concatemer," as used herein in the context of nucleic acid molecules, refers to a nucleic acid molecule that contains multiple copies of the same DNA sequences linked in a series. For example, a concatemer comprising ten copies of a specific sequence of nucleotides (e.g., $[XYZ]_{10}$), would comprise ten copies of the same specific sequence linked to each other in series, e.g., 5'-XYZXYZXYZXYZXYZX-YZXYZXYZXYZXYZ-3'. A concatemer may comprise any number of copies of the repeat unit or sequence, e.g., at least 2 copies, at least 3 copies, at least 4 copies, at least 5 copies, at least 10 copies, at least 100 copies, at least 1000 copies, etc. An example of a concatemer of a nucleic acid sequence comprising a nuclease target site and a constant insert sequence would be [(target site)-(constant insert sequence)]$_{300}$. A concatemer may be a linear nucleic acid molecule, or may be circular.

The terms "conjugating," "conjugated," and "conjugation" refer to an association of two entities, for example, of two molecules such as two proteins, two domains (e.g., a binding domain and a cleavage domain), or a protein and an agent, e.g., a protein binding domain and a small molecule. In some aspects, the association is between a protein (e.g., RNA-programmable nuclease) and a nucleic acid (e.g., a guide RNA). The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other, e.g., a binding domain and a cleavage domain of an engineered nuclease, to form a protein fusion, the two proteins may be conjugated via a polypeptide linker, e.g., an amino acid sequence connecting the C-terminus of one protein to the N-terminus of the other protein.

The term "consensus sequence," as used herein in the context of nucleic acid sequences, refers to a calculated sequence representing the most frequent nucleotide residues found at each position in a plurality of similar sequences. Typically, a consensus sequence is determined by sequence alignment in which similar sequences are compared to each other and similar sequence motifs are calculated. In the context of nuclease target site sequences, a consensus sequence of a nuclease target site may, in some embodiments, be the sequence most frequently bound, or bound with the highest affinity, by a given nuclease. With respect to RNA-programmable nuclease (e.g., Cas9) target site sequences, the consensus sequence may, in some embodiments, be the sequence or region to which a gRNA, or a plurality of gRNAs, is expected or designed to bind, e.g., based on complementary base pairing.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. As will be appreciated by the skilled artisan, the effective amount of an agent, e.g., a nuclease, a hybrid protein, or a polynucleotide, may vary depending on various factors as, for example, on the desired biological response, the specific allele, genome, target site, cell, or tissue being targeted, and the agent being used.

The term "enediyne," as used herein, refers to a class of bacterial natural products characterized by either nine- and ten-membered rings containing two triple bonds separated by a double bond (see, e.g., K. C. Nicolaou; A. L. Smith; E. W. Yue (1993). "Chemistry and biology of natural and designed enediynes". PNAS 90 (13): 5881-5888; the entire contents of which are incorporated herein by reference). Some enediynes are capable of undergoing Bergman cyclization, and the resulting diradical, a 1,4-dehydrobenzene derivative, is capable of abstracting hydrogen atoms from the sugar backbone of DNA which results in DNA strand cleavage (see, e.g., S. Walker; R. Landovitz; W. D. Ding; G. A. Ellestad; D. Kahne (1992). "Cleavage behavior of calicheamicin gamma 1 and calicheamicin T". Proc Natl Acad Sci U.S.A. 89 (10): 4608-12; the entire contents of which are incorporated herein by reference). Their reactivity with DNA confers an antibiotic character to many enediynes, and some enediynes are clinically investigated as anticancer antibiotics. Nonlimiting examples of enediynes are dynemicin, neocarzinostatin, calicheamicin, esperamicin (see, e.g., Adrian L. Smith and K. C. Bicolaou, "The Enediyne Antibiotics" J. Med. Chem., 1996, 39 (11), pp 2103-2117; and Donald Borders, "Enediyne antibiotics as antitumor agents," Informa Healthcare; 1$^{st}$ edition (Nov. 23, 1994, ISBN-10: 0824789385; the entire contents of which are incorporated herein by reference).

The term "homing endonuclease," as used herein, refers to a type of restriction enzymes typically encoded by introns or inteins Edgell D R (February 2009). "Selfish DNA: homing endonucleases find a home". Curr Biol 19 (3): R115-R117; Jasin M (June 1996). "Genetic manipulation of genomes with rare-cutting endonucleases". Trends Genet 12 (6): 224-8; Burt A, Koufopanou V (December 2004). "Homing endonuclease genes: the rise and fall and rise again of a selfish element". Curr Opin Genet Dev 14 (6): 609-15; the entire contents of which are incorporated herein by reference. Homing endonuclease recognition sequences are long enough to occur randomly only with a very low probability (approximately once every 7×10$^{10}$ bp), and are normally found in only one instance per genome.

The term "library," as used herein in the context of nucleic acids or proteins, refers to a population of two or more different nucleic acids or proteins, respectively. For example, a library of nuclease target sites comprises at least two nucleic acid molecules comprising different nuclease target sites. In some embodiments, a library comprises at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$ different nucleic acids or proteins. In some embodiments, the members of the library may comprise randomized sequences, for example, fully or partially randomized sequences. In some embodiments, the library comprises nucleic acid molecules that are unrelated to each other, e.g., nucleic acids comprising fully randomized sequences. In other embodiments, at least some members of the library may be related, for example, they may be variants or derivatives of a particular sequence, such as a consensus target site sequence.

The term "linker," as used herein, refers to a chemical group or a molecule linking two adjacent molecules or moieties, e.g., a binding domain and a cleavage domain of a nuclease. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety.

The term "nuclease," as used herein, refers to an agent, for example a protein or a small molecule, capable of cleaving a phosphodiester bond connecting nucleotide residues in a nucleic acid molecule. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease is a RNA-guided (i.e., RNA-programmable) nuclease, which complexes with (e.g., binds with) an RNA having a sequence that complements a target site, thereby providing the sequence specificity of the nuclease. In some embodiments, a nuclease recognizes a single stranded target site, while in other embodiments, a nuclease recognizes a double-stranded target site, for example a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 3' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and also, in some cases, specifically binds to a target site, and a "cleavage domain" that catalyzes the cleavage of the phosphodiester bond within the nucleic acid backbone. In some embodiments a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be fused to create nucleases binding specific target sites, are well known to those of skill in the art. For example, zinc fingers or transcriptional activator like elements can be used as binding domains to specifically bind a desired target site, and fused or conjugated to a cleavage domain, for example, the cleavage domain of FokI, to create an engineered nuclease cleaving the target site.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject in the context of treatment of a disease or disorder. In some embodiments, a pharmaceutical composition comprises an active ingredient, e.g., a nuclease or a nucleic acid encoding a nuclease, and a pharmaceutically acceptable excipient.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA.

The term "randomized," as used herein in the context of nucleic acid sequences, refers to a sequence or residue within a sequence that has been synthesized to incorporate a mixture of free nucleotides, for example, a mixture of all four nucleotides A, T, G, and C. Randomized residues are typically represented by the letter N within a nucleotide sequence. In some embodiments, a randomized sequence or residue is fully randomized, in which case the randomized residues are synthesized by adding equal amounts of the nucleotides to be incorporated (e.g., 25% T, 25% A, 25% G, and 25% C) during the synthesis step of the respective sequence residue. In some embodiments, a randomized sequence or residue is partially randomized, in which case the randomized residues are synthesized by adding non-equal amounts of the nucleotides to be incorporated (e.g., 79% T, 7% A, 7% G, and 7% C) during the synthesis step of the respective sequence residue. Partial randomization allows for the generation of sequences that are templated on a given sequence, but have incorporated mutations at a desired frequency. For example, if a known nuclease target site is used as a synthesis template, partial randomization in which at each step the nucleotide represented at the respective residue is added to the synthesis at 79%, and the other three nucleotides are added at 7% each, will result in a mixture of partially randomized target sites being synthesized, which still represent the consensus sequence of the original target site, but which differ from the original target site at each residue with a statistical frequency of 21% for each residue so synthesized (distributed binomially). In some embodiments, a partially randomized sequence differs from the consensus sequence by more than 5%, more than 10%, more than 15%, more than 20%, more than 25%, or more than 30% on average, distributed binomially. In some embodiments, a partially randomized sequence differs from the consensus site by no more than 10%, no more than 15%, no more than 20%, no more than 25%, nor more than 30%, no more than 40%, or no more than 50% on average, distributed binomially.

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease:RNA complex. Typically, the bound RNA(s) is referred to as a guide RNA (gRNA) or a single-guide RNA (sgRNA). The gRNA/sgRNA comprises a nucleotide sequence that complements a target site, which mediates binding of the nuclease/RNA complex to said target site and providing the sequence specificity of the nuclease:RNA complex. In some embodiments, the RNA-programmable nuclease is the (CRISPR-associated system) Cas9 endonuclease, for example Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference Because RNA-programmable nucleases (e.g., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (See e.g., Cong, L. et al. Multiplex genome engineering using CRISPR/Cas systems. *Science* 339, 819-823 (2013); Mali, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M.

et al. RNA-programmed genome editing in human cells. *eLife* 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

The terms "small molecule" and "organic compound" are used interchangeably herein and refer to molecules, whether naturally-occurring or artificially created (e.g., via chemical synthesis) that have a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, organic compounds are monomeric and have a molecular weight of less than about 1500 g/mol. In certain embodiments, the molecular weight of the small molecule is less than about 1000 g/mol or less than about 500 g/mol. In certain embodiments, the small molecule is a drug, for example, a drug that has already been deemed safe and effective for use in humans or animals by the appropriate governmental agency or regulatory body. In certain embodiments, the organic molecule is known to bind and/or cleave a nucleic acid. In some embodiments, the organic compound is an enediyne. In some embodiments, the organic compound is an antibiotic drug, for example, an anticancer antibiotic such as dynemicin, neocarzinostatin, calicheamicin, esperamicin, bleomycin, or a derivative thereof.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode.

The terms "target nucleic acid," and "target genome," as used herein in the context of nucleases, refer to a nucleic acid molecule or a genome, respectively, that comprises at least one target site of a given nuclease.

The term "target site," used herein interchangeably with the term "nuclease target site," refers to a sequence within a nucleic acid molecule that is bound and cleaved by a nuclease. A target site may be single-stranded or double-stranded. In the context of nucleases that dimerize, for example, nucleases comprising a FokI DNA cleavage domain, a target sites typically comprises a left-half site (bound by one monomer of the nuclease), a right-half site (bound by the second monomer of the nuclease), and a spacer sequence between the half sites in which the cut is made. This structure ([left-half site]-[spacer sequence]-[right-half site]) is referred to herein as an LSR structure. In some embodiments, the left-half site and/or the right-half site is between 10-18 nucleotides long. In some embodiments, either or both half-sites are shorter or longer. In some embodiments, the left and right half sites comprise different nucleic acid sequences. In the context of zinc finger nucleases, target sites may, in some embodiments comprise two half-sites that are each 6-18 bp long flanking a non-specified spacer region that is 4-8 bp long. In the context of TALENs, target sites may, in some embodiments, comprise two half-sites sites that are each 10-23 bp long flanking a non-specified spacer region that is 10-30 bp long. In the context of RNA-guided (e.g., RNA-programmable) nucleases, a target site typically comprises a nucleotide sequence that is complementary to the sgRNA of the RNA-programmable nuclease, and a protospacer adjacent motif (PAM) at the 3' end adjacent to the sgRNA-complementary sequence. For the RNA-guided nuclease Cas9, the target site may be, in some embodiments, 20 base pairs plus a 3 base pair PAM (e.g., NNN, wherein N represents any nucleotide). Typically, the first nucleotide of a PAM can be any nucleotide, while the two downstream nucleotides are specified depending on the specific RNA-guided nuclease. Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to NNA-GAAW and NAAR (see, e.g., Esvelt and Wang, Molecular Systems Biology, 9:641 (2013), the entire contents of which are incorporated herein by reference). For example, the target site of an RNA-guided nuclease, such as, e.g., Cas9, may comprise the structure $[N_z]$-[PAM], where each N is, independently, any nucleotide, and z is an integer between 1 and 50. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20.

The term "Transcriptional Activator-Like Effector," (TALE) as used herein, refers to bacterial proteins comprising a DNA binding domain, which contains a highly conserved 33-34 amino acid sequence comprising a highly variable two-amino acid motif (Repeat Variable Diresidue, RVD). The RVD motif determines binding specificity to a nucleic acid sequence, and can be engineered according to methods well known to those of skill in the art to specifically bind a desired DNA sequence (see, e.g., Miller, Jeffrey; et. al. (February 2011). "A TALE nuclease architecture for efficient genome editing". *Nature Biotechnology* 29 (2): 143-8; Zhang, Feng; et. al. (February 2011). "Efficient construction of sequence-specific TAL effectors for modulating mammalian transcription". *Nature Biotechnology* 29 (2): 149-53; Geißler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Boch, Jens (February 2011). "TALEs of genome targeting". *Nature Biotechnology* 29 (2): 135-6; Boch, Jens; et. al. (December 2009). "Breaking the Code of DNA Binding Specificity of TAL-Type III Effectors". *Science* 326 (5959): 1509-12; and Moscou, Matthew J.; Adam J. Bogdanove (December 2009). "A Simple Cipher Governs DNA Recognition by TAL Effectors". *Science* 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs.

The term "Transcriptional Activator-Like Element Nuclease," (TALEN) as used herein, refers to an artificial nuclease comprising a transcriptional activator like effector DNA binding domain to a DNA cleavage domain, for example, a FokI domain. A number of modular assembly schemes for generating engineered TALE constructs have been reported (see e.g., Zhang, Feng; et. al. (February 2011). "Efficient construction of sequence-specific TAL effectors for modulating mammalian transcription". *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Bailer, J. A.; Somia, N. V. et al. (2011). "Efficient design and assembly of custom TALEN and other TAL effector-based constructs for DNA targeting". *Nucleic Acids Research*; Morbitzer, R.; Elsaesser, J.; Hausner, J.; Lahaye, T. (2011). "Assembly of custom TALE-type DNA binding domains by modular cloning". *Nucleic Acids Research*; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". *Nucleic Acids Research*; Weber, E.; Gruetzner, R.; Werner, S.; Engler, C.; Marillonnet, S. (2011). Bendahmane, Mohammed. ed. "Assembly of Designer TAL Effectors by Golden Gate Cloning". *PLoS ONE* 6 (5): e19722; the entire contents of each of which are incorporated herein by reference).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "zinc finger," as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). "Zinc fingers: a novel protein fold for nucleic acid recognition". Cold Spring Harb. Symp. Quant. Biol. 52: 473-82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different type of zinc finger motifs are known to those of skill in the art, including, but not limited to, $Cys_2His_2$, Gag knuckle, Treble clef, Zinc ribbon, $Zn_2/Cys_6$, and TAZ2 domain-like motifs (see, e.g., Krishna S S, Majumdar I, Grishin N V (January 2003). "Structural classification of zinc fingers: survey and summary". *Nucleic Acids Res.* 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo C O, Peisach E, Grant R A (2001). "Design and selection of novel cys2His2 Zinc finger proteins". *Annual Review of Biochemistry* 70: 313-340; Jamieson A C, Miller J C, Pabo C O (2003). "Drug discovery with engineered zinc-finger proteins". *Nature Reviews Drug Discovery* 2 (5): 361-368; and Liu Q, Segal D J, Ghiara J B, Barbas C F (May 1997). "Design of polydactyl zinc-finger proteins for unique addressing within complex genomes". *Proc. Natl. Acad. Sci. U.S.A.* 94 (11); the entire contents of each of which are incorporated herein by reference). Fusions between engineered zinc finger arrays and protein domains that cleave a nucleic acid can be used to generate a "zinc finger nuclease." A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

The term "zinc finger nuclease," as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to the design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway. Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo C O (May 1991). "Zinc finger-DNA recognition: crystal structure of a Zif268-DNA complex at 2.1 A". *Science* 252 (5007): 809-17, the entire contents of which are incorporated herein). In some embodiments, separate zinc fingers that each recognize a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length. Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this nonlimiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

DETAILED DESCRIPTION OF CERTAIN EMBODIMENTS OF THE INVENTION

Introduction

Site-specific nucleases are powerful tools for targeted genome modification in vitro or in vivo. Some site specific nucleases can theoretically achieve a level of specificity for a target cleavage site that would allow one to target a single unique site in a genome for cleavage without affecting any other genomic site. It has been reported that nuclease cleavage in living cells triggers a DNA repair mechanism that frequently results in a modification of the cleaved, repaired genomic sequence, for example, via homologous recombination. Accordingly, the targeted cleavage of a specific unique sequence within a genome opens up new avenues for gene targeting and gene modification in living cells, including cells that are hard to manipulate with conventional gene targeting methods, such as many human somatic or embryonic stem cells. Nuclease-mediated modification of disease-related sequences, e.g., the CCR-5 allele in HIV/AIDS patients, or of genes necessary for tumor neovascularization, can be used in the clinical context, and two site specific nucleases are currently in clinical trials.

One important aspect in the field of site-specific nuclease-mediated modification are off-target nuclease effects, e.g., the cleavage of genomic sequences that differ from the intended target sequence by one or more nucleotides. Undesired side effects of off-target cleavage range from insertion into unwanted loci during a gene targeting event to severe complications in a clinical scenario. Off-target cleavage of sequences encoding essential gene functions or tumor suppressor genes by an endonuclease administered to a subject may result in disease or even death of the subject. Accordingly, it is desirable to characterize the cleavage preferences of a nuclease before using it in the laboratory or the clinic in order to determine its efficacy and safety. Further, the characterization of nuclease cleavage properties allows for the selection of the nuclease best suited for a specific task from a group of candidate nucleases, or for the selection of evolution products obtained from a plurality of nucleases. Such a characterization of nuclease cleavage properties may also inform the de-novo design of nucleases with enhanced properties, such as enhanced specificity or efficiency.

In many scenarios where a nuclease is employed for the targeted manipulation of a nucleic acid, cleavage specificity is a crucial feature. The imperfect specificity of some engineered nuclease binding domains can lead to off-target cleavage and undesired effects both in vitro and in vivo. Current methods of evaluating site-specific nuclease specificity, including ELISA assays, microarrays, one-hybrid systems, SELEX, and its variants, and Rosetta-based computational predictions, are all premised on the assumption that the binding specificity of the nuclease is equivalent or proportionate to their cleavage specificity.

It was previously discovered that the prediction of nuclease off-target binding effects constitute an imperfect approximation of a nuclease's off-target cleavage effects that may result in undesired biological effects (see PCT Application WO 2013/066438; and Pattanayak, V., Ramirez, C. L., Joung, J. K. & Liu, D. R. Revealing off-target cleavage specificities of zinc-finger nucleases by in vitro selection. *Nature methods* 8, 765-770 (2011), the entire contents of each of which are incorporated herein by reference). This finding was consistent with the notion that the reported toxicity of some site specific DNA nucleases results from off-target DNA cleavage, rather than off-target binding alone.

The methods and reagents of the present disclosure represent, in some aspects, an improvement over previous methods and allow for an accurate evaluation of a given nuclease's target site specificity and provide strategies for the selection of suitable unique target sites and the design or selection of highly specific nucleases for the targeted cleavage of a single site in the context of a complex genome. For example, some previously reported methods for determining nuclease target site specificity profiles by screening libraries of nucleic acid molecules comprising candidate target sites relied on a "two-cut" in vitro selection method which requires indirect reconstruction of target sites from sequences of two half-sites resulting from two adjacent cuts of the nuclease of a library member nucleic acid (see e.g., Pattanayak, V. et al., *Nature Methods* 8, 765-770 (2011)). In contrast to such "two-cut" strategies, the methods of the present disclosure utilize a "one cut" screening strategy, which allows for the identification of library members that have been cut at least once by the nuclease. The "one-cut" selection strategies provided herein are compatible with single end high-throughput sequencing methods and do not require computational reconstruction of cleaved target sites from cut half-sites because they feature, in some embodiments, direct sequencing of an intact target nuclease sequence in a cut library member nucleic acid.

Additionally, the presently disclosed "one-cut" screening methods utilize concatemers of a candidate nuclease target site and constant insert region that are about 10-fold shorter than previously reported constructs used for two-cut strategies (~50 bp repeat sequence length versus ~500 bp repeat sequence length in previous reports). This difference in repeat sequence length in the concatemers of the library allows for the generation of highly complex libraries of candidate nuclease target sites, e.g., of libraries comprising $10^{12}$ different candidate nuclease target sequences. As described herein, an exemplary library of such complexity has been generated, templated on a known Cas9 nuclease target site by varying the sequence of the known target site. The exemplary library demonstrated that a greater than 10-fold coverage of all sequences with eight or fewer mutations of the known target site can be achieved using the strategies provided herein. The use of a shorter repeat sequence also allows the use of single-end sequencing, since both a cut half-site and an adjacent uncut site of the same library member are contained within a 100 nucleotide sequencing read.

The strategies, methods, libraries, and reagents provided herein can be utilized to analyze the sequence preferences and specificity of any site-specific nuclease, for example, to Zinc Finger Nucleases (ZFNs), Transcription Activator-Like Effector Nucleases (TALENs), homing endonucleases, organic compound nucleases, and enediyne antibiotics (e.g., dynemicin, neocarzinostatin, calicheamicin, esperamicin, bleomycin). Suitable nucleases in addition to the ones described herein will be apparent to those of skill in the art based on this disclosure.

Further, the methods, reagents, and strategies provided herein allow those of skill in the art to identify, design, and/or select nucleases with enhanced specificity and minimize the off-target effects of any given nuclease (e.g., site-specific nucleases such as ZFNs, and TALENS which produce cleavage products with sticky ends, as well as RNA-programmable nucleases, for example Cas9, which produce cleavage products having blunt ends). While of particular relevance to DNA and DNA-cleaving nucleases, the inventive concepts, methods, strategies, and reagents provided herein are not limited in this respect, but can be applied to any nucleic acid:nuclease pair.

Identifying Nuclease Target Sites Cleaved by a Site-Specific Nuclease

Some aspects of this disclosure provide improved methods and reagents to determine the nucleic acid target sites cleaved by any site-specific nuclease. The methods provided herein can be used for the evaluation of target site preferences and specificity of both nucleases that create blunt ends and nucleases that create sticky ends. In general, such methods comprise contacting a given nuclease with a library of target sites under conditions suitable for the nuclease to bind and cut a target site, and determining which target sites the nuclease actually cuts. A determination of a nuclease's target site profile based on actual cutting has the advantage over methods that rely on binding in that it measures a parameter more relevant for mediating undesired off-target effects of site-specific nucleases. In general, the methods provided herein comprise ligating an adapter of a known sequence to nucleic acid molecules that have been cut by a nuclease of interest via 5'-phosphate-dependent ligation. Accordingly, the methods provided herein are particularly useful for identifying target sites cut by nucleases that leave a phosphate moiety at the 5'-end of the cut nucleic acid strand when cleaving their target site. After ligating an adapter to the 5'-end of a cut nucleic acid strand, the cut strand can directly be sequenced using the adapter as a sequencing linker, or a part of the cut library member concatemer comprising an intact target site identical to the cut target site can be amplified via PCR and the amplification product can then be sequenced.

In some embodiments, the method comprises (a) providing a nuclease that cuts a double-stranded nucleic acid target site, wherein cutting of the target site results in cut nucleic acid strands comprising a 5'-phosphate moiety; (b) contacting the nuclease of (a) with a library of candidate nucleic acid molecules, wherein each nucleic acid molecule comprises a concatemer of a sequence comprising a candidate nuclease target site and a constant insert sequence, under conditions suitable for the nuclease to cut a candidate nucleic acid molecule comprising a target site of the nuclease; and (c) identifying nuclease target sites cut by the nuclease in (b) by determining the sequence of an uncut nuclease target site on the nucleic acid strand that was cut by the nuclease in step (b).

In some embodiments, the method comprises providing a nuclease and contacting the nuclease with a library of candidate nucleic acid molecules comprising candidate target sites. In some embodiments, the candidate nucleic acid molecules are double-stranded nucleic acid molecules. In some embodiments, the candidate nucleic acid molecules are DNA molecules. In some embodiments, each nucleic acid molecule in the library comprises a concatemer of a sequence comprising a candidate nuclease target site and a constant insert sequence. For example, in some embodiments, the library comprises nucleic acid molecules that comprise the structure $R_1$-[(candidate nuclease target site)-(constant insert sequence)]$_n$-$R_2$, wherein $R_1$ and $R_2$ are, independently, nucleic acid sequences that may comprise a fragment of the [(candidate nuclease target site)-(constant insert sequence)] structure, and n is an integer between 2 and y. In some embodiments, y is at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$. In some embodiments, y is less than $10^2$, less than $10^3$, less than $10^4$, less than $10^5$, less than $10^6$, less than $10^7$, less than $10^8$, less than $10^9$, less than $10^{10}$, less than $10^{11}$, less than $10^{12}$, less than $10^{13}$, less than $10^{14}$, or less than $10^{15}$ For example, in some embodiments, the candidate nucleic acid molecules of the library comprise a candidate nuclease target site of the structure [($N_Z$)-(PAM)], and, thus, the nucleic acid molecules of the library comprise the structure $R_1$-[($N_Z$)-(PAM)-(constant region)]$_x$-$R_2$, wherein $R_1$ and $R_2$ are, independently, nucleic acid sequences that may comprise a fragment of the [($N_Z$)-(PAM)-(constant region)] repeat unit; each N represents, independently, any nucleotide; Z is an integer between 1 and 50; and X is an integer between 2 and y. In some embodiments, y is at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$. In some embodiments, y is less than $10^2$, less than $10^3$, less than $10^4$, less than $10^5$, less than $10^6$, less than $10^7$, less than $10^8$, less than $10^9$, less than $10^{10}$, less than $10^{11}$, less than $10^{12}$, less than $10^{13}$, less than $10^{14}$, or less than $10^{15}$. In some embodiments, Z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, Z is 20. Each N represents, independently, any nucleotide. Accordingly, a sequence provided as $N_Z$ with $z$=2 would be NN, with each N, independently, representing A, T, G, or C. Accordingly, $N_Z$ with $z$=2 can represent AA, AT, AG, AC, TA, TT, TG, TC, GA, GT, GG, GC, CA, CT, CG, and CC.

In other embodiments, the candidate nucleic acid molecules of the library comprise a candidate nuclease target site of the structure [left-half site]-[spacer sequence]-[right-half site] ("LSR"), and, thus, the nucleic acid molecules of the library comprise the structure $R_1$-[(LSR)-(constant region)]$_x$-$R_2$, wherein $R_1$ and $R_2$ are, independently, nucleic acid sequences that may comprise a fragment of the [(LSR)-(constant region)] repeat unit, and X is an integer between 2 and y. In some embodiments, y is at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$. In some embodiments, y is less than $10^2$, less than $10^3$, less than $10^4$, less than $10^5$, less than $10^6$, less than $10^7$, less than $10^8$, less than $10^9$, less than $10^{10}$, less than $10^{11}$, less than $10^{12}$, less than $10^{13}$, less than $10^{14}$, or less than $10^{15}$. The constant region, in some embodiments, is of a length that allows for efficient self-ligation of a single repeat unit. Suitable lengths will be apparent to those of skill in the art. For example, in some embodiments, the constant region is between 5 and 100 base pairs long, for example, about 5 base pairs, about 10 base pairs, about 15 base pairs, about 20 base pairs, about 25 base pairs, about 30 base pairs, about 35 base pairs, about 40 base pairs, about 50 base pairs, about 60 base pairs, about 70 base pairs, about 80 base pairs, about 90 base pairs, or about 100 base pairs long. In some embodiments, the constant region is 16 base pairs long. In some embodiments, the nuclease cuts a double-stranded nucleic acid target site and creates blunt ends. In other embodiments, the nuclease creates a 5'-overhang. In some such embodiments, the target site comprises a [left-half site]-[spacer sequence]-[right-half site] (LSR) structure, and the nuclease cuts the target site within the spacer sequence.

In some embodiments, a nuclease cuts a double-stranded target site and creates blunt ends. In some embodiments, a nuclease cuts a double-stranded target site and creates an overhang, or sticky end, for example, a 5'-overhang. In some such embodiments, the method comprises filling in the 5'-overhangs of nucleic acid molecules produced from a nucleic acid molecule that has been cut once by the nuclease, wherein the nucleic acid molecules comprise a constant insert sequence flanked by a left or right half-site and cut spacer sequence on one side, and an uncut target site sequence on the other side, thereby creating blunt ends.

In some embodiments, the determining of step (c) comprises ligating a first nucleic acid adapter to the 5' end of a nucleic acid strand that was cut by the nuclease in step (b) via 5'-phosphate-dependent ligation. In some embodiments, the nuclease creates blunt ends. In such embodiments, an adapter can directly be ligated to the blunt ends resulting from the nuclease cut of the target site by contacting the cut library members with a double-stranded, blunt-ended adapter lacking 5' phosphorylation. In some embodiments, the nuclease creates an overhang (sticky end). In some such embodiments, an adapter may be ligated to the cut site by contacting the cut library member with an excess of adapter having a compatible sticky end. If a nuclease is used that cuts within a constant spacer sequence between variable half-sites, the sticky end can be designed to match the 5' overhang created from the spacer sequence. In embodiments, where the nuclease cuts within a variable sequence, a population of adapters having a variable overhang sequence and a constant annealed sequence (for use as a sequencing linker or PCR primer) may be used, or the 5' overhangs may be filled in to form blunt ends before adapter ligation.

In some embodiments, the determining of step (c) further comprises amplifying a fragment of the concatemer cut by the nuclease that comprises an uncut target site via PCR using a PCR primer that hybridizes with the adapter and a PCR primer that hybridizes with the constant insert sequence. Typically, the amplification of concatemers via PCR will yield amplicons comprising at least one intact candidate target site identical to the cut target sites because the target sites in each concatemer are identical. For single-direction sequencing, an enrichment of amplicons that comprise one intact target site, no more than two intact target sites, no more than three intact target sites, no more than four intact target sites, or no more than five intact target sites may be desirable. In embodiments where PCR is used for amplification of cut nucleic acid molecules, the PCR parameters can be optimized to favor the amplification of short sequences and disfavor the amplification of longer sequences, e.g., by using a short elongation time in the PCR cycle. Another possibility for enrichment of short amplicons is size fractionation, e.g., via gel electrophoresis or size exclusion chromatography. Size fractionation can be performed before and/or after amplification. Other suitable methods for enrichment of short amplicons will be apparent to those of skill in the art and the disclosure is not limited in this respect.

In some embodiments, the determining of step (c) comprises sequencing the nucleic acid strand that was cut by the nuclease in step (b), or a copy thereof obtained via amplification, e.g., by PCR. Sequencing methods are well known to those of skill in the art. The disclosure is not limited in this respect.

In some embodiments, the nuclease being profiled using the inventive system is an RNA-programmable nuclease that forms a complex with an RNA molecule, and wherein the nuclease:RNA complex specifically binds a nucleic acid sequence complementary to the sequence of the RNA molecule. In some embodiments, the RNA molecule is a single-guide RNA (sgRNA). In some embodiments, the sgRNA comprises 5-50 nucleotides, 10-30 nucleotides, 15-25 nucleotides, 18-22 nucleotides, 19-21 nucleotides, e.g., 10, 11, 12, 13, 14, 15, 16, 17, 18, 19, 20, 21, 22, 23, 24, 25, 26, 27, 28, 29, or 30 nucleotides. In some embodiments, the sgRNA comprises 5-50 nucleotides, 10-30 nucleotides, 15-25 nucleotides, 18-22 nucleotides, 19-21 nucleotides, e.g., 10, 11, 12, 13, 14, 15, 16, 17, 18, 19, 20, 21, 22, 23, 24, 25, 26, 27, 28, 29, or 30 nucleotides that are complementary to a sequence of the nuclease target site. In some embodiments, the sgRNA comprises 20 nucleotides that are complementary to the nuclease target site. In some embodiments, the nuclease is a Cas9 nuclease. In some embodiments, the nuclease target site comprises a [sgRNA-complementary sequence]-[protospacer adjacent motif (PAM)] structure, and the nuclease cuts the target site within the sgRNA-complementary sequence. In some embodiments, the sgRNA-complementary sequence comprises 5-50 nucleotides, 10-30 nucleotides, 15-25 nucleotides, 18-22 nucleotides, 19-21 nucleotides, e.g., 10, 11, 12, 13, 14, 15, 16, 17, 18, 19, 20, 21, 22, 23, 24, 25, 26, 27, 28, 29, or 30 nucleotides.

In some embodiments, the RNA-programmable nuclease is a Cas9 nuclease. The RNA-programmable Cas9 endonuclease cleaves double-stranded DNA (dsDNA) at sites adjacent to a two-base-pair PAM motif and complementary to a guide RNA sequence (sgRNA). Typically, the sgRNA sequence that is complementary to the target site sequence is about 20 nucleotides long, but shorter and longer complementary sgRNA sequences can be used as well. For example, in some embodiments, the sgRNA comprises 5-50 nucleotides, 10-30 nucleotides, 15-25 nucleotides, 18-22 nucleotides, 19-21 nucleotides, e.g., 10, 11, 12, 13, 14, 15, 16, 17, 18, 19, 20, 21, 22, 23, 24, 25, 26, 27, 28, 29, or 30 nucleotides. The Cas9 system has been used to modify genomes in multiple cell types, demonstrating its potential as a facile genome-engineering tool.

In some embodiments, the nuclease comprises an unspecific nucleic acid cleavage domain. In some embodiments, the nuclease comprises a FokI cleavage domain. In some embodiments, the nuclease comprises a nucleic acid cleavage domain that cleaves a target sequence upon cleavage domain dimerization. In some embodiments, the nuclease comprises a binding domain that specifically binds a nucleic acid sequence. In some embodiments, the binding domain comprises a zinc finger. In some embodiments, the binding domain comprises at least 2, at least 3, at least 4, or at least 5 zinc fingers. In some embodiments, the nuclease is a Zinc Finger Nuclease. In some embodiments, the binding domain comprises a Transcriptional Activator-Like Element. In some embodiments, the nuclease is a Transcriptional Activator-Like Element Nuclease (TALEN). In some embodiments, the nuclease is a homing endonuclease. In some embodiments, the nuclease is an organic compound. In some embodiments, the nuclease comprises an enediyne functional group. In some embodiments, the nuclease is an antibiotic. In some embodiments, the compound is dynemicin, neocarzinostatin, calicheamicin, esperamicin, bleomycin, or a derivative thereof.

Incubation of the nuclease with the library nucleic acids will result in cleavage of those concatemers in the library that comprise target sites that can be bound and cleaved by the nuclease. If a given nuclease cleaves a specific target site with high efficiency, a concatemer comprising target sites will be cut, e.g., once or multiple times, resulting in the generation of fragments comprising a cut target site adjacent to one or more repeat units. Depending on the structure of the library members, an exemplary cut nucleic acid molecule released from a library member concatemer by a single nuclease cleavage may, for example, be of the structure (cut target site)-(constant region)-[(target site)-(constant region)]$_x$-R$_2$. For example, in the context of an RNA-guided nuclease, an exemplary cut nucleic acid molecule released from a library member concatemer by a single nuclease cleavage may, for example, be of the structure (PAM)-(constant region)-[(N$_Z$)—(PAM)-(constant region)]$_x$-R$_2$. And in the context of a nuclease cutting an LSR structure within the spacer region, an exemplary cut nucleic acid molecule released from a library member concatemer by a single nuclease cleavage may, for example, be of the structure (cut spacer region)-(right half site)-(constant region)-[(LSR)-(constant region)]$_x$-R$_2$. Such cut fragments released from library candidate molecules can then be isolated and/or the sequence of the target site cleaved by the nuclease identified by sequencing an intact target site (e.g., an intact (N$_Z$)-(PAM) site of released repeat units. See, e.g., FIG. 1B for an illustration.

Suitable conditions for exposure of the library of nucleic acid molecules will be apparent to those of skill in the art. In some embodiments, suitable conditions do not result in denaturation of the library nucleic acids or the nuclease and allow for the nuclease to exhibit at least 50%, at least 60%, at least 70%, at least 80%, at least 90%, at least 95%, or at least 98% of its nuclease activity.

Additionally, if a given nuclease cleaves a specific target site, some cleavage products will comprise a cut half site and an intact, or uncut target site. As described herein, such products can be isolated by routine methods, and because the insert sequence, in some aspects, is less than 100 base pairs, such isolated cleavage products may be sequenced in a single read-through, allowing identification of the target site sequence without reconstructing the sequence, e.g., from cut half sites.

Any method suitable for isolation and sequencing of the repeat units can be employed to elucidate the LSR sequence cleaved by the nuclease. For example, since the length of the constant region is known, individual released repeat units can be separated based on their size from the larger uncut library nucleic acid molecules as well as from fragments of library nucleic acid molecules that comprise multiple repeat units (indicating non-efficient targeted cleavage by the nuclease). Suitable methods for separating and/or isolating nucleic acid molecules based on their size are well-known to those of skill in the art and include, for example, size fractionation methods, such as gel electrophoresis, density gradient centrifugation, and dialysis over a semi-permeable membrane with a suitable molecular cutoff value. The separated/isolated nucleic acid molecules can then be further characterized, for example, by ligating PCR and/or sequencing adapters to the cut ends and amplifying and/or sequencing the respective nucleic acids. Further, if the length of the constant region is selected to favor self-ligation of individual released repeat units, such individual released repeat units may be enriched by contacting the nuclease treated library molecules with a ligase and subsequent amplification and/or sequencing based on the circularized nature of the self-ligated individual repeat units.

In some embodiments, where a nuclease is used that generates 5'-overhangs as a result of cutting a target nucleic acid, the 5'-overhangs of the cut nucleic acid molecules are filled in. Methods for filling in 5'-overhangs are well known to those of skill in the art and include, for example, methods using DNA polymerase I Klenow fragment lacking exonuclease activity (Klenow (3'→5' exo-)). Filling in 5'-overhangs results in the overhang-templated extension of the recessed strand, which, in turn, results in blunt ends. In the case of single repeat units released from library concatemers, the resulting structure is a blunt-ended S$_2$'R-(constant region)-LS$_1$', with S$_1$' and S$_2$' comprising blunt ends. PCR and/or sequencing adapters can then be added to the ends by blunt end ligation and the respective repeat units (including S$_2$'R and LS$_1$' regions) can be sequenced. From the sequence data, the original LSR region can be deduced. Blunting of the overhangs created during the nuclease cleavage process also allows for distinguishing between target sites that were properly cut by the respective nuclease and target sites that were non-specifically cut, e.g., based on non-nuclease effects such as physical shearing. Correctly cleaved nuclease target sites can be recognized by the existence of complementary S$_2$'R and LS$_1$' regions, which comprise a duplication of the overhang nucleotides as a result of the overhang fill in while target sites that were not cleaved by the respective nuclease are unlikely to comprise overhang nucleotide duplications. In some embodiments, the method comprises identifying the nuclease target site cut by the nuclease by determining the sequence of the left-half site, the right-half-site, and/or the spacer sequence of a released individual repeat unit. Any suitable method for amplifying and/or sequencing can be used to identify the LSR sequence of the target site cleaved by the respective nuclease. Methods for amplifying and/or sequencing nucleic acids are well known to those of skill in the art and the disclosure is not limited in this respect. In the case of nucleic acids released from library concatemers that comprise a cut half site and an uncut target site (e.g., comprises at least about 1.5 repeat sequences), filling in the 5'-overhangs also provides for assurance that the nucleic acid was cleaved by the nuclease. Because the nucleic acid also comprises an intact, or uncut target site, the sequence of said site can be determined without having to reconstruct the sequence from a left-half site, right-half site, and/or spacer sequence.

Some of the methods and strategies provided herein allow for the simultaneous assessment of a plurality of candidate target sites as possible cleavage targets for any given nuclease. Accordingly, the data obtained from such methods can be used to compile a list of target sites cleaved by a given nuclease, which is also referred to herein as a target site profile. If a sequencing method is used that allows for the generation of quantitative sequencing data, it is also possible to record the relative abundance of any nuclease target site detected to be cleaved by the respective nuclease. Target sites that are cleaved more efficiently by the nuclease will be detected more frequently in the sequencing step, while target sites that are not cleaved efficiently will only rarely release an individual repeat unit from a candidate concatemer, and thus, will only generate few, if any, sequencing reads. Such quantitative sequencing data can be integrated into a target site profile to generate a ranked list of highly preferred and less preferred nuclease target sites.

The methods and strategies of nuclease target site profiling provided herein can be applied to any site-specific nuclease, including, for example, ZFNs, TALENs, homing endonucleases, and RNA-programmable nucleases, such as Cas9 nucleases. As described in more detail herein, nuclease specificity typically decreases with increasing nuclease concentration, and the methods described herein can be used to determine a concentration at which a given nuclease efficiently cuts its intended target site, but does not efficiently cut any off-target sequences. In some embodiments, a maximum concentration of a therapeutic nuclease is determined at which the therapeutic nuclease cuts its intended nuclease target site but does not cut more than 10, more than 5, more than 4, more than 3, more than 2, more than 1, or any additional sites. In some embodiments, a therapeutic nuclease is administered to a subject in an amount effective to generate a final concentration equal or lower than the maximum concentration determined as described above.

In some embodiments, the library of candidate nucleic acid molecules used in the methods provided herein comprises at least $10^8$, at least $10^9$, at least $10^{10}$, at least $10^{11}$, or at least $10^{12}$ different candidate nuclease target sites.

In some embodiments, the nuclease is a therapeutic nuclease which cuts a specific nuclease target site in a gene associated with a disease. In some embodiments, the method further comprises determining a maximum concentration of the therapeutic nuclease at which the therapeutic nuclease cuts the specific nuclease target site and does not cut more than 10, more than 5, more than 4, more than 3, more than 2, more than 1, or no additional sites. In some embodiments, the method further comprises administering the therapeutic nuclease to a subject in an amount effective to generate a final concentration equal or lower than the maximum concentration.

Nuclease Target Site Libraries

Some embodiments of this disclosure provide libraries of nucleic acid molecules for nuclease target site profiling. In some embodiments, the candidate nucleic acid molecules of the library comprise the structure $R_1\text{-}[(N_Z)\text{-}(PAM)\text{-}(\text{constant region})]_x\text{-}R_2$, wherein $R_1$ and $R_2$ are, independently, nucleic acid sequences that may comprise a fragment of the $[(N_Z)\text{-}(PAM)\text{-}(\text{constant region})]$ repeat unit; each N represents, independently, any nucleotide; Z is an integer between 1 and 50; and X is an integer between 2 and y. In some embodiments, y is at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$. In some embodiments, y is less than $10^2$, less than $10^3$, less than $10^4$, less than $10^5$, less than $10^6$, less than $10^7$, less than $10^8$, less than $10^9$, less than $10^{10}$, less than $10^{11}$, less than $10^{12}$, less than $10^{13}$, less than $10^{14}$, or less than $10^{15}$. In some embodiments, Z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, Z is 20. Each N represents, independently, any nucleotide. Accordingly, a sequence provided as $N_Z$ with $z=2$ would be NN, with each N, independently, representing A, T, G, or C. Accordingly, $N_Z$ with $z=2$ can represent AA, AT, AG, AC, TA, TT, TG, TC, GA, GT, GG, GC, CA, CT, CG, and CC.

In some embodiments, a library is provided comprising candidate nucleic acid molecules that comprise target sites with a partially randomized left-half site, a partially randomized right-half site, and/or a partially randomized spacer sequence. In some embodiments, the library is provided comprising candidate nucleic acid molecules that comprise target sites with a partially randomized left half site, a fully randomized spacer sequence, and a partially randomized right half site. In some embodiments, a library is provided comprising candidate nucleic acid molecules that comprise target sites with a partially or fully randomized sequence, wherein the target sites comprise the structure $[N_Z\text{-}(PAM)]$, for example as described herein. In some embodiments, partially randomized sites differ from the consensus site by more than 5%, more than 10%, more than 15%, more than 20%, more than 25%, or more than 30% on average, distributed binomially.

In some embodiments such a library comprises a plurality of nucleic acid molecules, each comprising a concatemer of a candidate nuclease target site and a constant insert sequence, also referred to herein as a constant region. For example, in some embodiments, the candidate nucleic acid molecules of the library comprise the structure $R_1\text{-}[(\text{sgRNA-complementary sequence})\text{-}(PAM)\text{-}(\text{constant region})]_x\text{-}R_2$, or the structure $R_1\text{-}[(LSR)\text{-}(\text{constant region})]_x\text{-}R_2$, wherein the structure in square brackets ("[ . . . ]") is referred to as a repeat unit or repeat sequence; $R_1$ and $R_2$ are, independently, nucleic acid sequences that may comprise a fragment of the repeat unit, and X is an integer between 2 and y. In some embodiments, y is at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$. In some embodiments, y is less than $10^2$, less than $10^3$, less than $10^4$, less than $10^5$, less than $10^6$, less than $10^7$, less than $10^8$, less than $10^9$, less than $10^{10}$, less than $10^{11}$, less than $10^{12}$, less than $10^{13}$, less than $10^{14}$, or less than $10^{15}$. The constant region, in some embodiments, is of a length that allows for efficient self-ligation of a single repeat unit. In some embodiments, the constant region is of a length that allows for efficient separation of single repeat units from fragments comprising two or more repeat units. In some embodiments, the constant region is of a length allows for efficient sequencing of a complete repeat unit in one sequencing read. Suitable lengths will be apparent to those of skill in the art. For example, in some embodiments, the constant region is between 5 and 100 base pairs long, for example, about 5 base pairs, about 10 base pairs, about 15 base pairs, about 20 base pairs, about 25 base pairs, about 30 base pairs, about 35 base pairs, about 40 base pairs, about 50 base pairs, about 60 base pairs, about 70 base pairs, about 80 base pairs, about 90 base pairs, or about 100 base pairs long. In some embodiments, the constant region is 1, 2, 3, 4, 5, 6, 7, 8, 9, 0, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 base pairs long.

An LSR site typically comprises a [left-half site]-[spacer sequence]-[right-half site] structure. The lengths of the half-size and the spacer sequence will depend on the specific nuclease to be evaluated. In general, the half-sites will be 6-30 nucleotides long, and preferably 10-18 nucleotides long. For example, each half site individually may be 6, 7, 8, 9, 10, 11, 12, 13, 14, 15, 16, 17, 18, 19, 20, 21, 22, 23, 24, 25, 26, 27, 28, 29, or 30 nucleotides long. In some embodiments, an LSR site may be longer than 30 nucleotides. In some embodiments, the left half site and the right half site of an LSR are of the same length. In some embodiments, the left half site and the right half site of an LSR are of different lengths. In some embodiments, the left half site and the right half site of an LSR are of different sequences. In some embodiments, a library is provided that comprises candidate nucleic acids which comprise LSRs that can be cleaved by a FokI cleavage domain, a Zinc Finger Nuclease (ZFN), a Transcription Activator-Like Effector Nuclease (TALEN), a homing endonuclease, or an organic compound (e.g., an enediyne antibiotic such as dynemicin, neocarzinostatin, calicheamicin, and esperamicinl; and bleomycin).

In some embodiments, a library of candidate nucleic acid molecules is provided that comprises at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$ different candidate nuclease target sites. In some embodiments, the candidate nucleic acid molecules of the library are concatemers produced from a secularized templates by rolling cycle amplification. In some embodiments, the library comprises nucleic acid molecules, e.g., concatemers, of a molecular weight of at least 5 kDa, at least 6 kDa, at least 7 kDa, at least 8 kDa, at least 9 kDa, at least 10 kDa, at least 12 kDa, or at least 15 kDa. In some embodiments, the molecular weight of the nucleic acid molecules within the library may be larger than 15 kDa. In some embodiments, the library comprises nucleic acid molecules within a specific size range, for example, within a range of 5-7 kDa, 5-10 kDa, 8-12 kDa, 10-15 kDa, or 12-15 kDa, or 5-10 kDa or any possible subrange. While some methods suitable for generating nucleic acid concatemers according to some aspects of this disclosure result in the generation of nucleic acid molecules of greatly different molecular weights, such mixtures of nucleic acid molecules may be size fractionated to obtain a desired size distribution. Suitable methods for enriching nucleic acid molecules of a desired size or excluding nucleic acid molecules of a desired size are well known to those of skill in the art and the disclosure is not limited in this respect.

In some embodiments, partially randomized sites differ from the consensus site by no more than 10%, no more than 15%, no more than 20%, no more than 25%, nor more than 30%, no more than 40%, or no more than 50% on average, distributed binomially. For example, in some embodiments partially randomized sites differ from the consensus site by more than 5%, but by no more than 10%; by more than 10%, but by no more than 20%; by more than 20%, but by no more than 25%; by more than 5%, but by no more than 20%, and so on. Using partially randomized nuclease target sites in the library is useful to increase the concentration of library members comprising target sites that are closely related to the consensus site, for example, that differ from the consensus sites in only one, only two, only three, only four, or only five residues. The rationale behind this is that a given nuclease, for example a given ZFN or RNA-programmable nuclease, is likely to cut its intended target site and any closely related target sites, but unlikely to cut a target sites that is vastly different from or completely unrelated to the intended target site. Accordingly, using a library comprising partially randomized target sites can be more efficient than using libraries comprising fully randomized target sites without compromising the sensitivity in detecting any off-target cleavage events for any given nuclease. Thus, the use of partially randomized libraries significantly reduces the cost and effort required to produce a library having a high likelihood of covering virtually all off-target sites of a given nuclease. In some embodiments however it may be desirable to use a fully randomized library of target sites, for example, in embodiments, where the specificity of a given nuclease is to be evaluated in the context of any possible site in a given genome.

Selection and Design of Site-Specific Nucleases

Some aspects of this disclosure provide methods and strategies for selecting and designing site-specific nucleases that allow the targeted cleavage of a single, unique sites in the context of a complex genome. In some embodiments, a method is provided that comprises providing a plurality of candidate nucleases that are designed or known to cut the same consensus sequence; profiling the target sites actually cleaved by each candidate nuclease, thus detecting any cleaved off-target sites (target sites that differ from the consensus target site); and selecting a candidate nuclease based on the off-target site(s) so identified. In some embodiments, this method is used to select the most specific nuclease from a group of candidate nucleases, for example, the nuclease that cleaves the consensus target site with the highest specificity, the nuclease that cleaves the lowest number of off-target sites, the nuclease that cleaves the lowest number of off-target sites in the context of a target genome, or a nuclease that does not cleave any target site other than the consensus target site. In some embodiments, this method is used to select a nuclease that does not cleave any off-target site in the context of the genome of a subject at concentration that is equal to or higher than a therapeutically effective concentration of the nuclease.

The methods and reagents provided herein can be used, for example, to evaluate a plurality of different nucleases targeting the same intended targets site, for example, a plurality of variations of a given site-specific nuclease, for example a given zinc finger nuclease. Accordingly, such methods may be used as the selection step in evolving or designing a novel site-specific nucleases with improved specificity.

Identifying Unique Nuclease Target Sites within a Genome

Some embodiments of this disclosure provide a method for selecting a nuclease target site within a genome. As described in more detail elsewhere herein, it was surprisingly discovered that off target sites cleaved by a given nuclease are typically highly similar to the consensus target site, e.g., differing from the consensus target site in only one, only two, only three, only four, or only five nucleotide residues. Based on this discovery, a nuclease target sites within the genome can be selected to increase the likelihood of a nuclease targeting this site not cleaving any off target sites within the genome. For example, in some embodiments, a method is provided that comprises identifying a candidate nuclease target site; and comparing the candidate nuclease target site to other sequences within the genome. Methods for comparing candidate nuclease target sites to other sequences within the genome are well known to those of skill in the art and include for example sequence alignment methods, for example, using a sequence alignment software or algorithm such as BLAST on a general purpose computer. A suitable unique nuclease target site can then be selected based on the results of the sequence comparison. In some embodiments, if the candidate nuclease target site differs from any other sequence within the genome by at least 3, at least 4, at least 5, at least 6, at least 7, at least 8, at least 9, or at least 10 nucleotides, the nuclease target site is selected as a unique site within the genome, whereas if the site does not fulfill this criteria, the site may be discarded. In some embodiments, once a site is selected based on the sequence comparison, as outlined above, a site-specific nuclease targeting the selected site is designed. For example, a zinc finger nuclease may be designed to target any selected nuclease target site by constructing a zinc finger array binding the target site, and conjugating the zinc finger array to a DNA cleavage domain. In embodiments where the DNA cleavage domain needs to dimerize in order to cleave DNA, to zinc finger arrays will be designed, each binding a half site of the nuclease target site, and each conjugated to a cleavage domain. In some embodiments, nuclease designing and/or generating is done by recombinant technology. Suitable recombinant technologies are well known to those of skill in the art, and the disclosure is not limited in this respect.

In some embodiments, a site-specific nuclease designed or generated according to aspects of this disclosure is isolated and/or purified. The methods and strategies for designing site-specific nucleases according to aspects of this disclosure can be applied to design or generate any site-specific nuclease, including, but not limited to Zinc Finger Nucleases, Transcription Activator-Like Effector Nucleases (TALENs), a homing endonuclease, an organic compound nuclease, or an enediyne antibiotic (e.g., dynemicin, neocarzinostatin, calicheamicin, esperamicin, bleomycin).

Isolated Nucleases

Some aspects of this disclosure provide isolated site-specific nucleases with enhanced specificity that are designed using the methods and strategies described herein. Some embodiments, of this disclosure provide nucleic acids encoding such nucleases. Some embodiments of this disclosure provide expression constructs comprising such encoding nucleic acids. For example, in some embodiments an isolated nuclease is provided that has been engineered to cleave a desired target site within a genome, and has been evaluated according to a method provided herein to cut less than 1, less than 2, less than 3, less than 4, less than 5, less than 6, less than 7, less than 8, less than 9 or less than 10 off-target sites at a concentration effective for the nuclease to cut its intended target site. In some embodiments an isolated nuclease is provided that has been engineered to cleave a desired unique target site that has been selected to differ from any other site within a genome by at least 3, at least 4, at least 5, at least 6, at least 7, at least 8, at least 9, or at least 10 nucleotide residues. In some embodiments, the isolated nuclease is an RNA-programmable nuclease, such as a Cas9 nuclease; a Zinc Finger Nuclease (ZFN); or a Transcription Activator-Like Effector Nuclease (TALEN), a homing endonuclease, an organic compound nuclease, or an enediyne antibiotic (e.g., dynemicin, neocarzinostatin, calicheamicin, esperamicin, bleomycin). In some embodiments, the isolated nuclease cleaves a target site within an allele that is associated with a disease or disorder. In some embodiments, the isolated nuclease cleaves a target site the cleavage of which results in treatment or prevention of a disease or disorder. In some embodiments, the disease is HIV/AIDS, or a proliferative disease. In some embodiments, the allele is a CCR5 (for treating HIV/AIDS) or a VEGFA allele (for treating a proliferative disease).

In some embodiments, the isolated nuclease is provided as part of a pharmaceutical composition. For example, some embodiments provide pharmaceutical compositions comprising a nuclease as provided herein, or a nucleic acid encoding such a nuclease, and a pharmaceutically acceptable excipient. Pharmaceutical compositions may optionally comprise one or more additional therapeutically active substances.

In some embodiments, compositions provided herein are administered to a subject, for example, to a human subject, in order to effect a targeted genomic modification within the subject. In some embodiments, cells are obtained from the subject and contacted with a nuclease or a nuclease-encoding nucleic acid ex vivo, and re-administered to the subject after the desired genomic modification has been effected or detected in the cells. Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated in its entirety herein by reference) discloses various excipients used in formulating pharmaceutical compositions and known techniques for the preparation thereof. See also PCT application PCT/US2010/055131, incorporated in its entirety herein by reference, for additional suitable methods, reagents, excipients and solvents for producing pharmaceutical compositions comprising a nuclease. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Materials and Methods

Oligonucleotides.

All oligonucleotides used in this study were purchased from Integrated DNA Technologies. Oligonucleotide sequences are listed in Table 9.

Expression and Purification of *S. pyogenes* Cas9.

*E. coli* Rosetta (DE3) cells were transformed with plasmid pMJ806[11], encoding the *S. pyogenes* cas9 gene fused to an N-terminal 6×His-tag/maltose binding protein. The resulting expression strain was inoculated in Luria-Bertani (LB) broth containing 100 μg/mL of ampicillin and 30 μg/mL of chloramphenicol at 37° C. overnight. The cells were diluted 1:100 into the same growth medium and grown at 37° C. to $OD_{600}$ ~0.6. The culture was incubated at 18° C. for 30 min, and isopropyl β-D-1-thiogalactopyranoside (IPTG) was added at 0.2 mM to induce Cas9 expression. After ~17 h, the cells were collected by centrifugation at 8,000 g and resuspended in lysis buffer (20 mM tris(hydroxymethyl)-aminomethane (Tris)-HCl, pH 8.0, 1 M KCl, 20% glycerol, 1 mM tris (2-carboxyethyl)phosphine (TCEP)). The cells were lysed by sonication (10 sec pulse-on and 30 sec pulse-off for 10 min total at 6 W output) and the soluble lysate was obtained by centrifugation at 20,000 g for 30 min. The cell lysate was incubated with nickel-nitriloacetic acid (nickel-NTA) resin (Qiagen) at 4° C. for 20 min to capture His-tagged Cas9. The resin was transferred to a 20-mL column and washed with 20 column volumes of lysis buffer. Cas9 was eluted in 20 mM Tris-HCl (pH 8), 0.1 M KCl, 20% glycerol, 1 mM TCEP, and 250 mM imidazole, and concentrated by Amicon ultra centrifugal filter (Millipore, 30-kDa molecular weight cut-off) to ~50 mg/mL. The 6×His tag and maltose-binding protein were removed by TEV protease treatment at 4° C. for 20 h and captured by a second Ni-affinity purification step. The eluent, containing Cas9, was injected into a HiTrap SP FF column (GE Healthcare) in purification buffer containing 20 mM Tris-HCl (pH 8), 0.1 M KCl, 20% glycerol, and 1 mM TCEP. Cas9 was eluted with purification buffer containing a linear KCl gradient from 0.1 M to 1 M over five column volumes. The eluted Cas9 was further purified by a HiLoad Superdex 200 column in purification buffer, snap-frozen in liquid nitrogen, and stored in aliquots at −80° C.

In Vitro RNA Transcription.

100 pmol CLTA(#) v2.1 fwd and v2.1 template rev were incubated at 95° C. and cooled at 0.1° C./s to 37° C. in NEBuffer2 (50 mM sodium chloride, 10 mM Tris-HCl, 10 mM magnesium chloride, 1 mM dithiothreitol, pH 7.9) supplemented with 10 μM dNTP mix (Bio-Rad). 10 U of Klenow Fragment (3'→5' exo⁻) (NEB) were added to the reaction mixture and a double-stranded CLTA(#) v2.1 template was obtained by overlap extension for 1 h at 37° C. 200 nM CLTA(#) v2.1 template alone or 100 nM CLTA(#) template with 100 nM T7 promoter oligo was incubated overnight at 37° C. with 0.16 U/μL of T7 RNA Polymerase (NEB) in NEB RNAPol Buffer (40 mM Tris-HCl, pH 7.9, 6 mM magnesium chloride, 10 mM dithiothreitol, 2 mM spermidine) supplemented with 1 mM rNTP mix (1 mM rATP, 1 mM rCTP, 1 mM rGTP, 1 mM rUTP). In vitro transcribed RNA was precipitated with ethanol and purified by gel electrophoresis on a Criterion 10% polyacrylamide TBE-Urea gel (Bio-Rad). Gel-purified sgRNA was precipitated with ethanol and redissolved in water.

In Vitro Library Construction.

10 pmol of CLTA(#) lib oligonucleotides were separately circularized by incubation with 100 units of CircLigase II ssDNA Ligase (Epicentre) in 1× CircLigase II Reaction Buffer (33 mM Tris-acetate, 66 mM potassium acetate, 0.5 mM dithiothreitol, pH 7.5) supplemented with 2.5 mM manganese chloride in a total reaction volume of 20 μL for 16 hours at 60° C. The reaction mixture was incubated for 10 minutes at 85° C. to inactivate the enzyme. 5 μL (5 pmol) of the crude circular single-stranded DNA were converted into the concatemeric pre-selection libraries with the illustra TempliPhi Amplification Kit (GE Healthcare) according to the manufacturer's protocol. Concatemeric pre-selection libraries were quantified with the Quant-it PicoGreen dsDNA Assay Kit (Invitrogen).

In Vitro Cleavage of On-Target and Off-Target Substrates.

Plasmid templates for PCR were constructed by ligation of annealed oligonucleotides CLTA(#) site fwd/rev into HindIII/XbaI double-digested pUC19 (NEB). On-target substrate DNAs were generated by PCR with the plasmid templates and test fwd and test rev primers, then purified with the QIAquick PCR Purification Kit (Qiagen). Off-target substrate DNAs were generated by primer extension. 100 pmol off-target (#) fwd and off-target (#) rev primers were incubated at 95° C. and cooled at 0.1° C./s to 37° C. in NEBuffer2 (50 mM sodium chloride, 10 mM Tris-HCl, 10 mM magnesium chloride, 1 mM dithiothreitol, pH 7.9) supplemented with 10 μM dNTP mix (Bio-Rad). 10 U of Klenow Fragment (3'→5' exo-) (NEB) were added to the reaction mixture and double-stranded off-target templates were obtained by overlap extension for 1 h at 37° C. followed by enzyme inactivation for 20 min at 75° C., then purified with the QIAquick PCR Purification Kit (Qiagen). 200 nM substrate DNAs were incubated with 100 nM Cas9 and 100 nM (v1.0 or v2.1) sgRNA or 1000 nM Cas9 and 1000 nM (v1.0 or v2.1) sgRNA in Cas9 cleavage buffer (200 mM HEPES, pH 7.5, 1.5 M potassium chloride, 100 mM magnesium chloride, 1 mM EDTA, 5 mM dithiothreitol) for 10 min at 37° C. On-target cleavage reactions were purified with the QIAquick PCR Purification Kit (Qiagen), and off-target cleavage reactions were purified with the QIAquick Nucleotide Removal Kit (Qiagen) before electrophoresis in a Criterion 5% polyacrylamide TBE gel (Bio-Rad).

In Vitro Selection.

200 nM concatemeric pre-selection libraries were incubated with 100 nM Cas9 and 100 nM sgRNA or 1000 nM Cas9 and 1000 nM sgRNA in Cas9 cleavage buffer (200 mM HEPES, pH 7.5, 1.5 M potassium chloride, 100 mM magnesium chloride, 1 mM EDTA, 5 mM dithiothreitol) for 10 min at 37° C. Pre-selection libraries were also separately incubated with 2 U of BspMI restriction endonuclease (NEB) in NEBuffer3 (100 mM NaCl, 50 mM Tris-HCl, 10 mM MgCl2, 1 mM dithiothreitol, pH 7.9) for 1 h at 37° C. Blunt-ended post-selection library members or sticky-ended pre-selection library members were purified with the QIAQuick PCR Purification Kit (Qiagen) and ligated to 10 pmol adapter1/2(AACA) (Cas9:v2.1 sgRNA, 100 nM), adapter1/2(TTCA) (Cas9:v2.1 sgRNA, 1000 nM), adapter1/2 (Cas9:v2.1 sgRNA, 1000 nM), or lib adapter1/CLTA(#) lib adapter 2 (pre-selection) with 1,000 U of T4 DNA Ligase (NEB) in NEB T4 DNA Ligase Reaction Buffer (50 mM Tris-HCl, pH 7.5, 10 mM magnesium chloride, 1 mM ATP, 10 mM dithiothreitol) overnight (>10 h) at room temperature. Adapter-ligated DNA was purified with the QIAquick PCR Purification Kit and PCR-amplified for 10-13 cycles with Phusion Hot Start Flex DNA Polymerase (NEB) in Buffer HF (NEB) and primers CLTA(#) sel PCR/PE2 short (post-selection) or CLTA(#) lib seq PCR/lib fwd PCR (pre-selection). Amplified DNAs were gel purified, quantified with the KAPA Library Quantification Kit-Illumina (KAPA Biosystems), and subjected to single-read sequencing on an Illumina MiSeq or Rapid Run single-read sequencing on an Illumina HiSeq 2500 (Harvard University FAS Center for Systems Biology Core facility, Cambridge, Mass.).

Selection Analysis.

Pre-selection and post-selection sequencing data were analyzed as previously described[21], with modification (Algorithms) using scripts written in C++. Raw sequence data is not shown; see Table 2 for a curated summary. Specificity scores were calculated with the formulae: positive specificity score=(frequency of base pair at position[post-selection]−frequency of base pair at position[pre-selection])/(1−frequency of base pair at position[pre-selection]) and negative specificity score=(frequency of base pair at position[post-selection]−frequency of base pair at position[pre-selection])/(frequency of base pair at position[pre-selection]). Normalization for sequence logos was performed as previously described[22].

Cellular Cleavage Assays.

HEK293T cells were split at a density of $0.8 \times 10^5$ per well (6-well plate) before transcription and maintained in Dulbecco's modified eagle medium (DMEM) supplemented with 10% fetal bovine serum (FBS) in a 37° C. humidified incubator with 5% $CO_2$. After 1 day, cells were transiently transfected using Lipofectamine 2000 (Invitrogen) following the manufacturer's protocols. HEK293T cells were transfected at 70% confluency in each well of 6-well plate with 1.0 μg of the Cas9 expression plasmid (Cas9-HA-2× NLS-GFP-NLS) and 2.5 μg of the single-strand RNA expression plasmid pSilencer-CLTA (version 1.0 or 2.1). The transfection efficiencies were estimated to be ~70%, based on the fraction of GFP-positive cells observed by fluorescence microscopy. 48 h after transfection, cells were washed with phosphate buffered saline (PBS), pelleted and frozen at −80° C. Genomic DNA was isolated from 200 μL cell lysate using the DNeasy Blood and Tissue Kit (Qiagen) according to the manufacturer's protocol.

Off-Target Site Sequence Determination.

100 ng genomic DNA isolated from cells treated with Cas9 expression plasmid and single-strand RNA expression plasmid (treated cells) or Cas9 expression plasmid alone (control cells) were amplified by PCR with 10 s 72° C. extension for 35 cycles with primers CLTA(#)-(#)-(#) fwd and CLTA(#)-(#)-(#) rev and Phusion Hot Start Flex DNA Polymerase (NEB) in Buffer GC (NEB), supplemented with 3% DMSO. Relative amounts of crude PCR products were quantified by gel, and Cas9-treated (control) and Cas9: sgRNA-treated PCRs were separately pooled in equimolar concentrations before purification with the QIAquick PCR Purification Kit (Qiagen). Purified DNA was amplified by PCR with primers PE1-barcode# and PE2-barcode# for 7 cycles with Phusion Hot Start Flex DNA Polymerase (NEB) in Buffer HF (NEB). Amplified control and treated DNA pools were purified with the QIAquick PCR Purification Kit (Qiagen), followed by purification with Agencourt AMPure XP (Beckman Coulter). Purified control and treated DNAs were quantified with the KAPA Library Quantification Kit-Illumina (KAPA Biosystems), pooled in a 1:1 ratio, and subjected to paired-end sequencing on an Illumina MiSeq.

Statistical Analysis.

Statistical analysis was performed as previously described[21]. P-values in Table 1 and Table 6 were calculated for a one-sided Fisher exact test.

Algorithms

All scripts were written in C++. Algorithms used in this study are as previous reported (reference) with modification.

Sequence Binning.

1) designate sequence pairs starting with the barcode "AACA" or "TTCA" as post-selection library members. 2) for post-selection library members (with illustrated example):

example read:

```
                                               (SEQ ID NO: 42)
AACACATGGGTCGACACAAACACAACTCGGCAGGTACTTGCAGATGTAGT

CTTTCCACATGGGTCGACACAAACACAACTCGGCAGGTATCTCGTATGCC
``` i) search both paired reads for the positions, pos1 and pos2, of the constant sequence "CTCGGCAGGT" (SEQ ID NO:43). ii) keep only sequences that have identical sequences between the barcode and pos1 and preceding pos2. iii) keep the region between the two instances of the constant sequence (the region between the barcode and pos1 contains a cut half-site; the region that is between the two instances of the constant sequence contains a full site)

example:

```
                                        (SEQ ID NO: 44)
    ACTTGCAGATGTAGTCTTTCCACATGGGTCGACACAAACACAA
``` ii) search the sequence for a selection barcode

| ("TGTGTTTGTGTT" | (SEQ ID NO: 45) | for CLTA1,

| "AGAAGAAGAAGA" | (SEQ ID NO: 46) | for CLTA2,

| "TTCTCTTTCTCT" | (SEQ ID NO: 47) | for CLTA3,

| "ACACAAACACAA" | (SEQ ID NO: 48) | for CLTA4)
example:

```
                                             (SEQ ID NO: 49)
    ACTTGCAGATGTAGTCTTTCCACATGGGTCGACACAAACACAA

- CLTA4
``` iii) the sequence before the barcode is the full post-selection library member (first four and last four nucleotides are fully randomized flanking sequence)
example:

```
ACTT GCAGATGTAGTCTTTCCACATGG GTCG   (SEQ ID NO: 50)
``` iv) parse the quality scores for the positions corresponding to the 23 nucleotide post-selection library member
example read:

(SEQ ID NO: 51)
AACACATGGGTCGACACAAACACAACTCGGCAGGTACTT<u>GCAGATGTAGT</u>

<u>CTTTCCACATGGG</u>TCGACACAAACACAACTCGGCAGGTATCTCGTATGCC

CCCFFFFFHHHHHJJJJJJJJJJJJJJJJJJJJJGIJJJ<u>JIJIJJJIIIH</u>

<u>IIJJJHHHGHAEF</u>CDDDDDDDDDDDDDDDDDDDDDD?CDDEDD@DCCCD v) keep sequences only if the corresponding quality score string (underlined) FASTQ quality characters for the sequence are '?' or higher in ASCII code (Phred quality score>=30)

NHEJ Sequence Calling
example read:

(SEQ ID NO: 52)
CAATCTCCCGCATGCGCTCAGTCCTCATCTCCCTCAAGCAGGCCCC<u>GCTG</u>

<u>GTGCACTGAAGAGCCA</u>CCCTGTGAAACACTACATCTGC<u>AATATCTTAATC</u>

<u>CTACTCAGT</u>GAAGCTCTTCACAGTCATTGGATTAATTATGTTGAGTTCTT

TTGGACCAAACC example quality scores:

CCBCCFFFFCCCGGGGGGGGGGHHHHHHHHHHHHHHHHHHGGGGGGG

GHHHHHHHHHHHHHHHHHGHHHHHHHHHHHHHHHHHHHHHGHHHHHHHHH

HHHHHHHFHHHHHHHHHHHHHHHHHHHHHHHHHHHHHHHHHH

HHHGHFHHHHHF 1) identify the 20 base pairs flanking both sides of 20 base pair target site+three base pair PAM for each target site
example flanking sequences:

<u>GCTGGTGCACTGAAGAGCCA</u>    (SEQ ID NO: 53)

<u>AATATCTTAATCCTACTCAG</u>    (SEQ ID NO: 54)

2) search all sequence reads for the flanking sequences to identify the potential off-target site (the sequence between the flanking sequences)
example potential off-target site:

CCCTGTGAAACACTACATCTGC    (SEQ ID NO: 55)

Figure 3A:
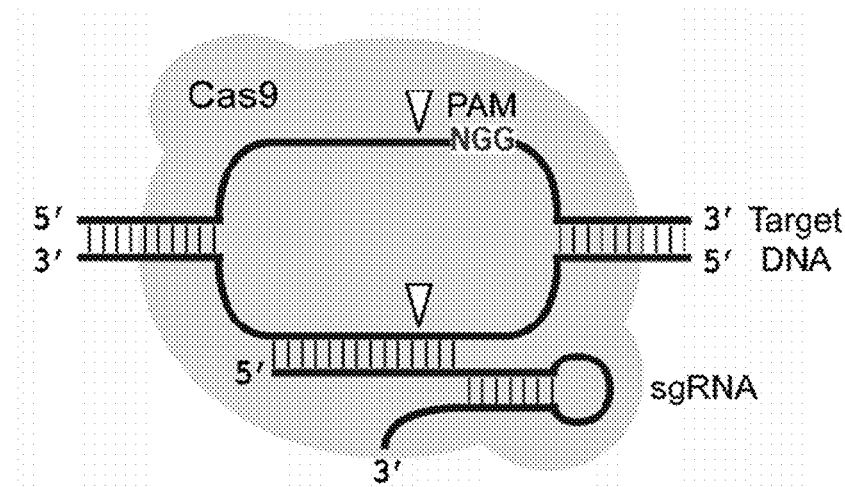
Figure 3B:
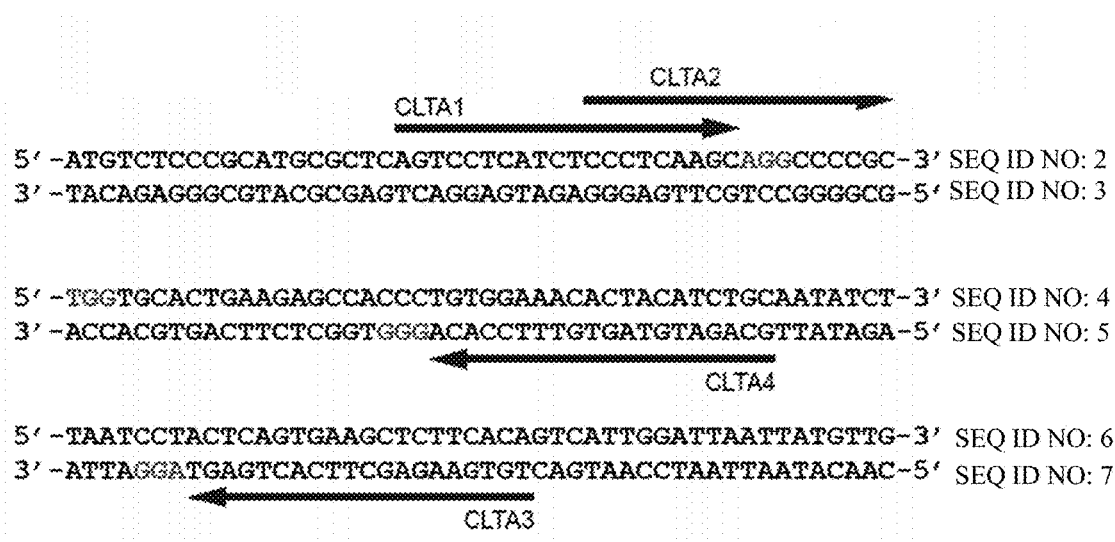

3) if the potential off-target site contains indels (length is less than 23), keep sequence as potential off-target site if all corresponding FASTQ quality characters for the sequence are '?' or higher in ASCII code (Phred quality score>=30)
example potential off-target site length=22
example corresponding FASTQ quality characters:

HHGHHHHHHHHHHHHHHHHH 4) bin and manually inspect all sequences that pass steps 2 and 3 and keep sequences as potential modified sequences if they have at least one deletion involving position 16, 17, or 18 (of 20 counting from the non-PAM end) of if they have an insertion between position 17 and 18, consistent with the most frequent modifications observed for the intended target site (FIG. 3)

example potential off-target site (reverse complement, with positions labeled) with reference sequence:

```
         11111111112222
non-PAM end 12345678901234567890123 PAM end
GCAGATGTAGTGTTTC-ACAGGG         (SEQ ID NO: 56)

GCAGATGTAGTGTTTCCACAGGG         (SEQ ID NO: 57)
```

4) repeat steps 1-3 for read2 and keep only if the sequence is the same
5) compare overall counts in Cas9+sgRNA treated sample to Cas9 alone sample to identify modified sites Filter Based on Cleavage Site (for Post-Selection Sequences)

1) tabulate the cleavage site locations across the recognition site by identifying the first position in the full sequenced recognition site (between the two constant sequences) that is identical to the first position in the sequencing read after the barcode (before the first constant sequence).

2) after tabulation, repeat step 1, keeping only sequences with cleavage site locations that are present in at least 5% of the sequencing reads.

Results

Broad Off-Target DNA Cleavage Profiling Reveals RNA Programmed Cas9 Nuclease Specificity.

Sequence-specific endonucleases including zinc-finger nucleases (ZFNs) and transcription activator-like effector nucleases (TALENs) have become important tools to modify genes in induced pluripotent stem cells (iPSCs),[1-3] in multicellular organisms,[4-8] and in ex vivo gene therapy clinical trials.[9, 10] Although ZFNs and TALENs have proved effective for such genetic manipulation, a new ZFN or TALEN protein must be generated for each DNA target site. In contrast, the RNA-guided Cas9 endonuclease uses RNA:DNA hybridization to determine target DNA cleavage sites, enabling a single monomeric protein to cleave, in principle, any sequence specified by the guide RNA.[11]

Previous studies[12-17] demonstrated that Cas9 mediates genome editing at sites complementary to a 20-nucleotide sequence in a bound guide RNA. In addition, target sites must include a protospacer adjacent motif (PAM) at the 3' end adjacent to the 20-nucleotide target site; for *Streptococcus pyogenes* Cas9, the PAM sequence is NGG. Cas9-mediated DNA cleavage specificity both in vitro and in cells has been inferred previously based on assays against small collections of potential single-mutation off-target sites. These studies suggested that perfect complementarity between guide RNA and target DNA is required in the 7-12 base pairs adjacent to the PAM end of the target site (3' end of the guide RNA) and mismatches are tolerated at the non-PAM end (5' end of the guide RNA).[11, 12, 17-19]

Although such a limited number of nucleotides specifying Cas9:guide RNA target recognition would predict multiple sites of DNA cleavage in genomes of moderate to large size (>~$10^7$ bp), Cas9:guide RNA complexes have been successfully used to modify both cells[12, 13, 15] and organisms.[14] A study using Cas9:guide RNA complexes to modify zebrafish embryos observed toxicity at a rate similar to that of ZFNs and TALENs.[14] A recent, broad study of the specificity of DNA binding (transcriptional repression) in *E. coli* of a catalytically inactive Cas9 mutant using high-throughput sequencing found no detectable off-target transcriptional repression in the relatively small *E. coli* transcriptome.[20] While these studies have substantially advanced our basic understanding of Cas9, a systematic and comprehensive profile of Cas9:guide RNA-mediated DNA cleavage specificity generated from measurements of Cas9 cleavage on a large number of related mutant target sites has not been described. Such a specificity profile is needed to understand and improve the potential of Cas9:guide RNA complexes as research tools and future therapeutic agents.

Figure 1B:
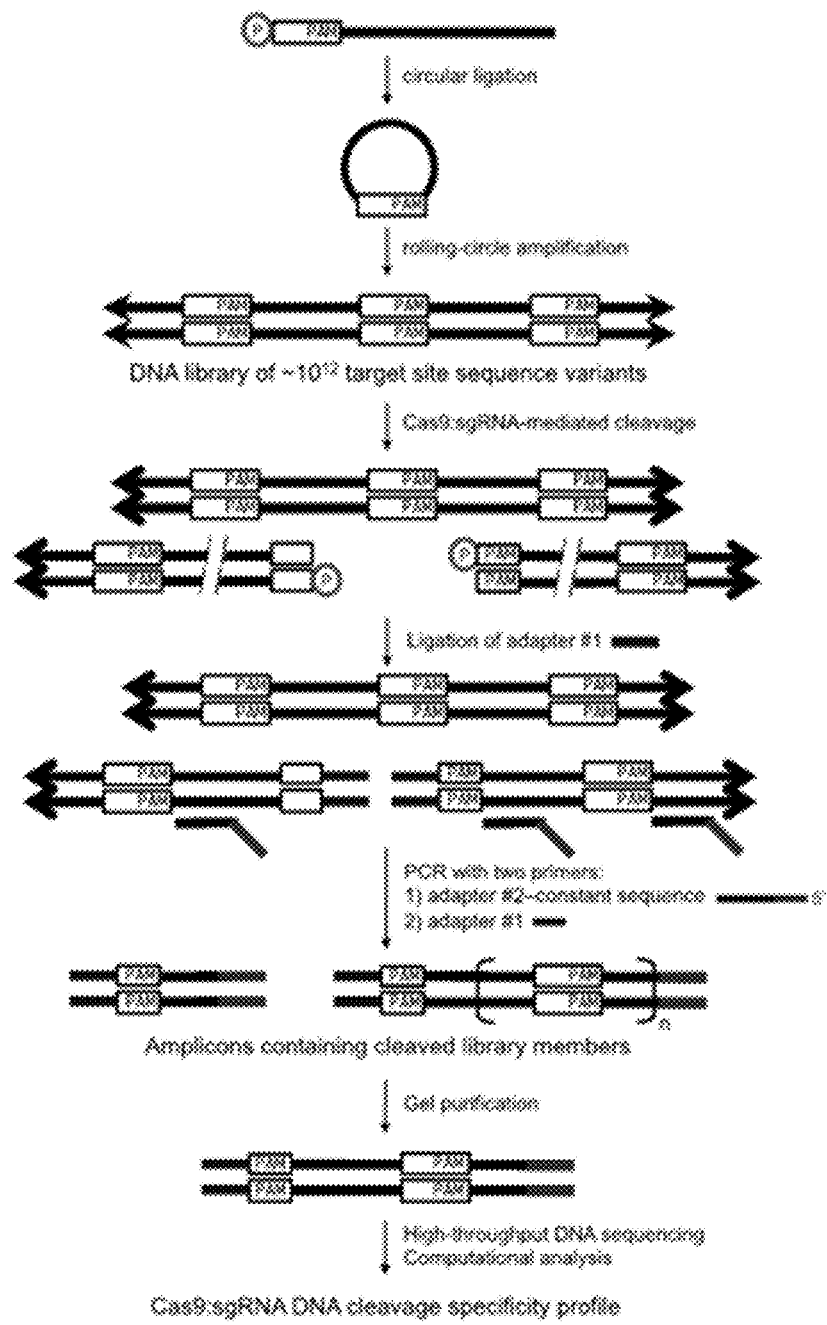

We modified our previously published in vitro selection,[21] adapted to process the blunt-ended cleavage products produced by Cas9 compared to the overhang-containing products of ZFN cleavage, to determine the off-target DNA cleavage profiles of Cas9:single guide RNA (sgRNA)[11] complexes. Each selection experiment used DNA substrate libraries containing ~$10^{12}$ sequences, a size sufficiently large to include ten-fold coverage of all sequences with eight or fewer mutations relative to each 22-base pair target sequence (including the two-base pair PAM) (FIG. 1). We used partially randomized nucleotide mixtures at all 22 target-site base pairs to create a binomially distributed library of mutant target sites with an expected mean of 4.62 mutations per target site. In addition, target site library members were flanked by four fully randomized base pairs on each side to test for specificity patterns beyond those imposed by the canonical 20-base pair target site and PAM.

Pre-selection libraries of $10^{12}$ individual potential off-target sites were generated for each of four different target sequences in the human clathrin light chain A (CLTA) gene (FIG. 3). Synthetic 5'-phosphorylated 53-base oligonucleotides were self-ligated into circular single-stranded DNA in vitro, then converted into concatemeric 53-base pair repeats through rolling-circle amplification. The resulting pre-selection libraries were incubated with their corresponding Cas9:sgRNA complexes. Cleaved library members containing free 5' phosphates were separated from intact library members through the 5' phosphate-dependent ligation of non-phosphorylated double-stranded sequencing adapters. The ligation-tagged post-selection libraries were amplified by PCR. The PCR step generated a mixture of post-selection DNA fragments containing 0.5, 1.5, or 2.5, etc. repeats of library members cleaved by Cas9, resulting from amplification of an adapter-ligated cut half-site with or without one or more adjacent corresponding full sites (FIG. 1). Post-selection library members with 1.5 target-sequence repeats were isolated by gel purification and analyzed by high-throughput sequencing. In a final computational selection step to minimize the impact of errors during DNA amplification or sequencing, only sequences with two identical copies of the repeated cut half-site were analyzed.

Figure 4:
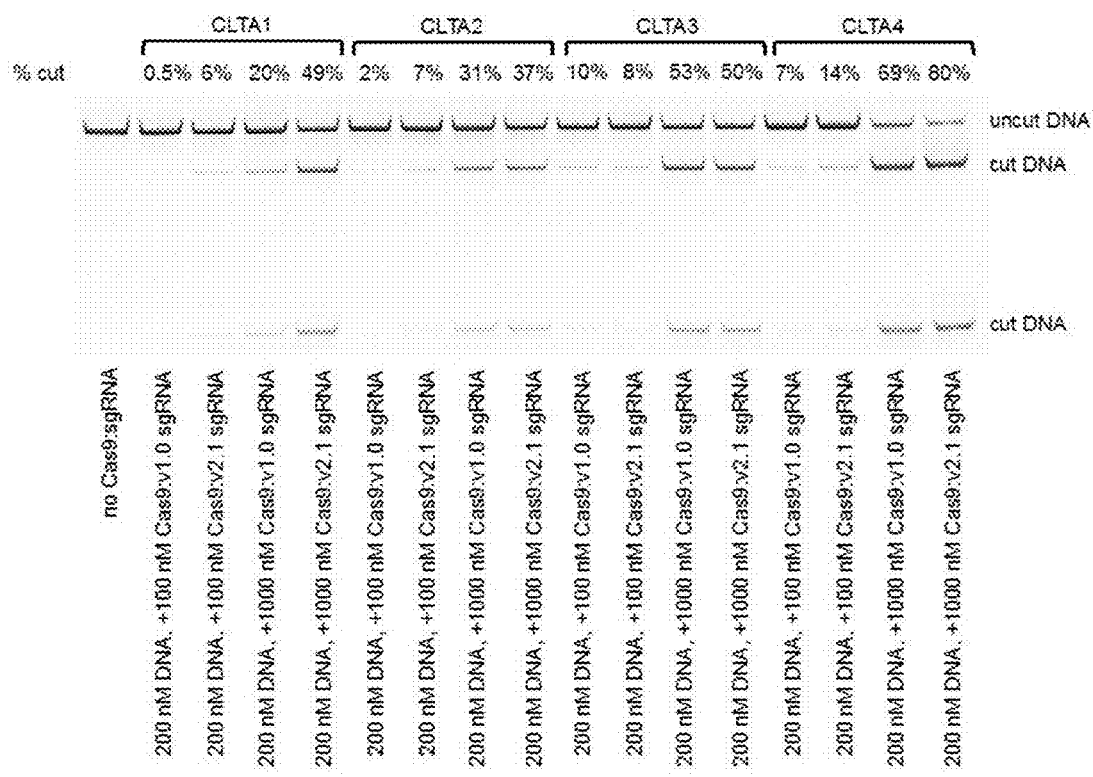
FIG. 4. Cas9:guide RNA cleavage of on-target DNA sequences in vitro. Discrete DNA cleavage assays on an approximately 1-kb linear substrate were performed with 200 nM on-target site and 100 nM Cas9:v1.0 sgRNA, 100 nM Cas9:v2.1 sgRNA, 1000 nM Cas9:v1.0 sgRNA, and 1000 nM Cas9:v2.1 sgRNA for each of four CLTA target sites. For CLTA1, CLTA2, and CLTA4, Cas9:v2.1 sgRNA shows higher activity than Cas9:v1.0 sgRNA. For CLTA3, the activities of the Cas9:v1.0 sgRNA and Cas9:v2.1 sgRNA were comparable.
Figure 5A:
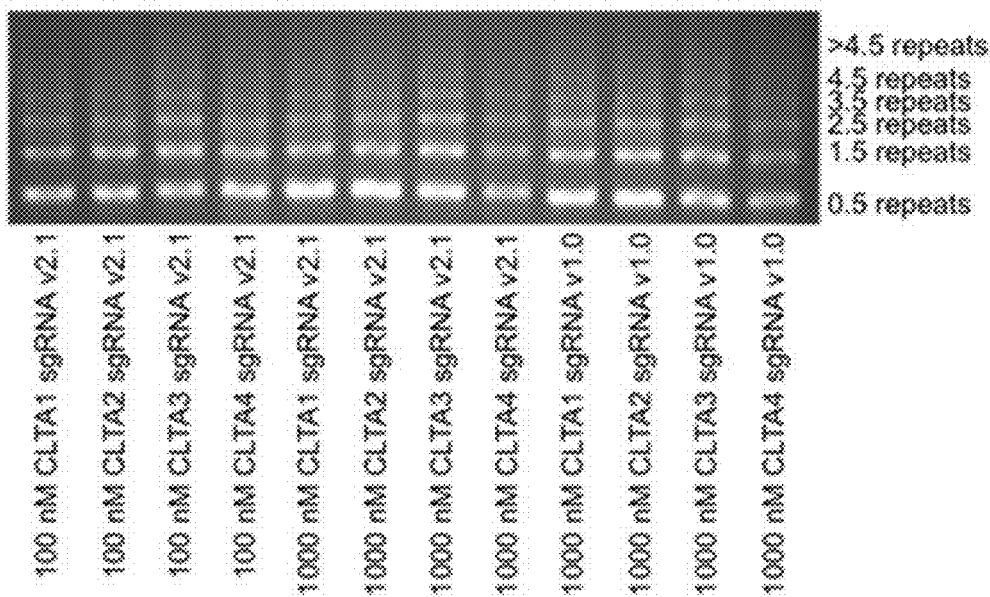
FIGS. 5A-5E. In vitro selection results for four target sites. In vitro selections were performed on 200 nM pre-selection library with 100 nM Cas9:sgRNA v2.1, 1000 nM Cas9:sgRNA v1.0, or 1000 nM Cas9:sgRNA v2.1.
Figure 5B:
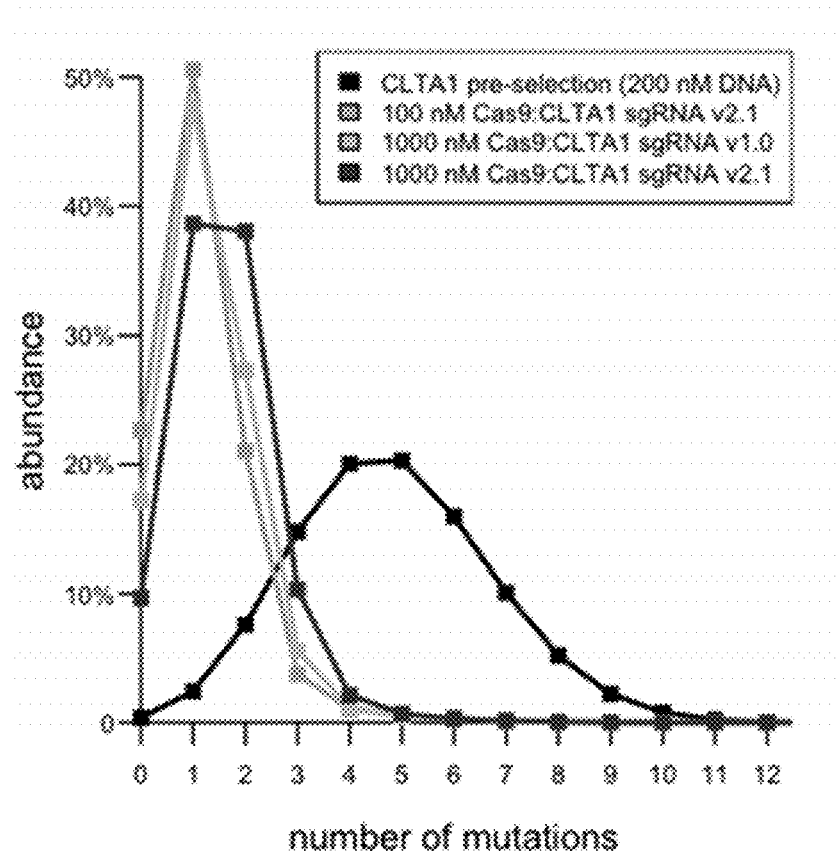
Figure 5C:
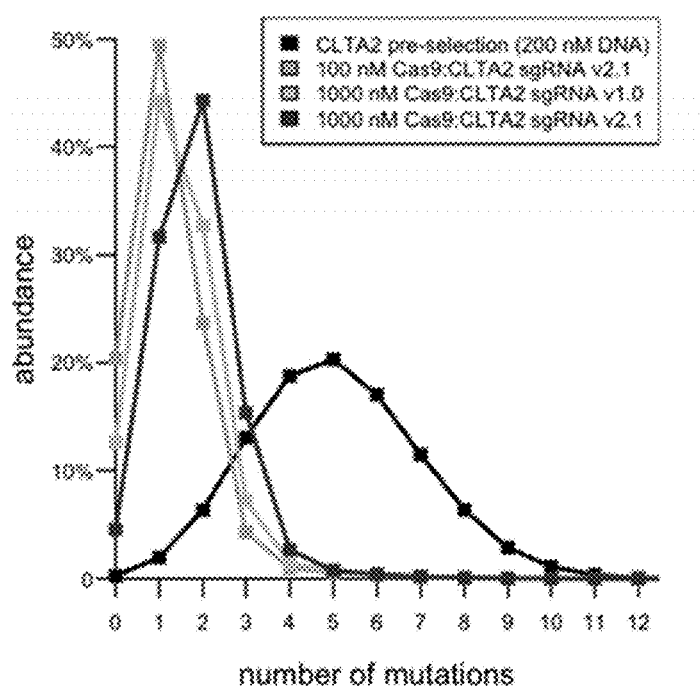
Figure 5D:
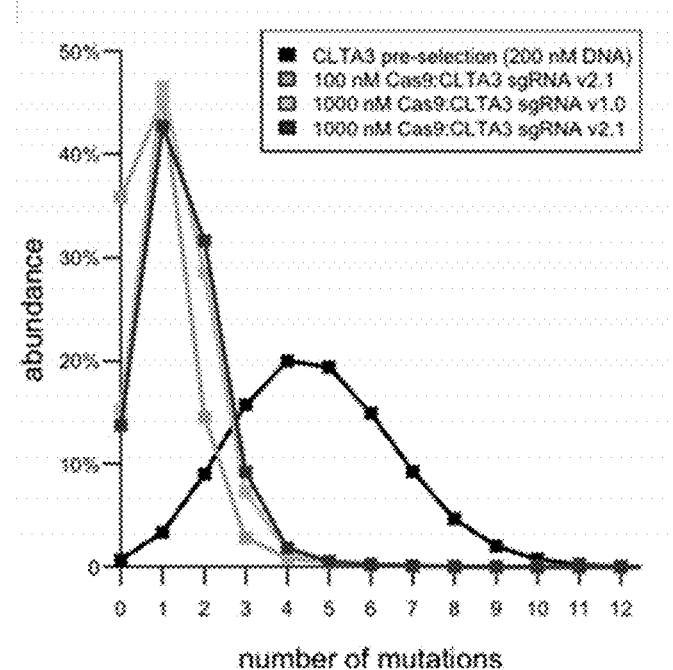
Figure 5E:
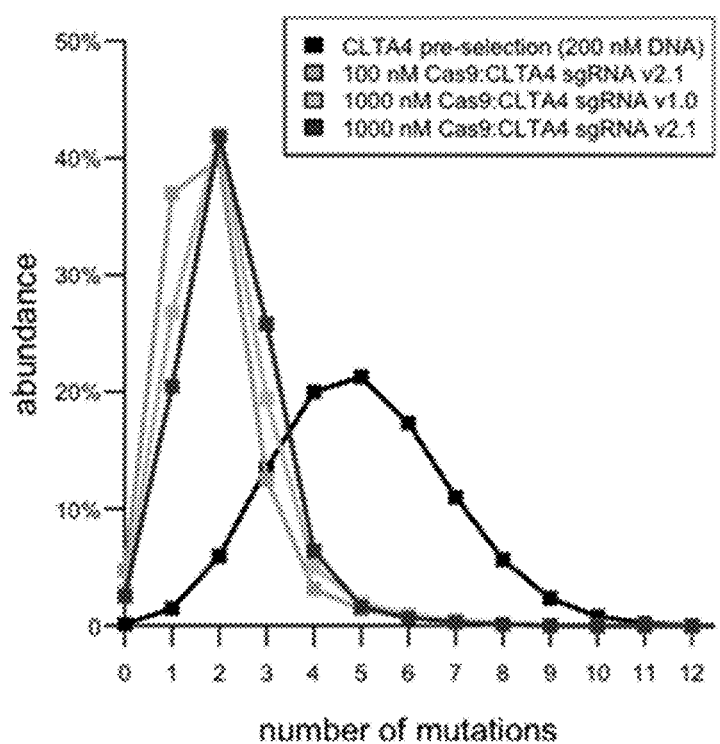
Figure 6A:
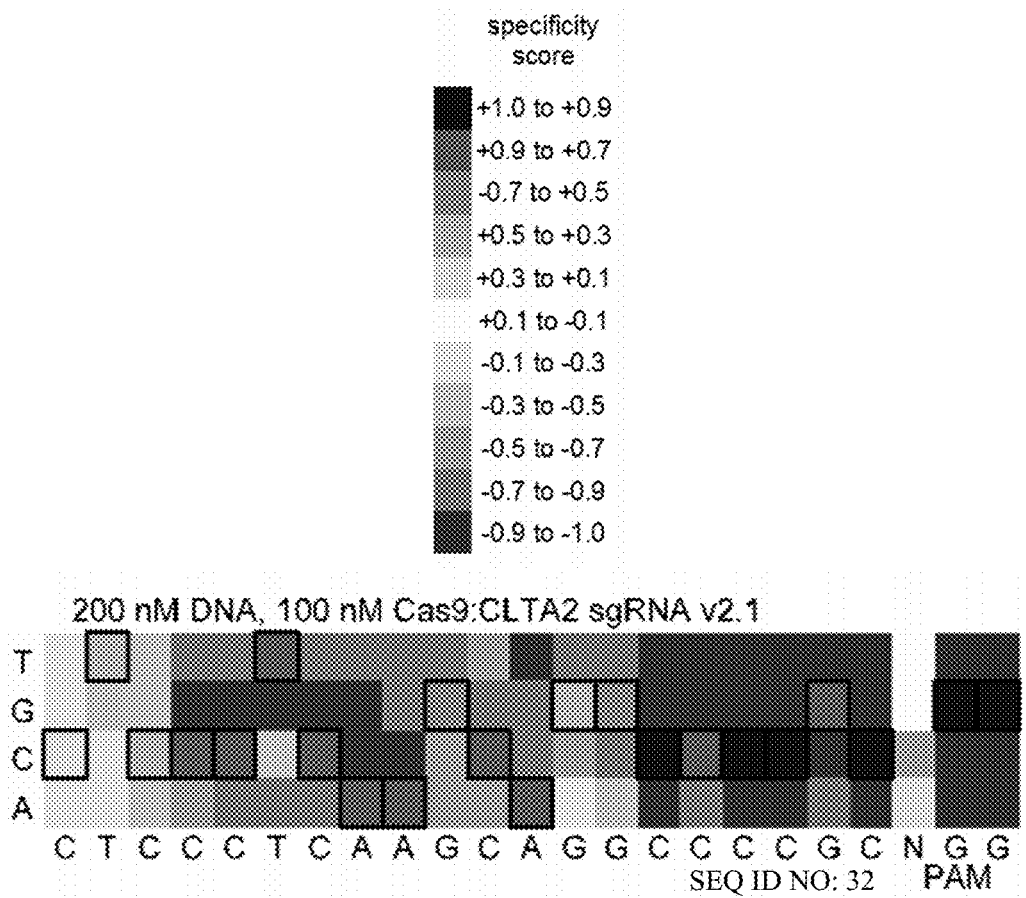
FIGS. 6A-6F. In vitro selection results for Cas9:CLTA2 sgRNA. Heat maps[24] show the specificity profiles of Cas9:CLTA2 sgRNA v2.1 under enzyme-limiting conditions (FIGS. 6A, 6B), Cas9:CLTA2 sgRNA v1.0 under enzyme-excess conditions (FIGS. 6C, 6D), and Cas9:CLTA2 sgRNA v2.1 under enzyme-excess conditions (FIGS. 6E, 6F). Heat maps show all post-selection sequences (FIGS. 6A, 6C, 6E) or only those sequences containing a single mutation in the 20-base pair sgRNA-specified target site and two-base pair PAM (FIGS. 6B, 6D, 6F). Specificity scores of 1.0 and −1.0 corresponds to 100% enrichment for and against, respectively, a particular base pair at a particular position. Black boxes denote the intended target nucleotides.
Figure 6B:
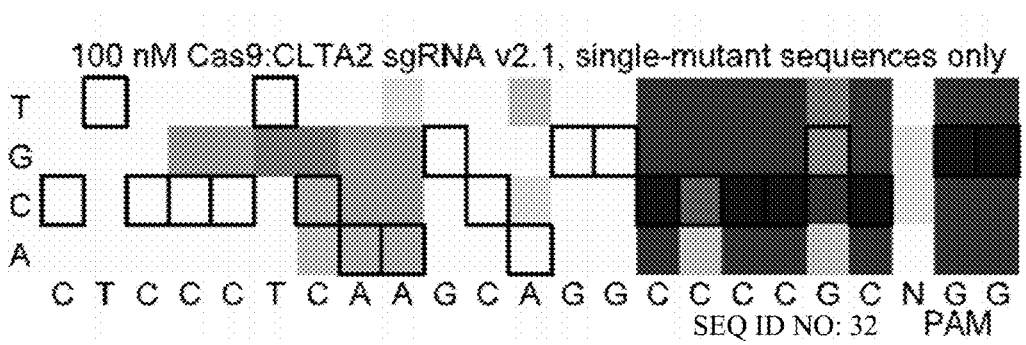
Figure 6C:
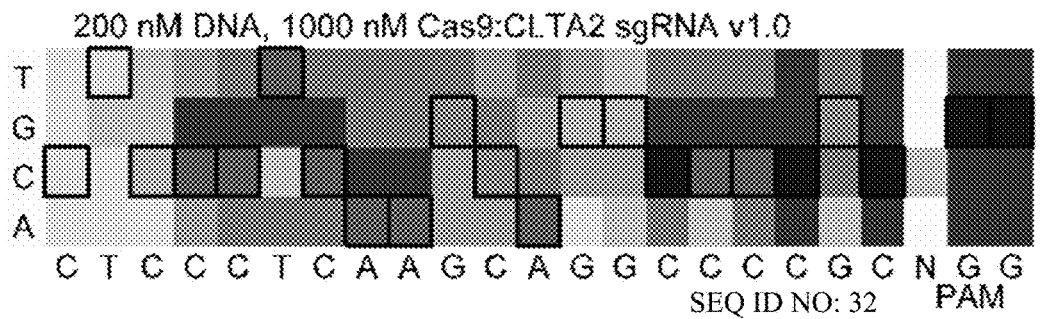
Figure 6D:
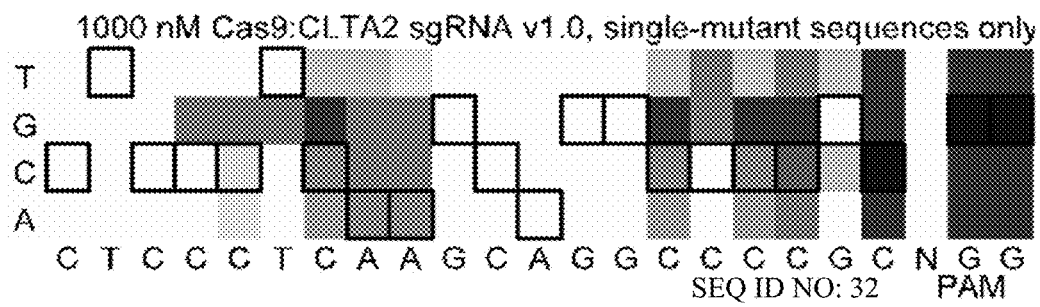
Figure 6E:
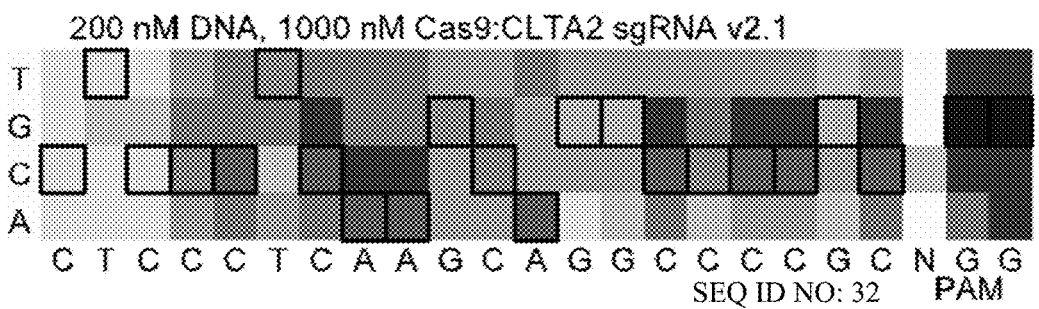
Figure 6F:
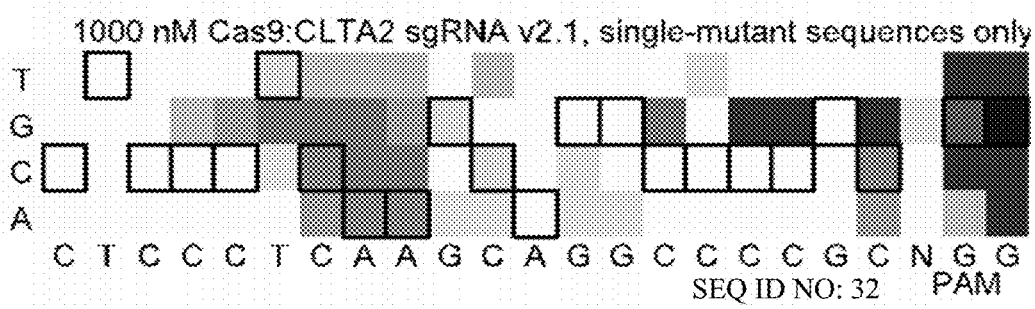
Figure 7A:
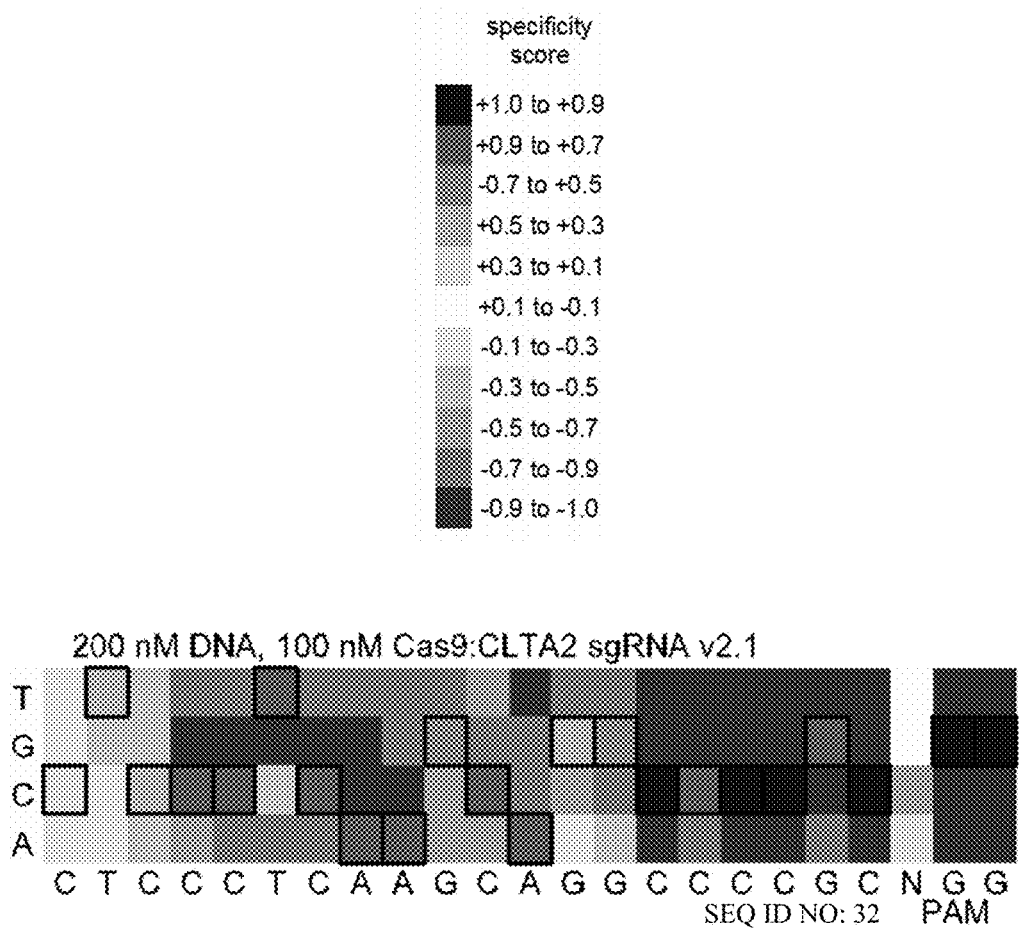
FIGS. 7A-7F. In vitro selection results for Cas9:CLTA3 sgRNA. Heat maps[24] show the specificity profiles of Cas9:CLTA3 sgRNA v2.1 under enzyme-limiting conditions (FIG. 7A, 7B), Cas9:CLTA3 sgRNA v1.0 under enzyme-excess conditions (FIGS. 7C, 7D), and Cas9:CLTA3 sgRNA v2.1 under enzyme-saturating conditions (FIGS. 7E, 7F). Heat maps show all post-selection sequences (FIGS. 7A, 7C, 7E) or only those sequences containing a single mutation in the 20-base pair sgRNA-specified target site and two-base pair PAM (FIGS. 7B, 7D, 7F). Specificity scores of 1.0 and −1.0 corresponds to 100% enrichment for and against, respectively, a particular base pair at a particular position. Black boxes denote the intended target nucleotides.
Figure 7B:
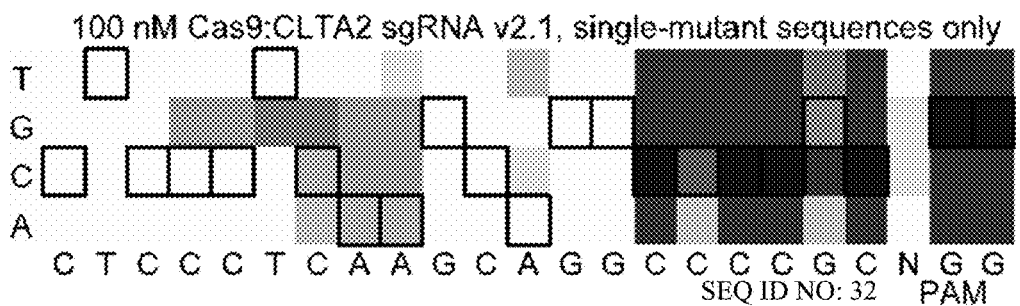
Figure 7C:
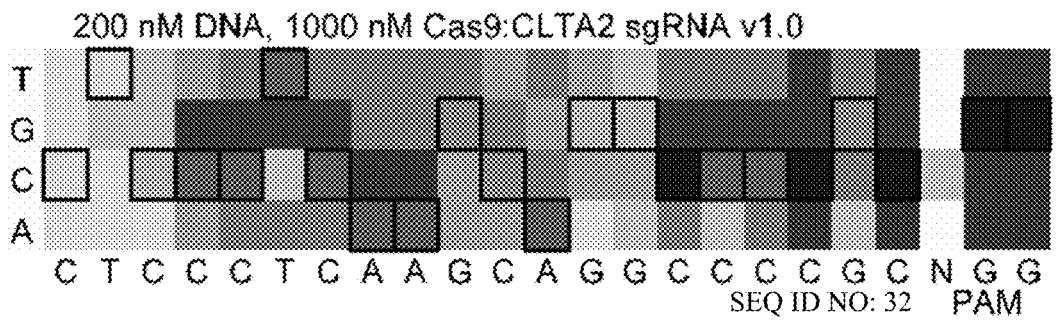
Figure 7D:
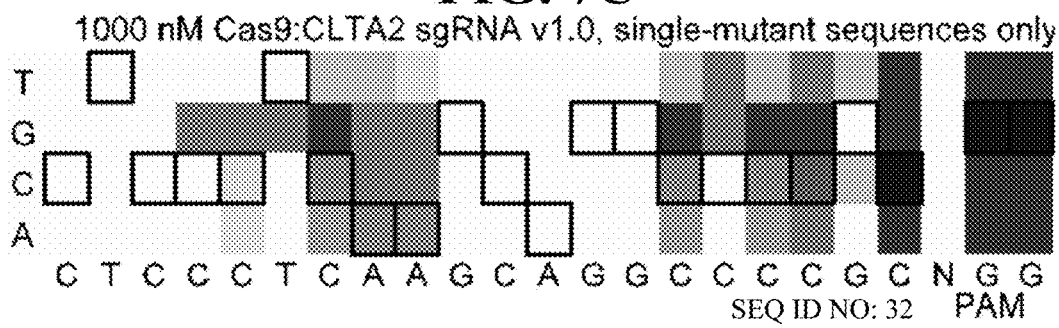
Figure 7E:
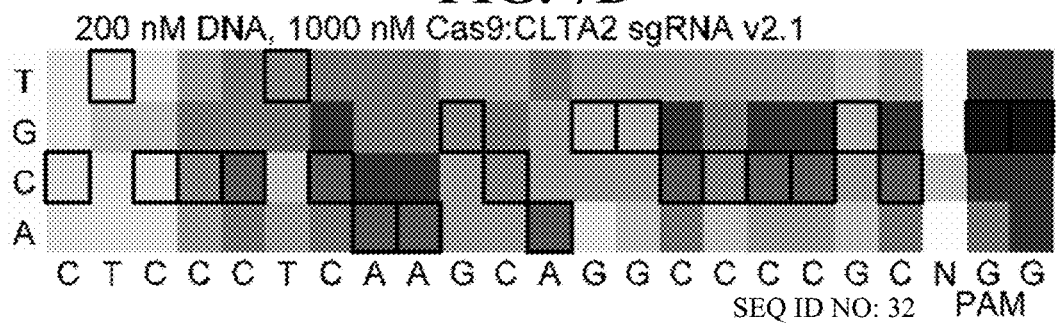
Figure 7F:
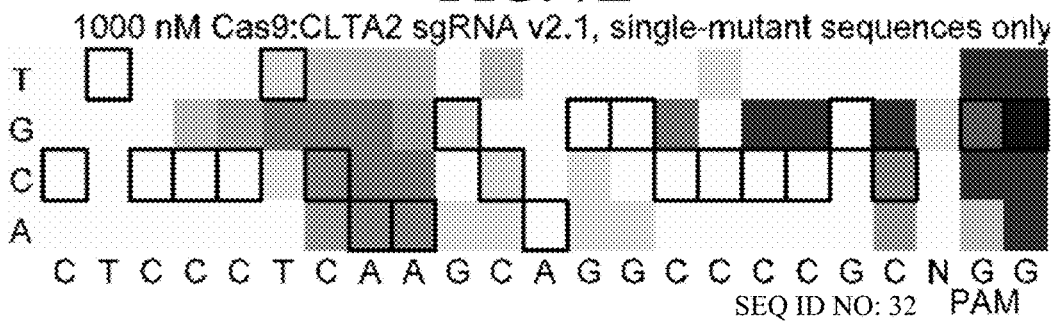
Figure 8A:
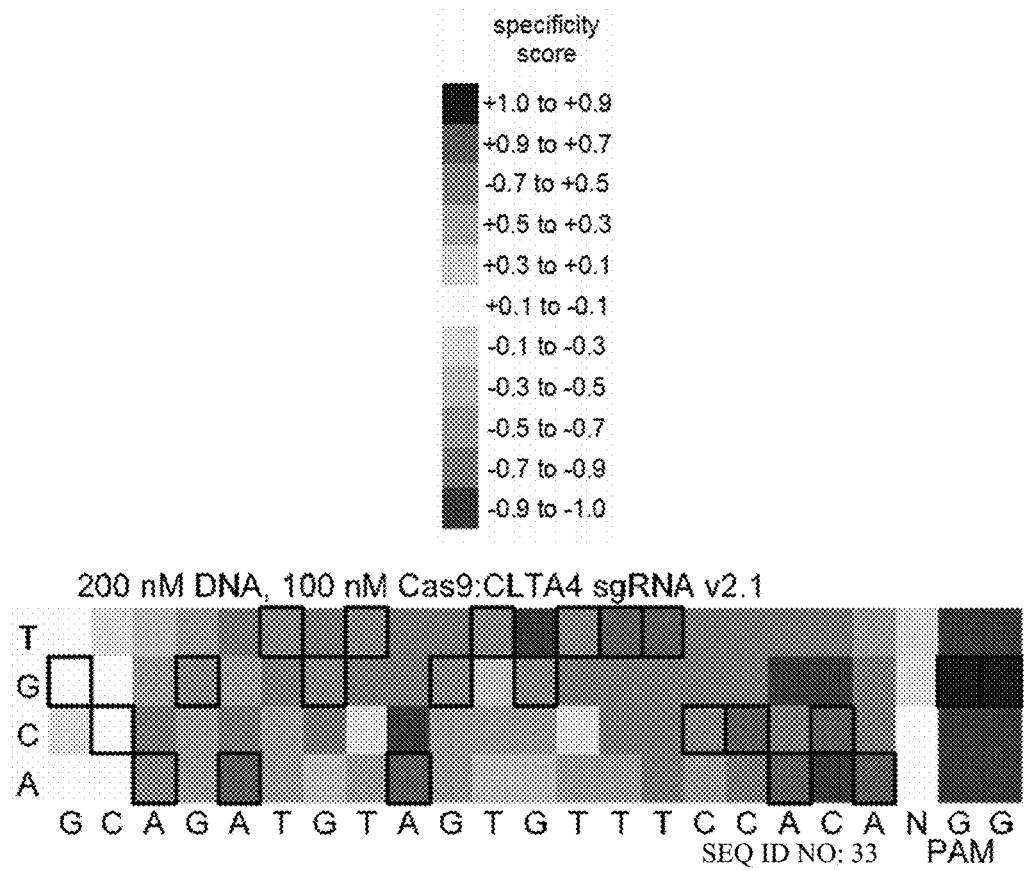
FIGS. 8A-8F. In vitro selection results for Cas9:CLTA4 sgRNA. Heat maps[24] show the specificity profiles of Cas9:CLTA4 sgRNA v2.1 under enzyme-limiting conditions (FIGS. 8A, 8B), Cas9:CLTA4 sgRNA v1.0 under enzyme-excess conditions (FIGS. 8C, 8D), and Cas9:CLTA4 sgRNA v2.1 under enzyme-saturating conditions (FIGS. 8E, 8F). Heat maps show all post-selection sequences (FIGS. 8A, 8C, 8E) or only those sequences containing a single mutation in the 20-base pair sgRNA-specified target site and two-base pair PAM (FIGS. 8B, 8D, 8F). Specificity scores of 1.0 and −1.0 corresponds to 100% enrichment for and against, respectively, a particular base pair at a particular position. Black boxes denote the intended target nucleotides.
Figure 8B:
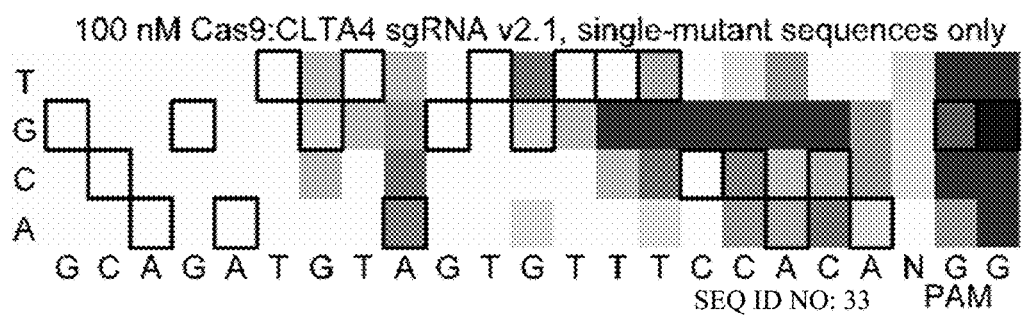
Figure 8C:
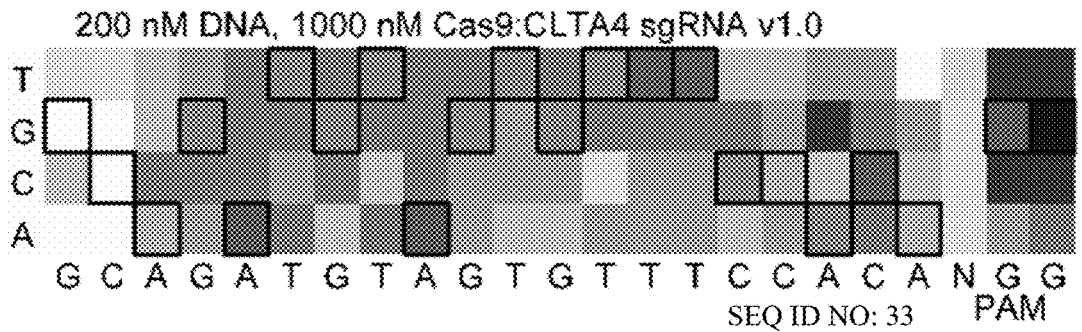
Figure 8D:
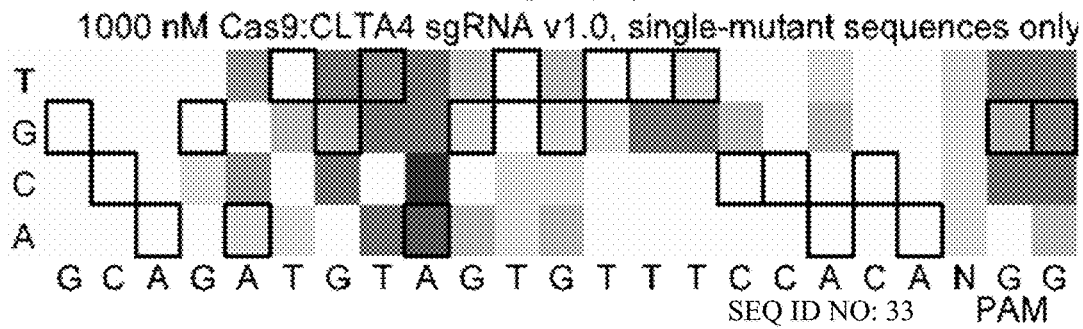
Figure 8E:
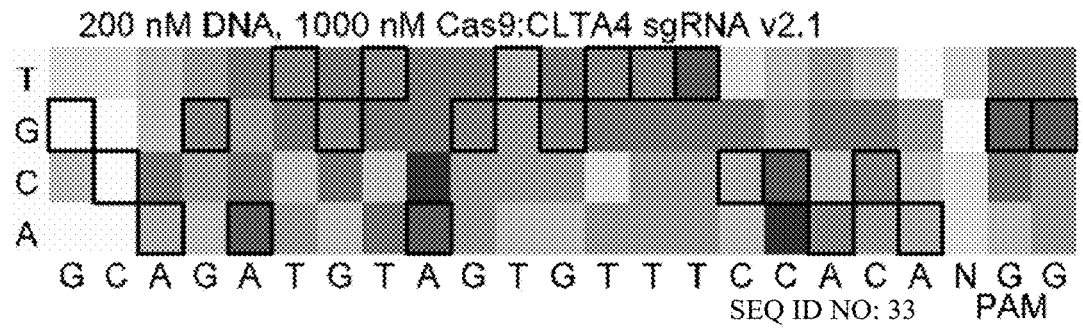
Figure 8F:
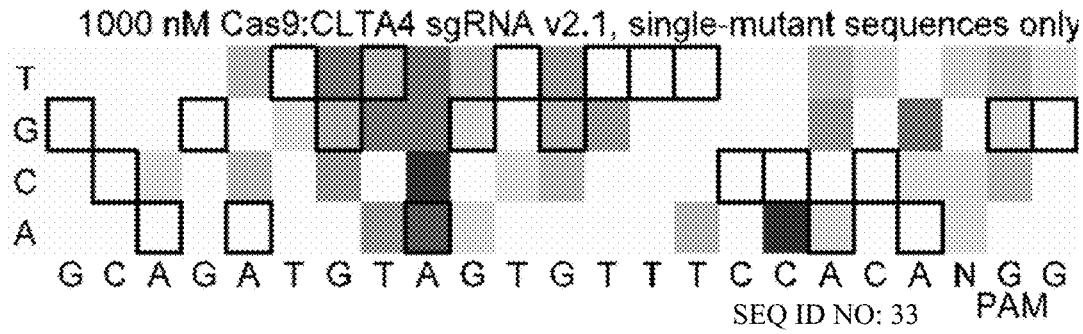
Figure 9A:
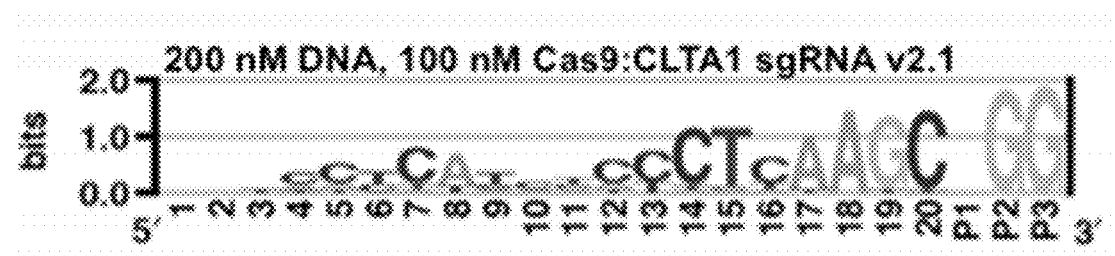
FIGS. 9A-9D. In vitro selection results as sequence logos. Information content is plotted[25] for each target site position (1-20) specified by CLTA1 (FIG. 9A), CLTA2 (FIG. 9B), CLTA3 (FIG. 9C), and CLTA4 (FIG. 9D) sgRNA v2.1 under enzyme-limiting conditions. Positions in the PAM are labelled "P1," "P2," and "P3." Information content is plotted in bits. 2.0 bits indicates absolute specificity and 0 bits indicates no specificity.
Figure 9B:
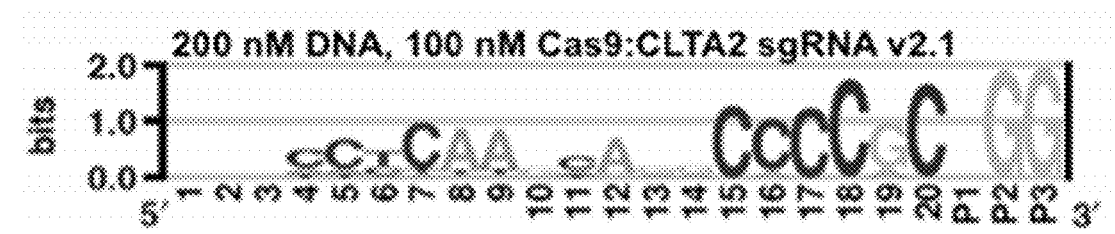
Figure 9C:
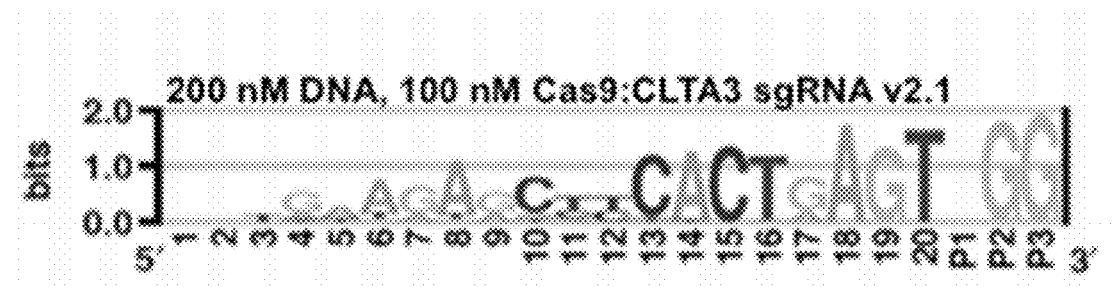
Figure 9D:
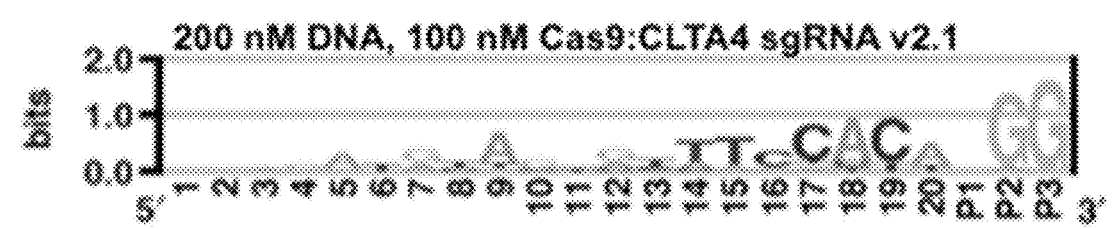
Figure 10A:
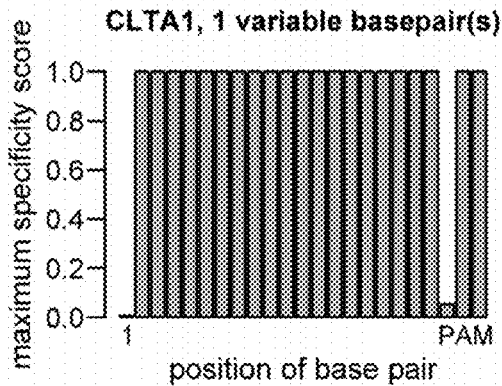
FIGS. 10A-10L. Tolerance of mutations distal to the PAM for CLTA1. The maximum specificity scores at each position are shown for the Cas9:CLTA1 v2.1 sgRNA selections when considering only those sequences with on-target base pairs in gray, while allowing mutations in the first 1-12 base pairs (FIGS. 10A-10L). The positions that are not constrained to on-target base pairs are indicated by dark bars. Higher specificity score values indicate higher specificity at a given position. The positions that were not allowed to contain any mutations (gray) were plotted with a specificity score of +1. For all panels, specificity scores were calculated from pre-selection library sequences and post-selection library sequences with an n≥5,130 and n≥74,538, respectively.
Figure 10B:
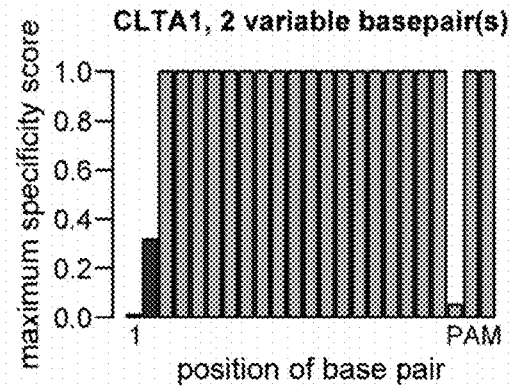
Figure 10C:
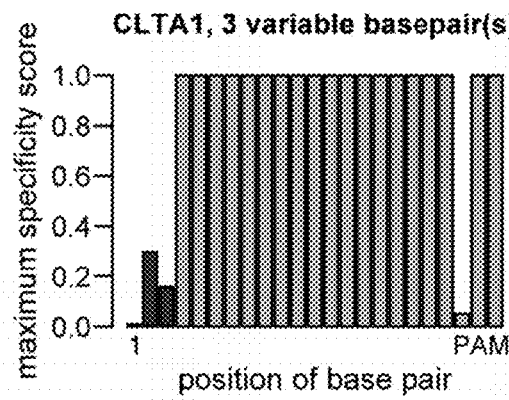
Figure 10D:
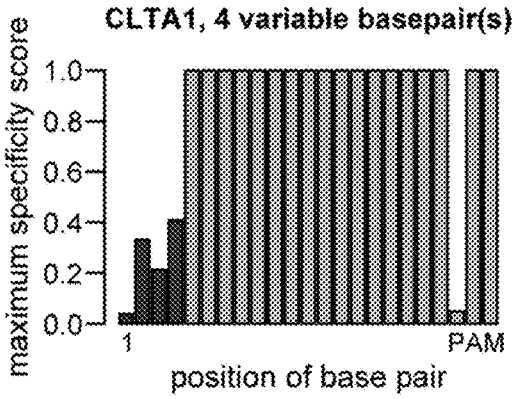
Figure 10E:
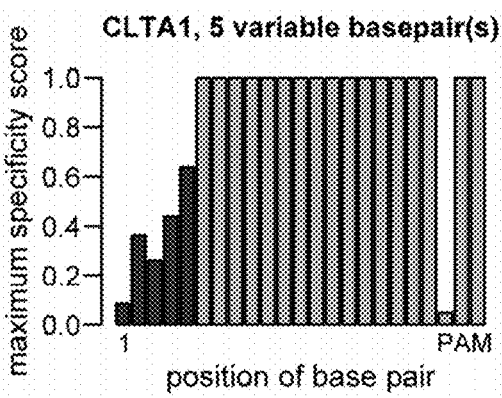
Figure 10F:
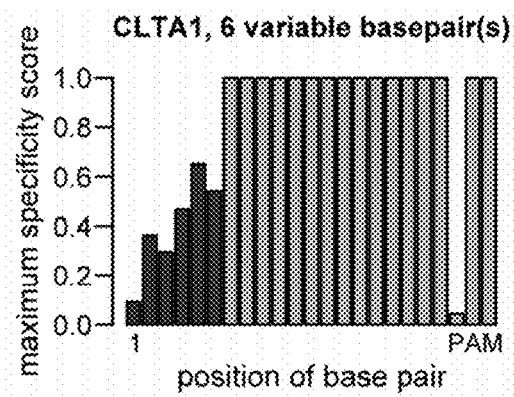
Figure 10G:
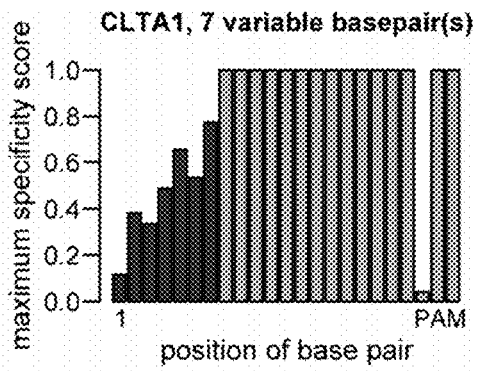
Figure 10H:
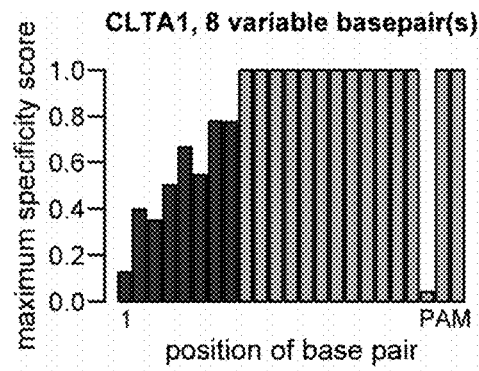
Figure 10I:
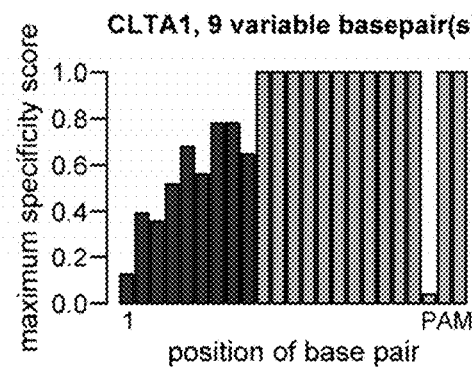
Figure 10J:
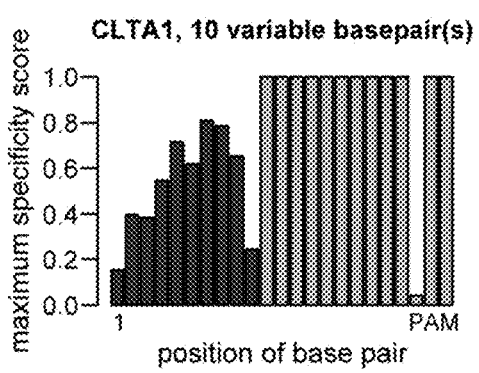
Figure 10K:
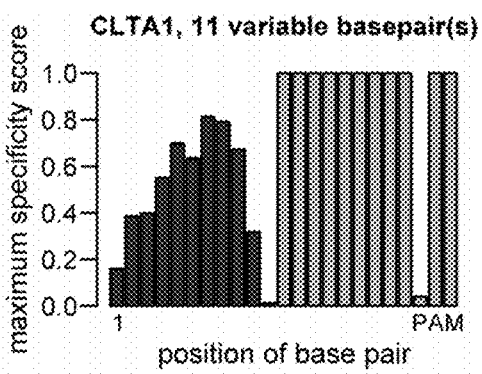
Figure 10L:
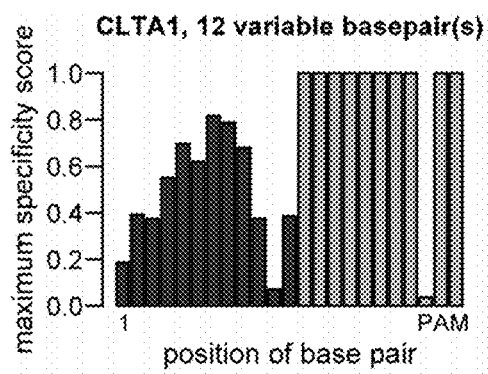
Figure 11A:
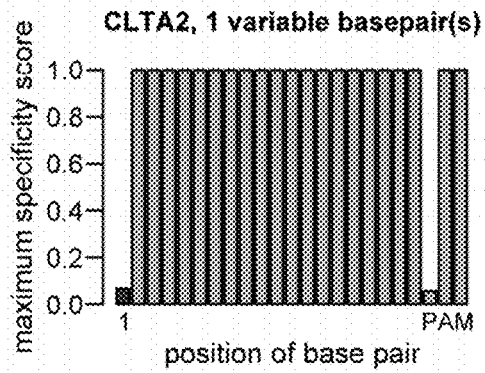
FIGS. 11A-11L. Tolerance of mutations distal to the PAM for CLTA2. The maximum specificity scores at each position are shown for the Cas9:CLTA2 v2.1 sgRNA selections when considering only those sequences with on-target base pairs in gray, while allowing mutations in the first 1-12 base pairs (FIGS. 11A-11L). The positions that are not constrained to on-target base pairs are indicated by dark bars. Higher specificity score values indicate higher specificity at a given position. The positions that were not allowed to contain any mutations (gray) were plotted with a specificity score of +1. For all panels, specificity scores were calculated from pre-selection library sequences and post-selection library sequences with an n≥3,190 and n≥25,365, respectively.
Figure 11B:
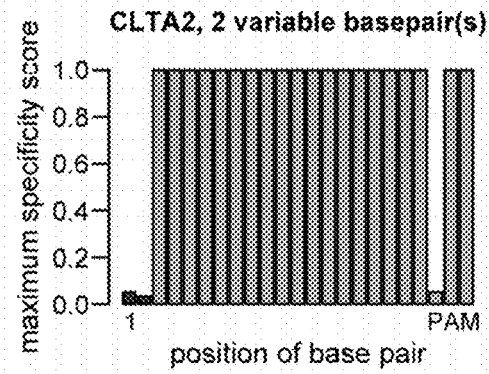
Figure 11C:
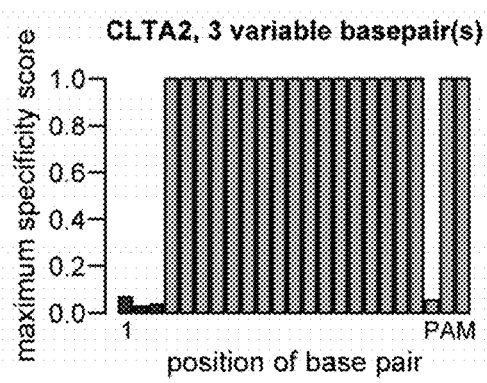
Figure 11D:
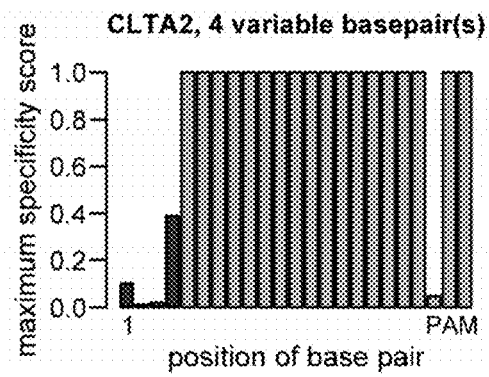
Figure 11E:
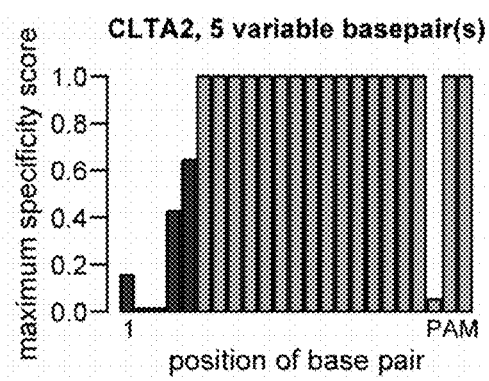
Figure 11F:
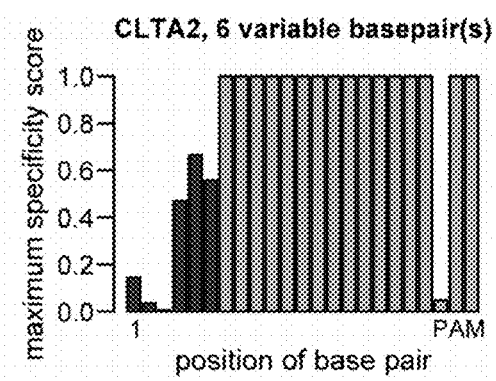
Figure 11G:
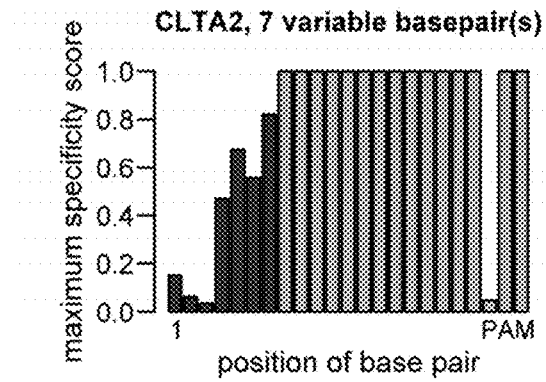
Figure 11H:
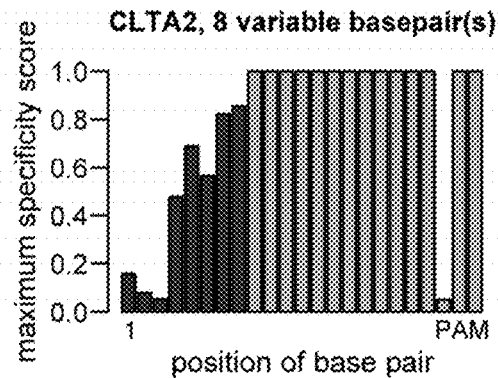
Figure 11I:
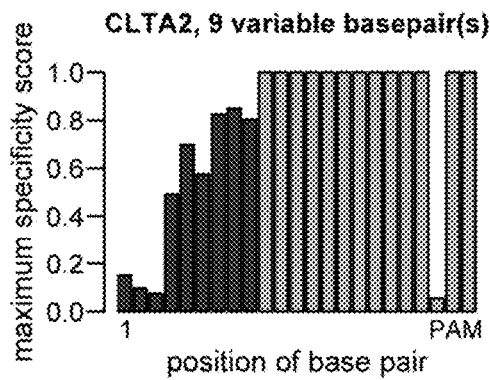
Figure 11J:
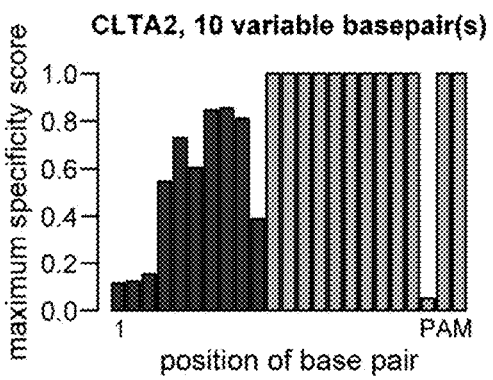
Figure 11K:
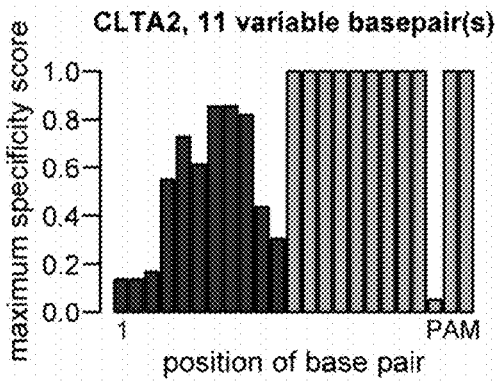
Figure 11L:
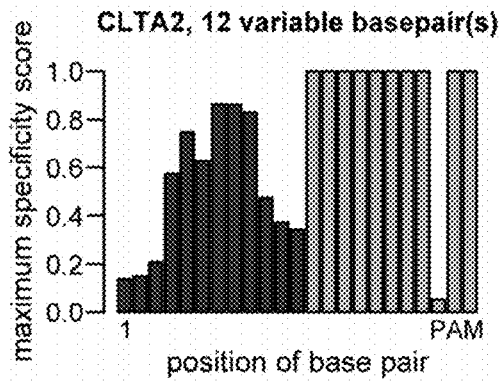
Figure 12A:
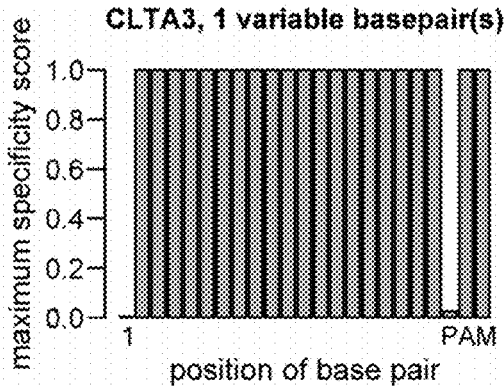
FIGS. 12A-12L. Tolerance of mutations distal to the PAM for CLTA3. The maximum specificity scores at each position are shown for the Cas9:CLTA3 v2.1 sgRNA selections when considering only those sequences with on-target base pairs in gray, while allowing mutations in the first 1-12 base pairs (FIGS. 12A-12L). The positions that are not constrained to on-target base pairs are indicated by dark bars. Higher specificity score values indicate higher specificity at a given position. The positions that were not allowed to contain any mutations (gray) were plotted with a specificity score of +1. For all panels, specificity scores were calculated from pre-selection library sequences and post-selection library sequences with an n≥5,604 and n≥158,424, respectively.
Figure 12B:
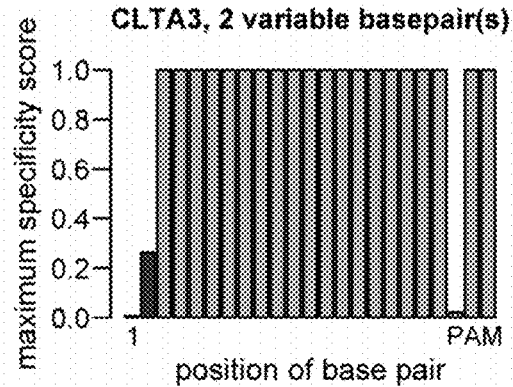
Figure 12C:
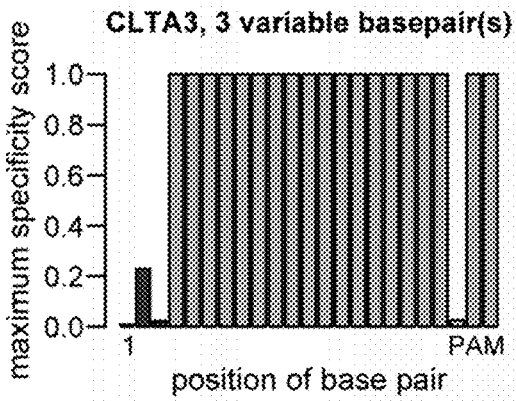
Figure 12D:
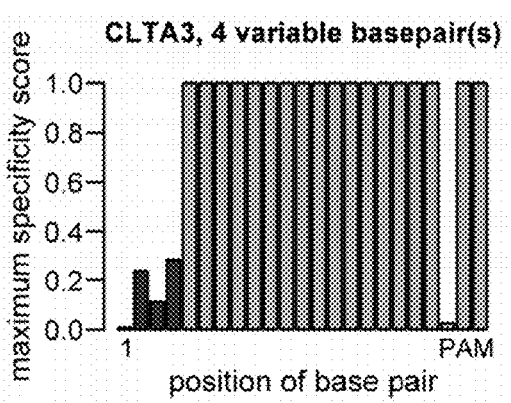
Figure 12E:
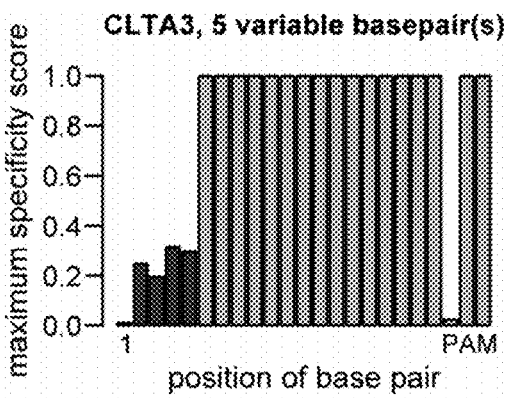
Figure 12F:
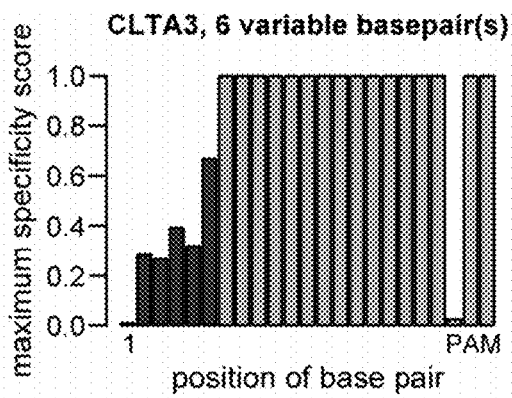
Figure 12G:
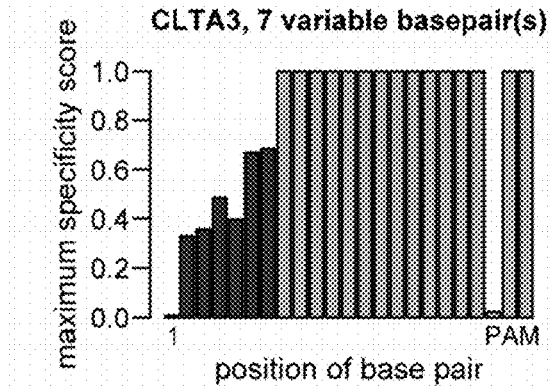
Figure 12H:
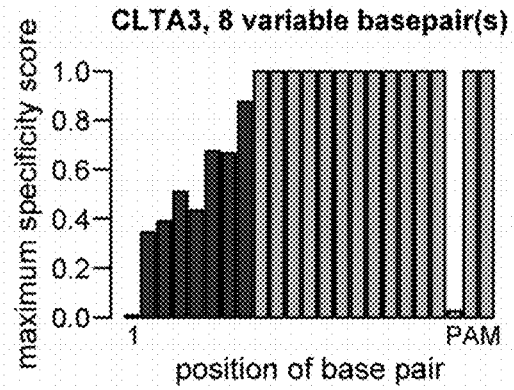
Figure 12I:
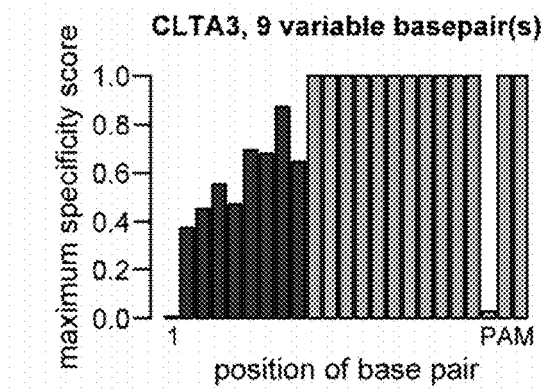
Figure 12J:
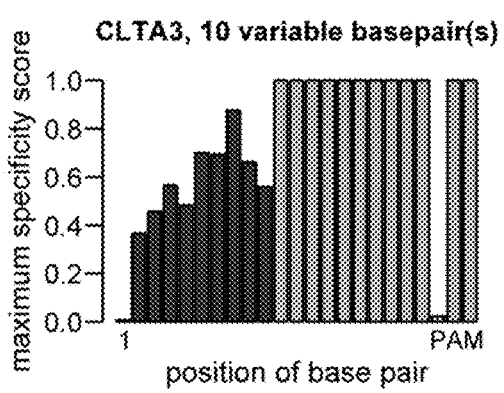
Figure 12K:
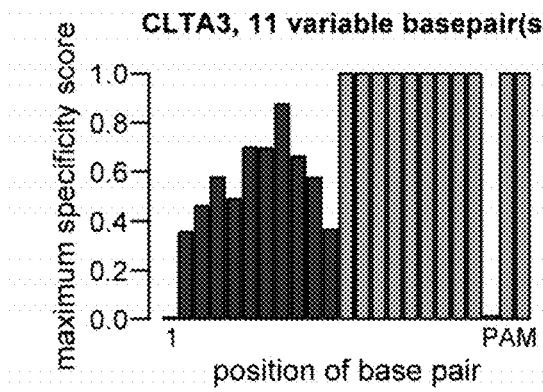
Figure 12L:
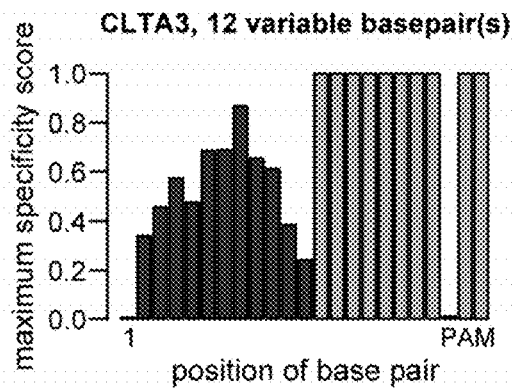
Figure 13A:
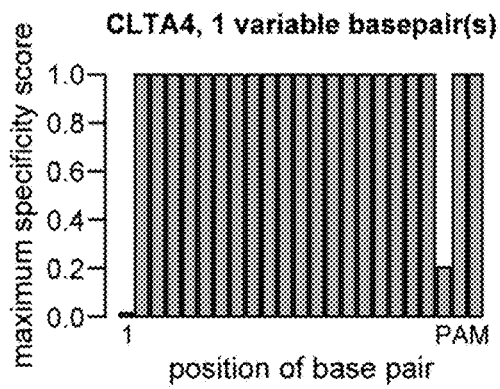
FIGS. 13A-13L. Tolerance of mutations distal to the PAM for CLTA4. The maximum specificity scores at each position are shown for the Cas9:CLTA4 v2.1 sgRNA selections when considering only those sequences with on-target base pairs in gray, while allowing mutations in the first 1-12 base pairs (FIGS. 13A-13L). The positions that are not constrained to on-target base pairs are indicated by dark bars. Higher specificity score values indicate higher specificity at a given position. The positions that were not allowed to contain any mutations (gray) were plotted with a specificity score of +1. For all panels, specificity scores were calculated from pre-selection library sequences and post-selection library sequences with an n≥2,323 and n≥21,819, respectively.
Figure 13B:
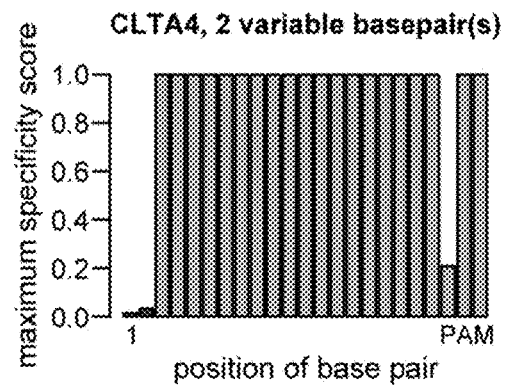
Figure 13C:
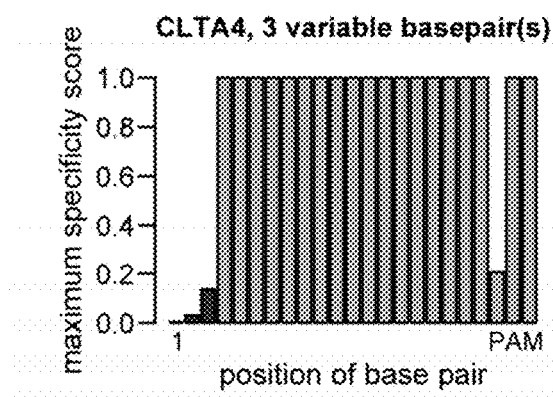
Figure 13D:
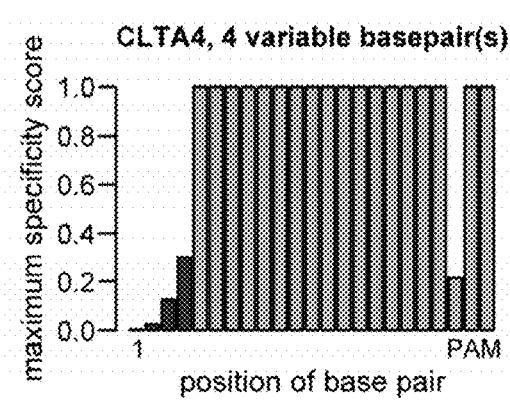
Figure 13E:
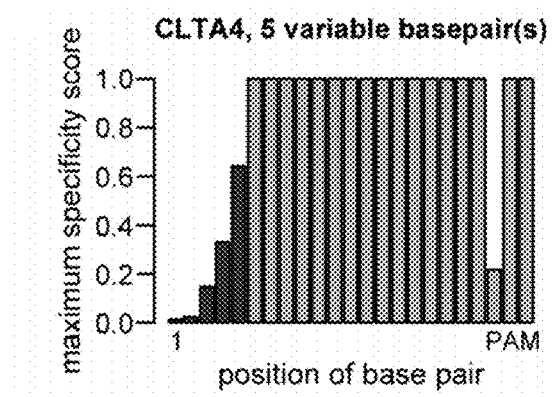
Figure 13F:
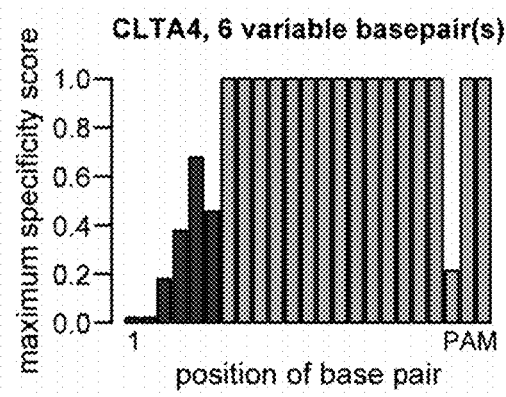
Figure 13G:
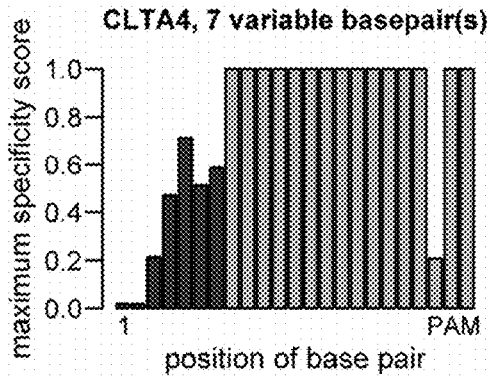
Figure 13H:
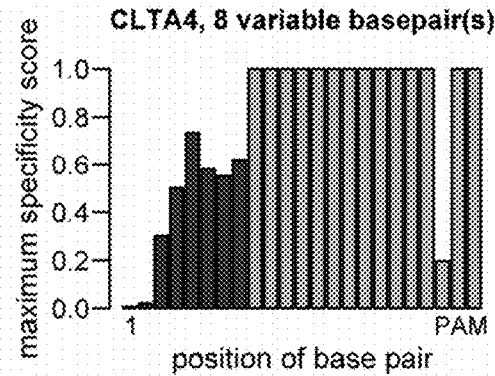
Figure 13I:
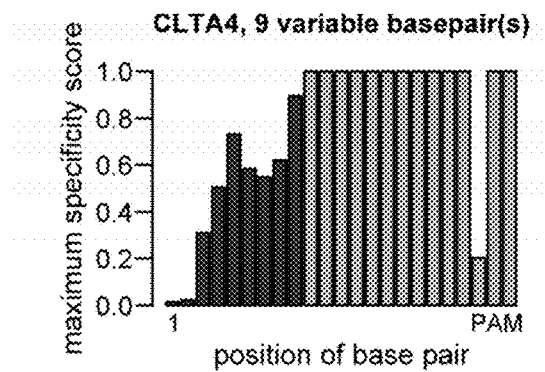
Figure 13J:
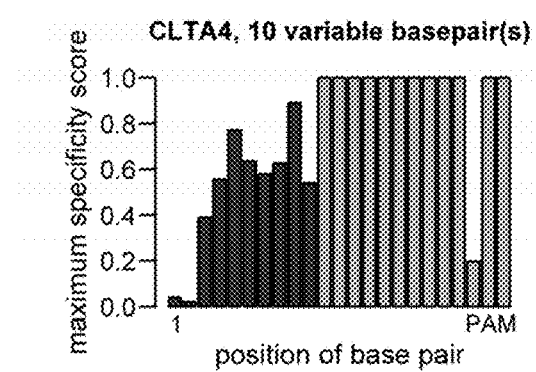
Figure 13K:
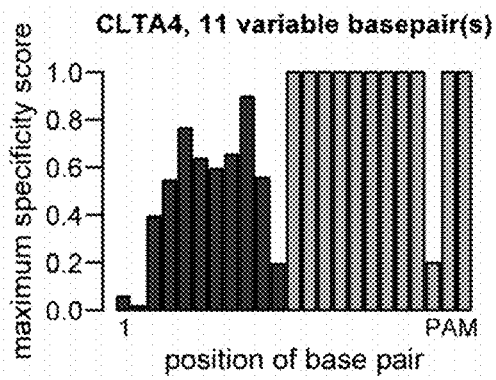
Figure 13L:
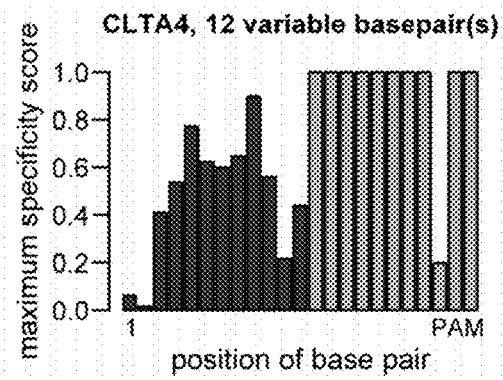
Figure 14A:
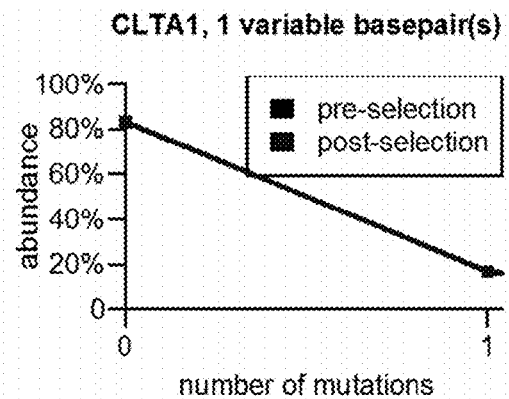
FIGS. 14A-14L. Tolerance of mutations distal to the PAM in CLTA1 target sites. Distributions of mutations are shown for in vitro selection on 200 nM pre-selection library with 1000 nM Cas9:CLTA1 sgRNA v2.1. The number of mutations shown are in a 1-12 base pair target site subsequence farthest from the PAM (FIG. 14A-14L) when the rest of the target site, including the PAM, contains only on-target base pairs. The pre-selection and post-selection distributions are similar for up to three base pairs, demonstrating tolerance for target sites with mutations in the three base pairs farthest from the PAM when the rest of the target sites have optimal interactions with the Cas9:sgRNA. For all panels, graphs were generated from pre-selection library sequences and post-selection library sequences with an n≥5,130 and n≥74,538, respectively.
Figure 14B:
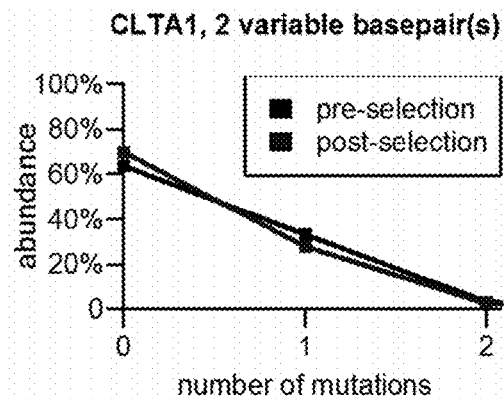
Figure 14C:
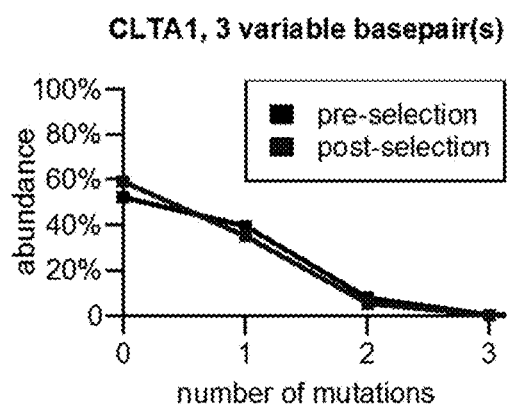
Figure 14D:
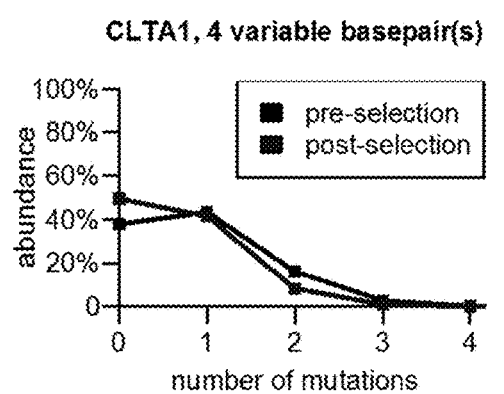
Figure 14E:
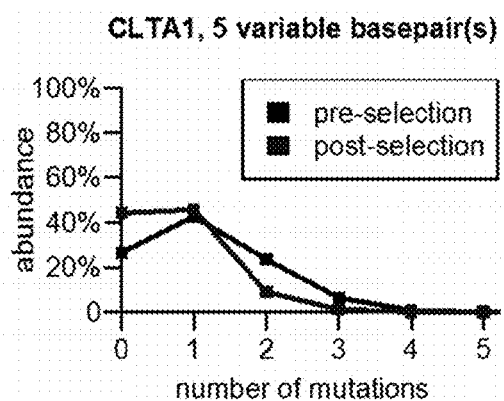
Figure 14F:
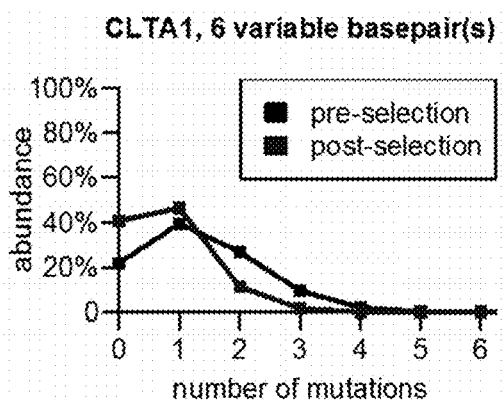
Figure 14G:
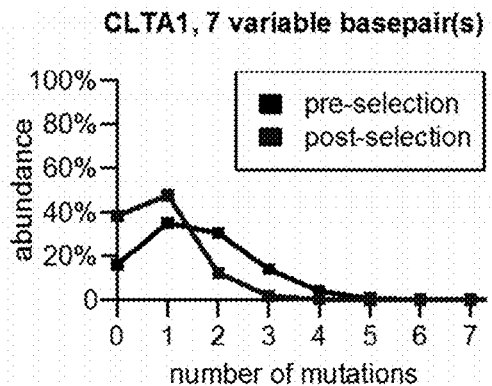
Figure 14H:
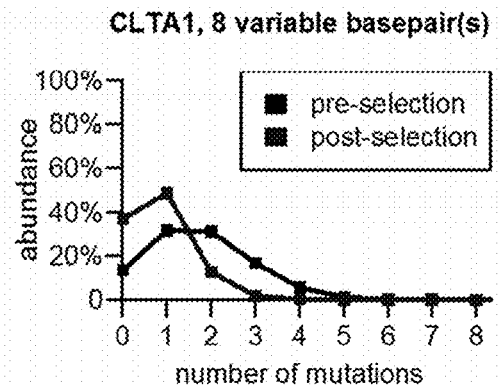
Figure 14I:
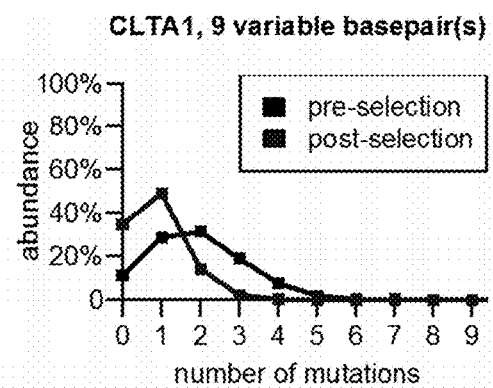
Figure 14J:
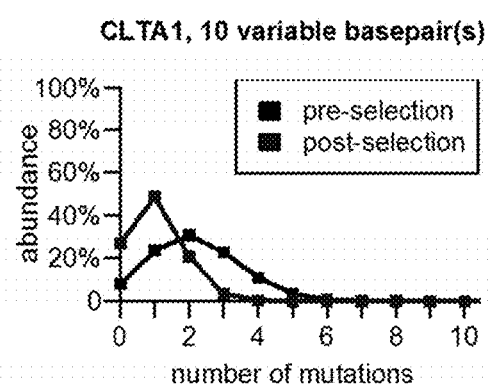
Figure 14K:
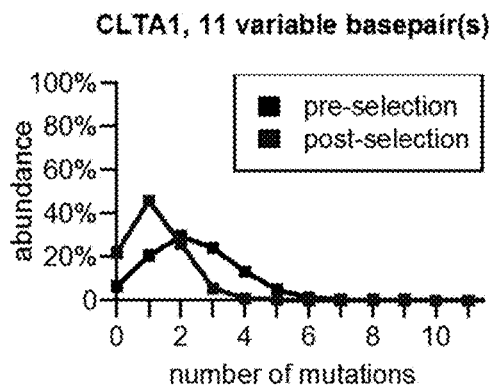
Figure 14L:
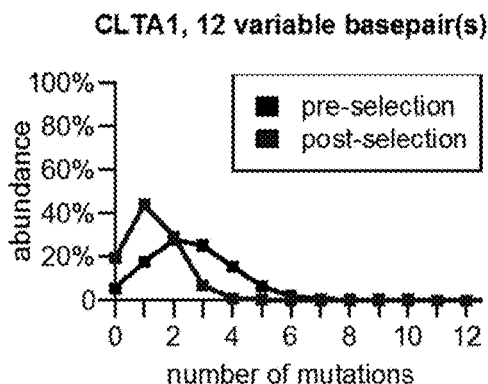
Figure 15A:
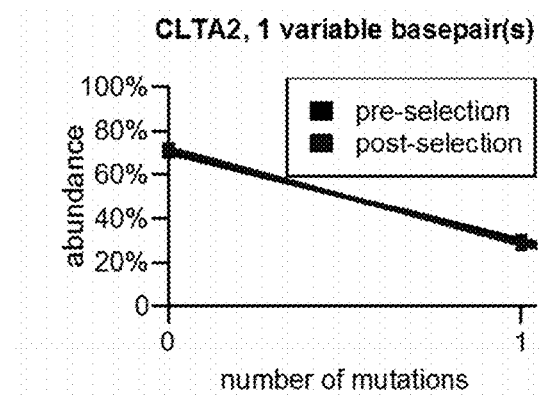
FIGS. 15A-15L. Tolerance of mutations distal to the PAM in CLTA2 target sites. Distributions of mutations are shown for in vitro selection on 200 nM pre-selection library with 1000 nM Cas9:CLTA2 sgRNA v2.1. The number of mutations shown are in a 1-12 base pair target site subsequence farthest from the PAM (FIGS. 15A-15L) when the rest of the target site, including the PAM, contains only on-target base pairs. The pre-selection and post-selection distributions are similar for up to three base pairs, demonstrating tolerance for target sites with mutations in the three base pairs farthest from the PAM when the rest of the target sites have optimal interactions with the Cas9:sgRNA. For all panels, graphs were generated from pre-selection library sequences and post-selection library sequences with an n≥3,190 and n≥21,265, respectively.
Figure 15B:
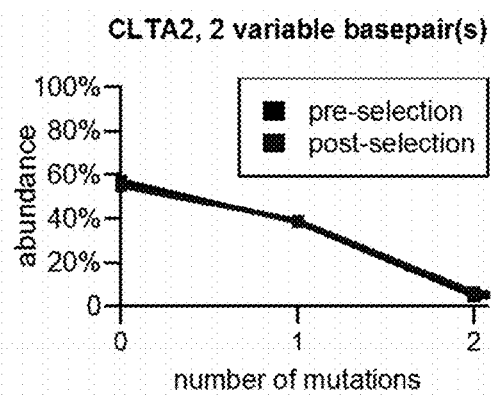
Figure 15C:
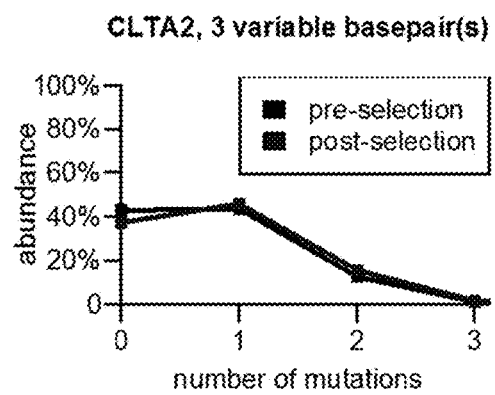
Figure 15D:
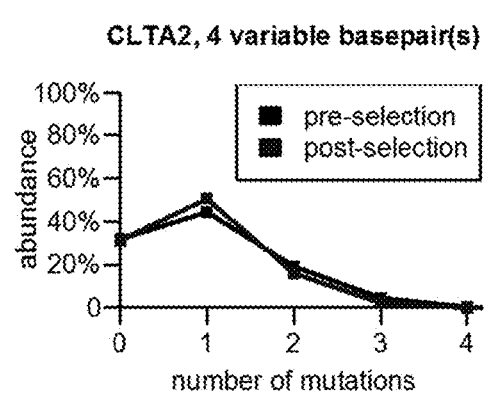
Figure 15E:
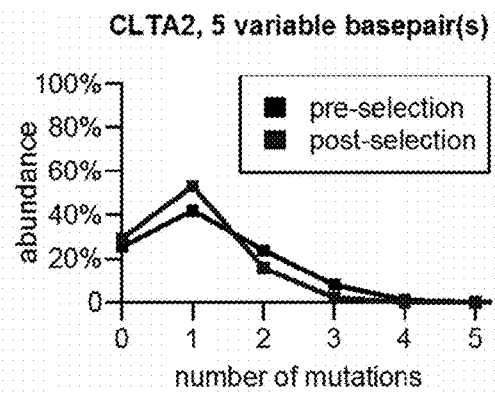
Figure 15F:
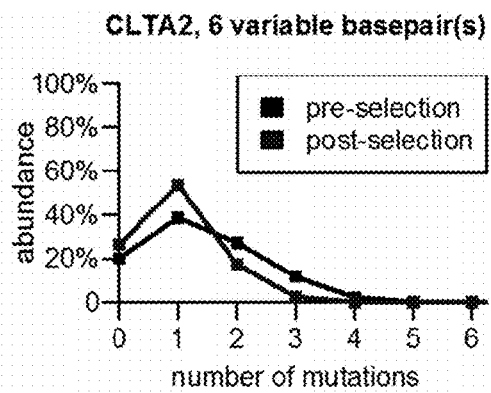
Figure 15G:
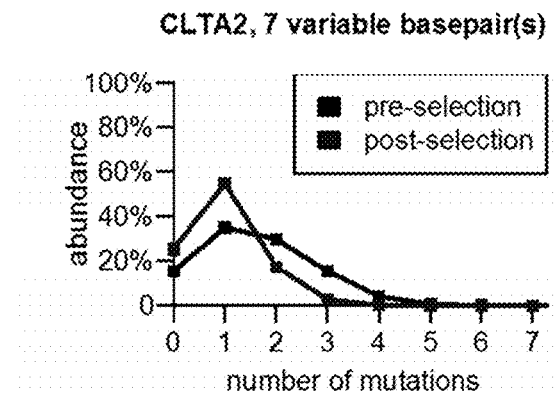
Figure 15H:
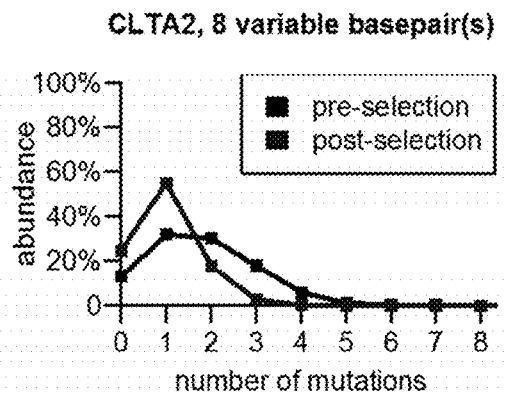
Figure 15I:
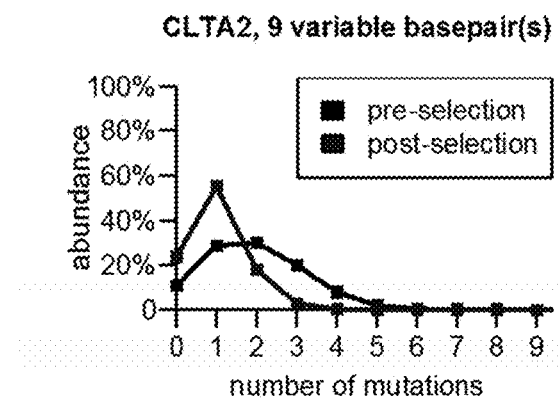
Figure 15J:
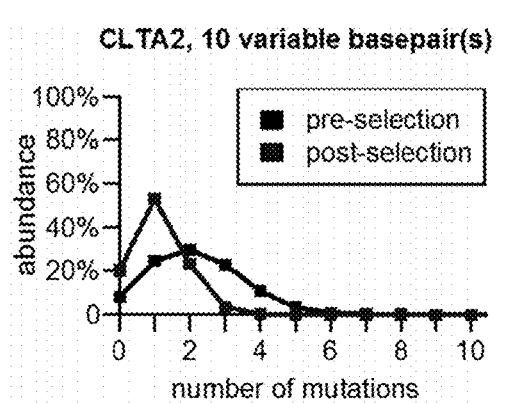
Figure 15K:
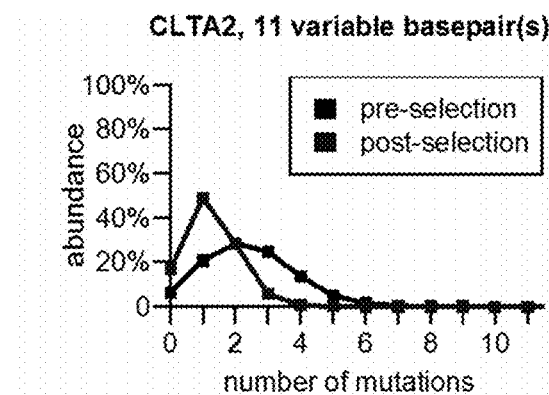
Figure 15L:
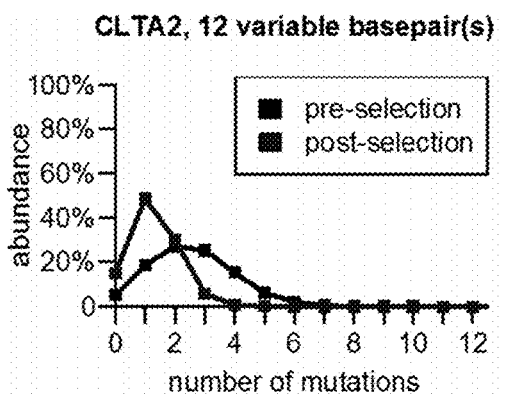
Figure 16A:
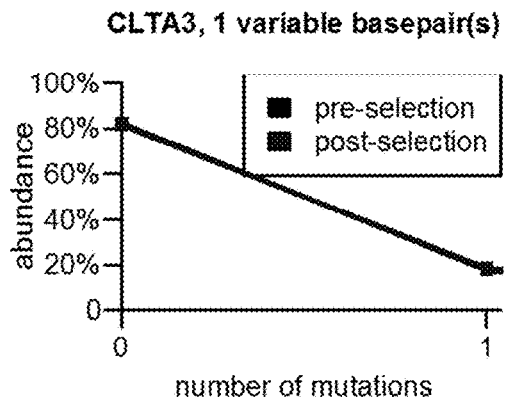
FIGS. 16A-16L. Tolerance of mutations distal to PAM in CLTA3 target sites. Distributions of mutations are shown for in vitro selection on 200 nM pre-selection library with 1000 nM Cas9:CLTA3 sgRNA v2.1. The number of mutations shown are in a 1-12 base pair target site subsequence farthest from the PAM (FIGS. 16A-16L) when the rest of the target site, including the PAM, contains only on-target base pairs. The pre-selection and post-selection distributions are similar for up to three base pairs, demonstrating tolerance for target sites with mutations in the three base pairs farthest from the PAM when the rest of the target sites have optimal interactions with the Cas9:sgRNA. For all panels, graphs were generated from pre-selection library sequences and post-selection library sequences with an n≥5,604 and n≥158,424, respectively.
Figure 16B:
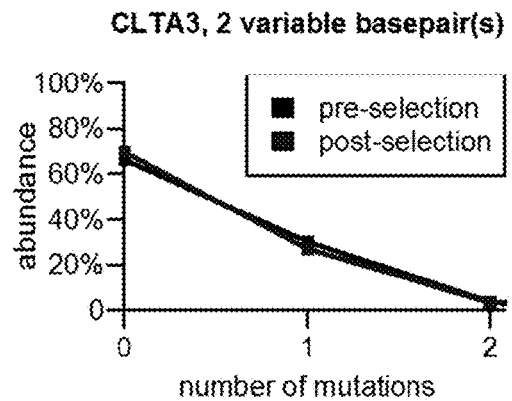
Figure 16C:
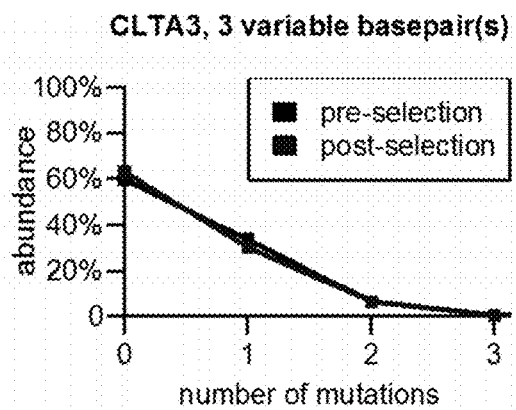
Figure 16D:
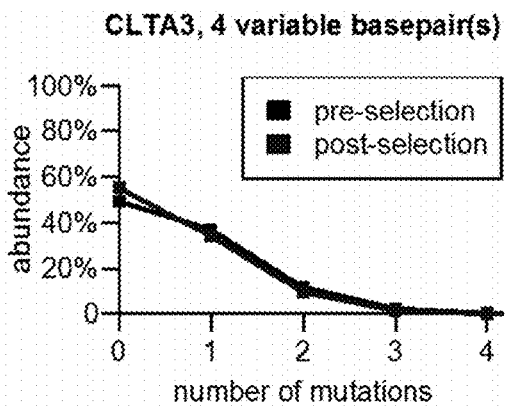
Figure 16E:
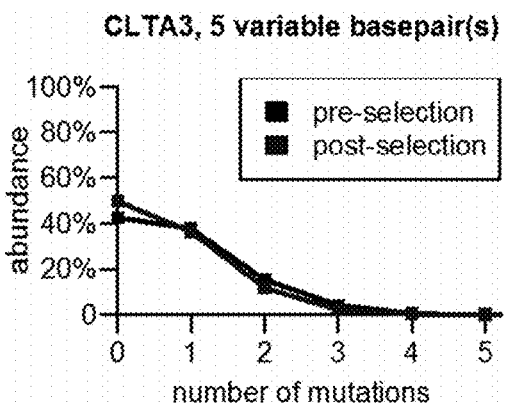
Figure 16F:
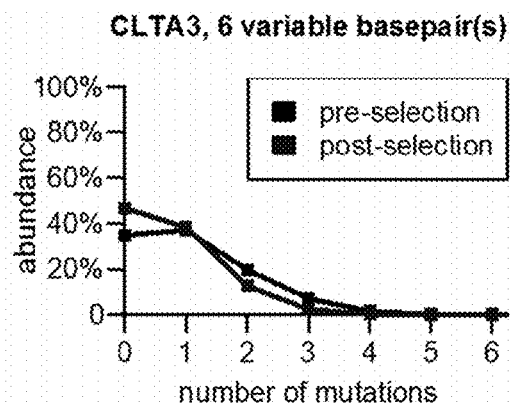
Figure 16G:
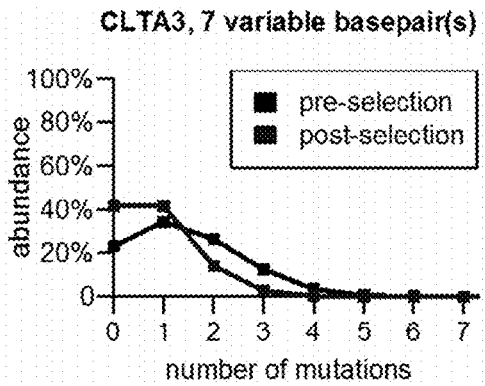
Figure 16H:
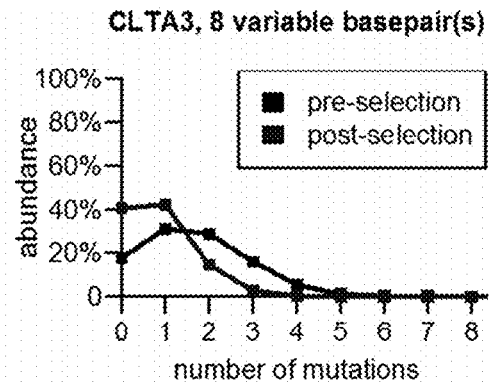
Figure 16I:
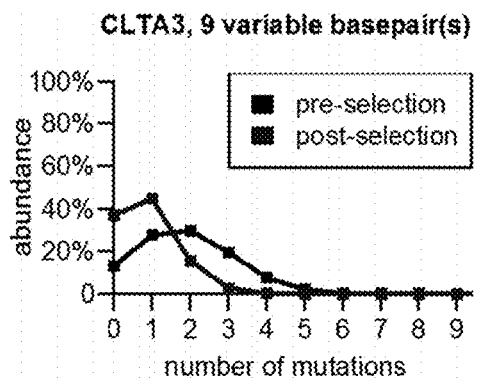
Figure 16J:
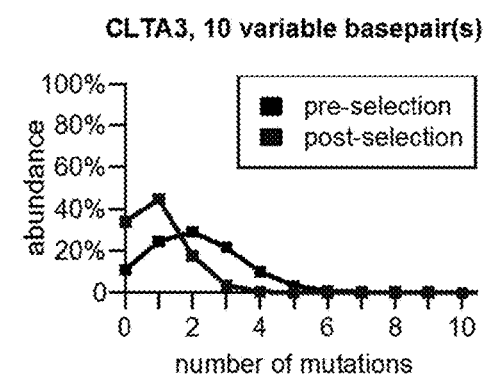
Figure 16K:
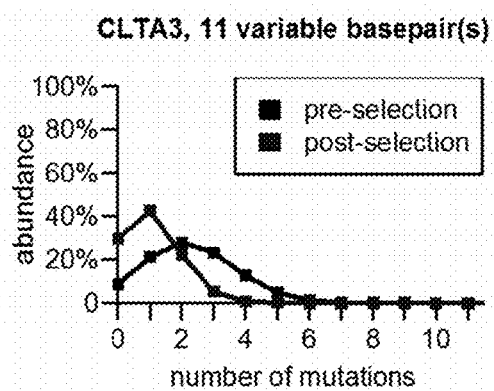
Figure 16L:
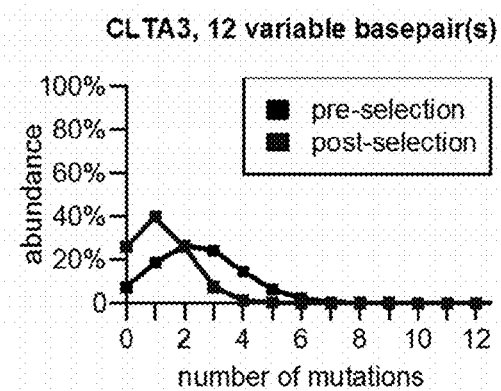
Figure 17A:
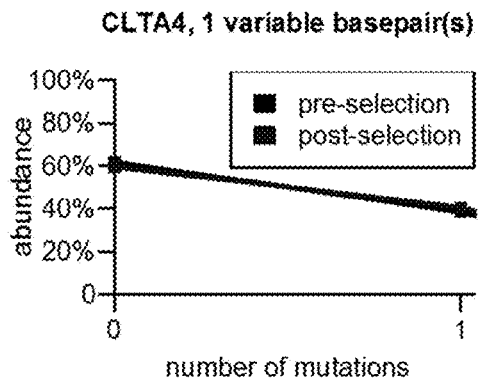
FIGS. 17A-17L. Tolerance of mutations distal to PAM in CLTA4 target sites. Distributions of mutations are shown for in vitro selection on 200 nM pre-selection library with 1000 nM Cas9:CLTA4 sgRNA v2.1. The number of mutations shown are in a 1-12 base pair target site subsequence farthest from the PAM (FIGS. 17A-17L) when the rest of the target site, including the PAM, contains only on-target base pairs. The pre-selection and post-selection distributions are similar for up to three base pairs, demonstrating tolerance for target sites with mutations in the three base pairs farthest from the PAM when the rest of the target sites have optimal interactions with the Cas9:sgRNA. For all panels, graphs were generated from pre-selection library sequences and post-selection library sequences with an n≥2,323 and n≥21,819, respectively.
Figure 17B:
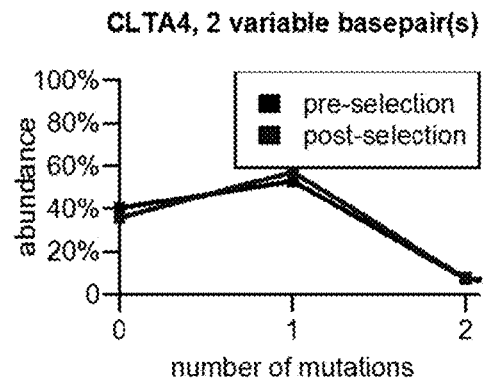
Figure 17C:
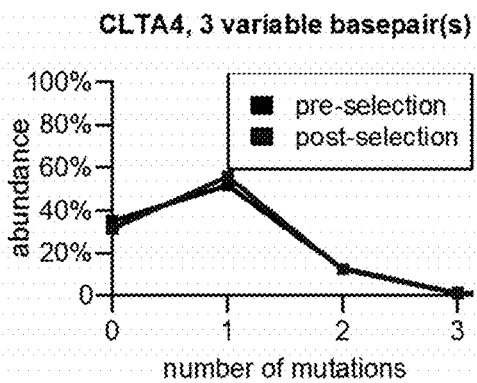
Figure 17D:
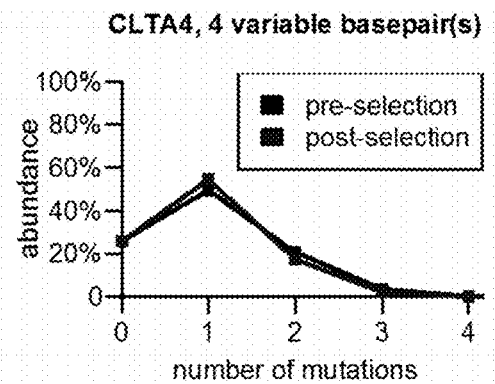
Figure 17E:
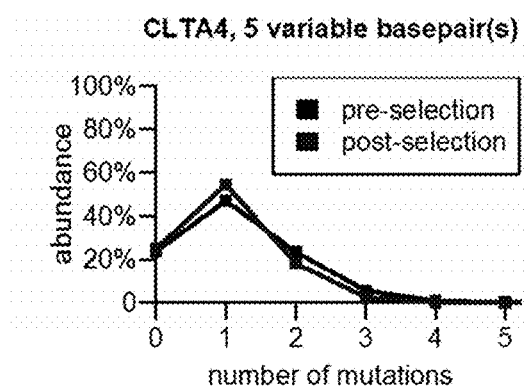
Figure 17F:
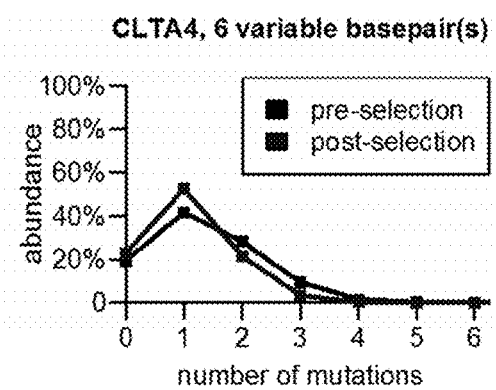
Figure 17G:
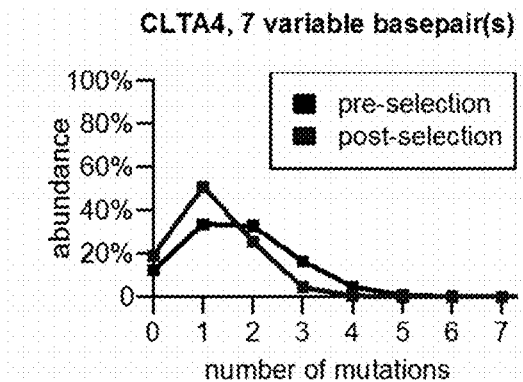
Figure 17H:
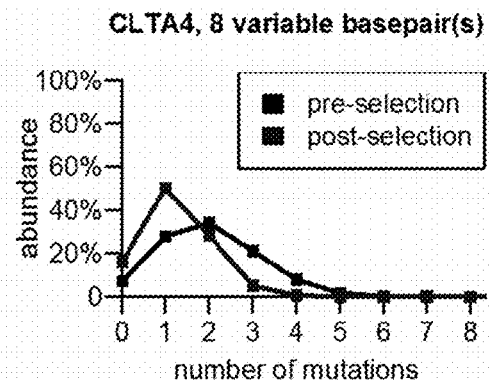
Figure 17I:
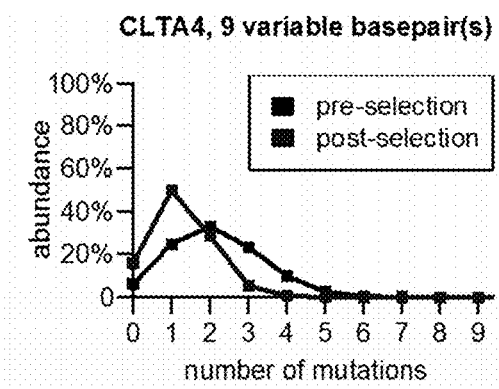
Figure 17J:
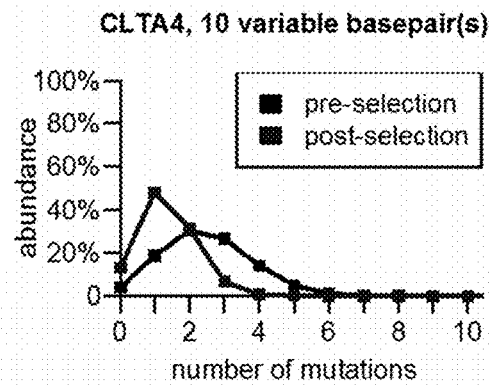
Figure 17K:
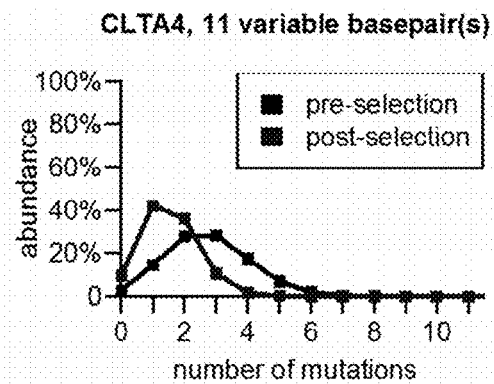
Figure 17L:
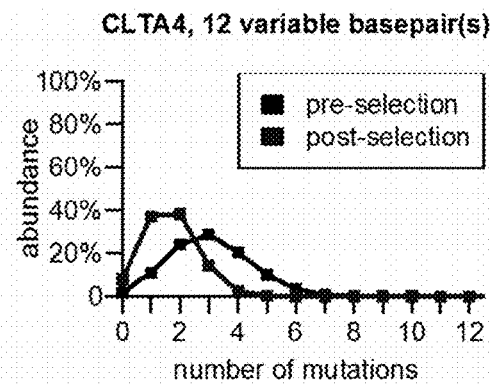
Figure 18A:
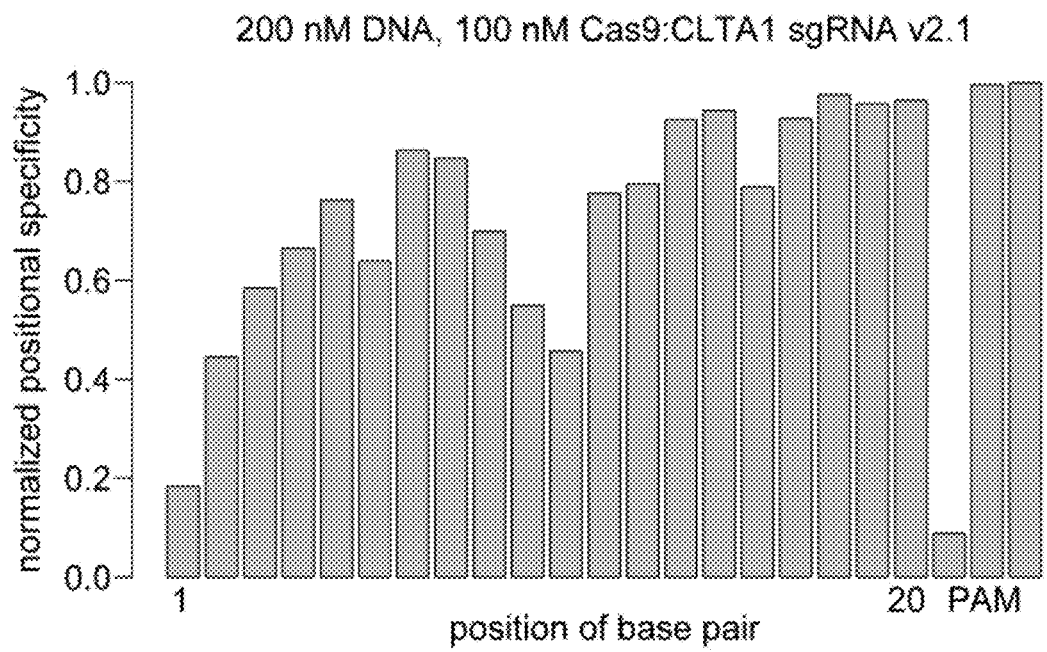
FIGS. 18A-18D. Positional specificity patterns for 100 nM Cas9:sgRNA v2.1. Positional specificity, defined as the sum of the magnitude of the specificity score for each of the four possible base pairs recognized at a certain position in the target site, is plotted for each target site under enzyme-limiting conditions for sgRNA v2.1 (FIGS. 18A-18D). The positional specificity is shown as a value normalized to the maximum positional specificity value of the target site. Positional specificity is highest at the end of the target site proximal to the PAM and is lowest in the middle of the target site and in the several nucleotides most distal to the PAM.
Figure 18B:
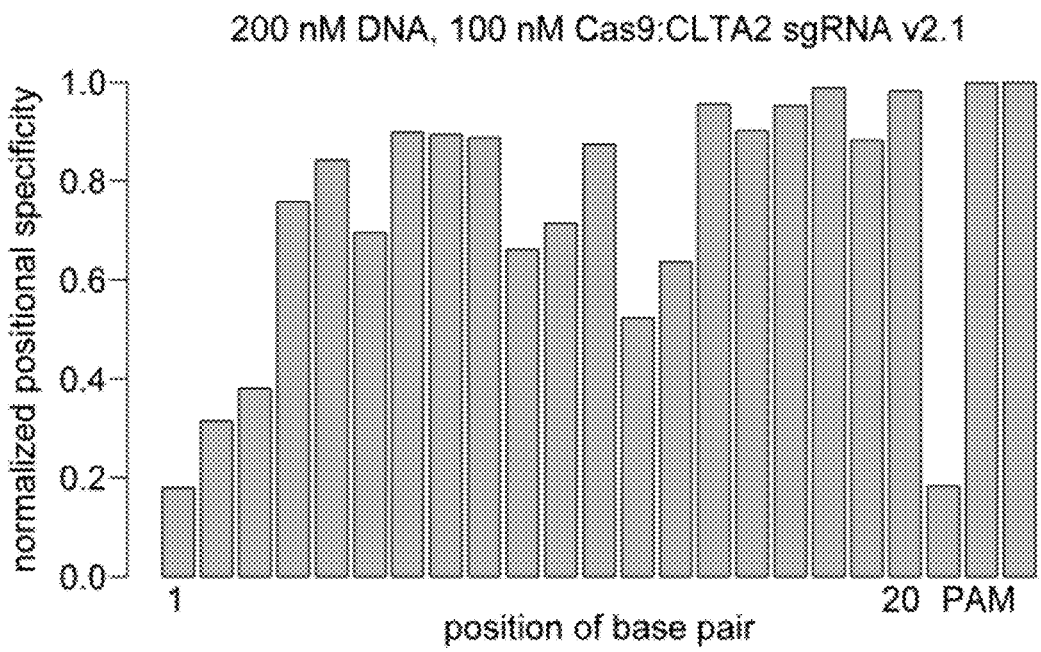
Figure 18C:
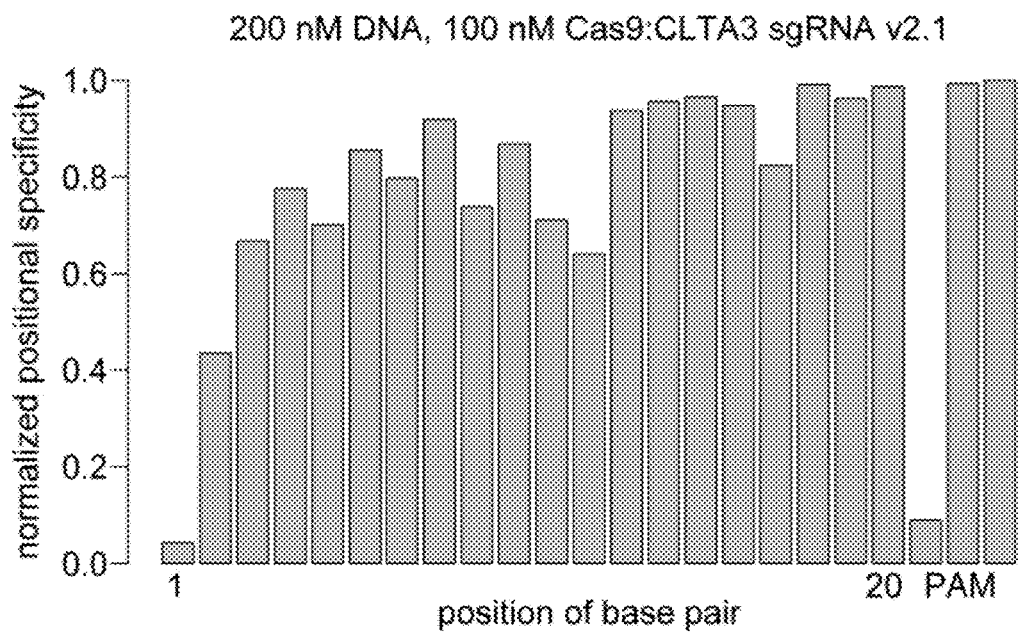
Figure 18D:
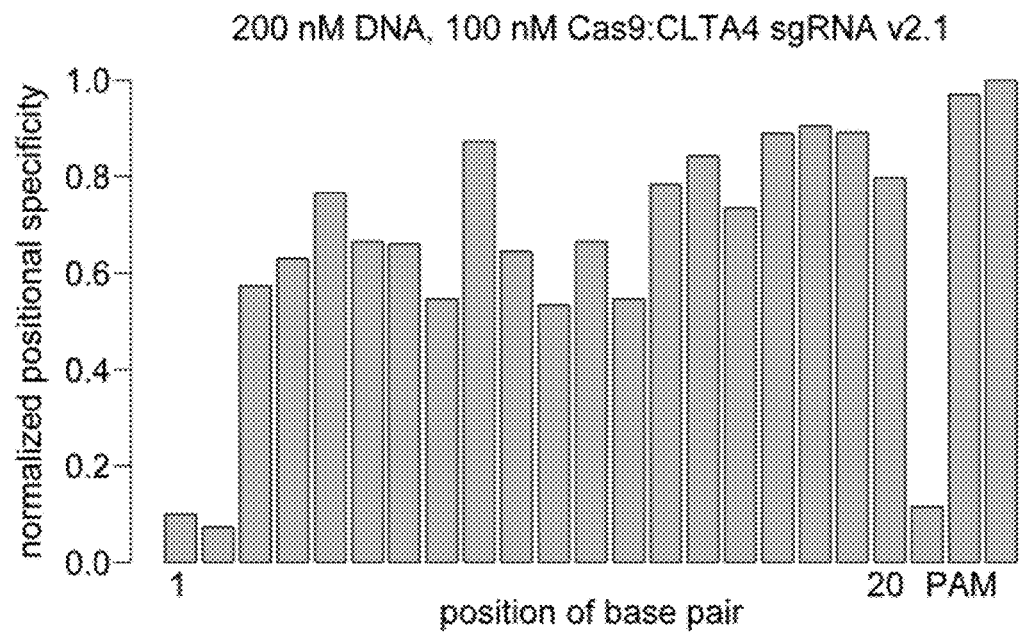
Figure 19A:
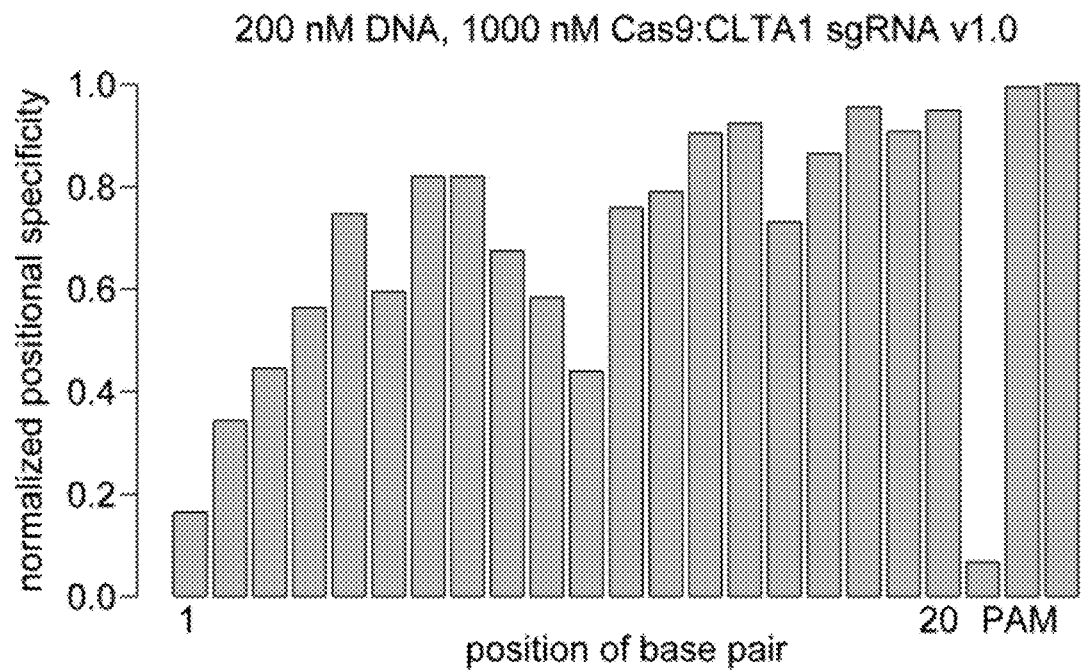
FIGS. 19A-19D. Positional specificity patterns for 1000 nM Cas9:sgRNA v1.0. Positional specificity, defined as the sum of the magnitude of the specificity score for each of the four possible base pairs recognized at a certain position in the target site, is plotted for each target site under enzyme-excess conditions with sgRNA v1.0 (FIGS. 19A-19D). The positional specificity is shown as a value normalized to the maximum positional specificity value of the target site. Positional specificity is relatively constant across the target site but is lowest in the middle of the target site and in the several nucleotides most distal to the PAM.
Figure 19B:
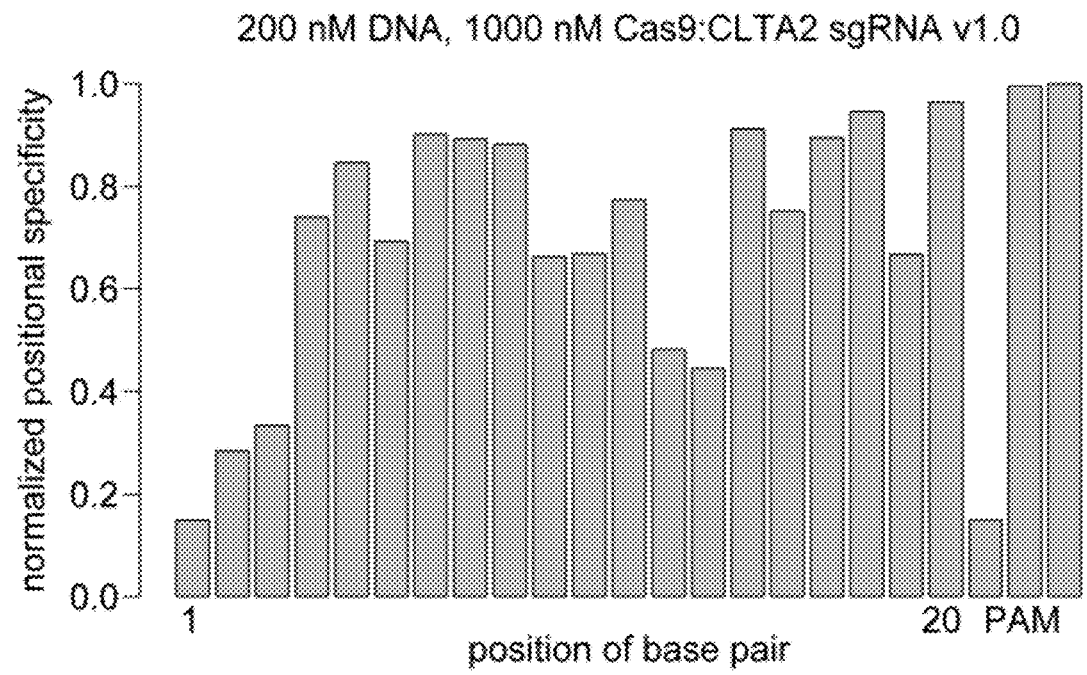
Figure 19C:
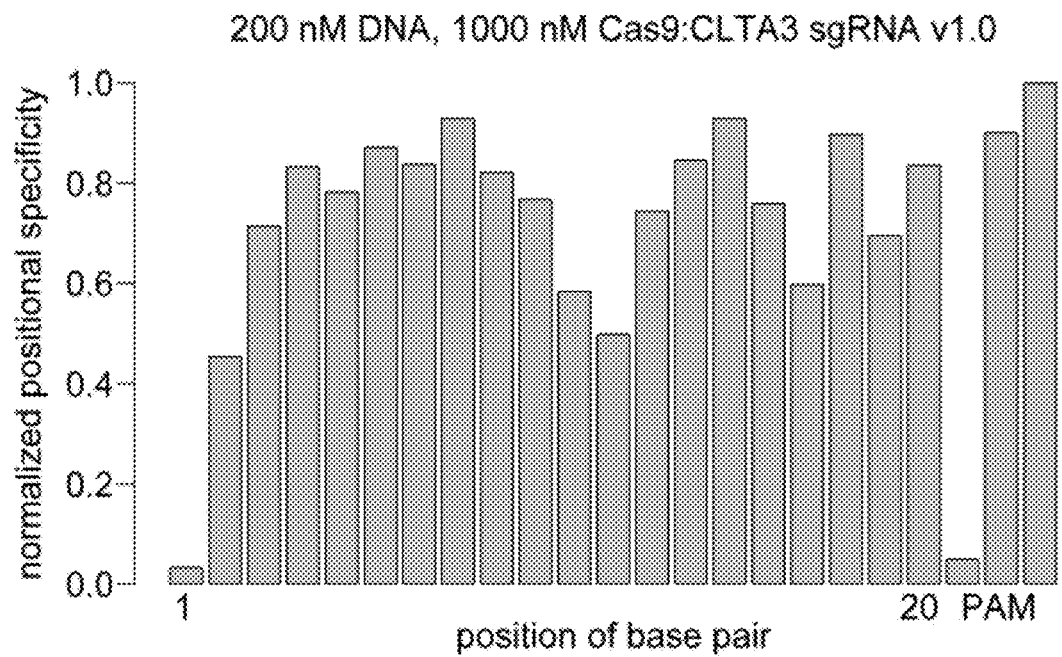
Figure 19D:
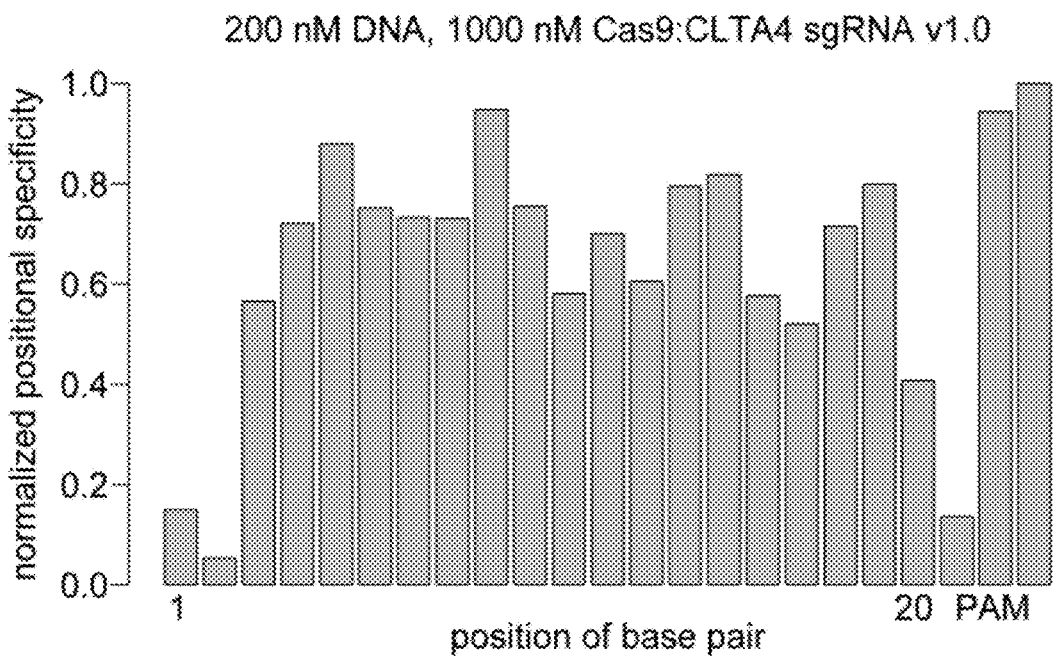
Figure 20A:
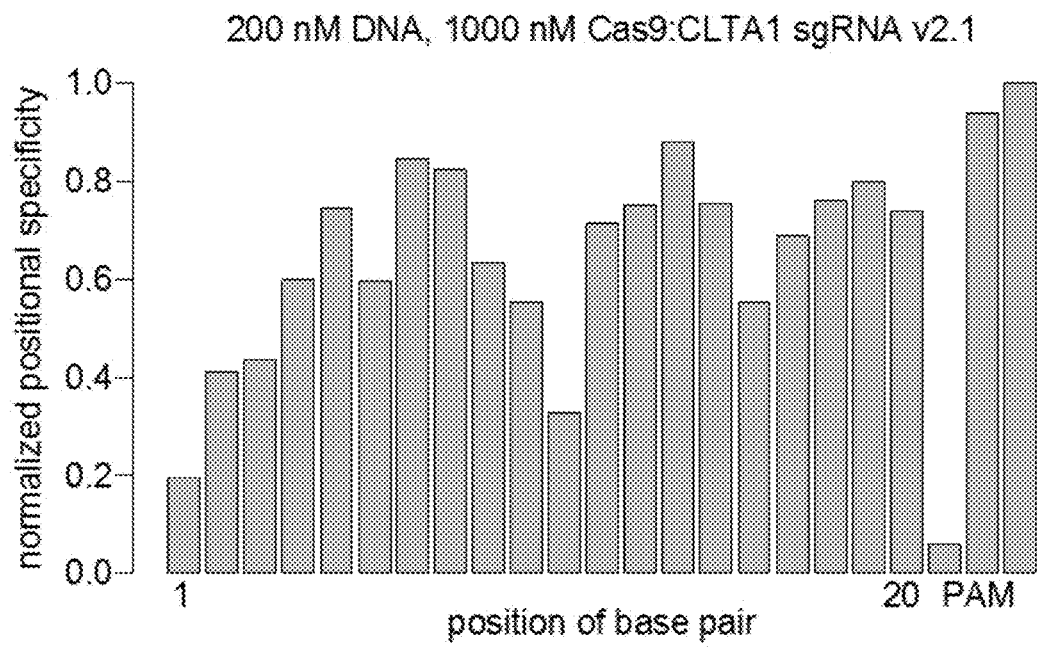
FIGS. 20A-20D. Positional specificity patterns for 1000 nM Cas9:sgRNA v2.1. Positional specificity, defined as the sum of the magnitude of the specificity score for each of the four possible base pairs recognized at a certain position in the target site, is plotted for each target site under enzyme-excess conditions with sgRNA v2.1 (FIGS. 20A-20D). The positional specificity is shown as a value normalized to the maximum positional specificity value of the target site. Positional specificity is relatively constant across the target site but is lowest in the middle of the target site and in the several nucleotides most distal to the PAM.
Figure 20B:
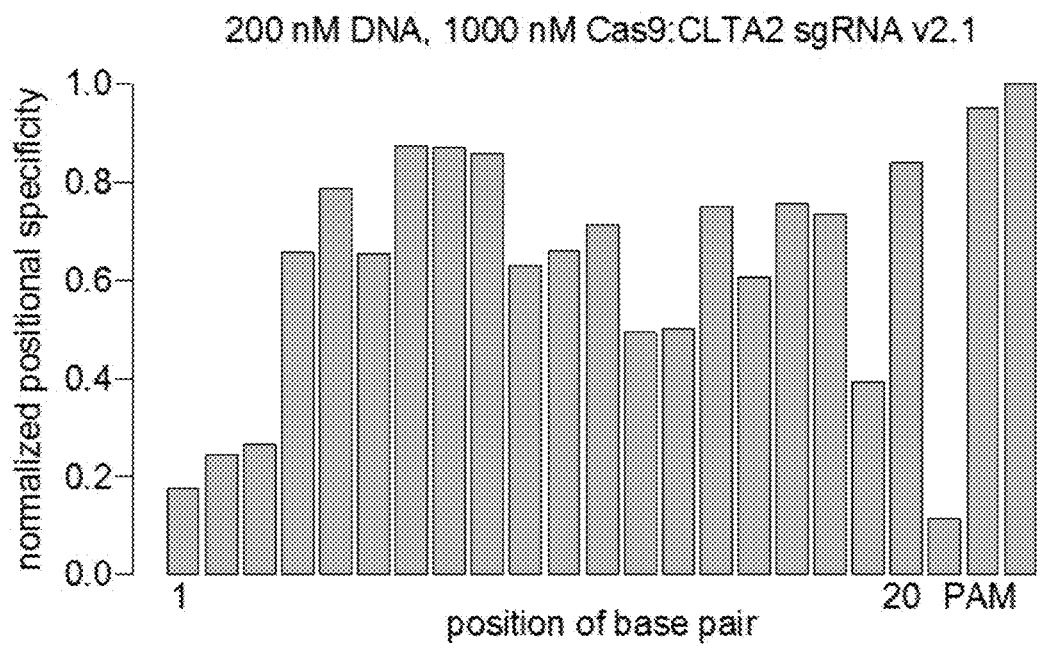
Figure 20C:
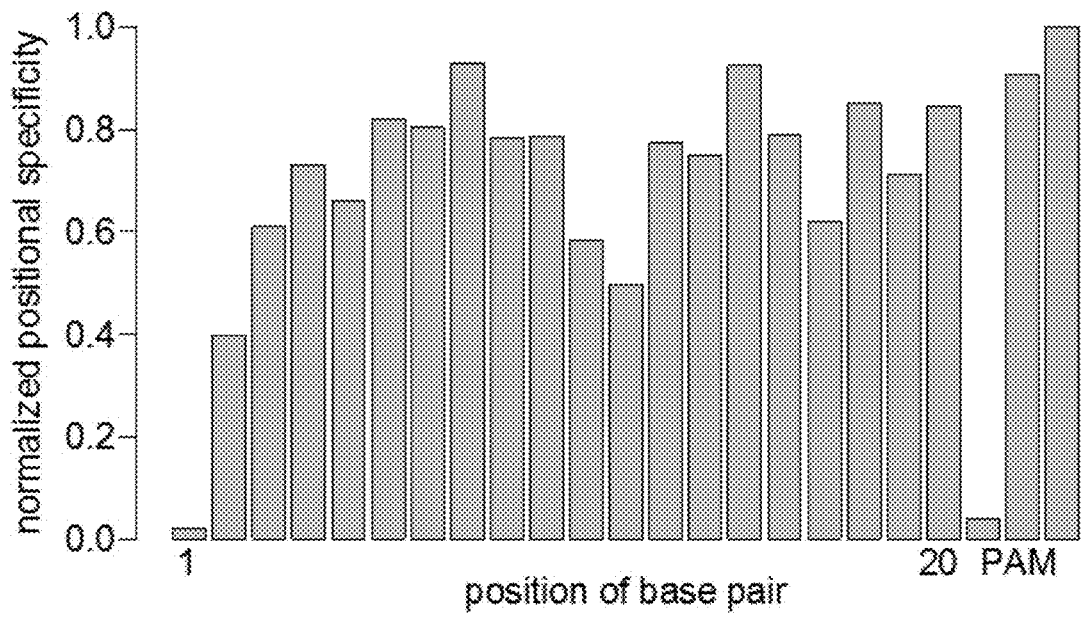
Figure 20D:
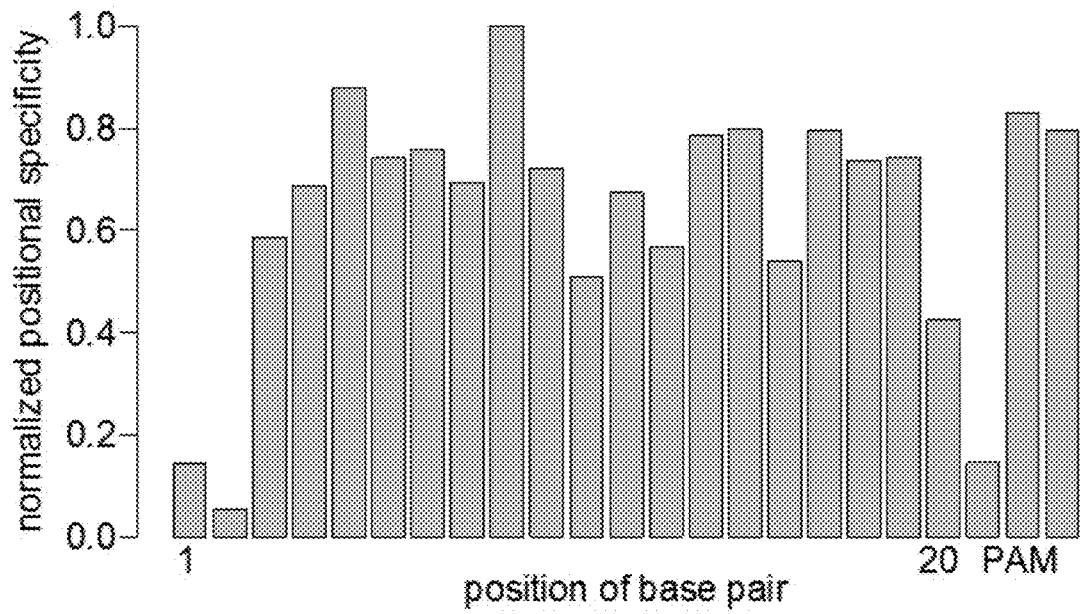
Figure 21A:
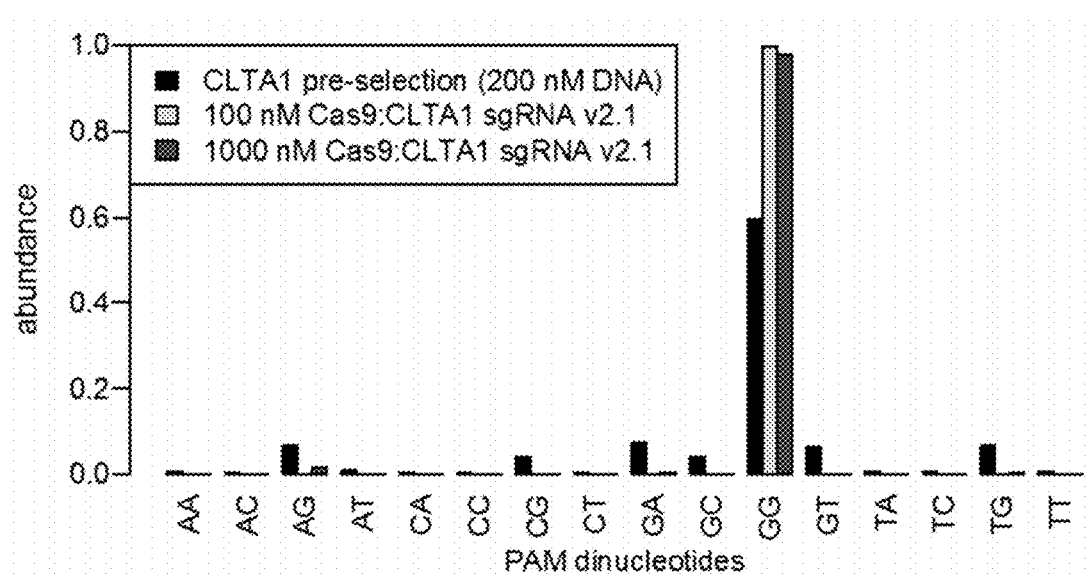
FIGS. 21A-21D. PAM nucleotide preferences. The abundance in the pre-selection library and post-selection libraries under enzyme-limiting or enzyme-excess conditions are shown for all 16 possible PAM dinucleotides for selections with CLTA1 (FIG. 21A), CLTA2 (FIG. 21B), CLTA3 (FIG. 21C), and CLTA4 (FIG. 21D) sgRNA v2.1. GG dinucleotides increased in abundance in the post-selection libraries, while the other possible PAM dinucleotides decreased in abundance after the selection.
Figure 21B:
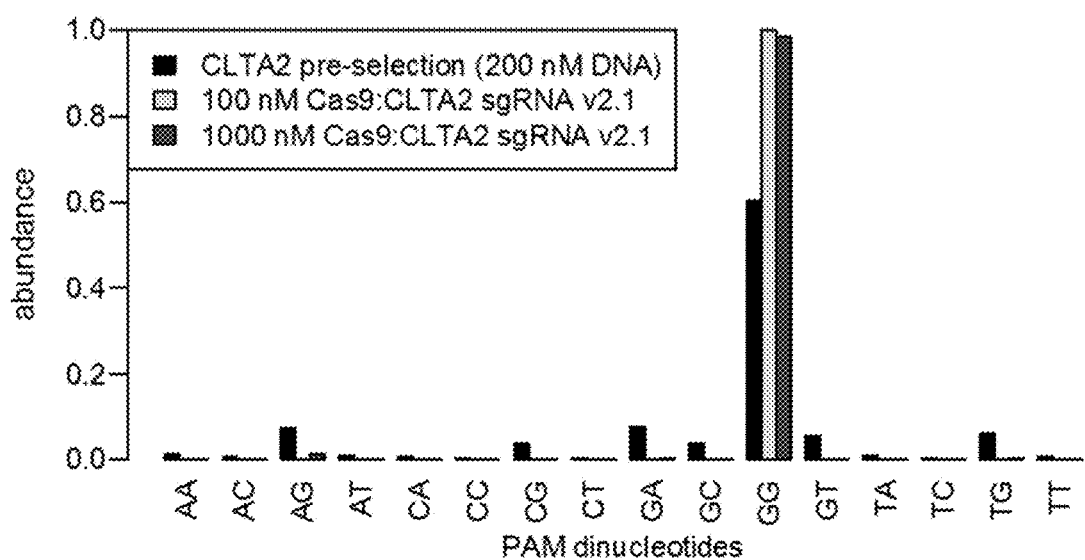
Figure 21C:
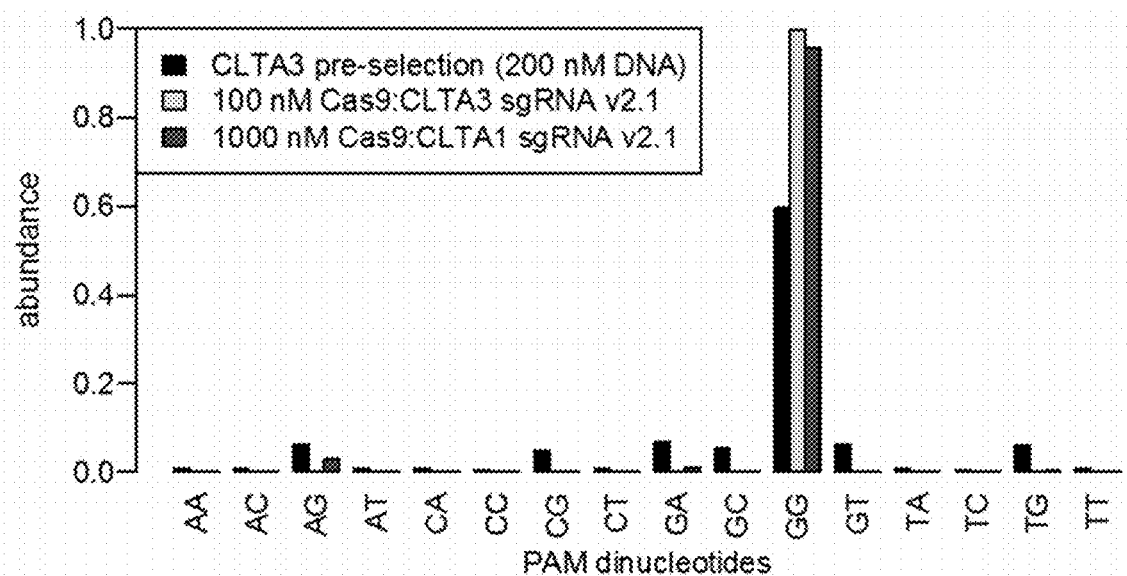
Figure 21D:
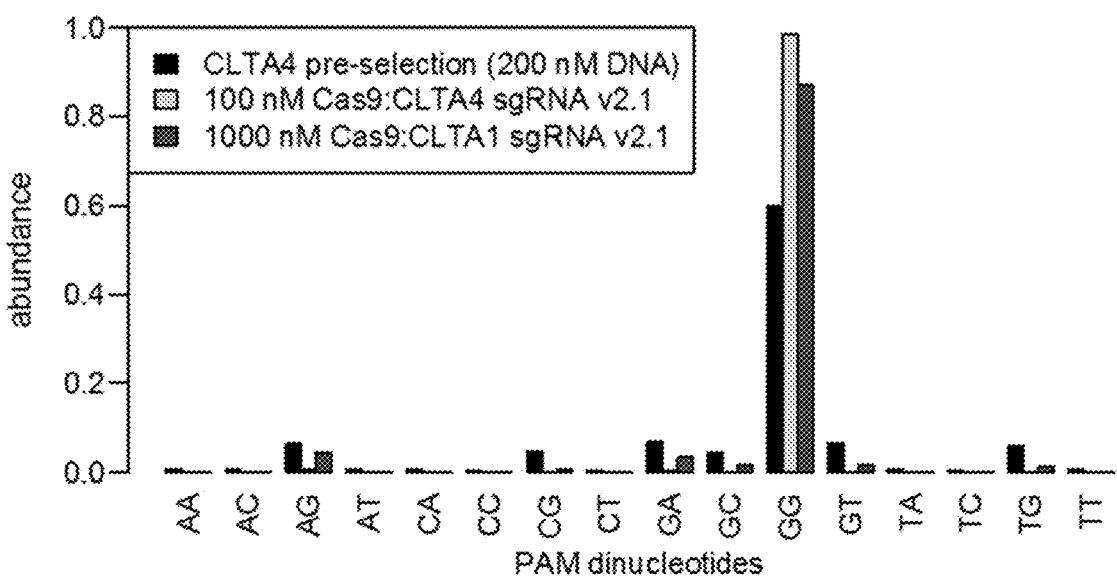
Figure 22A:
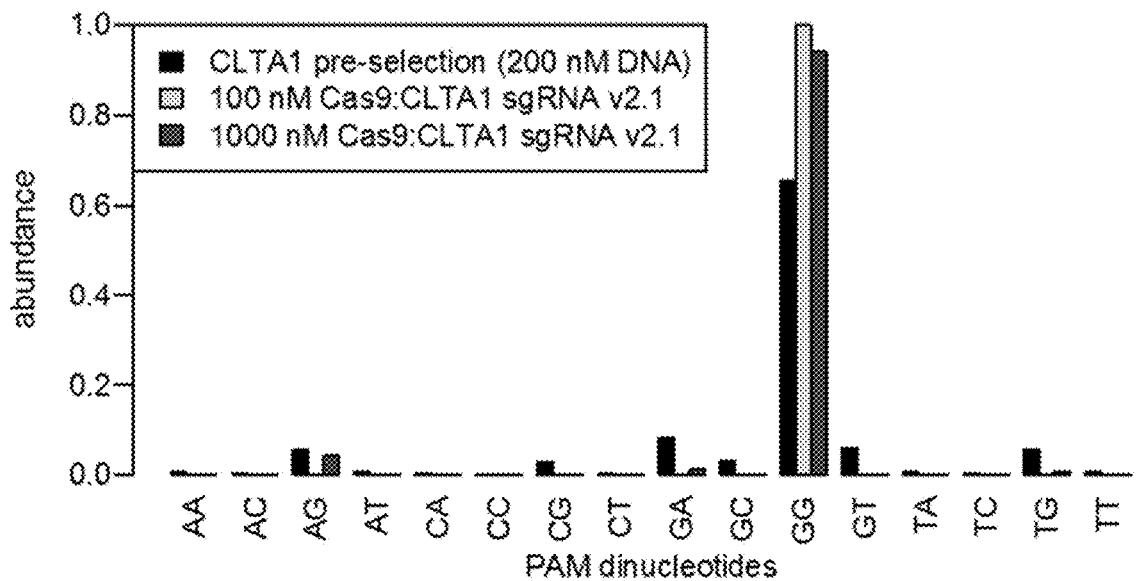
FIGS. 22A-22D. PAM nucleotide preferences for on-target sites. Only post-selection library members containing no mutations in the 20 base pairs specified by the guide RNAs were included in this analysis. The abundance in the pre-selection library and post-selection libraries under enzyme-limiting and enzyme-excess conditions are shown for all 16 possible PAM dinucleotides for selections with CLTA1 (FIG. 22A), CLTA2 (FIG. 22B), CLTA3 (FIG. 22C), and CLTA4 (FIG. 22D) sgRNA v2.1. GG dinucleotides increased in abundance in the post-selection libraries, while the other possible PAM dinucleotides generally decreased in abundance after the selection, although this effect for the enzyme-excess concentrations of Cas9:sgRNA was modest or non-existent for many dinucleotides.
Figure 22B:
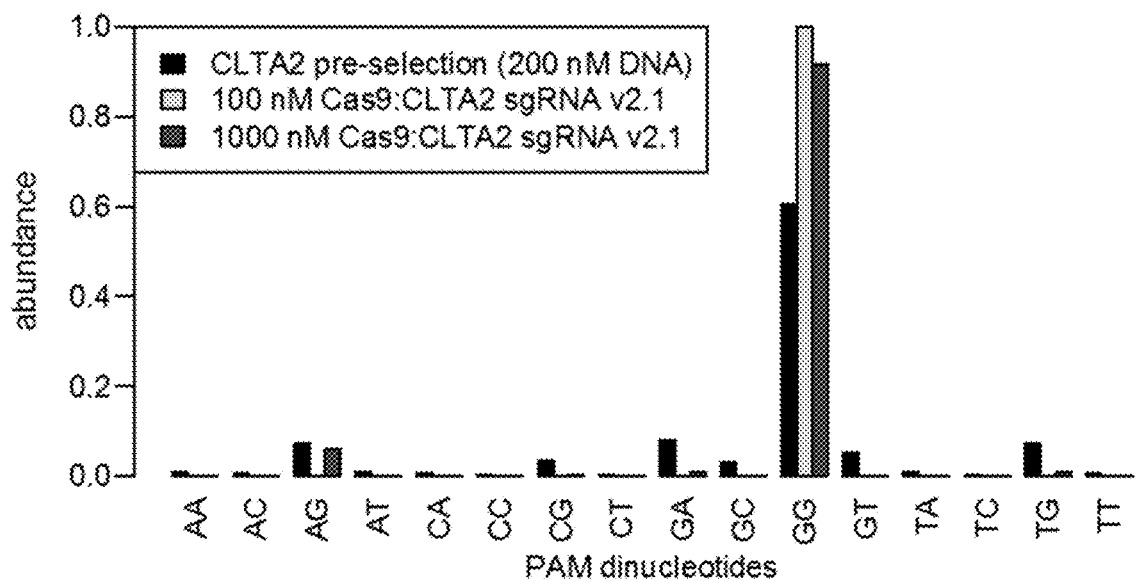
Figure 22C:
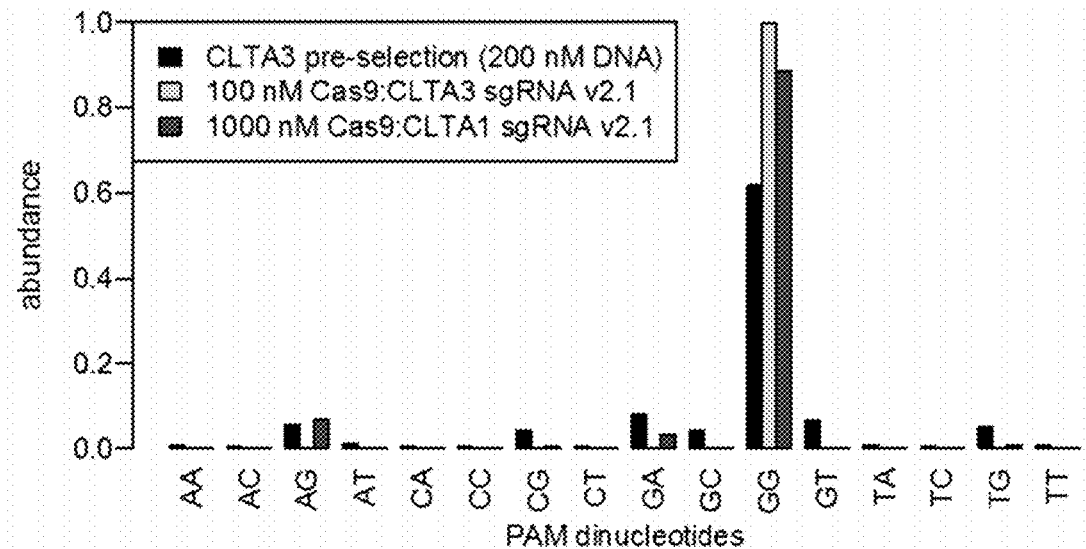
Figure 22D:
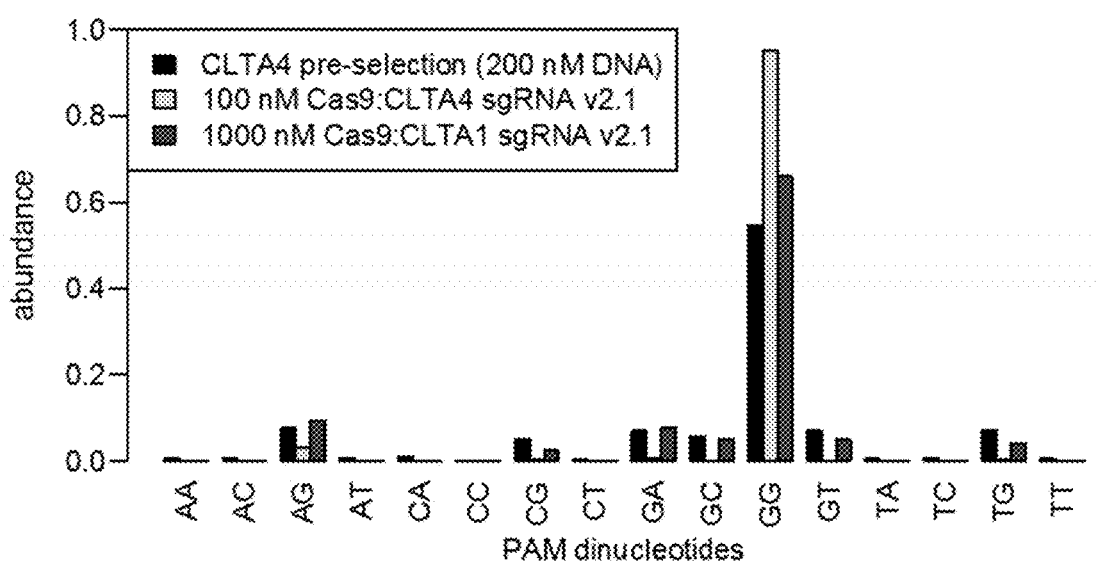
Figure 23A:
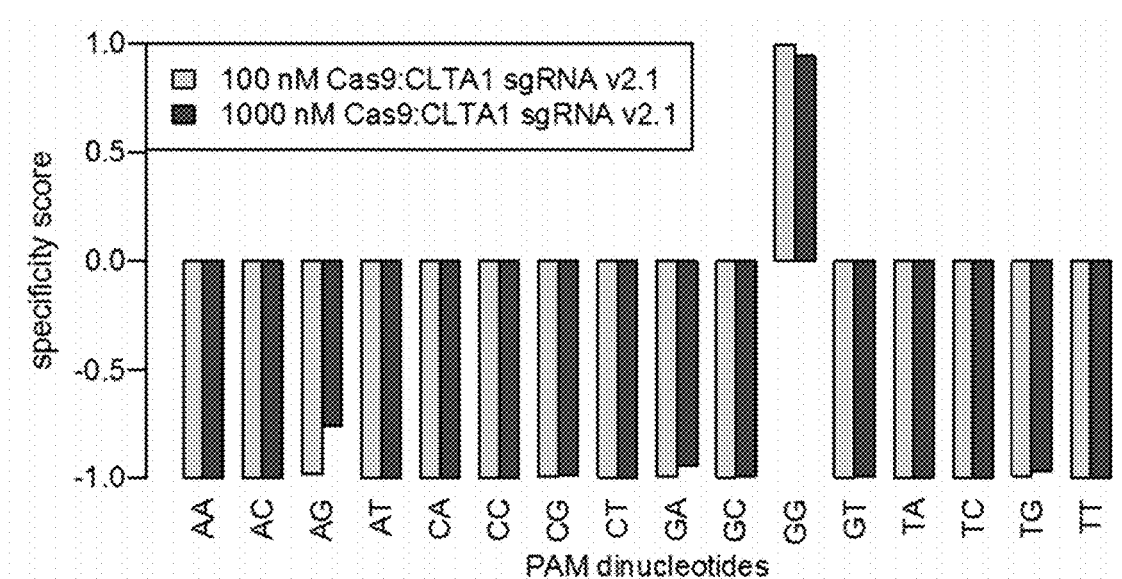
FIGS. 23A-23D. PAM dinucleotide specificity scores. The specificity scores under enzyme-limiting and enzyme-excess conditions are shown for all 16 possible PAM dinucleotides (positions 2 and 3 of the three-nucleotide NGG PAM) for selections with CLTA1 (FIG. 23A), CLTA2
Figure 23B:
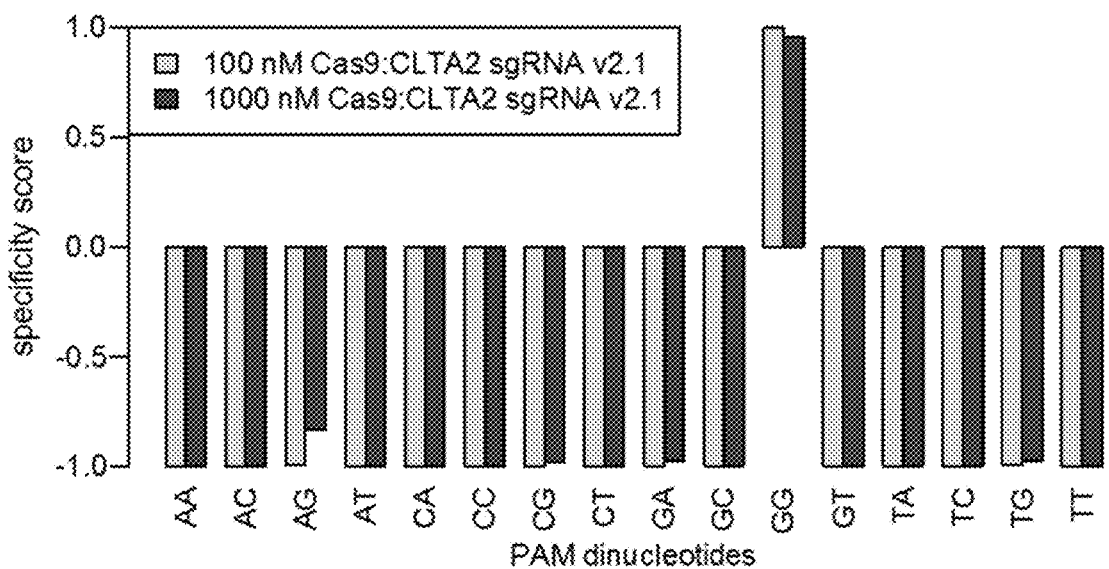
Figure 23C:
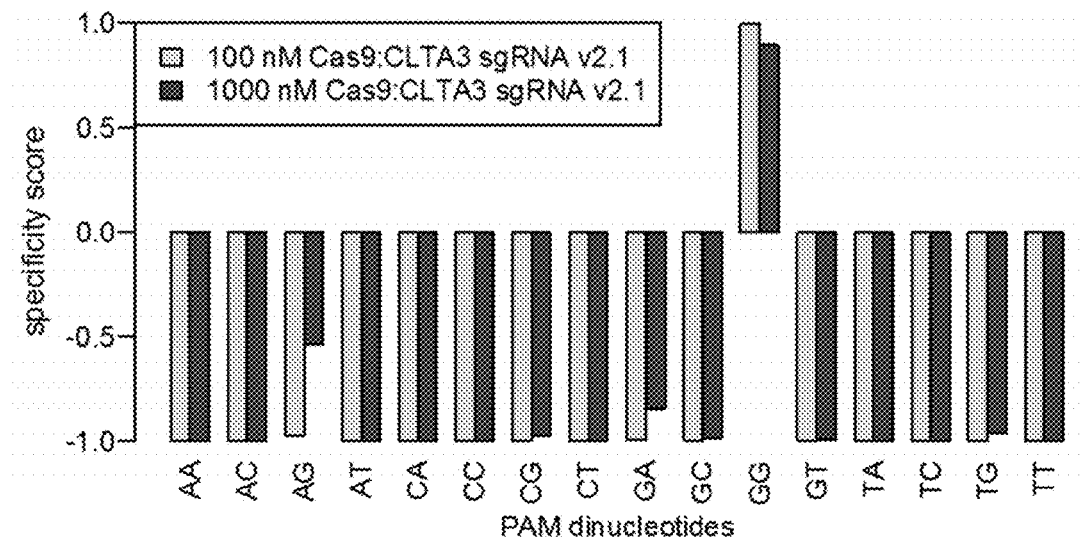
Figure 23D:
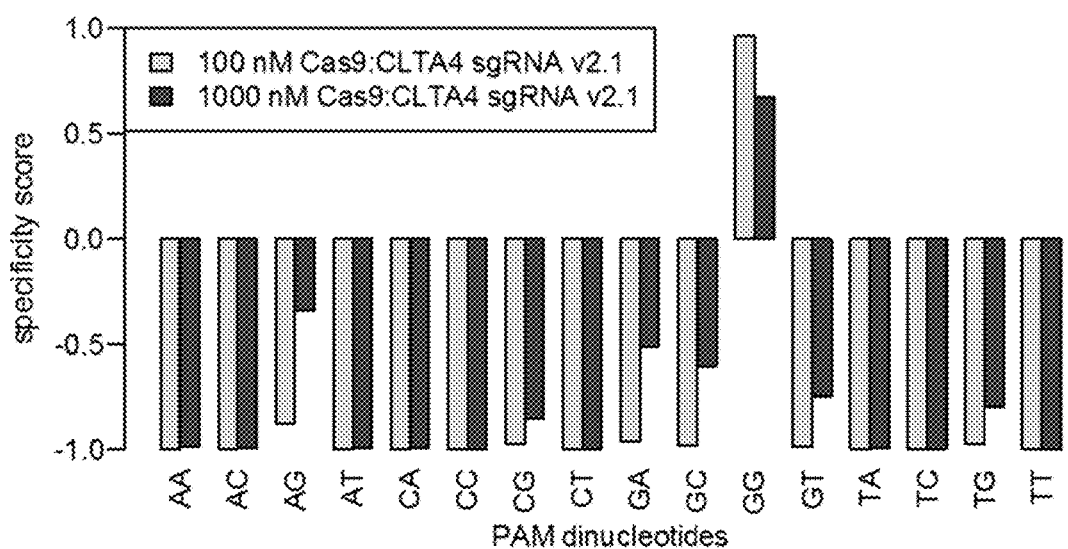
Figure 24A:
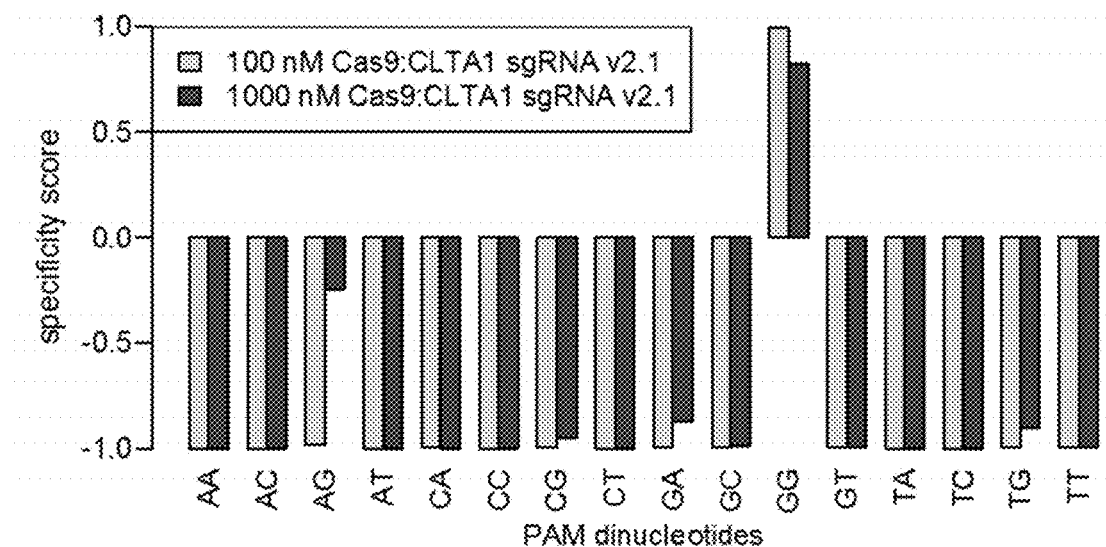
FIGS. 24A-24D. PAM dinucleotide specificity scores for on-target sites. Only post-selection library members containing no mutations in the 20 base pairs specified by the guide RNAs were included in this analysis. The specificity scores under enzyme-limiting and enzyme-excess conditions are shown for all 16 possible PAM dinucleotides (positions 2 and 3 of the three-nucleotide NGG PAM) for selections with CLTA1 (FIG. 24A), CLTA2 (FIG. 24B), CLTA3 (FIG. 24C), and CLTA4 (FIG. 24D) sgRNA v2.1. The specificity score indicates the enrichment of the PAM dinucleotide in the post-selection library relative to the pre-selection library, normalized to the maximum possible enrichment of that dinucleotide. A specificity score of +1.0 indicates that a dinucleotide is 100% enriched in the post-selection library, and a specificity score of −1.0 indicates that a dinucleotide is 100% de-enriched. GG dinucleotides were the most enriched in the post-selection libraries, AG and GA nucleotides were neither enriched or de-enriched in at least one selection condition, and GC, GT, and TG show less relative de-enrichment compared to the other possible PAM dinucleotides.
Figure 24B:
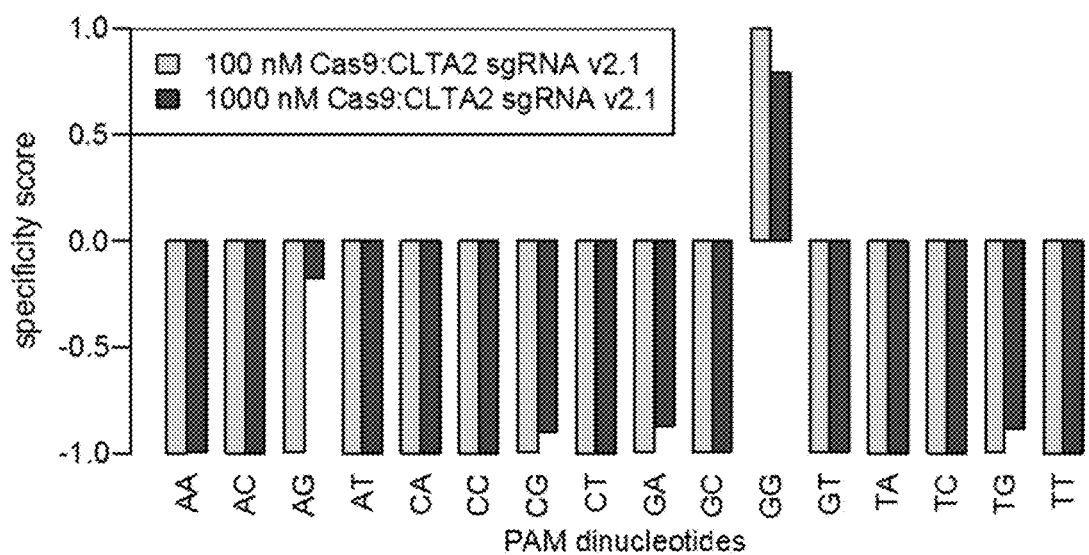
Figure 24C:
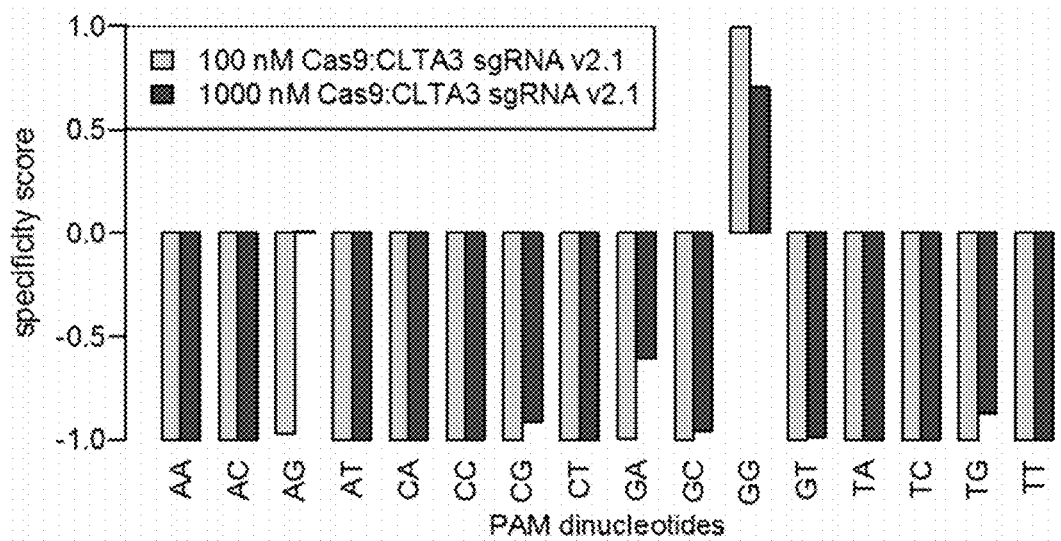
Figure 24D:
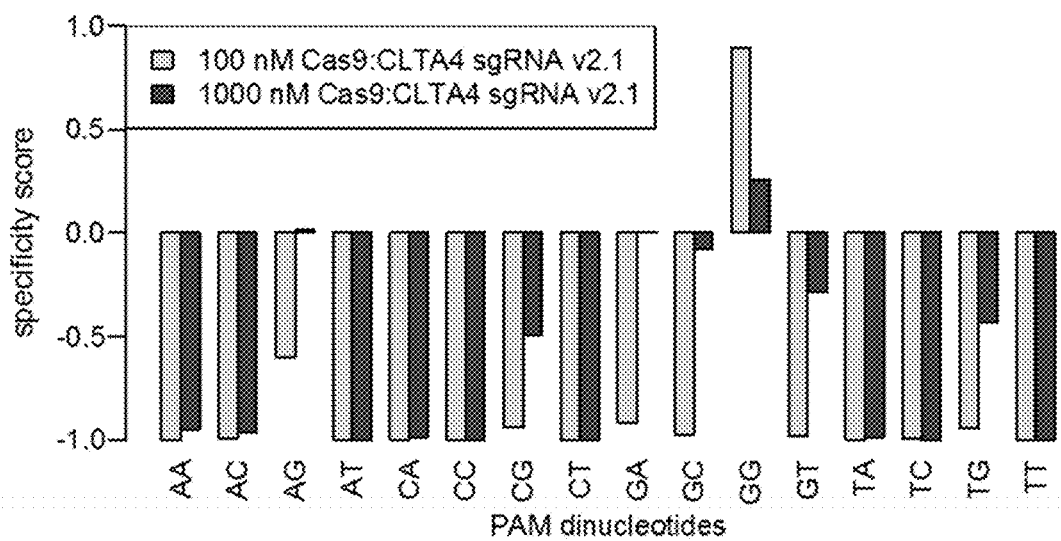
Figure 25A:
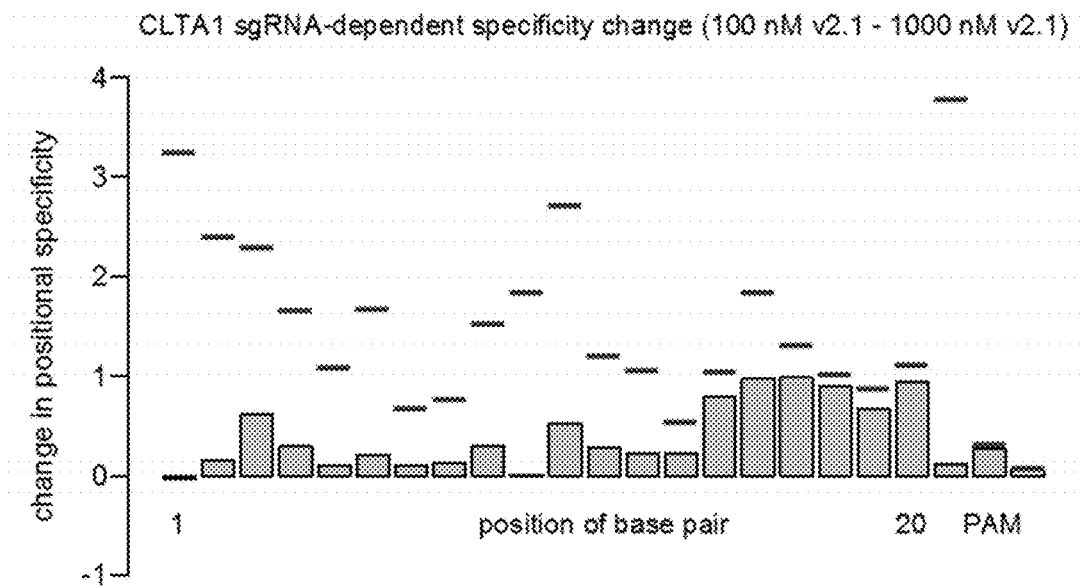
FIGS. 25A-25D. Effects of Cas9:sgRNA concentration on specificity. Positional specificity changes between enzyme-limiting (200 nM DNA, 100 nM Cas9:sgRNA v2.1) and enzyme-excess (200 nM DNA, 1000 nM Cas9:sgRNA v2.1) conditions are shown for selections with sgRNAs targeting CLTA1 (FIG. 25A), CLTA2 (FIG. 25B), CLTA3 (FIG. 25C), and CLTA4 (FIG. 25D) target sites. Lines indicate the maximum possible change in positional specificity for a given position. The highest changes in specificity occur proximal to the PAM as enzyme concentration is increased.
Figure 25B:
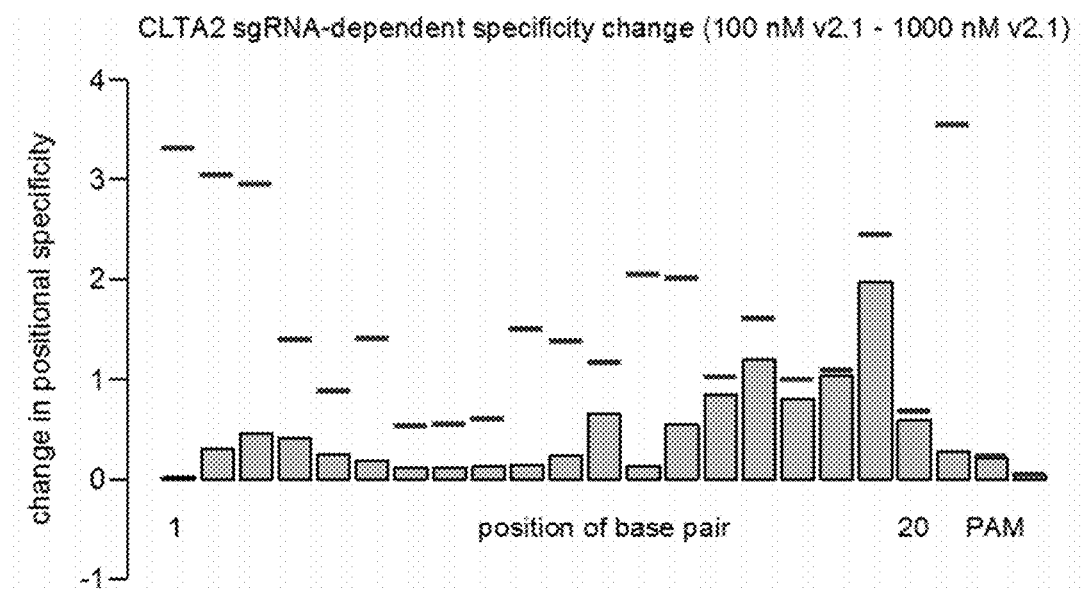
Figure 25C:
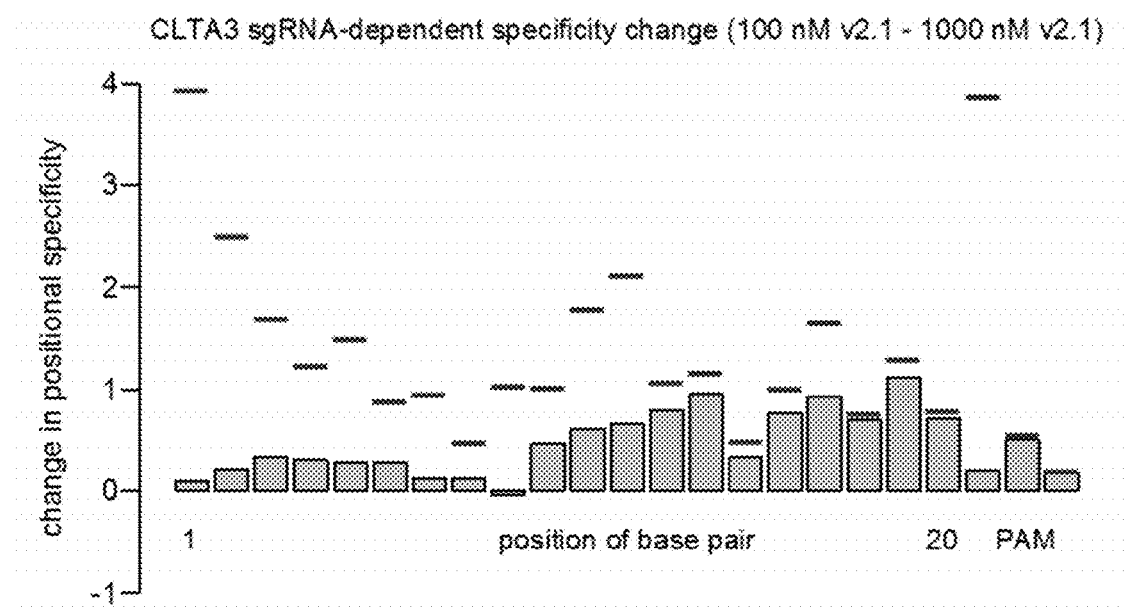
Figure 25D:
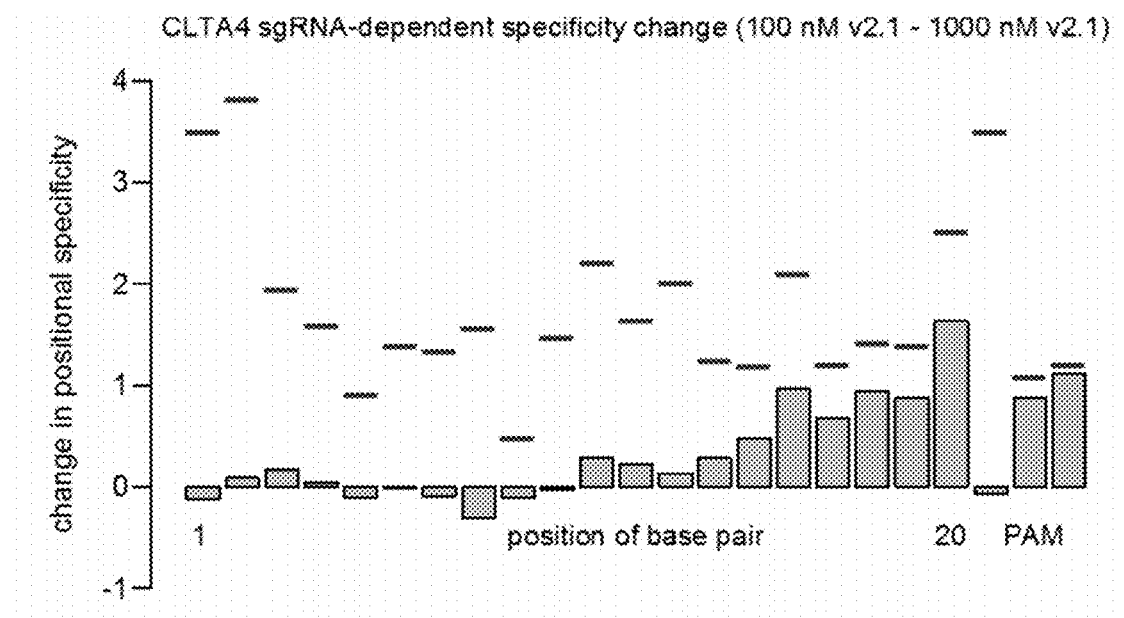
Figure 26A:
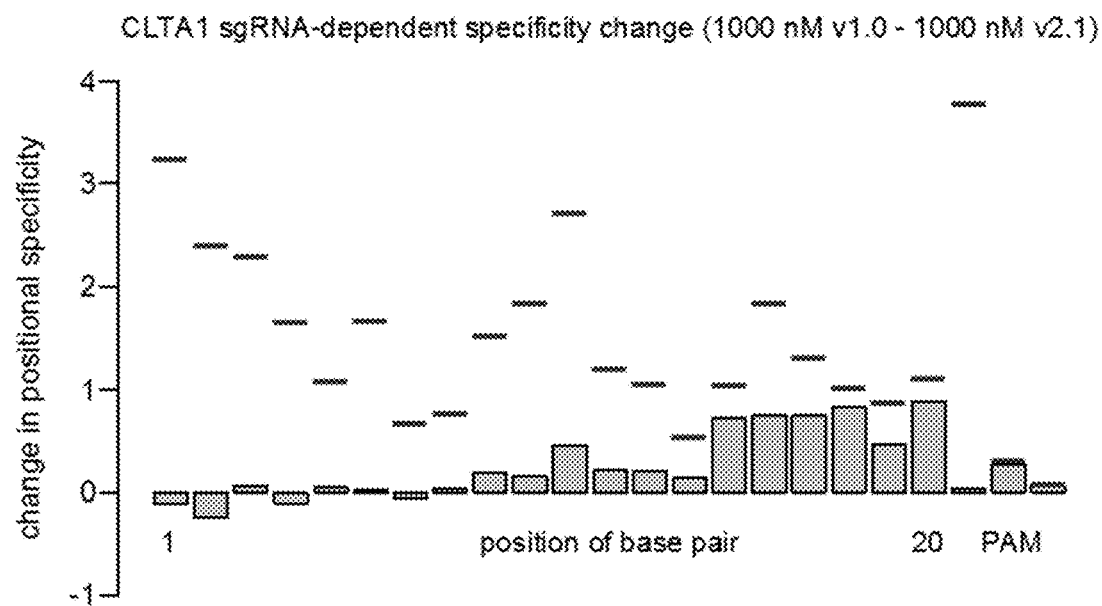
FIGS. 26A-26D. Effects of sgRNA architecture on specificity. Positional specificity changes between Cas9:sgRNA v1.0 and Cas9:sgRNA v2.1 under enzyme-excess (200 nM DNA, 1000 nM Cas9:sgRNA v2.1) conditions are shown for selections with sgRNAs targeting CLTA1 (FIG. 26A), CLTA2 (FIG. 26B), CLTA3 (FIG. 26C), and CLTA4 (FIG. 26D) target sites. Lines indicate the maximum possible change in positional specificity for a given position.
Figure 26B:
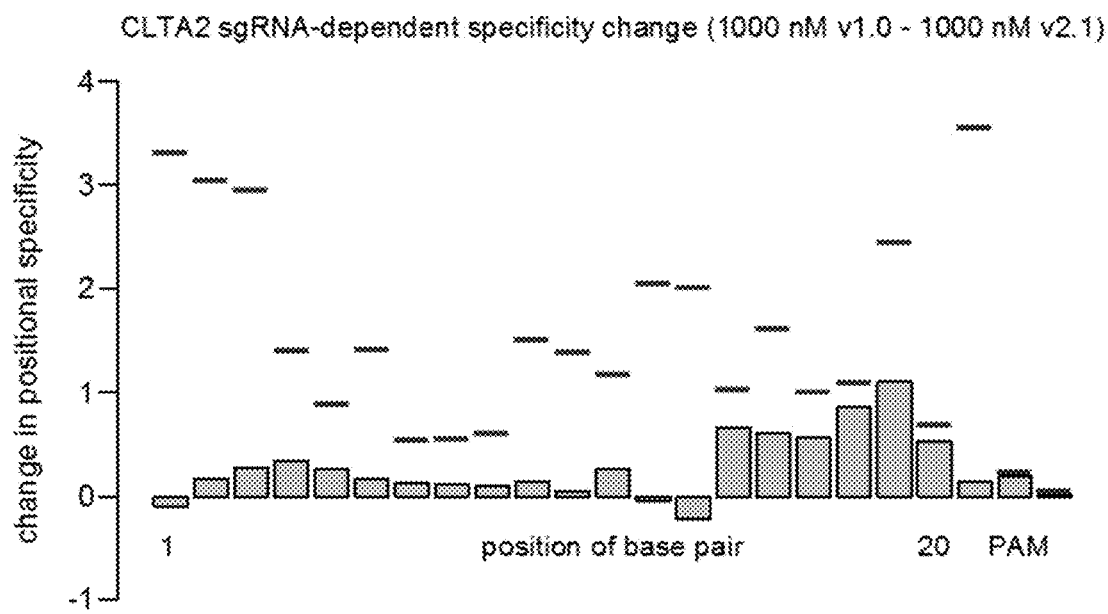
Figure 26C:
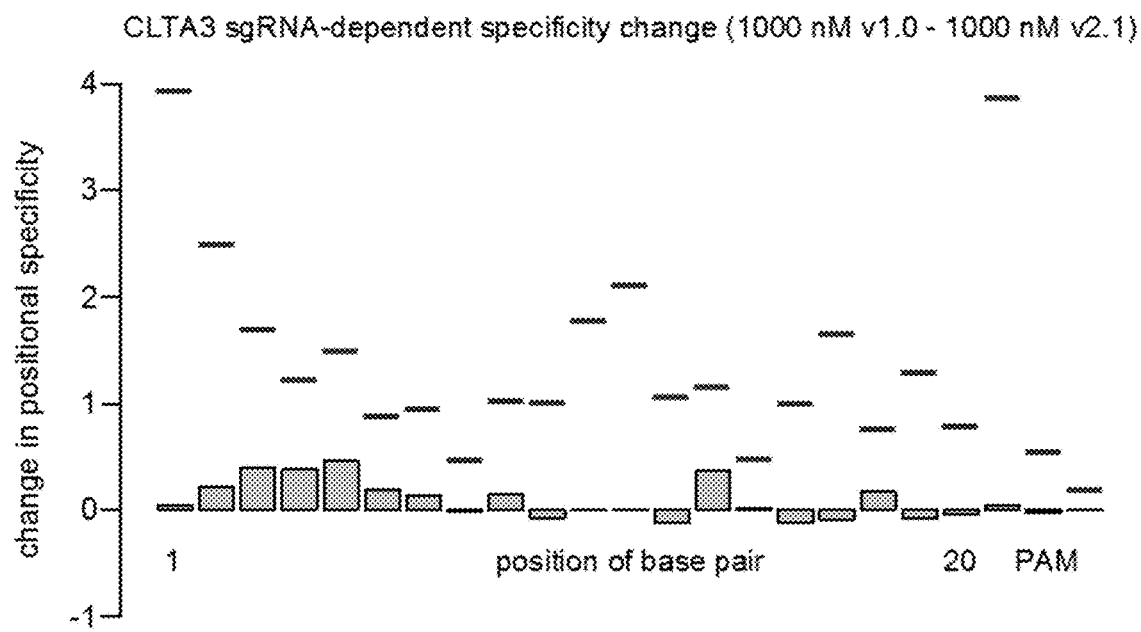
Figure 26D:
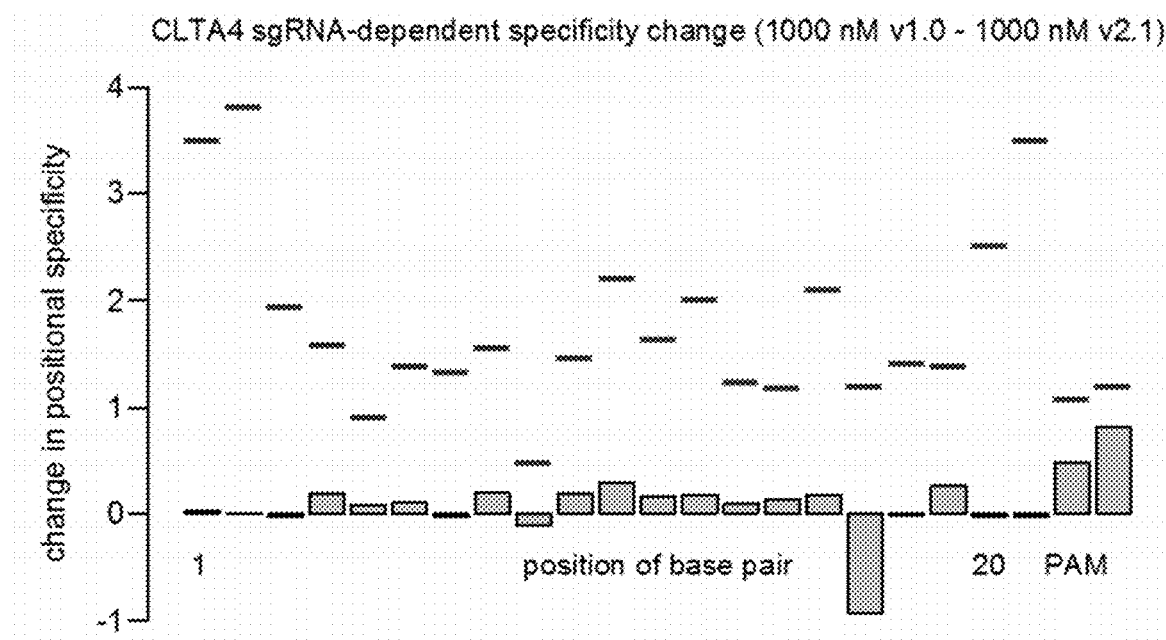

Pre-selection libraries were incubated under enzyme-limiting conditions (200 nM target site library, 100 nM Cas9:sgRNA v2.1) or enzyme-saturating conditions (200 nM target site library, 1000 nM Cas9:sgRNA v2.1) for each of the four guide RNAs targets tested (CLTA1, CLTA2, CLTA3, and CLTA4) (FIGS. 3C and 3D). A second guide RNA construct, sgRNA v1.0, which is less active than sgRNA v2.1, was assayed under enzyme-saturating conditions alone for each of the four guide RNA targets tested (200 nM target site library, 1000 nM Cas9:sgRNA v1.0). The two guide RNA constructs differ in their length (FIG. 3) and in their DNA cleavage activity level under the selection conditions, consistent with previous reports[15] (FIG. 4). Both pre-selection and post-selection libraries were characterized by high-throughput DNA sequencing and computational analysis. As expected, library members with fewer mutations were significantly enriched in post-selection libraries relative to pre-selection libraries (FIG. 5).

Pre- and Post-Selection Library Composition.

The pre-selection libraries for CLTA1, CLTA2, CLTA3, and CLTA4 had observed mean mutation rates of 4.82 (n=1,129,593), 5.06 (n=847,618), 4.66 (n=692,997), and 5.00 (n=951,503) mutations per 22-base pair target site, including the two-base pair PAM, respectively. The post-selection libraries treated under enzyme-limiting conditions with Cas9 plus CLTA1, CLTA2, CLTA3, or CLTA4 v.2.1 sgRNAs contained means of 1.14 (n=1,206,268), 1.21 (n=668,312), 0.91 (n=1,138,568), and 1.82 (n=560,758) mutations per 22-base pair target site. Under enzyme-excess conditions, the mean number of mutations among sequences surviving selection increased to 1.61 (n=640,391), 1.86 (n=399,560), 1.46 (n=936,414), and 2.24 (n=506,179) mutations per 22-base pair target site, respectively, for CLTA1, CLTA2, CLTA3, or CLTA4 v2.1 sgRNAs. These results reveal that the selection significantly enriched library members with fewer mutations for all Cas9:sgRNA complexes tested, and that enzyme-excess conditions resulted in the putative cleavage of more highly mutated library members compared with enzyme-limiting conditions (FIG. 5).

We calculated specificity scores to quantify the enrichment level of each base pair at each position in the post-selection library relative to the pre-selection library, normalized to the maximum possible enrichment of that base pair. Positive specificity scores indicate base pairs that were enriched in the post-selection library and negative specificity scores indicate base pairs that were de-enriched in the post-selection library. For example, a score of +0.5 indicates that a base pair is enriched to 50% of the maximum enrichment value, while a score of −0.5 indicates that a base pair is de-enriched to 50% of the maximum de-enrichment value.

In addition to the two base pairs specified by the PAM, all 20 base pairs targeted by the guide RNA were enriched in the sequences from the CLTA1 and CLTA2 selections (FIG. 2, FIGS. 6 and 9, and Table 2). For the CLTA3 and CLTA4 selections (FIGS. 7 and 8, and Table 2), guide RNA-specified base pairs were enriched at all positions except for the two most distal base pairs from the PAM (5' end of the guide RNA), respectively. At these non-specified positions farthest from the PAM, at least two of the three alternate base pairs were nearly as enriched as the specified base pair. Our finding that the entire 20 base-pair target site and two base pair PAM can contribute to Cas9:sgRNA DNA cleavage specificity contrasts with the results from previous single-substrate assays suggesting that only 7-12 base pairs and two base pair PAM are specified.[11, 12, 15]

All single-mutant pre-selection (n≥14,569) and post-selection library members (n≥103,660) were computationally analyzed to provide a selection enrichment value for every possible single-mutant sequence. The results of this analysis (FIG. 2 and FIGS. 6 and 8) show that when only single-mutant sequences are considered, the six to eight base pairs closest to the PAM are generally highly specified and the non-PAM end is poorly specified under enzyme-limiting conditions, consistent with previous findings.[11, 12, 17-19] Under enzyme-saturating conditions, however, single mutations even in the six to eight base pairs most proximal to the PAM are tolerated, suggesting that the high specificity at the PAM end of the DNA target site can be compromised when enzyme concentrations are high relative to substrate (FIG. 2). The observation of high specificity against single mutations close to the PAM only applies to sequences with a single mutation and the selection results do not support a model in which any combination of mutations is tolerated in the region of the target site farthest from the PAM (FIG.

10-15). Analyses of pre- and post-selection library composition are described elsewhere herein, position-dependent specificity patterns are illustrated in FIGS. 18-20, PAM nucleotide specificity is illustrated in FIGS. 21-24, and more detailed effects of Cas9:sgRNA concentration on specificity are described in FIG. 2G and FIG. 25).

Specificity at the Non-PAM End of the Target Site.

To assess the ability of Cas9:v2.1 sgRNA under enzyme-excess conditions to tolerate multiple mutations distal to the PAM, we calculated maximum specificity scores at each position for sequences that contained mutations only in the region of one to 12 base pairs at the end of the target site most distal from the PAM (FIG. 10-17).

The results of this analysis show no selection (maximum specificity score~0) against sequences with up to three mutations, depending on the target site, at the end of the molecule farthest from the PAM when the rest of the sequence contains no mutations. For example, when only the three base pairs farthest from the PAM are allowed to vary (indicated by dark bars in FIG. 11C) in the CLTA2 target site, the maximum specificity scores at each of the three variable positions are close to zero, indicating that there was no selection for any of the four possible base pairs at each of the three variable positions. However, when the eight base pairs farthest from the PAM are allowed to vary (FIG. 11H), the maximum specificity scores at positions 4-8 are all greater than +0.4, indicating that the Cas9:sgRNA has a sequence preference at these positions even when the rest of the substrate contains preferred, on-target base pairs.

We also calculated the distribution of mutations (FIG. 15-17), in both pre-selection and v2.1 sgRNA-treated post-selection libraries under enzyme-excess conditions, when only the first 1-12 base pairs of the target site are allowed to vary. There is significant overlap between the pre-selection and post-selection libraries for only a subset of the data (FIG. 15-17, a-c), demonstrating minimal to no selection in the post-selection library for sequences with mutations only in the first three base pairs of the target site. These results collectively show that Cas9:sgRNA can tolerate a small number of mutations (~one to three) at the end of the sequence farthest from the PAM when provided with maximal sgRNA:DNA interactions in the rest of the target site.

Specificity at the PAM End of the Target Site.

We plotted positional specificity as the sum of the magnitudes of the specificity scores for all four base pairs at each position of each target site, normalized to the same sum for the most highly specified position (FIG. 18-20). Under both enzyme-limiting and enzyme-excess conditions, the PAM end of the target site is highly specified. Under enzyme-limiting conditions, the PAM end of the molecule is almost absolutely specified (specificity score≥+0.9 for guide RNA-specified base pairs) by CLTA1, CTLA2, and CLTA3 guide RNAs (FIG. 2 and FIG. 6-9), and highly specified by CLTA4 guide RNA (specificity score of +0.7 to +0.9). Within this region of high specificity, specific single mutations, consistent with wobble pairing between the guide RNA and target DNA, that are tolerated. For example, under enzyme-limiting conditions for single-mutant sequences, a dA:dT off-target base pair and a guide RNA-specified dG:dC base pair are equally tolerated at position 17 out of 20 (relative to the non-PAM end of the target site) of the CLTA3 target site. At this position, an rG:dT wobble RNA:DNA base pair may be formed, with minimal apparent loss of cleavage activity.

Figure 2A:
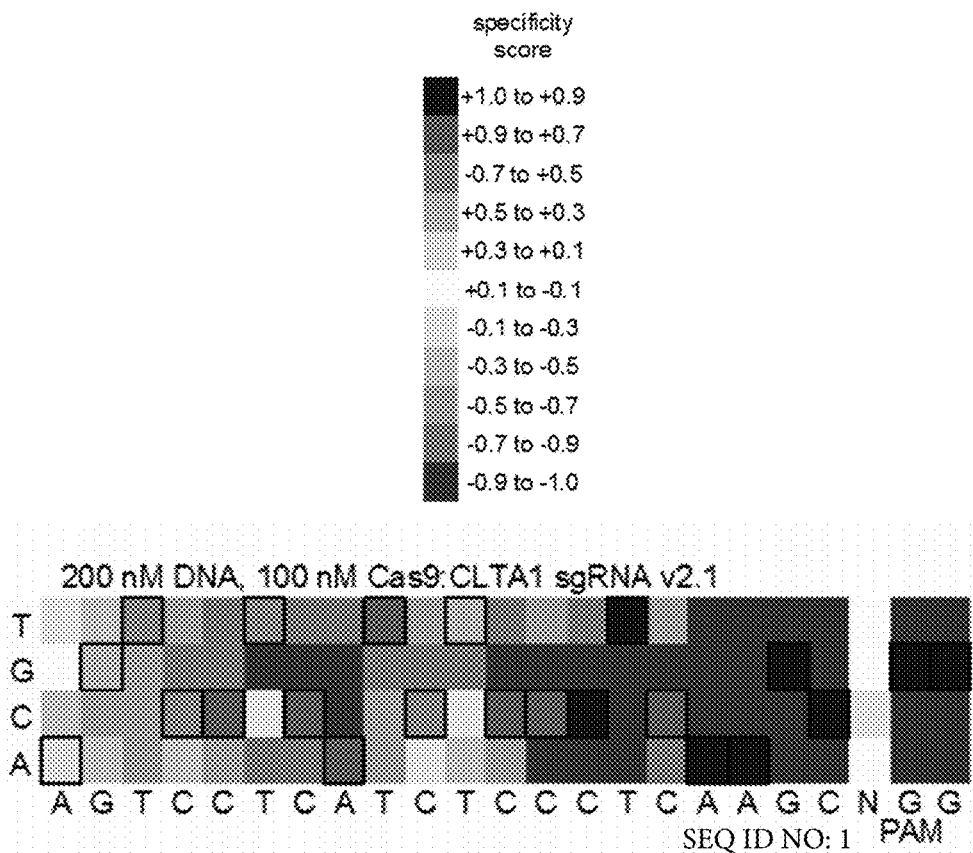
FIGS. 2A-2H. In vitro selection results for Cas9:CLTA1 sgRNA. Heat maps[21] show the specificity profiles of Cas9:CLTA1 sgRNA v2.1 under enzyme-limiting conditions (FIGS. 2A, 2B), Cas9:CLTA1 sgRNA v1.0 under enzyme-saturating conditions (FIGS. 2C, 2D), and Cas9:CLTA1 sgRNA v2.1 under enzyme-saturating conditions (FIGS. 2E, 2F). Heat maps show all post-selection sequences (FIGS. 2A, 2C, 2E) or only those sequences containing a single mutation in the 20-base pair sgRNA-specified target site and two-base pair PAM (FIGS. 2B, 2D, 2F). Specificity scores of 1.0 and −1.0 corresponds to 100% enrichment for and against, respectively, a particular base pair at a particular position. Black boxes denote the intended target nucleotides.
Figure 2B:
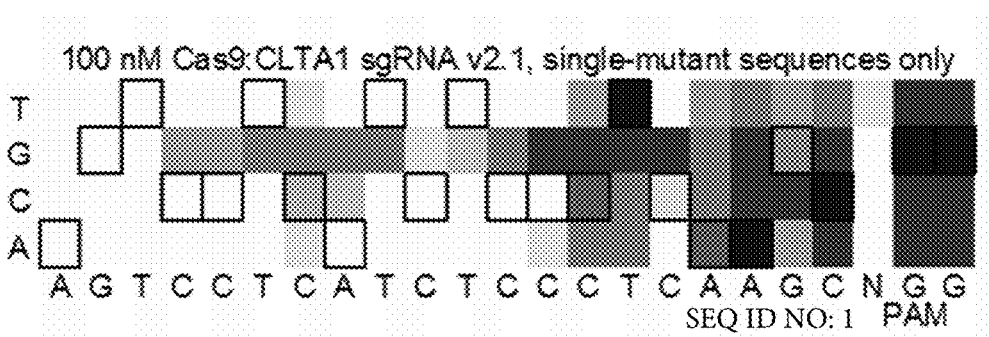
Figure 2C:
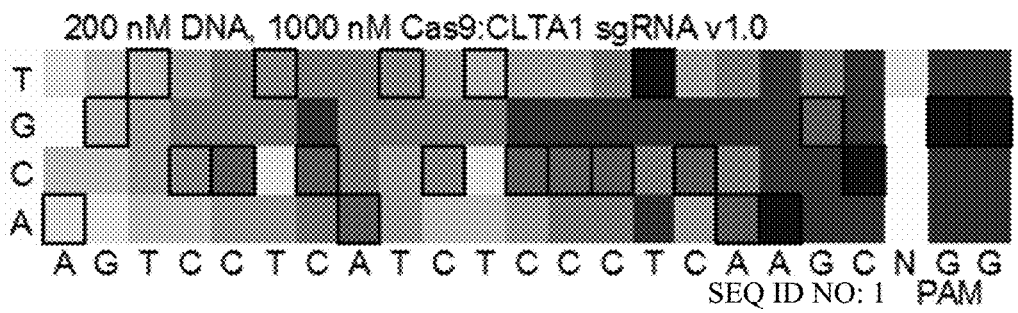
Figure 2D:
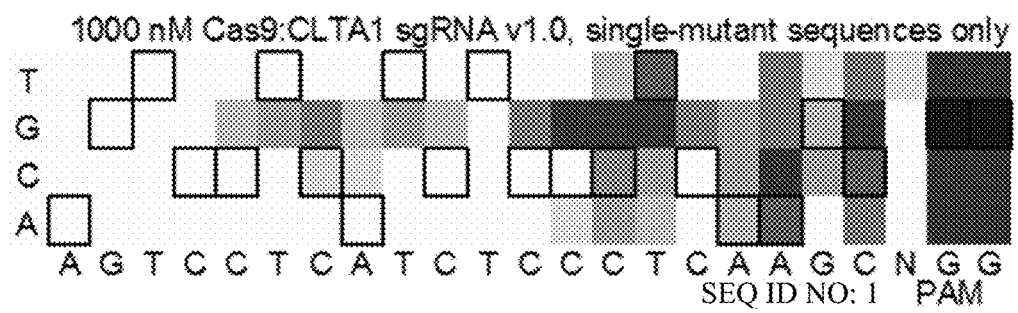
Figure 2E:
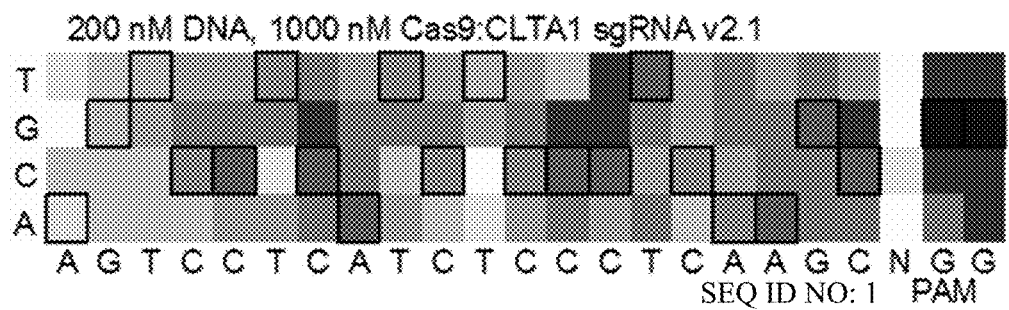
Figure 2F:
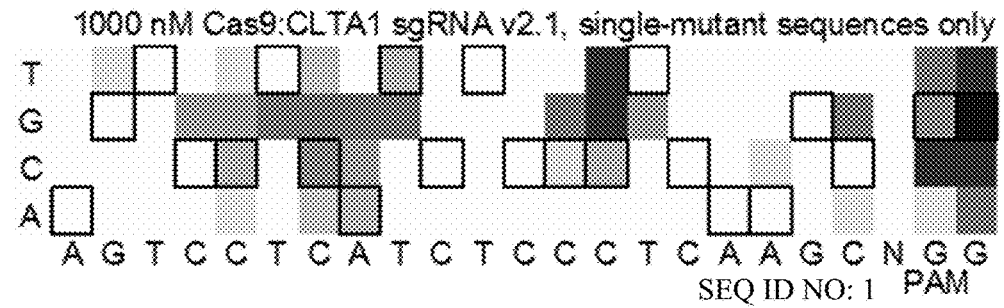
Figure 2G:
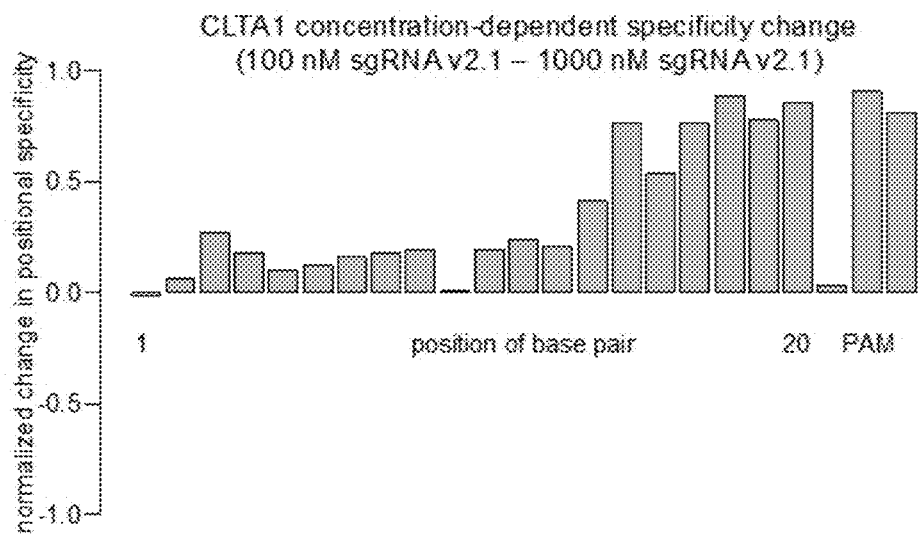
Figure 2H:
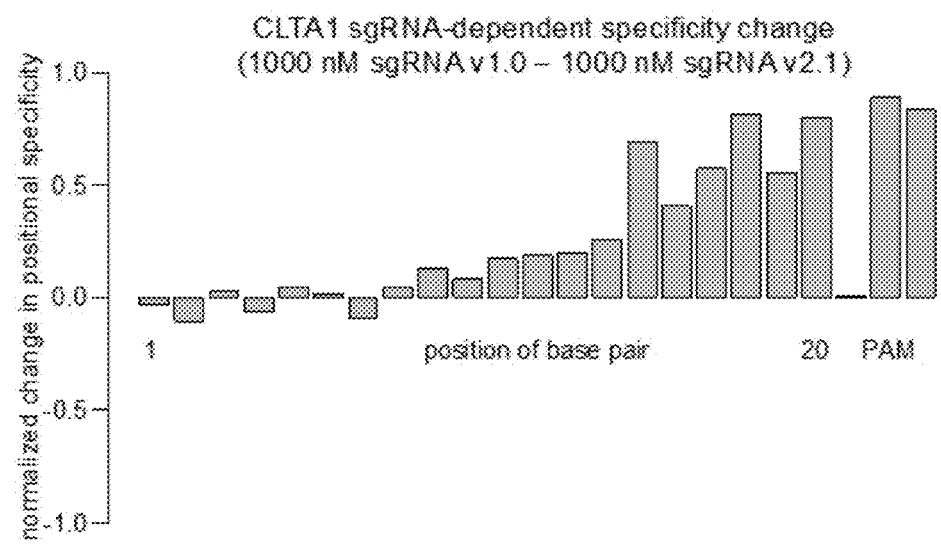

Importantly, the selection results also reveal that the choice of guide RNA hairpin affects specificity. The shorter, less-active sgRNA v1.0 constructs are more specific than the longer, more-active sgRNA v2.1 constructs when assayed under identical, enzyme-saturating conditions that reflect an excess of enzyme relative to substrate in a cellular context (FIG. 2 and FIGS. 5-8). The higher specificity of sgRNA v1.0 over sgRNA v2.1 is greater for CLTA1 and CLTA2 (~40-90% difference) than for CLTA3 and CLTA4 (<40% difference). Interestingly, this specificity difference is localized to different regions of the target site for each target sequence (FIGS. 2H and 26). Collectively, these results indicate that different guide RNA architectures result in different DNA cleavage specificities, and that guide RNA-dependent changes in specificity do not affect all positions in the target site equally. Given the inverse relationship between Cas9:sgRNA concentration and specificity described above, we speculate that the differences in specificity between guide RNA architectures arises from differences in their overall level of DNA-cleavage activities.

Effects of Cas9:sgRNA Concentration on DNA Cleavage Specificity.

To assess the effect of enzyme concentration on patterns of specificity for the four target sites tested, we calculated the concentration-dependent difference in positional specificity and compared it to the maximal possible change in positional specificity (FIG. 25). In general, specificity was higher under enzyme-limiting conditions than enzyme-excess conditions. A change from enzyme-excess to enzyme-limiting conditions generally increased the specificity at the PAM end of the target by ≥80% of the maximum possible change in specificity. Although a decrease in enzyme concentration generally induces small (~30%) increases in specificity at the end of the target sites farthest from the PAM, concentration decreases induce much larger increases in specificity at the end of the target site nearest the PAM. For CLTA4, a decrease in enzyme concentration is accompanied by a small (~30%) decrease in specificity at some base pairs near the end of the target site farthest from the PAM.

Specificity of PAM Nucleotides.

To assess the contribution of the PAM to specificity, we calculated the abundance of all 16 possible PAM dinucleotides in the pre-selection and post-selection libraries, considering all observed post-selection target site sequences (FIG. 21) or considering only post-selection target site sequences that contained no mutations in the 20 base pairs specified by the guide RNA (FIG. 22). Considering all observed post-selection target site sequences, under enzyme-limiting conditions, GG dinucleotides represented 99.8%, 99.9%, 99.8%, and 98.5% of the post-selection PAM dinucleotides for selections with CLTA1, CLTA2, CLTA3, and CLTA4 v2.1 sgRNAs, respectively. In contrast, under enzyme-excess conditions, GG dinucleotides represented 97.7%, 98.3%, 95.7%, and 87.0% of the post-selection PAM dinucleotides for selections with CLTA1, CLTA2, CLTA3, and CLTA4 v2.1 sgRNAs, respectively. These data demonstrate that an increase in enzyme concentration leads to increased cleavage of substrates containing non-canonical PAM dinucleotides.

To account for the pre-selection library distribution of PAM dinucleotides, we calculated specificity scores for the PAM dinucleotides (FIG. 23). When only on-target post-selection sequences are considered under enzyme-excess conditions (FIG. 24), non-canonical PAM dinucleotides with a single G rather than two Gs are relatively tolerated. Under enzyme-excess conditions, Cas9:CLTA4 sgRNA 2.1 exhibited the highest tolerance of non-canonical PAM dinucleotides of all the Cas9:sgRNA combinations tested. AG and GA dinucleotides were the most tolerated, followed by GT, TG, and CG PAM dinucleotides. In selections with Cas9:

CLTA1, 2, or 3 sgRNA 2.1 under enzyme-excess conditions, AG was the predominate non-canonical PAM (FIGS. 23 and 24). Our results are consistent with another recent study of PAM specificity, which shows that Cas9:sgRNA can recognize AG PAM dinucleotides[23]. In addition, our results show that under enzyme-limiting conditions, GG PAM dinucleotides are highly specified, and under enzyme-excess conditions, non-canonical PAM dinucleotides containing a single G can be tolerated, depending on the guide RNA context.

Figure 27:
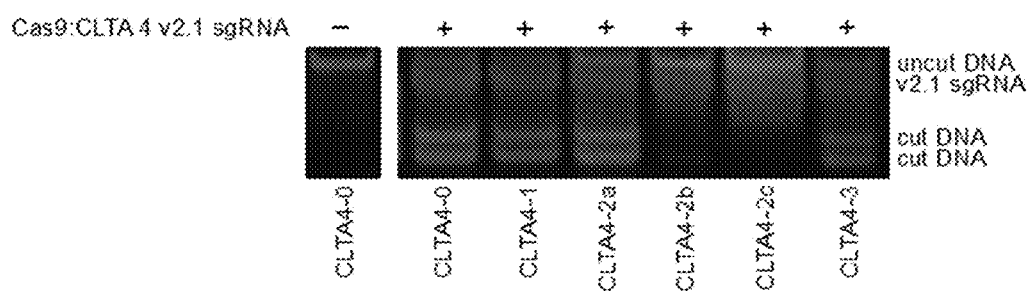
FIG. 27. Cas9:guide RNA cleavage of off-target DNA sequences in vitro. Discrete DNA cleavage assays on a 96-bp linear substrate were performed with 200 nM DNA and 1000 nM Cas9:CLTA4 v2.1 sgRNA for the on-target CLTA4 site (CLTA4-0) and five CLTA4 off-target sites identified by in vitro selection. Enrichment values shown are from the in vitro selection with 1000 nM Cas9:CLTA4 v2.1 sgRNA. CLTA4-1 and CLTA4-3 were the most highly enriched sequences under these conditions. CLTA4-2a, CLTA4-2b, and CLTA4-2c are two-mutation sequences that represent a range of enrichment values from high enrichment to no enrichment to high de-enrichment. Lowercase letters indicate mutations relative to the on-target CLTA4 site. The enrichment values are qualitatively consistent with the observed amount of cleavage in vitro.
Figure 28:
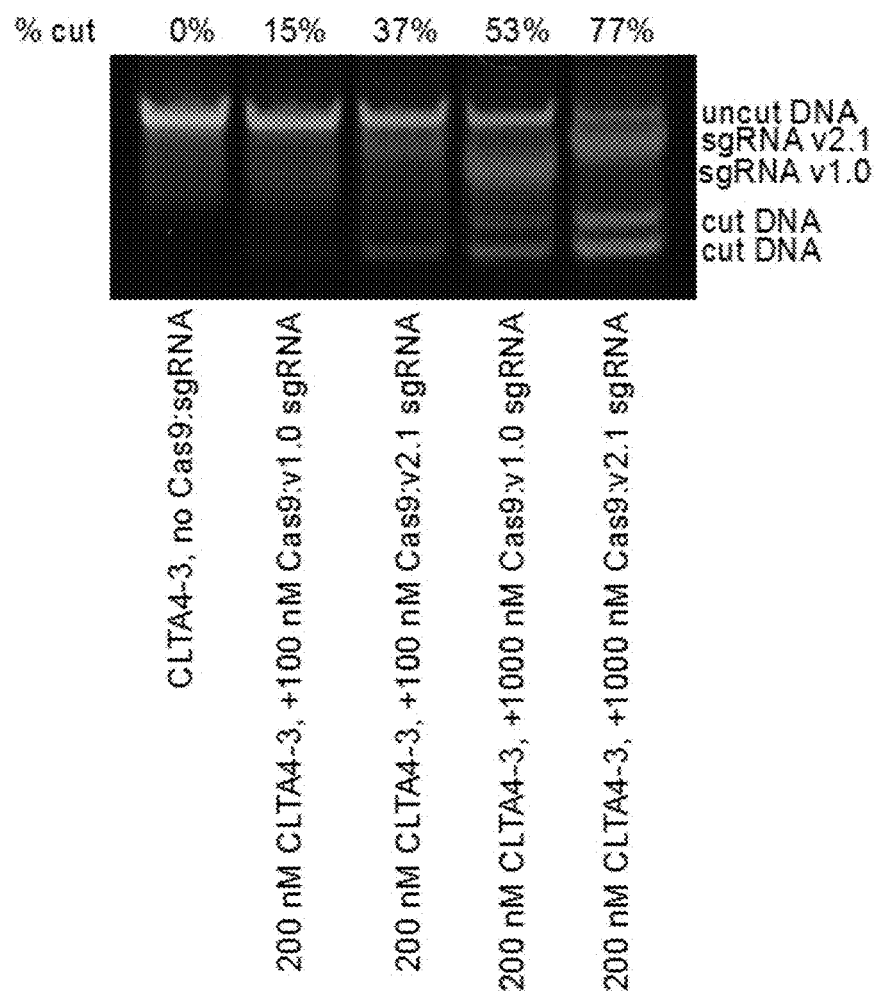
FIG. 28. Effect of guide RNA architecture and Cas9: sgRNA concentration on in vitro cleavage of an off-target site. Discrete DNA cleavage assays on a 96-bp linear substrate were performed with 200 nM DNA and 100 nM Cas9:v1.0 sgRNA, 100 nM Cas9:v2.1 sgRNA, 1000 nM Cas9:v1.0 sgRNA, or 1000 nM Cas9:v2.1 sgRNA for the CLTA4-3 off-target site (5' GggGATGTAGTGTTTC-CACtGGG—mutations are shown in lowercase letters). DNA cleavage is observed under all four conditions tested, and cleavage rates are higher under enzyme-excess conditions, or with v2.1 sgRNA compared with v1.0 sgRNA.

To confirm that the in vitro selection results accurately reflect the cleavage behavior of Cas9 in vitro, we performed discrete cleavage assays of six CLTA4 off-target substrates containing one to three mutations in the target site. We calculated enrichment values for all sequences in the post-selection libraries for the Cas9:CLTA4 v2.1 sgRNA under enzyme-saturating conditions by dividing the abundance of each sequence in the post-selection library by the calculated abundance in the pre-selection library. Under enzyme-saturating conditions, the single one, two, and three mutation sequences with the highest enrichment values (27.5, 43.9, and 95.9) were cleaved to ≥71% completion (FIG. 27). A two-mutation sequence with an enrichment value of 1.0 was cleaved to 35%, and a two-mutation sequence with an enrichment value near zero (0.064) was not cleaved. The three-mutation sequence, which was cleaved to 77% by CLTA4 v2.1 sgRNA, was cleaved to a lower efficiency of 53% by CLTA4 v1.0 sgRNA (FIG. 28). These results indicate that the selection enrichment values of individual sequences are predictive of in vitro cleavage efficiencies.

To determine if results of the in vitro selection and in vitro cleavage assays pertain to Cas9:guide RNA activity in human cells, we identified 51 off-target sites (19 for CLTA1 and 32 for CLTA4) containing up to eight mutations that were both enriched in the in vitro selection and present in the human genome (Tables 3-5). We expressed Cas9:CLTA1 sgRNA v1.0, Cas9:CLTA1 sgRNA v2.1, Cas9:CLTA4 sgRNA v1.0, Cas9:CLTA4 sgRNA v2.1, or Cas9 without sgRNA in HEK293T cells by transient transfection and used genomic PCR and high-throughput DNA sequencing to look for evidence of Cas9:sgRNA modification at 46 of the 51 off-target sites as well as at the on-target loci; no specific amplified DNA was obtained for five of the 51 predicted off-target sites (three for CLTA1 and two for CLTA4).

Deep sequencing of genomic DNA isolated from HEK293T cells treated with Cas9:CLTA1 sgRNA or Cas9:CLTA4 sgRNA identified sequences evident of non-homologous end-joining (NHEJ) at the on-target sites and at five of the 49 tested off-target sites (CLTA1-1-1, CLTA1-2-2, CLTA4-3-1, CLTA4-3-3, and CLTA4-4-8) (Tables 1 and 6-8). The CLTA4 target site was modified by Cas9:CLTA4 v2.1 sgRNA at a frequency of 76%, while off-target sites, CLTA4-3-1 CLTA4-3-3, and CLTA4-4-8, were modified at frequencies of 24%, 0.47% and 0.73%, respectively. The CLTA1 target site was modified by Cas9:CLTA1 v2.1 sgRNA at a frequency of 0.34%, while off-target sites, CLTA1-1-1 and CLTA1-2-2, were modified at frequencies of 0.09% and 0.16%, respectively.

Under enzyme-saturating conditions with the v2.1 sgRNA, the two verified CLTA1 off-target sites, CLTA1-1-1 and CLTA1-2-2, were two of the three most highly enriched sequences identified in the in vitro selection. CLTA4-3-1 and CLTA4-3-3 were the highest and third-highest enriched sequences of the seven CLTA4 three-mutation sequences enriched in the in vitro selection that are also present in the genome. The in vitro selection enrichment values of the four-mutation sequences were not calculated, since 12 out of the 14 CLTA4 sequences in the genome containing four mutations, including CLTA4-4-8, were observed at a level of only one sequence count in the post-selection library. Taken together, these results confirm that several of the off-target substrates identified in the in vitro selection that are present in the human genome are indeed cleaved by Cas9:sgRNA complexes in human cells, and also suggest that the most highly enriched genomic off-target sequences in the selection are modified in cells to the greatest extent.

The off-target sites we identified in cells were among the most-highly enriched in our in vitro selection and contain up to four mutations relative to the intended target sites. While it is possible that heterochromatin or covalent DNA modifications could diminish the ability of a Cas9:guide RNA complex to access genomic off-target sites in cells, the identification of five out of 49 tested cellular off-target sites in this study, rather than zero or many, strongly suggests that Cas9-mediated DNA cleavage is not limited to specific targeting of only a 7-12-base pair target sequence, as suggested in recent studies.[11, 12, 19]

The cellular genome modification data are also consistent with the increase in specificity of sgRNA v1.0 compared to sgRNA v2.1 sgRNAs observed in the in vitro selection data and discrete assays. Although the CLTA1-2-2, CLTA4-3-3, and CLTA4-4-8 sites were modified by the Cas9-sgRNA v2.1 complexes, no evidence of modification at any of these three sites was detected in Cas9:sgRNA v1.0-treated cells. The CLTA4-3-1 site, which was modified at 32% of the frequency of on-target CLTA4 site modification in Cas9: v2.1 sgRNA-treated cells, was modified at only 0.5% of the on-target modification frequency in v1.0 sgRNA-treated cells, representing a 62-fold change in selectivity. Taken together, these results demonstrate that guide RNA architecture can have a significant influence on Cas9 specificity in cells. Our specificity profiling findings present an important caveat to recent and ongoing efforts to improve the overall DNA modification activity of Cas9:guide RNA complexes through guide RNA engineering.[11, 15]

Overall, the off-target DNA cleavage profiling of Cas9 and subsequent analyses show that (i) Cas9:guide RNA recognition extends to 18-20 specified target site base pairs and a two-base pair PAM for the four target sites tested; (ii) increasing Cas9:guide RNA concentrations can decrease DNA-cleaving specificity in vitro; (iii) using more active sgRNA architectures can increase DNA-cleavage specificity both in vitro and in cells but impair DNA-cleavage specificity both in vitro and in cells; and (iv) as predicted by our in vitro results, Cas9:guide RNA can modify off-target sites in cells with up to four mutations relative to the on-target site. Our findings provide key insights to our understanding of RNA-programmed Cas9 specificity, and reveal a previously unknown role for sgRNA architecture in DNA-cleavage specificity. The principles revealed in this study may also apply to Cas9-based effectors engineered to mediate functions beyond DNA cleavage.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

TABLES

Table 1. Cellular Modification Induced by Cas9:CLTA4 sgRNA.

33 human genomic DNA sequences were identified that were enriched in the Cas9:CLTA4 v2.1 sgRNA in vitro selections under enzyme-limiting or enzyme-saturating conditions. Sites shown with underline contain insertions or deletions (indels) that are consistent with significant Cas9:sgRNA-mediated modification in HEK293T cells. In vitro enrichment values for selections with Cas9:CLTA4 v1.0 sgRNA or Cas9:CLTA4 v2.1 sgRNA are shown for sequences with three or fewer mutations. Enrichment values were not calculated for sequences with four or more mutations due to low numbers of in vitro selection sequence counts. Modification frequencies (number of sequences with indels divided by total number of sequences) in HEK293T cells treated with Cas9 without sgRNA ("no sgRNA"), Cas9 with CLTA4 v1.0 sgRNA, or Cas9 with CLTA4 v2.1 sgRNA. P-values are listed for those sites that show significant modification in v1.0 sgRNA- or v2.1 sgRNA-treated cells compared to cells treated with Cas9 without sgRNA. "Not tested (n.t.)" indicates that PCR of the genomic sequence failed to provide specific amplification products.

Table 2: Raw Selection Sequence Counts.

Positions −4 to −1 are the four nucleotides preceding the 20-base pair target site. PAM1, PAM2, and PAM3 are the PAM positions immediately following the target site. Positions +4 to +7 are the four nucleotides immediately following the PAM.

Table 3: CLTA1 Genomic Off-Target Sequences.

20 human genomic DNA sequences were identified that were enriched in the Cas9:CLTA1 v2.1 sgRNA in vitro selections under enzyme-limiting or enzyme-excess conditions. "m" refers to number of mutations from on-target sequence with mutations shown in lower case. Sites shown with underline contain insertions or deletions (indels) that are consistent with significant Cas9:sgRNA-mediated modification in HEK293T cells. Human genome coordinates are shown for each site (assembly GRCh37). CLTA1-0-1 is present at two loci, and sequence counts were pooled from both loci. Sequence counts are shown for amplified and sequenced DNA for each site from HEK293T cells treated with Cas9 without sgRNA ("no sgRNA"), Cas9 with CLTA1 v1.0 sgRNA, or Cas9 with CLTA1 v2.1 sgRNA.

Table 4: CLTA4 Genomic Off-Target Sequences.

33 human genomic DNA sequences were identified that were enriched in the Cas9:CLTA4 v2.1 sgRNA in vitro selections under enzyme-limiting or enzyme-excess conditions. "m" refers to number of mutations from on-target sequence with mutations shown in lower case. Sites shown with underline contain insertions or deletions (indels) that are consistent with significant Cas9:sgRNA-mediated modification in HEK293T cells. Human genome coordinates are shown for each site (assembly GRCh37). Sequence counts are shown for amplified and sequenced DNA for each site from HEK293T cells treated with Cas9 without sgRNA ("no sgRNA"), Cas9 with CLTA4 v1.0 sgRNA, or Cas9 with CLTA4 v2.1 sgRNA.

Table 5: Genomic Coordinates of CLTA1 and CLTA4 Off-Target Sites.

54 human genomic DNA sequences were identified that were enriched in the Cas9:CLTA1 v2.1 sgRNA and Cas9:CLTA4 v2.1 sgRNA in vitro selections under enzyme-limiting or enzyme-excess conditions. Human genome coordinates are shown for each site (assembly GRCh37).

Table 6: Cellular Modification Induced by Cas9:CLTA1 sgRNA.

20 human genomic DNA sequences were identified that were enriched in the Cas9:CLTA1 v2.1 sgRNA in vitro selections under enzyme-limiting or enzyme-excess conditions. Sites shown with underline contain insertions or deletions (indels) that are consistent with significant Cas9:sgRNA-mediated modification in HEK293T cells. In vitro enrichment values for selections with Cas9:CLTA1 v1.0 sgRNA or Cas9:CLTA1 v2.1 sgRNA are shown for sequences with three or fewer mutations. Enrichment values were not calculated for sequences with four or more mutations due to low numbers of in vitro selection sequence counts. Modification frequencies (number of sequences with indels divided by total number of sequences) in HEK293T cells treated with Cas9 without sgRNA ("no sgRNA"), Cas9 with CLTA1 v1.0 sgRNA, or Cas9 with CLTA1 v2.1 sgRNA. P-values of sites that show significant modification in v1.0 sgRNA- or v2.1 sgRNA-treated cells compared to cells treated with Cas9 without sgRNA were 1.1E−05 (v1.0) and 6.9E−55 (v2.1) for CLTA1-0-1, 2.6E−03 (v1.0) and 2.0E−10 (v2.1) for CLTA1-1-1, and 4.6E−08 (v2.1) for CLTA1-2-2. P-values were calculated using a one-sided Fisher exact test. "Not tested (n.t.)" indicates that the site was not tested or PCR of the genomic sequence failed to provide specific amplification products.

Table 7: CLTA1 Genomic Off-Target Indel Sequences.

Insertion and deletion-containing sequences from cells treated with amplified and sequenced DNA for the on-target genomic sequence (CLTA1-0-1) and each modified off-target site from HEK293T cells treated with Cas9 without sgRNA ("no sgRNA"), Cas9 with CLTA1 v1.0 sgRNA, or Cas9 with CLTA1 v2.1 sgRNA. "ref" refers to the human genome reference sequence for each site, and the modified sites are listed below. Mutations relative to the on-target genomic sequence are shown in lowercase letters. Insertions and deletions are shown in underlined bold letters or dashes, respectively. Modification percentages are shown for those conditions (v1.0 sgRNA or v2.1 sgRNA) that show statistically significant enrichment of modified sequences compared to the control (no sgRNA).

Table 8: CLTA4 Genomic Off-Target Indel Sequences.

Insertion and deletion-containing sequences from cells treated with amplified and sequenced DNA for the on-target genomic sequence (CLTA4-0-1) and each modified off-target site from HEK293T cells treated with Cas9 without sgRNA ("no sgRNA"), Cas9 with CLTA4 v1.0 sgRNA, or Cas9 with CLTA4 v2.1 sgRNA. "ref" refers to the human genome reference sequence for each site, and the modified sites are listed below. Mutations relative to the on-target genomic sequence are shown in lowercase letters. Insertions and deletions are shown in underlined bold letters or dashes, respectively. Modification percentages are shown for those conditions (v1.0 sgRNA or v2.1 sgRNA) that show statistically significant enrichment of modified sequences compared to the control (no sgRNA).

Table 9: Oligonucleotides Used in this Study.

All oligonucleotides were purchased from Integrated DNA Technologies. An asterisk (*) indicates that the preceding nucleotide was incorporated as a hand mix of phosphoramidites consisting of 79 mol % of the phosphoramidite corresponding to the preceding nucleotide and 4 mol % of each of the other three canonical phosphoramidites. "/5Phos/" denotes a 5' phosphate group installed during synthesis.

TABLE 1

| | # of Mutations | sequence | SEQ ID NO. | gene | in vitro enrichment v1.0 | in vitro enrichment v2.1 | modification frequency in HEK293T cells no sgRNA | modification frequency in HEK293T cells v1.0 | modification frequency in HEK293T cells v2.1 | P-value v1.0 | P-value v2.1 |
|---|---|---|---|---|---|---|---|---|---|---|---|
| CLTA4-0-1 | 0 | GCAGATGTAGTGTTTCCACAGGG | SEQ ID NO: 58 | CLTA | 20 | 7.95 | 0.021% | 11% | 76% | <1E-55 | <1E-55 |
| CLTA4-3-1 | 3 | aCAtATGTAGTaTTTCCACAGGG | SEQ ID NO: 59 | | 16.5 | 12.5 | 0.006% | 0.055% | 24% | 6.0E-04 | <1E-55 |
| CLTA4-3-2 | 3 | GCAtATGTAGTGTTTCCAaATGt | SEQ ID NO: 60 | | 2.99 | 6.97 | 0.017% | 0% | 0.014% | | |
| CLTA4-3-3 | 3 | cCAGATGTAGTaTTcCCACAGGG | SEQ ID NO: 61 | CELF1 | 1.00 | 4.95 | 0% | 0% | 0.469% | | 2.5E-21 |
| CLTA4-3-4 | 3 | GCAGtTtTAGTGTTTtCACAGGG | SEQ ID NO: 62 | BC073807 | 0.79 | 3.12 | 0% | 0% | 0% | | |
| CLTA4-3-5 | 3 | GCAGAgtTAGTGTTTCCACACAG | SEQ ID NO: 63 | MPPED2 | 0 | 1.22 | 0.005% | 0.015% | 0.018% | | |
| CLTA4-3-6 | 3 | GCAGATGgAGgGTTTCCACAGGG | SEQ ID NO: 64 | DCHS2 | 1.57 | 1.17 | 0.015% | 0.023% | 0.021% | | |
| CLTA4-3-7 | 3 | GgAaATTTAGTGTTTCCACAGGG | SEQ ID NO: 65 | | 0.43 | 0.42 | 0.005% | 0.012% | 0.003% | | |
| CLTA4-4-1 | 4 | aaAGAaGTAGTaTTTCCACATGG | SEQ ID NO: 66 | | | | n.t. | n.t. | n.t. | | |
| CLTA4-4-2 | 4 | aaAGATGTAGTcATTCCACAAGG | SEQ ID NO: 67 | | | | 0.004% | 0% | 0.005% | | |
| CLTA4-4-3 | 4 | aaAtATGTAGTcTTTCCACAGGG | SEQ ID NO: 68 | | | | 0.004% | 0.009% | 0% | | |
| CLTA4-4-4 | 4 | atAGATGTAGTGTTTCCAaAGGa | SEQ ID NO: 69 | NR1H4 | | | 0.032% | 0.006% | 0.052% | | |
| CLTA4-4-5 | 4 | cCAGATGTAGTGcTcCCACAGGG | SEQ ID NO: 70 | | | | 0.005% | 0.006% | 0.007% | | |
| CLTA4-4-6 | 4 | cCAGATGTgagGTTTCCACAAGG | SEQ ID NO: 71 | XKR6 | | | 0.018% | 0% | 0.007% | | |
| CLTA4-4-7 | 4 | ctAcATGTAGTGTTTCCAtATGG | SEQ ID NO: 72 | HKR1 | | | 0.006% | 0% | 0.008% | | |
| CLTA4-4-8 | 4 | ctAGATGaAGTGcTTCCACATGG | SEQ ID NO: 73 | CDK8 | | | 0.009% | 0.013% | 0.730% | | 9.70E-21 |
| CLTA4-4-9 | 4 | GaAaATGaAGTGTTTaCACATGG | SEQ ID NO: 74 | | | | 0% | 0% | 0.004% | | |
| CLTA4-4-10 | 4 | GCAaATGaAGTGTcaCCACAAGG | SEQ ID NO: 75 | | | | 0.004% | 0% | 0% | | |
| CLTA4-4-11 | 4 | GCAtATGTAtTaTTTCCActAGG | SEQ ID NO: 76 | NOV | | | 0% | 0% | 0% | | |
| CLTA4-4-12 | 4 | GCAGATGTAGctTTTgtACATGG | SEQ ID NO: 77 | | | | 0% | 0.00% | 0% | | |
| CLTA4-4-13 | 4 | GCAGcTtaAGTGTTTtCACATGG | SEQ ID NO: 78 | GRHL2 | | | 0.020% | 0.02% | 0.030% | | |
| CLTA4-4-14 | 4 | ttAcATGTAGTGTTTaCACACGG | SEQ ID NO: 79 | LINC00535 | | | n.t. | n.t. | n.t. | | |
| CLTA4-5-1 | 5 | GaAGAggGaAGTGTTTgcccCAGGG | SEQ ID NO: 80 | RNH1 | | | 0.004% | 0.01% | 0.006% | | |

TABLE 1-continued

| | # of Mutations | sequence | SEQ ID NO. | gene | in vitro enrichment v1.0 | in vitro enrichment v2.1 | modification frequency in HEK293T cells no sgRNA | modification frequency in HEK293T cells v1.0 | modification frequency in HEK293T cells v2.1 | P-value v1.0 | P-value v2.1 |
|---|---|---|---|---|---|---|---|---|---|---|---|
| CLTA4-5-2 | 5 | GaAGATGTGgGaGTTgaCACATGG | SEQ ID NO: 81 | FZD3 | | | 0.004% | 0.00% | 0% | | |
| CLTA4-5-3 | 5 | GCAGAaGTAcTGTTgtTACAAGG | SEQ ID NO: 82 | | | | 0.002% | 0.00% | 0.003% | | |
| CLTA4-5-4 | 5 | GCAGATGTgGaaTTaCaACAGGG | SEQ ID NO: 83 | SLC9A2 | | | 0% | 0.00% | 0% | | |
| CLTA4-5-5 | 5 | GCAGtcaTAGTGTaTaCACATGG | SEQ ID NO: 84 | | | | 0.004% | 0.00% | 0.005% | | |
| CLTA4-5-6 | 5 | taAGATGTAGTaTTTCCaAaAAGt | SEQ ID NO: 85 | | | | 0.007% | 0.01% | 0% | | |
| CLTA4-6-1 | 6 | GCAGcTGgcaTtTcTCCACACGG | SEQ ID NO: 86 | | | | n.t. | n.t. | n.t. | | |
| CLTA4-6-2 | 6 | GgAGATcTgaTGgTTCTACAAGG | SEQ ID NO: 87 | | | | 0.007% | 0.00% | 0.009% | | |
| CLTA4-6-3 | 6 | taAaATGcAGTGTaTCCAtATGG | SEQ ID NO: 88 | SMA4 | | | 0.015% | 0.00% | 0% | | |
| CLTA4-7-1 | 7 | GCcagaaTAGTTTTTCaACAAGG | SEQ ID NO: 89 | SEPHS2 | | | 0% | 0.00% | 0.007% | | |
| CLTA4-7-2 | 8 | ttgtATTTAGaGaTTgCACAAGG | SEQ ID NO: 90 | RORB | | | 0% | 0.00% | 0% | | |

TABLE 2

| position | −4 | −3 | −2 | −1 | 1 | 2 | 3 | 4 | 5 | 6 | 7 |
|---|---|---|---|---|---|---|---|---|---|---|---|
| 100 nM Cas9:CLTA1 v2.1 sgRNA ||||||||||||
| A | 212906 | 240335 | 195549 | 240068 | 1.04E+06 | 72751 | 40206 | 62972 | 41734 | 17376 | 18710 |
| C | 285295 | 248395 | 263973 | 260202 | 37925 | 32496 | 24822 | 1.10E+06 | 1.12E+06 | 42444 | 1.16E+06 |
| G | 214213 | 219078 | 220275 | 189578 | 61062 | 1.04E+06 | 25785 | 11117 | 9125 | 5423 | 5745 |
| T | 493854 | 498460 | 526471 | 516420 | 64694 | 59173 | 1.12E+06 | 35336 | 34236 | 1.14E+06 | 20532 |
| 1000 nM Cas9:CLTA1 v1.0 sgRNA ||||||||||||
| A | 154613 | 184336 | 154288 | 177436 | 805105 | 66777 | 43354 | 56461 | 32941 | 15531 | 19465 |
| C | 227144 | 201856 | 215667 | 220894 | 30269 | 30133 | 24249 | 825333 | 865486 | 35164 | 889622 |
| G | 163868 | 174062 | 177891 | 148150 | 47940 | 784264 | 26342 | 17972 | 10299 | 6332 | 5785 |
| T | 389059 | 374430 | 386838 | 388204 | 51370 | 53510 | 840739 | 34918 | 25958 | 877657 | 19812 |
| 1000 nM Cas9:CLTA1 v2.1 sgRNA ||||||||||||
| A | 104782 | 127116 | 103361 | 124521 | 554601 | 40232 | 29541 | 38710 | 23659 | 10435 | 11462 |
| C | 154144 | 136337 | 145670 | 146754 | 20057 | 19440 | 17922 | 569754 | 590426 | 25233 | 612203 |
| G | 113998 | 119668 | 120741 | 103026 | 32861 | 547445 | 18468 | 9314 | 6346 | 3908 | 4295 |
| T | 267467 | 257270 | 270619 | 266090 | 32872 | 33274 | 574460 | 22613 | 19960 | 600815 | 12431 |
| CLTA1 pre-selection library ||||||||||||
| A | 241543 | 217144 | 209045 | 198284 | 943175 | 103452 | 76259 | 106919 | 124476 | 59762 | 108373 |
| C | 254366 | 269805 | 276090 | 322860 | 52984 | 65855 | 58943 | 834238 | 812029 | 52168 | 839963 |
| G | 230024 | 196574 | 210445 | 180859 | 60496 | 857631 | 66782 | 89366 | 85315 | 67098 | 77499 |
| T | 403590 | 446000 | 433943 | 427520 | 72868 | 102585 | 927538 | 99000 | 107703 | 950495 | 103688 |
| 100 nM Cas9:CLTA2 v2.1 sgRNA ||||||||||||
| A | 109129 | 135587 | 94032 | 141748 | 5.74E+04 | 44802 | 48284 | 24464 | 11611 | 16668 | 6282 |
| C | 155710 | 138970 | 207735 | 220443 | 529643 | 24503 | 566049 | 6.27E+05 | 6.46E+05 | 19040 | 6.52E+05 |
| G | 136555 | 142038 | 118241 | 105620 | 39991 | 2.11E+04 | 26481 | 3756 | 3627 | 2889 | 2488 |
| T | 266918 | 251717 | 248304 | 200501 | 41277 | 577893 | 2.75E+04 | 13008 | 7318 | 6.30E+05 | 7487 |
| 1000 nM Cas9:CLTA2 v1.0 sgRNA ||||||||||||
| A | 94138 | 115628 | 85485 | 120876 | 52411 | 41438 | 46093 | 22399 | 9065 | 14310 | 5351 |
| C | 140695 | 125708 | 179224 | 191394 | 452192 | 21517 | 481298 | 538392 | 557549 | 16233 | 562576 |
| G | 113243 | 118054 | 101836 | 91048 | 35101 | 18969 | 22797 | 3440 | 2802 | 2960 | 2526 |
| T | 228367 | 217053 | 209898 | 173125 | 36739 | 494519 | 26255 | 12212 | 7026 | 542940 | 5990 |
| 1000 nM Cas9:CLTA2 v2.1 sgRNA ||||||||||||
| A | 64249 | 81812 | 58977 | 65387 | 35172 | 29833 | 33434 | 19419 | 9272 | 13136 | 4907 |
| C | 96983 | 87918 | 124642 | 187760 | 316077 | 14548 | 327166 | 364874 | 380987 | 11360 | 387025 |
| G | 77913 | 80500 | 68612 | 64299 | 23522 | 15749 | 19664 | 3856 | 3035 | 2752 | 2062 |
| T | 160415 | 149330 | 147329 | 122114 | 94789 | 339431 | 19296 | 11411 | 6266 | 372312 | 5566 |
| CLTA2 pre-selection library ||||||||||||
| A | 203147 | 173899 | 167999 | 170203 | 89970 | 73770 | 88239 | 88611 | 76114 | 78589 | 75016 |
| C | 181430 | 214835 | 246369 | 272618 | 632831 | 41977 | 641062 | 644565 | 670872 | 40877 | 649838 |
| G | 177090 | 153006 | 151178 | 140868 | 58664 | 49976 | 60827 | 56077 | 52341 | 49259 | 55484 |
| T | 285951 | 305878 | 282072 | 263929 | 66153 | 681895 | 57490 | 58365 | 48291 | 678893 | 67280 |
| 100 nM Cas9:CLTA3 v2.1 sgRNA ||||||||||||
| A | 212836 | 248582 | 202151 | 249368 | 9.13E+04 | 77392 | 19048 | 39738 | 1078520 | 1106930 | 46196 |
| C | 233270 | 241259 | 274819 | 305120 | 37894 | 35918 | 13930 | 5.61E+03 | 1.22E+04 | 3774 | 6.35E+03 |
| G | 211701 | 187534 | 185281 | 196614 | 66632 | 9.88E+05 | 26572 | 1074020 | 12936 | 9205 | 1066570 |
| T | 480761 | 461193 | 476317 | 387466 | 942707 | 37284 | 1.08E+06 | 19204 | 34885 | 1.87E+04 | 19450 |
| 1000 nM Cas9:CLTA3 v1.0 sgRNA ||||||||||||
| A | 219833 | 263464 | 207913 | 264018 | 97886 | 78562 | 20663 | 39724 | 1136320 | 1151200 | 42966 |
| C | 240570 | 261247 | 311444 | 333414 | 39996 | 40484 | 13961 | 5323 | 11099 | 5475 | 10323 |
| G | 221683 | 206195 | 199246 | 215583 | 76580 | 1032080 | 24785 | 1126840 | 12654 | 12465 | 1114450 |
| T | 506611 | 457791 | 470094 | 375682 | 974235 | 37571 | 1129290 | 16811 | 28626 | 19560 | 20956 |
| 1000 nM Cas9:CLTA3 v2.1 sgRNA ||||||||||||
| A | 169775 | 206549 | 166197 | 201768 | 75243 | 67150 | 20449 | 36549 | 876154 | 898360 | 39901 |
| C | 197800 | 209445 | 243688 | 264177 | 32775 | 34540 | 14250 | 7885 | 14793 | 4878 | 7791 |
| G | 174766 | 158928 | 158824 | 168325 | 58121 | 801768 | 26558 | 356689 | 13343 | 12052 | 868394 |
| T | 394073 | 361492 | 367705 | 302144 | 770275 | 32956 | 875157 | 25291 | 32124 | 21124 | 20328 |
| CLTA3 pre-selection library ||||||||||||
| A | 173122 | 135327 | 133244 | 142593 | 50365 | 69485 | 37040 | 56315 | 575295 | 566722 | 70243 |
| C | 143788 | 158534 | 162046 | 177240 | 25902 | 40142 | 28129 | 34669 | 38933 | 36129 | 61591 |
| G | 137601 | 132826 | 130592 | 128304 | 42860 | 534378 | 42217 | 531723 | 29873 | 34068 | 479149 |
| T | 238486 | 266310 | 261515 | 244854 | 573870 | 48391 | 595611 | 60291 | 48596 | 56079 | 82008 |
| 100 nM Cas9:CLTA4 v2.1 sgRNA ||||||||||||
| A | 55030 | 78101 | 78867 | 81833 | 8.09E+04 | 58148 | 525585 | 29962 | 544918 | 19446 | 54151 |
| C | 168401 | 162082 | 139480 | 130495 | 22088 | 428628 | 4498 | 1.21E+04 | 5.14E+03 | 15601 | 7.10E+03 |
| G | 89302 | 75785 | 82959 | 133275 | 415632 | 4.70E+04 | 14868 | 504358 | 6156 | 9951 | 493432 |
| T | 248025 | 244790 | 259452 | 215155 | 42090 | 26956 | 1.58E+04 | 14300 | 4541 | 5.16E+05 | 6071 |

TABLE 2-continued

| | | | | 1000 nM Cas9:CLTA4 v1.0 sgRNA | | | | | | |
|---|---|---|---|---|---|---|---|---|---|---|
| A | 95188 | 141261 | 145156 | 141850 | 151224 | 116745 | 928773 | 50295 | 975924 | 29201 | 95476 |
| C | 305024 | 297215 | 260676 | 243819 | 34420 | 745345 | 8606 | 17266 | 7541 | 29948 | 10779 |
| G | 159888 | 139073 | 153474 | 225343 | 742232 | 85777 | 29776 | 907007 | 9285 | 13455 | 883325 |
| T | 438973 | 421524 | 439767 | 388061 | 71197 | 51206 | 31918 | 24505 | 6323 | 926469 | 9493 |
| | | | | 1000 nM Cas9:CLTA4 v2.1 sgRNA | | | | | | |
| A | 47674 | 70467 | 71535 | 72698 | 72554 | 54587 | 471218 | 27627 | 493315 | 16818 | 47470 |
| C | 154985 | 151636 | 133622 | 122579 | 18730 | 384037 | 4452 | 10916 | 4303 | 16232 | 5436 |
| G | 80869 | 69972 | 76726 | 118084 | 379024 | 42360 | 14989 | 453870 | 5084 | 6863 | 448784 |
| T | 222651 | 214104 | 224296 | 192818 | 35871 | 25195 | 15520 | 13766 | 3477 | 466266 | 4489 |
| | | | | CLTA4 pre-selection library | | | | | | |
| A | 106798 | 131577 | 131941 | 132368 | 127160 | 103294 | 820923 | 103844 | 840417 | 99163 | 133349 |
| C | 304597 | 297419 | 277233 | 283453 | 50833 | 722264 | 29748 | 65558 | 44890 | 59551 | 73916 |
| G | 146240 | 137027 | 134399 | 183111 | 695802 | 68240 | 51484 | 708098 | 30709 | 62837 | 673752 |
| T | 393868 | 385480 | 407930 | 352571 | 77708 | 57705 | 49348 | 74003 | 35487 | 729952 | 70486 |

| position | 8 | 9 | 10 | 11 | 12 | 13 | 14 | 15 | 16 | 17 |
|---|---|---|---|---|---|---|---|---|---|---|
| | | | | 100 nM Cas9:CLTA1 v2.1 sgRNA | | | | | | |
| A | 1.17E+06 | 24455 | 83195 | 46083 | 33528 | 8551 | 9668 | 4582 | 32237 | 1.19E+06 |
| C | 5339 | 22096 | 1.06E+06 | 48105 | 1.14E+06 | 1.14E+06 | 1.18E+06 | 4090 | 1.13E+06 | 4363 |
| G | 5121 | 8080 | 14905 | 8906 | 3732 | 3294 | 3867 | 3597 | 7260 | 3400 |
| T | 24018 | 1.15E+06 | 50488 | 1.10E+06 | 32417 | 57980 | 13065 | 1.19E+06 | 36826 | 8959 |
| | | | | 1000 nM Cas9:CLTA1 v1.0 sgRNA | | | | | | |
| A | 904223 | 19696 | 56566 | 35200 | 26674 | 7925 | 9269 | 4859 | 32891 | 910633 |
| C | 5488 | 17340 | 828521 | 36975 | 876790 | 880022 | 908816 | 4419 | 859691 | 5694 |
| G | 5938 | 9185 | 11560 | 10641 | 3020 | 2819 | 3185 | 2994 | 6763 | 3631 |
| T | 19035 | 888463 | 38037 | 851868 | 28200 | 43918 | 13414 | 922412 | 35339 | 14726 |
| | | | | 1000 nM Cas9:CLTA1 v2.1 sgRNA | | | | | | |
| A | 618404 | 14608 | 41826 | 27762 | 19590 | 8961 | 19434 | 9549 | 35083 | 604115 |
| C | 3834 | 15297 | 561351 | 26392 | 592757 | 594469 | 616112 | 11645 | 553993 | 13212 |
| G | 3719 | 5851 | 10887 | 15360 | 5605 | 3378 | 3517 | 5896 | 22551 | 8658 |
| T | 14434 | 604635 | 26327 | 570877 | 22439 | 33583 | 1328 | 613301 | 28764 | 14406 |
| | | | | CLTA1 pre-selection library | | | | | | |
| A | 937511 | 65477 | 110282 | 67774 | 96299 | 88029 | 109977 | 62686 | 119399 | 931093 |
| C | 54708 | 43285 | 831610 | 50109 | 861358 | 841819 | 817157 | 51676 | 797914 | 60106 |
| G | 59257 | 71824 | 89579 | 68090 | 66121 | 86080 | 96496 | 81367 | 104949 | 52143 |
| T | 78047 | 948937 | 98052 | 943550 | 105745 | 113595 | 105893 | 933794 | 107261 | 86181 |
| | | | | 100 nM Cas9:CLTA2 v2.1 sgRNA | | | | | | |
| A | 6.58E+05 | 655917 | 28909 | 24210 | 656617 | 59160 | 36601 | 2974 | 12980 | 3.27E+03 |
| C | 2951 | 2577 | 1.30E+04 | 617274 | 2.64E+03 | 1.48E+04 | 9.12E+03 | 660929 | 6.50E+05 | 660305 |
| G | 3025 | 3202 | 609865 | 8312 | 5889 | 581322 | 606454 | 1564 | 2134 | 1819 |
| T | 4920 | 6.62E+03 | 16554 | 1.85E+04 | 3165 | 13024 | 16134 | 2.85E+03 | 3253 | 2918 |
| | | | | 1000 nM Cas9:CLTA2 v1.0 sgRNA | | | | | | |
| A | 567337 | 565061 | 24132 | 23848 | 558483 | 49577 | 39401 | 5425 | 30774 | 6408 |
| C | 1973 | 2127 | 11807 | 525901 | 4992 | 13617 | 13316 | 563557 | 535780 | 560658 |
| G | 2895 | 2793 | 526655 | 8738 | 8100 | 495156 | 496382 | 1789 | 3325 | 1846 |
| T | 4238 | 6462 | 13849 | 16956 | 4868 | 18093 | 27344 | 5672 | 6564 | 7531 |
| | | | | 1000 nM Cas9:CLTA2 v2.1 sgRNA | | | | | | |
| A | 391675 | 389930 | 13852 | 16657 | 383605 | 32780 | 22855 | 9722 | 25181 | 12518 |
| C | 1694 | 1815 | 8124 | 363374 | 5168 | 9569 | 9710 | 374342 | 355544 | 373485 |
| G | 2398 | 2439 | 360755 | 7431 | 6019 | 344511 | 350245 | 1559 | 5882 | 1339 |
| T | 3793 | 5376 | 10829 | 12098 | 4768 | 12700 | 16750 | 13937 | 12953 | 12819 |
| | | | | CLTA2 pre-selection library | | | | | | |
| A | 726091 | 712150 | 96111 | 90307 | 728931 | 91515 | 84764 | 79586 | 86205 | 87337 |
| C | 38931 | 44691 | 46591 | 628706 | 32296 | 49519 | 46571 | 641958 | 624548 | 637703 |
| G | 39801 | 38939 | 630670 | 55013 | 38368 | 627263 | 642878 | 59549 | 55292 | 53056 |
| T | 42795 | 51838 | 74246 | 73592 | 48023 | 79321 | 73405 | 66525 | 81573 | 69522 |
| | | | | 100 nM Cas9:CLTA3 v2.1 sgRNA | | | | | | |
| A | 1.12E+06 | 64461 | 11912 | 30992 | 21158 | 6465 | 1130430 | 4097 | 5750 | 4.71E+04 |
| C | 4063 | 6018 | 1.11E+06 | 27501 | 4.68E+04 | 1.12E+06 | 1.96E+04 | 1129400 | 1.82E+03 | 3421 |
| G | 7418 | 1050360 | 3828 | 3949 | 2231 | 2504 | 2471 | 1726 | 2881 | 1081680 |
| T | 11145 | 1.77E+04 | 13689 | 1.08E+06 | 1068370 | 9829 | 3709 | 3.34E+03 | 1128120 | 6398 |
| | | | | 1000 nM Cas9:CLTA3 v1.0 sgRNA | | | | | | |
| A | 1156400 | 49443 | 18669 | 44652 | 44644 | 44771 | 1152540 | 16264 | 30980 | 71714 |
| C | 6501 | 8456 | 1126310 | 36792 | 56203 | 1096280 | 8437 | 1156840 | 8448 | 25120 |

TABLE 2-continued

| | | | | | | | | | | |
|---|---|---|---|---|---|---|---|---|---|---|
| G | 12075 | 1113930 | 12078 | 19275 | 9014 | 7707 | 9466 | 2708 | 17195 | 1053760 |
| T | 13723 | 16864 | 31636 | 1087980 | 1078840 | 39940 | 18250 | 12883 | 1132070 | 38103 |

1000 nM Cas9:CLTA3 v2.1 sgRNA

| | | | | | | | | | | |
|---|---|---|---|---|---|---|---|---|---|---|
| A | 911344 | 44415 | 13218 | 37301 | 33080 | 26409 | 893670 | 6315 | 20807 | 52541 |
| C | 4636 | 7510 | 890531 | 28425 | 46269 | 870864 | 7991 | 910584 | 5931 | 19923 |
| G | 8837 | 867980 | 7923 | 14022 | 6553 | 3393 | 7912 | 1499 | 12906 | 836022 |
| T | 11597 | 16509 | 24682 | 856666 | 850512 | 35746 | 26841 | 18016 | 896770 | 27928 |

CLTA3 pre-selection library

| | | | | | | | | | | |
|---|---|---|---|---|---|---|---|---|---|---|
| A | 528947 | 72610 | 41265 | 61770 | 56547 | 75555 | 586476 | 61203 | 51740 | 70943 |
| C | 52201 | 46032 | 559715 | 32233 | 34830 | 519328 | 30904 | 540977 | 24982 | 45344 |
| G | 49753 | 501888 | 41949 | 43243 | 30118 | 38922 | 34282 | 34082 | 37275 | 515778 |
| T | 82036 | 72467 | 50068 | 555751 | 571502 | 59192 | 41335 | 56735 | 579000 | 60932 |

100 nM Cas9:CLTA4 v2.1 sgRNA

| | | | | | | | | | | |
|---|---|---|---|---|---|---|---|---|---|---|
| A | 2.59E+04 | 550200 | 29521 | 34194 | 38891 | 26542 | 23991 | 15243 | 25122 | 5.36E+03 |
| C | 35217 | 2481 | 2.35E+04 | 16846 | 2.03E+04 | 3.69E+04 | 8.47E+03 | 5182 | 5.22E+05 | 547711 |
| G | 14899 | 4528 | 498832 | 27411 | 497382 | 6729 | 3344 | 3716 | 3926 | 3162 |
| T | 484788 | 3.55E+03 | 8877 | 4.82E+05 | 4222 | 490573 | 524958 | 5.37E+05 | 9437 | 4528 |

1000 nM Cas9:CLTA4 v1.0 sgRNA

| | | | | | | | | | | |
|---|---|---|---|---|---|---|---|---|---|---|
| A | 30383 | 980248 | 50181 | 65094 | 77253 | 42674 | 41050 | 32933 | 55244 | 39984 |
| C | 47831 | 5069 | 32501 | 30389 | 29610 | 61641 | 25910 | 21400 | 887446 | 900777 |
| G | 19640 | 8303 | 902733 | 44730 | 879985 | 16677 | 7879 | 8429 | 12432 | 17373 |
| T | 901219 | 5453 | 13658 | 858860 | 12225 | 878081 | 924234 | 936311 | 43951 | 40939 |

1000 nM Cas9:CLTA4 v2.1 sgRNA

| | | | | | | | | | | |
|---|---|---|---|---|---|---|---|---|---|---|
| A | 17728 | 498471 | 29769 | 40021 | 41618 | 24741 | 23050 | 16409 | 27974 | 2697 |
| C | 28594 | 1961 | 19017 | 19152 | 18001 | 35213 | 12845 | 13497 | 445302 | 480543 |
| G | 10260 | 3281 | 450120 | 23076 | 439828 | 7741 | 5091 | 5456 | 7558 | 7112 |
| T | 449597 | 2466 | 7273 | 423930 | 6732 | 438484 | 465193 | 470817 | 25345 | 15827 |

CLTA4 pre-selection library

| | | | | | | | | | | |
|---|---|---|---|---|---|---|---|---|---|---|
| A | 123366 | 824537 | 126564 | 115133 | 122618 | 108492 | 107761 | 96384 | 99908 | 76163 |
| C | 77470 | 45318 | 84973 | 73106 | 90384 | 78280 | 76978 | 66776 | 738550 | 776738 |
| G | 89897 | 49093 | 672860 | 88125 | 663922 | 67768 | 53472 | 58440 | 47550 | 41427 |
| T | 660770 | 32555 | 67106 | 675139 | 74579 | 696963 | 713292 | 729903 | 65495 | 57175 |

| position | 18 | 19 | 20 | PAM1 | PAM2 | PAM3 | +4 | +5 | +6 | +7 |
|---|---|---|---|---|---|---|---|---|---|---|

100 nM Cas9:CLTA1 v2.1 sgRNA

| | | | | | | | | | | |
|---|---|---|---|---|---|---|---|---|---|---|
| A | 1.20E+06 | 2032 | 4237 | 261056 | 1386 | 574 | 235167 | 223887 | 222343 | 301956 |
| C | 628 | 969 | 1.19E+06 | 210095 | 167 | 152 | 211027 | 273777 | 264354 | 309690 |
| G | 2474 | 1.19E+06 | 1301 | 238989 | 1.20E+06 | 1.21E+06 | 205765 | 222282 | 240526 | 217260 |
| T | 3966 | 9354 | 8065 | 496128 | 475 | 211 | 554309 | 486322 | 479045 | 377362 |

1000 nM Cas9:CLTA1 v1.0 sgRNA

| | | | | | | | | | | |
|---|---|---|---|---|---|---|---|---|---|---|
| A | 925527 | 3595 | 5976 | 183479 | 1390 | 413 | 182704 | 171051 | 174062 | 221899 |
| C | 776 | 2120 | 920211 | 180463 | 120 | 88 | 180657 | 220438 | 211411 | 245967 |
| G | 2894 | 916417 | 1415 | 193418 | 932808 | 934044 | 172551 | 172071 | 176484 | 161703 |
| T | 5487 | 12552 | 7082 | 377324 | 366 | 139 | 398772 | 371124 | 372727 | 305115 |

1000 nM Cas9:CLTA1 v2.1 sgRNA

| | | | | | | | | | | |
|---|---|---|---|---|---|---|---|---|---|---|
| A | 607264 | 4665 | 16515 | 125225 | 10391 | 2519 | 125288 | 114575 | 120476 | 149847 |
| C | 4438 | 5146 | 590160 | 116022 | 329 | 138 | 123802 | 154249 | 146572 | 166531 |
| G | 12770 | 613580 | 3712 | 121392 | 628464 | 637588 | 118800 | 113560 | 118464 | 111278 |
| T | 15919 | 17000 | 30004 | 277752 | 1207 | 146 | 272501 | 258007 | 254879 | 212735 |

CLTA1 pre-selection library

| | | | | | | | | | | |
|---|---|---|---|---|---|---|---|---|---|---|
| A | 908362 | 64248 | 111479 | 190574 | 97896 | 104002 | 183367 | 178912 | 198049 | 219754 |
| C | 52998 | 42317 | 813253 | 239201 | 56843 | 59450 | 289074 | 295400 | 289007 | 284268 |
| G | 77389 | 918970 | 96000 | 192652 | 879150 | 870948 | 196672 | 202194 | 196499 | 202544 |
| T | 90774 | 103988 | 108791 | 507096 | 95634 | 95123 | 460410 | 453017 | 445968 | 422957 |

100 nM Cas9:CLTA2 v2.1 sgRNA

| | | | | | | | | | | |
|---|---|---|---|---|---|---|---|---|---|---|
| A | 1.09E+03 | 17686 | 689 | 193742 | 284 | 129 | 143150 | 165553 | 136708 | 146056 |
| C | 656122 | 1314 | 6.65E+05 | 42664 | 48 | 43 | 162563 | 111729 | 143442 | 177253 |
| G | 89 | 6.44E+05 | 505 | 137388 | 6.68E+05 | 6.68E+05 | 103305 | 146355 | 139972 | 124772 |
| T | 1016 | 4886 | 2608 | 294518 | 146 | 48 | 259294 | 244675 | 248190 | 220231 |

1000 nM Cas9:CLTA2 v1.0 sgRNA

| | | | | | | | | | | |
|---|---|---|---|---|---|---|---|---|---|---|
| A | 5055 | 36081 | 2573 | 148145 | 782 | 243 | 132801 | 126862 | 118528 | 122897 |
| C | 567693 | 4938 | 569653 | 46472 | 70 | 45 | 133402 | 123970 | 130555 | 148756 |
| G | 166 | 519782 | 520 | 125177 | 575295 | 576103 | 118877 | 108849 | 104210 | 103370 |
| T | 3529 | 15642 | 3697 | 256649 | 196 | 52 | 191363 | 216762 | 223150 | 201420 |

TABLE 2-continued

| | | | | | | | | | | | |
|---|---|---|---|---|---|---|---|---|---|---|---|
| | | colspan="10" | 1000 nM Cas9:CLTA2 v2.1 sgRNA | | | | | | | | |
| A | 17950 | 28198 | 5471 | 100745 | 4933 | 834 | 89339 | 87351 | 82615 | 85108 |
| C | 370343 | 11652 | 378841 | 40532 | 238 | 34 | 93621 | 87920 | 91380 | 105625 |
| G | 391 | 331376 | 1034 | 74803 | 393760 | 398660 | 79776 | 75927 | 74068 | 70435 |
| T | 10876 | 28334 | 14214 | 183480 | 629 | 32 | 136824 | 148362 | 151497 | 138392 |
| | colspan="10" | CLTA2 pre-selection library | | | | | | | | |
| A | 85547 | 92983 | 100316 | 177716 | 84144 | 88017 | 177831 | 180209 | 176904 | 174190 |
| C | 635473 | 51727 | 594349 | 136372 | 41282 | 41689 | 216880 | 206368 | 210039 | 235263 |
| G | 57979 | 616575 | 86553 | 158929 | 656315 | 654970 | 162242 | 160704 | 157741 | 138890 |
| T | 68619 | 86333 | 86400 | 374601 | 65877 | 62942 | 290665 | 300337 | 302934 | 299275 |
| | colspan="10" | 100 nM Cas9:CLTA3 v2.1 sgRNA | | | | | | | | |
| A | 1.14E+06 | 6151 | 2047 | 305062 | 1993 | 394 | 213566 | 240851 | 230230 | 252637 |
| C | 167 | 1451 | 6.66E+02 | 261609 | 103 | 82 | 313990 | 253055 | 261338 | 293644 |
| G | 876 | 1.13E+06 | 600 | 228865 | 1.14E+06 | 1.14E+06 | 142425 | 192720 | 220683 | 227840 |
| T | 1320 | 4480 | 1135260 | 343032 | 211 | 69 | 462587 | 451942 | 426317 | 364447 |
| | colspan="10" | 1000 nM Cas9:CLTA3 v1.0 sgRNA | | | | | | | | |
| A | 1156700 | 47106 | 27658 | 276285 | 26304 | 12701 | 219034 | 239515 | 244440 | 255360 |
| C | 4351 | 24685 | 9473 | 297135 | 1331 | 939 | 354289 | 298216 | 277740 | 292917 |
| G | 10278 | 1085310 | 10308 | 238545 | 1148550 | 1174510 | 171862 | 193096 | 217301 | 239319 |
| T | 17372 | 31596 | 1141260 | 376732 | 2514 | 550 | 443512 | 457870 | 449216 | 401101 |
| | colspan="10" | 1000 nM Cas9:CLTA3 v2.1 sgRNA | | | | | | | | |
| A | 903619 | 33690 | 20904 | 205940 | 26623 | 9880 | 172210 | 182986 | 187305 | 196429 |
| C | 4977 | 18171 | 6508 | 223797 | 1163 | 693 | 283240 | 240802 | 224453 | 236469 |
| G | 9011 | 859600 | 8302 | 190011 | 906628 | 925513 | 132620 | 153591 | 172169 | 187623 |
| T | 18807 | 24953 | 900700 | 310666 | 2000 | 328 | 348344 | 359035 | 352487 | 315893 |
| | colspan="10" | CLTA3 pre-selection library | | | | | | | | |
| A | 563277 | 70484 | 50807 | 130402 | 57527 | 61702 | 110207 | 118993 | 126967 | 127707 |
| C | 35359 | 44014 | 35778 | 174938 | 42259 | 46083 | 201434 | 190347 | 184768 | 207347 |
| G | 36956 | 516177 | 45203 | 137307 | 539445 | 527404 | 113323 | 119846 | 118423 | 127230 |
| T | 51405 | 62322 | 561209 | 250350 | 53766 | 57808 | 268033 | 263811 | 262839 | 230713 |
| | colspan="10" | 100 nM Cas9:CLTA4 v2.1 sgRNA | | | | | | | | |
| A | 5.51E+05 | 1994 | 540029 | 47731 | 4642 | 1401 | 77633 | 56902 | 63224 | 54815 |
| C | 5715 | 546119 | 3.02E+03 | 152056 | 655 | 473 | 141123 | 164035 | 146401 | 190955 |
| G | 554 | 1.45E+03 | 4637 | 72296 | 5.55E+05 | 5.58E+05 | 84257 | 77627 | 75123 | 91454 |
| T | 3692 | 11194 | 13069 | 288675 | 911 | 495 | 257745 | 262194 | 276010 | 223534 |
| | colspan="10" | 1000 nM Cas9:CLTA4 v1.0 sgRNA | | | | | | | | |
| A | 942989 | 19900 | 887311 | 80159 | 28536 | 12390 | 142460 | 96664 | 110844 | 99920 |
| C | 34590 | 940504 | 23749 | 257985 | 4791 | 2556 | 252462 | 297152 | 258929 | 338099 |
| G | 4103 | 7346 | 20095 | 139488 | 964013 | 976818 | 154302 | 139784 | 136512 | 165750 |
| T | 17391 | 31323 | 67918 | 521441 | 3968 | 5074 | 449849 | 465473 | 492788 | 395304 |
| | colspan="10" | 1000 nM Cas9:CLTA4 v2.1 sgRNA | | | | | | | | |
| A | 478335 | 12667 | 451298 | 36128 | 22041 | 16967 | 68943 | 49017 | 56451 | 51102 |
| C | 15631 | 469503 | 11832 | 122541 | 3529 | 8965 | 126313 | 153105 | 134293 | 171499 |
| G | 3083 | 5302 | 10184 | 87517 | 474540 | 471647 | 85849 | 72063 | 71600 | 85239 |
| T | 9130 | 18707 | 32865 | 259993 | 6069 | 8600 | 225074 | 231994 | 243835 | 198339 |
| | colspan="10" | CLTA4 pre-selection library | | | | | | | | |
| A | 806675 | 75877 | 793806 | 87755 | 82110 | 83605 | 111015 | 103082 | 109315 | 101198 |
| C | 55522 | 754283 | 42168 | 278602 | 57603 | 55530 | 266156 | 281433 | 258029 | 295144 |
| G | 42574 | 54424 | 59162 | 151536 | 740525 | 732891 | 163824 | 158224 | 146268 | 151560 |
| T | 46732 | 66919 | 56347 | 433410 | 71265 | 79477 | 410508 | 408764 | 437891 | 403601 |

TABLE 3

| | | | no sgRNA | | v1.0 sgRNA | | v2.1 sgRNA | |
|---|---|---|---|---|---|---|---|---|
| | m | sequence | modified sequences | total sequences | modified sequences | total sequences | modified sequences | total sequences |
| CLTA1-0-1 | 0 | AGTCCTCATCTCCCTCAAGCAGG (SEQ ID NO: 91) | 2 | 58889 | 18 | 42683 | 178 | 52845 |
| CLTA1-1-1 | 1 | AGTCCTCAaCTCCCTCAACCACC (SEQ ID NO: 92) | 1 | 39804 | 9 | 29000 | 37 | 40588 |
| CLTA1-2-1 | 2 | AGcCCTCATtTCCCTCAAGCAGG (SEQ ID NO: 93) | 0 | 16276 | 0 | 15032 | 0 | 18277 |

TABLE 3-continued

| | m | sequence | no sgRNA | | v1.0 sgRNA | | v2.1 sgRNA | |
|---|---|---|---|---|---|---|---|---|
| | | | modified sequences | total sequences | modified sequences | total sequences | modified sequences | total sequences |
| CLTA1-2-2 | 2 | AcTCCTCATCcCCCTCAAGCCGG (SEQ ID NO: 94) | 3 | 21267 | 1 | 20042 | 33 | 22579 |
| CLTA1-2-3 | 2 | AGTCaTCATCTCCCTCAAGCAGa (SEQ ID NO: 95) | 0 | 0 | 0 | 0 | 0 | 0 |
| CLTA1-3-1 | 3 | cGTCCTCcTCTCCCcCAAGCAGG (SEQ ID NO: 96) | 2 | 53901 | 0 | 42194 | 0 | 52205 |
| CLTA1-3-2 | 3 | tGTCCTCtTCTCCCTCAAGCAGa (SEQ ID NO: 97) | 0 | 14890 | 0 | 14231 | 0 | 15937 |
| CLTA1-4-1 | 4 | AagCtTCATCTCtCTCAAGCTGG (SEQ ID NO: 98) | 0 | 49579 | 2 | 31413 | 0 | 41234 |
| CLTA1-4-2 | 4 | AGTaCTCtTtTCCCTCAgGCTGG (SEQ ID NO: 99) | 2 | 30013 | 1 | 23470 | 4 | 26999 |
| CLTA1-4-3 | 4 | AGTCtTaAatTCCCTCAAGCAGG (SEQ ID NO: 100) | 2 | 63792 | 0 | 52321 | 1 | 73007 |
| CLTA1-4-4 | 4 | AGTgCTCATCTaCCagAAGCTGG (SEQ ID NO: 101) | 1 | 12585 | 0 | 11339 | 0 | 12066 |
| CLTA1-4-5 | 4 | ccTCCTCATCTCCCTgcAGCAGG (SEQ ID NO: 102) | 4 | 30568 | 1 | 23810 | 0 | 27870 |
| CLTA1-4-6 | 4 | ctaCaTCATCTCCCTCAAGCTGG (SEQ ID NO: 103) | 0 | 13200 | 1 | 12886 | 2 | 12843 |
| CLTA1-4-7 | 4 | gGTCCTCATCTCCCTaAAaCAGa (SEQ ID NO: 104) | 1 | 8697 | 3 | 8188 | 0 | 8783 |
| CLTA1-4-8 | 4 | tGTCCTCATCggCCTCAgGCAGG (SEQ ID NO: 105) | 0 | 13169 | 0 | 8805 | 2 | 12830 |
| CLTA1-5-1 | 5 | AGaCacCATCTCCCTtgAGCTGG (SEQ ID NO: 106) | 0 | 46109 | 1 | 32515 | 2 | 35567 |
| CLTA1-5-2 | 5 | AGgCaTCATCTaCaTCAAGtTGG (SEQ ID NO: 107) | 0 | 41280 | 0 | 28896 | 0 | 35152 |
| CLTA1-5-3 | 5 | AGTaaTCActTCCaTCAAGCCGG (SEQ ID NO: 108) | 0 | 0 | 0 | 0 | 0 | 0 |
| CLTA1-5-4 | 5 | tccCCTCAcCTCCCTaAAGCAGG (SEQ ID NO: 109) | 2 | 24169 | 5 | 17512 | 1 | 23483 |
| CLTA1-5-5 | 5 | tGTCtTtATtTCCCTCtAGCTGG (SEQ ID NO: 110) | 0 | 11527 | 0 | 10481 | 1 | 11027 |
| CLTA1-6-1 | 6 | AGTCCTCATCTCCCTCAAGCAGG (SEQ ID NO: 111) | 0 | 6537 | 0 | 5654 | 0 | 6741 |

TABLE 4

| | m | sequence | no sgRNA | | v1.0 sgRNA | | v2.1 sgRNA | |
|---|---|---|---|---|---|---|---|---|
| | | | modified sequences | total sequences | modified sequences | total sequences | modified sequences | total sequences |
| CLTA4-0-1 | 0 | GCAGATGTAGTGTTTCCACAGGG (SEQ ID NO: 112) | 6 | 29191 | 2005 | 18640 | 14970 | 19661 |
| CLTA4-3-1 | 3 | aCAtATGTAGTaTTTCCACAGGC (SEQ ID NO: 113) | 2 | 34165 | 11 | 20018 | 3874 | 16082 |
| CLTA4-3-2 | 3 | GCAtATGTAGTGTTTCCAaATGt (SEQ ID NO: 114) | 3 | 17923 | 0 | 11688 | 2 | 13880 |
| CLTA4-3-3 | 3 | cCAGATGTAGTaTTcCCACAGGG (SEQ ID NO: 115) | 0 | 16559 | 0 | 12007 | 52 | 11082 |

TABLE 4-continued

| | m | sequence | no sgRNA | | v1.0 sgRNA | | v2.1 sgRNA | |
|---|---|---|---|---|---|---|---|---|
| | | | modified sequences | total sequences | modified sequences | total sequences | modified sequences | total sequences |
| CLTA4-3-4 | 3 | GCAGtTtTAGTGTTTtCACAGGG (SEQ ID NO: 116) | 0 | 21722 | 0 | 12831 | 0 | 15726 |
| CLTA4-3-5 | 3 | GCAGAgtTAGTGTTTCCACACaG (SEQ ID NO: 117) | 1 | 21222 | 2 | 13555 | 3 | 16425 |
| CLTA4-3-6 | 3 | GCAGATGgAGgGTTTtCACAGGG (SEQ ID NO: 118) | 3 | 20342 | 3 | 12804 | 3 | 14068 |
| CLTA4-3-7 | 3 | GgAaATtTAGTGTTTCCACAGGG (SEQ ID NO: 119) | 2 | 38894 | 3 | 24017 | 1 | 29347 |
| CLTA4-4-1 | 4 | aaAGAaGTAGTaTTTCCACATGG (SEQ ID NO: 120) | 0 | 0 | 0 | 0 | 0 | 0 |
| CLTA4-4-2 | 4 | aaAGATGTAGTcaTTCCACAAGG (SEQ ID NO: 121) | 1 | 27326 | 0 | 17365 | 1 | 18941 |
| CLTA4-4-3 | 4 | aaAtATGTAGTcTTTCCACAGGG (SEQ ID NO: 122) | 2 | 46232 | 3 | 32264 | 0 | 32638 |
| CLTA4-4-4 | 4 | atAGATGTAGTGTTTCCAaAGGa (SEQ ID NO: 123) | 9 | 27821 | 1 | 16223 | 8 | 15388 |
| CLTA4-4-5 | 4 | cCAGAgGTAGTGcTcCCACAGGG (SEQ ID NO: 124) | 1 | 20979 | 1 | 15674 | 1 | 15086 |
| CLTA4-4-6 | 4 | cCAGATGTgagGTTTCCACAAGG (SEQ ID NO: 125) | 4 | 22021 | 0 | 15691 | 1 | 14253 |
| CLTA4-4-7 | 4 | ctAcATGTAGTGTTTCCAtATGG (SEQ ID NO: 126) | 2 | 35942 | 0 | 23076 | 1 | 11867 |
| <u>CLTA4-4-8</u> | <u>4</u> | <u>ctAGATGaAGTGcTTCCACATGC</u> (SEQ ID NO: 127) | <u>1</u> | <u>10692</u> | <u>1</u> | <u>7609</u> | <u>59</u> | <u>8077</u> |
| CLTA4-4-9 | 4 | GaAaATGgAGTGTTTaCACATGG (SEQ ID NO: 128) | 0 | 34616 | 0 | 22302 | 1 | 24671 |
| CLTA4-4-10 | 4 | GCAaATGaAGTGTcaCCACAAGG (SEQ ID NO: 129) | 1 | 25210 | 0 | 16187 | 0 | 16974 |
| CLTA4-4-11 | 4 | GCAaATGTAtTaTTTCCACtAGG (SEQ ID NO: 130) | 0 | 34144 | 1 | 24770 | 0 | 22547 |
| CLTA4-4-12 | 4 | GCAGATGTAGctTTTgtACATGG (SEQ ID NO: 131) | 0 | 14254 | 0 | 9616 | 0 | 9994 |
| CLTA4-4-13 | 4 | GCAGcTtaAGTGTTTtCACATGG (SEQ ID NO: 132) | 8 | 39466 | 1 | 7609 | 5 | 16525 |
| CLTA4-4-14 | 4 | ttAcATGTAGTGTTTaCACACGG (SEQ ID NO: 133) | 0 | 0 | 0 | 22302 | 0 | 0 |
| CLTA4-5-1 | 5 | GaAGAgGaAGTGTTTgCcCAGGG (SEQ ID NO: 134) | 1 | 27616 | 1 | 16319 | 1 | 16140 |
| CLTA4-5-2 | 5 | GaAGATGTgGaGTTgaCACATGG (SEQ ID NO: 135) | 1 | 22533 | 0 | 14292 | 0 | 15013 |
| CLTA4-5-3 | 5 | GCAGAaGTAcTGTTgttACAAGG (SEQ ID NO: 136) | 1 | 44243 | 1 | 29391 | 1 | 29734 |
| CLTA4-5-4 | 5 | GCAGATGTgGaaTTaCaACAGGG (SEQ ID NO: 137) | 0 | 27321 | 0 | 13640 | 0 | 14680 |
| CLTA4-5-5 | 5 | GCAGtcaTAGTGTaTaCACATGG (SEQ ID NO: 138) | 1 | 26538 | 0 | 18449 | 1 | 20559 |
| CLTA4-5-6 | 5 | taAGATGTAGTaTTTCCAaAAGt (SEQ ID NO: 139) | 1 | 15145 | 1 | 8905 | 0 | 7911 |
| CLTA4-6-1 | 6 | GCAGcTGgcaTtTcTCCACACGG (SEQ ID NO: 140) | 0 | 2 | 0 | 0 | 0 | 0 |

TABLE 4-continued

| | | | no sgRNA | | v1.0 sgRNA | | v2.1 sgRNA | |
|---|---|---|---|---|---|---|---|---|
| | m | sequence | modified sequences | total sequences | modified sequences | total sequences | modified sequences | total sequences |
| CLTA4-6-2 | 6 | GgAGATcTgaTGgTTCtACAAGG (SEQ ID NO: 141) | 2 | 27797 | 0 | 19450 | 2 | 21709 |
| CLTA4-6-3 | 6 | taAaATGCAGTGTaTCCAtATGG (SEQ ID NO: 142) | 4 | 27551 | 0 | 18424 | 0 | 18783 |
| CLTA4-7-1 | 7 | GCcagaaTAGTtTTTCaACAAGG (SEQ ID NO: 143) | 0 | 20942 | 0 | 13137 | 1 | 13792 |
| CLTA4-7-2 | 8 | ttgtATtTAGaGaTTgCACAAGG (SEQ ID NO: 144) | 0 | 28470 | 0 | 18104 | 0 | 20416 |

TABLE 5

| Off-target site | Human genome coordinates |
|---|---|
| CLTA1-0-1 | 9(+): 36,211,732-36,211,754 |
| | 12(+): 7,759,893-7,759,915 |
| CLTA1-1-1 | 8(−): 15,546,437-15,546,459 |
| CLTA1-2-1 | 3(−): 54,223,111-54,223,133 |
| CLTA1-2-2 | 15(+): 89,388,670-89,388,692 |
| CLTA1-2-3 | 5(+): 88716920-88,716,942 |
| CLTA1-3-1 | 21(+): 27,972,462-27,972,484 |
| CLTA1-3-2 | 4(−): 17,179,924-17,179,946 |
| CLTA1-4-1 | 1(+): 147,288,742-147,288,764 |
| CLTA1-4-2 | 10(+): 97,544,444-97,544,466 |
| CLTA1-4-3 | 2+30: 161,873,870-161,873,892 |
| CLTA1-4-4 | 1(+): 196,172,702-196,172,724 |
| CLTA1-4-5 | 13(+): 56,574,636-56,574,658 |
| CLTA1-4-6 | 2(+): 241,357,827-241,357,849 |
| CLTA1-4-7 | 3(−): 121,248,627-121,248,649 |
| CLTA1-4-8 | 12(+): 132,937,319-132,937,341 |
| CLTA1-5-1 | 9(−): 80,930,919 -80,930,941 |
| CLTA1-5-2 | 2(+): 140,901,875-14,0901,897 |
| CLTA1-5-3 | 3(+): 45,016,841-45,016,863 |
| CLTA1-5-4 | X(+): 40,775,684-40,775,706 |
| CLTA1-5-5 | 2(−): 185,151,622-185,151,644 |
| CLTA1-6-1 | X(+): 150,655,097-150,655,119 |
| CLTA4-0-1 | 9(−): 36,211,779-36,211,801 |
| CLTA4-3-1 | 12(−): 50,679,419-50,679,441 |
| CLTA4-3-2 | X(−): 143,939,483-143,939,505 |
| CLTA4-3-3 | 11(−): 47,492,611-47,492,633 |
| CLTA4-3-4 | 3(−): 162,523,715-162,523,737 |
| CLTA4-3-5 | 11(+): 30,592,975-30,592,997 |
| CLTA4-3-6 | 4(−): 155,252,699-155,252,721 |
| CLTA4-3-7 | 18(+): 39,209,441-39,209,463 |
| CLTA4-4-1 | 17(−): 36,785,650-36,785,672 |
| CLTA4-4-2 | 1(−): 241,537,119-241,537,141 |
| CLTA4-4-3 | 8(−): 120,432,103-120,432,125 |
| CLTA4-4-4 | 6(−): 106,204,600-106,204,622 |
| CLTA4-4-5 | 8(+): 102,527,804-102,527,826 |
| CLTA4-4-6 | 8(−): 94,685,538-94,685,560 |
| CLTA4-4-7 | 2(+): 35,820,054-35,820,076 |
| CLTA4-4-8 | 3(−): 36,590,352-36,590,374 |
| CLTA4-4-9 | 12(+): 100,915,498-100,915,520 |
| CLTA4-4-10 | 21(+): 33,557,705-33,557,727 |
| CLTA4-4-11 | 8(+): 10, 764,183-10, 764,205 |
| CLTA4-4-12 | 19(+): 37,811,645-37,811,667 |
| CLTA4-4-13 | 13(−): 26,832,673-26,832,695 |
| CLTA4-4-14 | 6(+): 19,349,572-19,349,594 |
| CLTA4-5-1 | 11(−): 502,300-502,322 |
| CLTA4-5-2 | 8(−): 28,389,683-28,389,705 |
| CLTA4-5-3 | 2(−): 118,557,405-118,557,427 |
| CLTA4-5-4 | 2(−): 103,248,360-103,248,382 |
| CLTA4-5-5 | 21(−): 42,929,085-42,929,107 |
| CLTA4-5-6 | 13(−): 83,097,278-83,097,300 |
| CLTA4-6-1 | 2(+): 43,078,423-43,078,445 |
| CLTA4-6-2 | 7(−): 11,909,384-11,909,406 |
| CLTA4-6-3 | 5(−): 69,775,482-69,775,504 |
| CLTA4-7-1 | 16(+): 30,454,945-30,454,967 |
| CLTA4-7-2 | 9(−): 77,211,328-77,211,350 |

TABLE 6

| | number of mutations | sequence | gene | in vitro enrichment | | modification frequency in HEK293T cells | | |
|---|---|---|---|---|---|---|---|---|
| | | | | v1.0 | v2.1 | no sgRNA | v1.0 | v2.1 |
| CLTA1-0-1 | 0 | AGTCCTCATCTCCCTCAAGCAGG (SEQ ID NO: 145) | CLTA | 41.4 | 23.3 | 0.003% | 0.042% | 0.337% |
| CLTA1-1-1 | 1 | AGTCCTCAaCTCCCTCAACCAGG (SEQ ID NO: 146) | TUSC3 | 25.9 | 14 | 0.003% | 0.031% | 0.091% |
| CLTA1-2-1 | 2 | AGcCCTCATtTCCCTCAAGCAGG (SEQ ID NO: 147) | CACNA2D3 | 15.4 | 26.2 | 0% | 0% | 0% |
| CLTA1-2-2 | 2 | AcTCCTCATCcCCCTCAAGCCGG (SEQ ID NO: 148) | ACAN | 29.2 | 18.8 | 0.014% | 0.005% | 0.146% |
| CLTA1-2-3 | 2 | AGTCaTCATCTCCCTCAAGCAGa (SEQ ID NO: 149) | | 0.06 | 1.27 | n.t. | n.t. | n.t. |
| CLTA1-3-1 | 3 | cGTCCTCcTCTCCCcCAAGCAGG (SEQ ID NO: 150) | | 0 | 2.07 | 0.004% | 0% | 0% |

TABLE 6-continued

| | number of mutations | sequence | gene | in vitro enrichment | | modification frequency in HEK293T cells | | |
|---|---|---|---|---|---|---|---|---|
| | | | | v1.0 | v2.1 | no sgRNA | v1.0 | v2.1 |
| CLTA1-3-2 | 3 | tGTCCTCtTCTCCCTCAAGCAGa (SEQ ID NO: 151) | BC029598 | 0 | 1.47 | 0% | 0% | 0% |
| CLTA1-4-1 | 4 | AagCtTCATCTCtCTCAAGCTGG (SEQ ID NO: 152) | | | | 0% | 0.006% | 0% |
| CLTA1-4-2 | 4 | AGTaCTCtTtTCCCTCAgGCTGG (SEQ ID NO: 153) | ENTPD1 | | | 0.007% | 0.004% | 0.015% |
| CLTA1-4-3 | 4 | AGTCtTaAatTCCCTCAAGCAGG (SEQ ID NO: 154) | | | | 0.003% | 0% | 0.001% |
| CLTA1-4-4 | 4 | AGTgCTCATCTaCCagAAGCTGG (SEQ ID NO: 155) | | | | 0.008% | 0% | 0% |
| CLTA1-4-5 | 4 | ccTCCTCATCTCCCTgcAGCAGG (SEQ ID NO: 156) | | | | 0.013% | 0.004% | 0% |
| CLTA1-4-6 | 4 | ctaCaTCATCTCCCTCAAGCTGG (SEQ ID NO: 157) | | | | 0% | 0.008% | 0.016% |
| CLTA1-4-7 | 4 | gGTCCTCATCTCCCTaAAaCAGa (SEQ ID NO: 158) | POLQ (coding) | | | 0.011% | 0.037% | 0% |
| CLTA1-4-8 | 4 | tGTCCTCATCggCCTCAgGCAGG (SEQ ID NO: 159) | | | | 0% | 0% | 0.016% |
| CLTA1-5-1 | 5 | AGaCacCATCTCCCTtgAGCTGG (SEQ ID NO: 160) | PSAT1 | | | 0% | 0.003% | 0.006% |
| CLTA1-5-2 | 5 | AGgCaTCATCTaCaTCAAGtTGG (SEQ ID NO: 161) | | | | 0% | 0% | 0% |
| CLTA1-5-3 | 5 | AGTaaTCActTCCaTCAAGCCGG (SEQ ID NO: 162) | ZDHHC3, EXOSC7 | | | n.t. | n.t. | n.t. |
| CLTA1-5-4 | 5 | tccCCTCAcCTCCCTaAAGCAGG (SEQ ID NO: 163) | | | | 0.008% | 0.029% | 0.004% |
| CLTA1-5-5 | 5 | tGTCtTtATtTCCCTCtAGCTGG (SEQ ID NO: 164) | | | | 0% | 0% | 0.009% |
| CLTA1-6-1 | 6 | AGTCCTCATCTCCCTCAAGCAGG (SEQ ID NO: 165) | | | | 0% | 0% | 0% |

TABLE 7

| | sequence | # of sequences | | |
|---|---|---|---|---|
| | | no sgRNA | v1.0 sgRNA | v2.1 sgRNA |
| | CLTA1-0-1 | | | |
| ref | AGTCCTCATCTCCCTCAAGCAGG (SEQ ID NO: 166) | 58,887 | 42,665 | 52,667 |
| | AGTCCTCATCTCCCTCAAAGCAGG (SEQ ID NO: 167) | 0 | 0 | 66 |
| | AGTCCTCATCTCCCTC-AGCAGG (SEQ ID NO: 168) | 0 | 2 | 28 |
| | AGTCCTCAT-------------- | 0 | 0 | 13 |
| | AGTCCTCATCTCCCTCATAGCAGG (SEQ ID NO: 169) | 0 | 0 | 11 |
| | AGTCCTCAT--------AGCAGG (SEQ ID NO: 170) | 0 | 0 | 9 |
| | AGTCCTCATCT------AGCAGG (SEQ ID NO: 171) | 0 | 0 | 8 |

TABLE 7-continued

|     | sequence | # of sequences | | |
|-----|----------|----------------|---|---|
|     |          | no sgRNA | v1.0 sgRNA | v2.1 sgRNA |
|     | AGTCCTCA---------AGCAGG (SEQ ID NO: 172) | 0 | 0 | 6 |
|     | AGTCCTCATCTCCCTCAAAGGCAGTGTTTGTTACTTGAGTTTGTCAGCAGG (SEQ ID NO: 173) | 0 | 0 | 4 |
|     | AGTCCTCATCTCCCTCATTAGCAGG (SEQ ID NO: 174) | 0 | 0 | 4 |
|     | AGTCCTCATCTCCCTCAGGGCTTGTTTACAGCTCACCTTTGAATTTGCACAAGCGTGCAAGCAGG (SEQ ID NO: 175) | 0 | 0 | 3 |
|     | AGTCCTCATCTCCCT-AGCAGG (SEQ ID NO: 176) | 0 | 11 | 0 |
|     | AGTCCTCATCCCTC-AAGCAGG (SEQ ID NO: 177) | 0 | 3 | 0 |
|     | AGTCCTCATCTCCCT-AAGCAGG (SEQ ID NO: 178) | 1 | 2 | 0 |
|     | other | 1 | 0 | 26 |
|     | modified total | 2 | 18 (0.042%) | 178 (0.34%) |
|     | CLTA1-1-1 | | | |
| ref | AGTCCTCAaCTCCCTCAAGCAGG (SEQ ID NO: 179) | 39,803 | 28,991 | 40,551 |
|     | AGTCCTCAaCTCCCTCAAAGCAGG (SEQ ID NO: 180) | 0 | 4 | 13 |
|     | AGTCCTCAaACTCCCTCA------ (SEQ ID NO: 181) | 0 | 0 | 12 |
|     | AGTCCTCAaCTCCCTC-AGCAGG (SEQ ID NO: 182) | 0 | 2 | 4 |
|     | AGTCCTCAaCTCCCTCAAGAAAGGTGTTGAAAATCAGAAAGAGAGAAACAAGCAGG (SEQ ID NO: 183) | 0 | 0 | 3 |
|     | AGTCCTCAaCTCCCTCAATCTACGGTCCATTCCCGTTTCCACTCACCTTGCGCCGCAGCAGG (SEQ ID NO: 184) | 0 | 0 | 2 |
|     | AGTCCTCAaCTCCCT-AAGCAGG (SEQ ID NO: 185) | 0 | 3 | 1 |
|     | AGTCCTCAaCTCCCTCAACCAACTTTAACATCCTGCTGGTTCTGTCATTAATAAGTTGAAAGCAGG (SEQ ID NO: 186) | 0 | 0 | 1 |
|     | AGTCCTCAaCTCCCTCACAGCAAATAAAAAAGTTGTTTATGCATATTCAGATAAGCAAAGCAGG (SEQ ID NO: 187) | 0 | 0 | 1 |
|     | AGTCCTCAaCTCCC-AAGCAGG (SEQ ID NO: 188) | 1 | 0 | 0 |
|     | modified total | 1 | 9 (0.031%) | 37 (0.091%) |
|     | CLTA1-2-2 | | | |
| ref | AcTCCTCATCcCCCTCAAGCCGG (SEQ ID NO: 189) | 21,264 | 20,041 | 22,546 |
|     | AcTCCTCATCcCCCTCAAAGCCGG (SEQ ID NO: 190) | 0 | 0 | 8 |
|     | AcTCCTCATCcCCCTCAGAGCCGG (SEQ ID NO: 191) | 0 | 0 | 7 |

TABLE 7-continued

| | | # of sequences | | |
|---|---|---|---|---|
| | sequence | no sgRNA | v1.0 sgRNA | v2.1 sgRNA |
| | AcTCCTC----------AGCCGG (SEQ ID NO: 192) | 0 | 0 | 5 |
| | AcTCCTCATCcCCCTCAAAAGCCGG (SEQ ID NO: 193) | 0 | 0 | 2 |
| | AcTCCTCATCcCCCTCAGCAGCCGG (SEQ ID NO: 194) | 0 | 0 | 2 |
| | AcTCCTCATCcCCCTCATAGCCGG (SEQ ID NO: 195) | 0 | 0 | 2 |
| | AcTCCTCATCcCCCTCATCCCCGG (SEQ ID NO: 196) | 0 | 0 | 2 |
| | ACTCCTCATCCC-----AGCCGG (SEQ ID NO: 197) | 0 | 0 | 2 |
| | ACTCCTCATCCCCCTA-AGCCGG (SEQ ID NO: 198) | 3 | 1 | 1 |
| | AcTCCTCATCcCCCTCAATAGCCGG (SEQ ID NO: 199) | 0 | 0 | 1 |
| | AcTCCTCACCcCCCTCAGCAGCCGG (SEQ ID NO: 200) | 0 | 0 | 1 |
| | modified total | 3 | 1 | 33 (0.15%) |

TABLE 8

| | | # of sequences | | |
|---|---|---|---|---|
| | sequence | control | v1.0 sgRNA | v2.1 sgRNA |
| | CLTA4-0-1 | | | |
| ref | GCAGATGTAGTGTTTCCACAGGG (SEQ ID NO: 201) | 29,185 | 16,635 | 17,555 |
| | GCAGATGTAGTGTTTC-ACAGGG (SEQ ID NO: 202) | 1 | 891 | 5,937 |
| | GCAGATGTAGTGTTTCCCACAGGG (SEQ ID NO: 203) | 0 | 809 | 5,044 |
| | GCAGATGTAGTG----CACAGGG (SEQ ID NO: 204) | 0 | 14 | 400 |
| | GCAGATGTAGTGTTTCC-CAGGG (SEQ ID NO: 205) | 0 | 19 | 269 |
| | GCAGATGTAC-------ACAGGG (SEQ ID NO: 206) | 0 | 17 | 262 |
| | GCAGATGTAGTGTCA---CAGGG (SEQ ID NO: 207) | 2 | 6 | 254 |
| | GCAGATGTAGTGTTCA-CAGGG (SEQ ID NO: 208) | 0 | 21 | 229 |
| | GCAGATGTAGTGTTTC-CAGGG (SEQ ID NO: 209) | 1 | 14 | 188 |
| | GCAGATGTAGT-----CACAGGG (SEQ ID NO: 210) | 0 | 0 | 152 |
| | GCAGATGT----------AGGG (SEQ ID NO: 211) | 0 | 6 | 129 |

TABLE 8-continued

|  | sequence | # of sequences | | |
|---|---|---|---|---|
|  |  | control | v1.0 sgRNA | v2.1 sgRNA |
|  | other | 2 | 208 | 2,106 |
|  | modified total | 6 | 2,005 (11%) | 14,970 (76%) |
|  | CLTA4-3-1 | | | |
| ref | aCAtATGTAGTaTTTCCACAGGG (SEQ ID NO: 212) | 34,163 | 20,007 | 12,208 |
|  | aCAtATGTAGTaTTTCCCACAGGG (SEQ ID NO: 213) | 0 | 8 | 1779 |
|  | aCAtATGTAGTaTTTCA-CAGGG (SEQ ID NO: 214) | 1 | 0 | 293 |
|  | aCAtATGTAGTaTTTC-CAGGG (SEQ ID NO: 215) | 1 | 0 | 227 |
|  | aCAtAT----------CACAGGG (SEQ ID NO: 216) | 0 | 0 | 117 |
|  | a----------------CAGGG | 0 | 0 | 96 |
|  | aCAt-----------CACAGGG (SEQ ID NO: 217) | 0 | 0 | 78 |
|  | aCAtATGTAGT-----CACAGGG (SEQ ID NO: 218) | 0 | 0 | 77 |
|  | aCAtATGTAGTaTTTCC------ (SEQ ID NO: 219) | 0 | 0 | 76 |
|  | aCAtATGT----------AGGG (SEQ ID NO: 220) | 0 | 0 | 68 |
|  | aCAtATGTAG------CACAGGG (SEQ ID NO: 221) | 0 | 0 | 64 |
|  | other | 0 | 3 | 999 |
|  | modified total | 2 | 11 (0.055%) | 3874 (24%) |
|  | CLTA4-3-3 | | | |
| ref | cCAGATGTAGTaTTcCCACAGGG (SEQ ID NO: 222) | 16,559 | 12,007 | 11,030 |
|  | cCAGATGTAGTaTTcCCCACAGGG (SEQ ID NO: 223) | 0 | 0 | 35 |
|  | ccAGATGTAGTaT----ACAGGG (SEQ ID NO: 224) | 0 | 0 | 5 |
|  | cCAGATGTAGTaT---CACAGGG (SEQ ID NO: 225) | 0 | 0 | 3 |
|  | cCAGATGTAGTaTTcCCAACACAGGG (SEQ ID NO: 226) | 0 | 0 | 2 |
|  | cCAGATGTAGTaTT-CACAGGG (SEQ ID NO: 227) | 0 | 0 | 2 |
|  | cCAGATGTAGTaTTcC-CAGGG (SEQ ID NO: 228) | 0 | 0 | 2 |
|  | ccAGATGTA-------------- | 0 | 0 | 2 |
|  | cCAGATGTAGTaTTcC-ACAGGG (SEQ ID NO: 229) | 0 | 0 | 1 |
|  | modified total | 0 | 0 | 52 (0.47%) |
|  | CLTA4-4-8 | | | |
| ref | ctAGATGaAGTGcTTCCACATGG (SEQ ID NO: 230) | 10,691 | 7,608 | 8,018 |
|  | ctAGATGaAGTGcTTCCCACATGG (SEQ ID NO: 231) | 0 | 0 | 49 |

TABLE 8-continued

| sequence | # of sequences control | v1.0 sgRNA | v2.1 sgRNA |
|---|---|---|---|
| ctAGATGaAGTGcTTC-ACATGG (SEQ ID NO: 232) | 0 | 0 | 6 |
| ctAGATGaAGTG---------- (SEQ ID NO: 233) | 0 | 0 | 2 |
| ctAGATGaAGTGcTTCCACACATGG (SEQ ID NO: 234) | 0 | 0 | 1 |
| ctAGATGaAGTGcTTC-CATGG (SEQ ID NO: 235) | 1 | 0 | 0 |
| ctAGATGaAGTGcTTCC-CATGG (SEQ ID NO: 236) | 0 | 1 | 0 |
| modified total | 1 | 1 | 59 (0.73%) |

TABLE 9

| oligonucleotide name | oligonucleotide sequence(5'->3') |
|---|---|
| CLTA1 v2.1 template fwd | TAA TAC GAC TCA CTA TAG GAG TCC TCA TCT CCC TCA AGC GTT TTA GAG CTA TGC TG (SEQ ID NO: 237) |
| CLTA2 v2.1 template fwd | TAA TAC GAC TCA CTA TAG GCT CCC TCA AGC AGG CCC CGC GTT TTA GAG CTA TGC TG (SEQ ID NO: 238) |
| CLTA3 v2.1 template fwd | TAA TAC GAC TCA CTA TAG GTG TGA AGA GCT TCA CTG AGT GTT TTA GAG CTA TGC TG (SEQ ID NO: 239) |
| CLTA4 v2.1 template fwd | TAA TAC GAC TCA CTA TAG GGC AGA TGT AGT GTT CCA CA GTT TTA GAG CTA TGC TG (SEQ ID NO: 240) |
| v2.1 template rev | GAT AAC GGA CTA GCC TTA TTT TAA CTT GCT ATG CTT TTC AGC ATA GCT CTA AAA C (SEQ ID NO: 241) |
| CLTA1 v1.0 template | CGG ACT AGC CTT ATT TTA ACT GCT ATT TC TAG CTC TAA AAC GCT TGA GGG AGA TGA GGA CTC CTA TAG TGA GTC GTA TTA (SEQ ID NO: 242) |
| CLTA2 v1.0 template | CGG ACT AGC CTT ATT TTA ACT GCT ATT TC TAG CTC TAA AAC GCG GGG CCT GCT TGA GGG AGC CTA TAG TGA GTC GTA TTA (SEQ ID NO: 243) |
| CLTA3 v1.0 template | CGG ACT AGC CTT ATT TTA ACT GCT ATT TC TAG CTC TAA AAC ACT CAG TGA AGC TCT TCA CAC CTA TAG TGA GTC GTA TTA (SEQ ID NO: 244) |
| CLTA4 v1.0 template | CGG ACT AGC CTT ATT TTA ACT GCT ATT TC TAG CTC TAA AAC TGT GGA AAC ACT ACA TCT GCC CTA TAG TGA GTC GTA TTA (SEQ ID NO: 245) |
| T7 promoter oligo | TAA TAC GAC TCA CTA TAG G (SEQ ID NO: 246) |
| CLTA1 lib | /5Phos/AAC ACA NNN NC*C* NGC* T*T*G* A*G*G* G*A*G* A*T*G* A*G*G* A*C*T* NNN NAC CTG CCG AGA ACA CA (SEQ ID NO: 247) |
| CLTA2 lib | /5Phos/TCT TCT NNN NC*C* NGC* G*G*G* G*C*C* T*G*C* T*T*G* A*G*G* G*A*G* NNN NAC CTG CCG AGT CTT CT (SEQ ID NO: 248) |
| CLTA3 lib | /5Phos/AGA GAA NNN NC*C* NA*C* T*C*A* G*T*G* A*A*G* C*T*C* T*T*C* A*C*A* NNN NAC CTG CCG AGA GAG AA (SEQ ID NO: 249) |
| CLTA4 lib | /5Phos/TTG TGT NNN NC*C* NT*G* T*G*G* A*A*A* C*A*C* T*A*C* A*T*C* T*G*C* NNN NAC CTG CCG AGT TGT GT (SEQ ID NO: 250) |
| CLTA1 site fwd | CTA GCA GTC CTC ATC TCC CTC AAG CAG GC (SEQ ID NO: 251) |
| CLTA1 site rev | AGC TGC CTG CTT GAG GGA GAT GAG GAC TG (SEQ ID NO: 252) |
| CLTA2 site fwd | CTA GTC CTC AAG CAG GCC CCG CTG GT (SEQ ID NO: 253) |
| CLTA2 site rev | AGC TAC CAG CGG GGC CTG CTT GAG GGA GA (SEQ ID NO: 254) |
| CLTA3 site fwd | CTA GCT GTG AAG AGC TTC ACT GAG TAG GA (SEQ ID NO: 255) |
| CLTA3 site rev | AGC TTC CTA CTC AGT GAA GCT CTT CAC AG (SEQ ID NO: 256) |

TABLE 9 -continued

| oligonucleotide name | oligonucleotide sequence(5'->3') |
|---|---|
| CLTA4 site fwd | CTA GTG CAG ATG TAG TGT TTC CAC AGG GT (SEQ ID NO: 257) |
| CLTA4 site rev | AGC TAC CCT GTG GAA ACA CTA CAT CTG CA (SEQ ID NO: 258) |
| test fwd | GCG ACA CGG AAA TGT TGA ATA CTC AT (SEQ ID NO: 259) |
| test rev | GGA GTC AGG CAA CTA GGA TGA ACA G (SEQ ID NO: 260) |
| off-target CLTA4-0 fwd | ACT GTG AAG AGC TTC ACT GAG TAG GAT TAA GAT ATT GCA GAT GTA GTG TTT CCA CAG GGT (SEQ ID NO: 261) |
| off-target CLTA4-1 fwd | ACT GTG AAG AGC TTC ACT GAG TAG GAT TAA GAT ATT GAA GAT GTA GTG TTT CCA CAG GGT (SEQ ID NO: 262) |
| off-target CLTA4-2a fwd | ACT GTG AAG AGC TTC ACT GAG TAG GAT TAA GAT ATT GAA GAT GTA GTG TTT CCA CTG GGT (SEQ ID NO: 263) |
| off-target CLTA4-2b fwd | ACT GTG AAG AGC TTC ACT GAG TAG GAT TAA GAT ATT GCA GAT GGA GGG TTT CCA CAG GGT (SEQ ID NO: 264) |
| off-target CLTA4-2c fwd | ACT GTG AAG AGC TTC ACT GAG TAG GAT TAA GAT ATT GCA GAT GTA GTG TTA CCA GAG GGT (SEQ ID NO: 265) |
| off-target CLTA4-3 fwd | ACT GTG AAG AGC TTC ACT GAG TAG GAT TAA GAT ATT GGG GAT GTA GTG TTT CCA CTG GGT (SEQ ID NO: 266) |
| off-target CLTA4-0 rev | TCC CTC AAG CAG GCC CCG CTG GTG CAC TGA AGA GCC ACC CTG TGG AAA CAC TAC ATC TGC (SEQ ID NO: 267) |
| off-target CLTA4-1 rev | TCC CTC AAG CAG GCC CCG CTG GTG CAC TGA AGA GCC ACC CTG TGG AAA CAC TAC ATC TTC (SEQ ID NO: 268) |
| off-target CLTA4-2a rev | TCC CTC AAG CAG GCC CCG CTG GTG CAC TGA AGA GCC ACC CAG TGG AAA CAC TAC ATC TTC (SEQ ID NO: 269) |
| off-target CLTA4-2b rev | TCC CTC AAG CAG GCC CCG CTG GTG CAC TGA AGA GCC ACC CTG TGG AAA CCC TCC ATC TGC (SEQ ID NO: 270) |
| off-target CLTA4-2c rev | TCC CTC AAG CAG GCC CCG CTG GTG CAC TGA AGA GCC ACC CTC TGG TAA CAC TAC ATC TGC (SEQ ID NO: 271) |
| off-target CLTA4-3 rev | TCC CTC AAG CAG GCC CCG CTG GTG CAC TGA AGA GCC ACC CAG TGG AAA CAC TAC ATC CCC (SEQ ID NO: 272) |
| adapter1(AACA) | AAT GAT ACG GCG ACC ACC GAG ATC TAC ACT CTT TCC CTA CAC GAC GCT CTT CCG ATC TAA CA (SEQ ID NO: 273) |
| adapter2(AACA) | TGT TAG ATC GGA AGA GCG TCG TGT AGG GAA AGA GTG TAG ATC TCG GTG G (SEQ ID NO: 274) |
| adapter1(TTCA) | AAT GAT ACG GCG ACC ACC GAG ATC TAC ACT CTT TCC CTA CAC GAC GCT CTT CCG ATC TTT CA (SEQ ID NO: 275) |
| adapter2(TTCA) | TGA AAG ATC GGA AGA GCG TCG TGT AGG GAA AGA GTG TAG ATC TCG GTG G (SEQ ID NO: 276) |
| adapter1 | AAT GAT ACG GCG ACC ACC GAG ATC TAC ACT CTT TCC CTA CAC GAC GCT CTT CCG ATC T (SEQ ID NO: 277) |
| adapter2 | AGA TCG GAA GAG CGT CGT GTA GGG AAA GAG TGT AGA TCT CGG TGG (SEQ ID NO: 278) |
| lib adapter1 | GAC GGC ATA CGA GAT (SEQ ID NO: 279) |
| CLTA1 lib adapter2 | AAC AAT CTC GTA TGC CGT CTT CTG CTT G (SEQ ID NO: 280) |
| CLTA2 lib adapter2 | TCT TAT CTC GTA TGC CGT CTT CTG CTT G (SEQ ID NO: 281) |
| CLTA3 lib adapter2 | AGA GAT CTC GTA TGC CGT CTT CTG CTT G (SEQ ID NO: 282) |
| CLTA4 lib adapter2 | TTG TAT CTC GTA TGC CGT CTT CTG CTT G (SEQ ID NO: 283) |
| CLTA1 sel PCR | CAA GCA GAA GAC GGC ATA CGA GAT TGT GTT CTC GGC AGG T (SEQ ID NO: 284) |
| CLTA2 sel PCR | CAA GCA GAA GAC GGC ATA CGA GAT AGA AGA CTC GGC AGG T (SEQ ID NO: 285) |
| CLTA3 sel PCR | CAA GCA GAA GAC GGC ATA CGA GAT TTC TCT CTC GGC AGG T (SEQ ID NO: 286) |

TABLE 9 -continued

| oligonucleotide name | oligonucleotide sequence(5'->3') |
|---|---|
| CLTA4 sel PCR | CAA GCA GAA GAC GGC ATA CGA GAT ACA CAA CTC GGC AGG T (SEQ ID NO: 287) |
| PE2 short | AAT GAT ACG GCG ACC ACC GA (SEQ ID NO: 288) |
| CLTA1 lib seq PCR | AAT GAT ACG GCG ACC ACC GAG ATC TAC ACT CTT TCC CTA CAC GAC GCT CTT CCG ATC TNN NNA CCT ACC TGC CGA GAA CAC A (SEQ ID NO: 289) |
| CLTA2 lib seq PCR | AAT GAT ACG GCG ACC ACC GAG ATC TAC ACT CTT TCC CTA CAC GAC GCT CTT CCG ATC TNN NNA CCT ACC TGC CGA GTC TTC T (SEQ ID NO: 290) |
| CLTA3 lib seq PCR | AAT GAT ACG GCG ACC ACC GAG ATC TAC ACT CTT TCC CTA CAC GAC GCT CTT CCG ATC TNN NNA CCT ACC TGC CGA GAG AGA A (SEQ ID NO: 291) |
| CLTA4 lib seq PCR | AAT GAT ACG GCG ACC ACC GAG ATC TAC ACT CTT TCC CTA CAC GAC GCT CTT CCG ATC TNN NNA CCT ACC TGC CGA GTT GTG T (SEQ ID NO: 292) |
| lib fwd PCR | CAA GCA GAA GAC GGC ATA CGA GAT (SEQ ID NO: 293) |
| CLTA1-0-1 (Chr. 9) fwd | ACA CTC TTT CCC TAC ACG ACG CTC TTC CGA TCT CAA GTC TAG CAA GCA GGC CA (SEQ ID NO: 294) |
| CLTA1-0-1 (Chr. 12) fwd | ACA CTC TTT CCC TAC ACG ACG CTC TTC CGA TCT CAG GCA CTG AGT GGG AAA GT (SEQ ID NO: 295) |
| CLTA1-1-1 fwd | ACA CTC TTT CCC TAC ACG ACG CTC TTC CGA TCT TAA CCC CAA GTC AGC AAG CA (SEQ ID NO: 296) |
| CLTA1-2-1 fwd | ACA CTC TTT CCC TAC ACG ACG CTC TTC CGA TCT TTG CTG GTC AAT ACC CTG GC (SEQ ID NO: 297) |
| CLTA1-2-2 fwd | ACA CTC TTT CCC TAC ACG ACG CTC TTC CGA TCT TGA GTA CCC CTG AAA TGG GC (SEQ ID NO: 298) |
| CLTA1-3-1 fwd | ACA CTC TTT CCC TAC ACG ACG CTC TTC CGA TCT TCG CTA CCA ATC AGG GCT TT (SEQ ID NO: 299) |
| CLTA1-3-2 fwd | ACA CTC TTT CCC TAC ACG ACG CTC TTC CGA TCT CCA TTG CCA CTT GTT TGC AT (SEQ ID NO: 300) |
| CLTA1-4-1 fwd | ACA CTC TTT CCC TAC ACG ACG CTC TTC CGA TCT CCT ACC CCA CAA CTT TGC T (SEQ ID NO: 301) |
| CLTA1-4-2 fwd | ACA CTC TTT CCC TAC ACG ACG CTC TTC CGA TCT GTG TAC ATC AGT GCA CC CA (SEQ ID NO: 302) |
| CLTA1-4-3 fwd | ACA CTC TTT CCC TAC ACG ACG CTC TTC CGA TCT TCG GAA AGG ACT TTG AAT ACT TGT (SEQ ID NO: 303) |
| CLTA1-4-4 fwd | ACA CTC TTT CCC TAC ACG ACG CTC TTC CGA TCT CGG CCC AAG ACC TCA TTC AC (SEQ ID NO: 304) |
| CLTA1-4-5 fwd | ACA CTC TTT CCC TAC ACG ACG CTC TTC CGA TCT GTC CTC TCT GGG GCA GAA GT (SEQ ID NO: 305) |
| CLTA1-4-6 fwd | ACA CTC TTT CCC TAC ACG ACG CTC TTC CGA TCT AGC TGA GTC ATG AGT TGT CTC C (SEQ ID NO: 306) |
| CLTA1-4-7 fwd | ACA CTC TTT CCC TAC ACG ACG CTC TTC CGA TCT CTG CCA GCT TCT CAC ACC AT (SEQ ID NO: 307) |
| CLTA1-4-8 fwd | ACA CTC TTT CCC TAC ACG ACG CTC TTC CGA TCT CTG AAG GAC AAA GGC GGG AA (SEQ ID NO: 308) |
| CLTA1-5-1 fwd | ACA CTC TTT CCC TAC ACG ACG CTC TTC CGA TCT AAG GTG CTA AAG GCT CCA CG (SEQ ID NO: 309) |
| CLTA1-5-2 fwd | ACA CTC TTT CCC TAC ACG ACG CTC TTC CGA TCT GAC CAT TGG TGA GCC CAG AG (SEQ ID NO: 310) |
| CLTA1-5-3 fwd | ACA CTC TTT CCC TAC ACG ACG CTC TTC CGA TCT TTT TTC GGG CAA CTG CTC AC (SEQ ID NO: 311) |
| CLTA1-5-4 fwd | ACA CTC TTT CCC TAC ACG ACG CTC TTC CGA TCT GCA AGC TTC TCT CC TCA GA (SEQ ID NO: 312) |
| CLTA1-5-5 fwd | ACA CTC TTT CCC TAC ACG ACG CTC TTC CGA TCT ACA CAA ACT TCC CTG AGA CCC (SEQ ID NO: 313) |

TABLE 9 -continued

| oligonucleotide name | oligonucleotide sequence(5'->3') |
|---|---|
| CLTA1-6-1 fwd | ACA CTC TTT CCC TAC ACG ACG CTC TTC CGA TCT TGA GTT AGC CCT GCT GTT CA (SEQ ID NO: 314) |
| CLTA4-0-1 fwd | ACA CTC TTT CCC TAC ACG ACG CTC TTC CGA TCT TGA AGA GCT TCA CTG AGT AGG A (SEQ ID NO: 315) |
| CLTA4-3-1 fwd | ACA CTC TTT CCC TAC ACG ACG CTC TTC CGA TCT TCC CCT TAC AGC CAA TTT CGT (SEQ ID NO: 316) |
| CLTA4-3-2 fwd | ACA CTC TTT CCC TAC ACG ACG CTC TTC CGA TCT TGC TGA TGA AAT GCA ATT AAG AGG T (SEQ ID NO: 317) |
| CLTA4-3-3 fwd | ACA CTC TTT CCC TAC ACG ACG CTC TTC CGA TCT GGT CCC TGC AAG CCA GTA TG (SEQ ID NO: 318) |
| CLTA4-3-4 fwd | ACA CTC TTT CCC TAC ACG ACG CTC TTC CGA TCT ATC AAA GCC TTG TAT CAC AGT T (SEQ ID NO: 319) |
| CLTA4-3-5 fwd | ACA CTC TTT CCC TAC ACG ACG CTC TTC CGA TCT CCC AAA TAA TGC AGG AGC CAA (SEQ ID NO: 320) |
| CLTA4-3-6 fwd | ACA CTC TTT CCC TAC ACG ACG CTC TTC CGA TCT CTG CCT TTA GTG GGA CAG ACT T (SEQ ID NO: 321) |
| CLTA4-3-7 fwd | ACA CTC TTT CCC TAC ACG ACG CTC TTC CGA TCT AGT AAC CCT AGT AGC CCT CCA (SEQ ID NO: 322) |
| CLTA4-4-1 fwd | ACA CTC TTT CCC TAC ACG ACG CTC TTC CGA TCT CAT TGC AGT GAG CCG AGA TTG (SEQ ID NO: 323) |
| CLTA4-4-2 fwd | ACA CTC TTT CCC TAC ACG ACG CTC TTC CGA TCT TGG CAA AGT TCA CTT CCA TGT (SEQ ID NO: 324) |
| CLTA4-4-3 fwd | ACA CTC TTT CCC TAC ACG ACG CTC TTC CGA TCT TGC TCT GTG ATG TCT GCC AC (SEQ ID NO: 325) |
| CLTA4-4-4 fwd | ACA CTC TTT CCC TAC ACG ACG CTC TTC CGA TCT TGT GTA GGA TTG TGA ACC AGC A (SEQ ID NO: 326) |
| CLTA4-4-5 fwd | ACA CTC TTT CCC TAC ACG ACG CTC TTC CGA TCT TCC CAG CCC AGC ATT TTT CT (SEQ ID NO: 327) |
| CLTA4-4-6 fwd | ACA CTC TTT CCC TAC ACG ACG CTC TTC CGA TCT AGG TTG CTT TGT GCA CAG TC (SEQ ID NO: 328) |
| CLTA4-4-7 fwd | ACA CTC TTT CCC TAC ACG ACG CTC TTC CGA TCT CCT GGC TTG GGA TGT TGG AA (SEQ ID NO: 329) |
| CLTA4-4-8 fwd | ACA CTC TTT CCC TAC ACG ACG CTC TTC CGA TCT TTG CCC AAG GTC ATA CTG CT (SEQ ID NO: 330) |
| CLTA4-4-9 fwd | ACA CTC TTT CCC TAC ACG ACG CTC TTC CGA TCT ACC CAC TAG GTA GCC ATA ATC CA (SEQ ID NO: 331) |
| CLTA4-4-10 fwd | ACA CTC TTT CCC TAC ACG ACG CTC TTC CGA TCT CGG TCA TGT CGC TTG GAA GA (SEQ ID NO: 332) |
| CLTA4-4-11 fwd | ACA CTC TTT CCC TAC ACG ACG CTC TTC CGA TCT TTG GCC CAT ATT GCT TTA TGC TG (SEQ ID NO: 333) |
| CLTA4-4-12 fwd | ACA CTC TTT CCC TAC ACG ACG CTC TTC CGA TCT ATT AGG GGT TGG CTG CAT GA (SEQ ID NO: 334) |
| CLTA4-4-13 fwd | ACA CTC TTT CCC TAC ACG ACG CTC TTC CGA TCT CCA AGA CGT GTT GCA TGC TG (SEQ ID NO: 335) |
| CLTA4-4-14 fwd | ACA CTC TTT CCC TAC ACG ACG CTC TTC CGA TCT TGG GAG GTG ATA AAT TCC CTA AAT (SEQ ID NO: 336) |
| CLTA4-5-1 fwd | ACA CTC TTT CCC TAC ACG ACG CTC TTC CGA TCT CCA GAG ACA AAG GTG GGG AG (SEQ ID NO: 337) |
| CLTA4-5-2 fwd | ACA CTC TTT CCC TAC ACG ACG CTC TTC CGA TCT TCA TAC AGA AGA GCA AAG TAC CA (SEQ ID NO: 338) |
| CLTA4-5-3 fwd | ACA CTC TTT CCC TAC ACG ACG CTC TTC CGA TCT CAA AGA GGG GTA TCG GGA GC (SEQ ID NO: 339) |

TABLE 9 -continued

| oligonucleotide name | oligonucleotide sequence(5'->3') |
|---|---|
| CLTA4-5-4 fwd | ACA CTC TTT CCC TAC ACG ACG CTC TTC CGA TCT AAA TGG AAG AAC CAA GTA GAT GAA (SEQ ID NO: 340) |
| CLTA4-5-5 fwd | ACA CTC TTT CCC TAC ACG ACG CTC TTC CGA TCT TTT GGG TTG ACA GAT GGC CAC A (SEQ ID NO: 341) |
| CLTA4-5-6 fwd | ACA CTC TTT CCC TAC ACG ACG CTC TTC CGA TCT TCT TAC TTG TGT GAT TTT AGA ACA A (SEQ ID NO: 342) |
| CLTA4-6-1 fwd | ACA CTC TTT CCC TAC ACG ACG CTC TTC CGA TCT GAT GGT TCA TGC AGA GGG CT (SEQ ID NO: 343) |
| CLTA4-6-2 fwd | ACA CTC TTT CCC TAC ACG ACG CTC TTC CGA TCT GCT GGT CTT TCC TGA GCT GT (SEQ ID NO: 344) |
| CLTA4-6-3 fwd | ACA CTC TTT CCC TAC ACG ACG CTC TTC CGA TCT CTC CAT CAG ATA CCT GTA CCC A (SEQ ID NO: 345) |
| CLTA4-7-1 fwd | ACA CTC TTT CCC TAC ACG ACG CTC TTC CGA TCT GGG AAA ACA CTC TCT CTC TGC T (SEQ ID NO: 346) |
| CLTA4-7-2 fwd | ACA CTC TTT CCC TAC ACG ACG CTC TTC CGA TCT GGA GGC CAC GAC ACA CAA TA (SEQ ID NO: 347) |
| CLTA1-0-1 (Chr. 9) rev | GTG ACT GGA GTT CAG ACG TGT GCT CTT CCG ATCT CAC AGG GTG GCT CTT CAG TG (SEQ ID NO: 348) |
| CLTA1-0-1 (Chr. 12) rev | GTG ACT GGA GTT CAG ACG TGT GCT CTT CCG ATCT TGC ACA TGT TTC CAC AGG GT (SEQ ID NO: 349) |
| CLTA1-1-1 rev | GTG ACT GGA GTT CAG ACG TGT GCT CTT CCG ATCT AGT GTT TCC AGG AGC GGT TT (SEQ ID NO: 350) |
| CLTA1-2-1 rev | GTG ACT GGA GTT CAG ACG TGT GCT CTT CCG ATCT AAG CCT CAG GCA CAA CTC TG (SEQ ID NO: 351) |
| CLTA1-2-2 rev | GTG ACT GGA GTT CAG ACG TGT GCT CTT CCG ATCT TAG GGG AGG GGC AAA GAC A (SEQ ID NO: 352) |
| CLTA1-3-1 rev | GTG ACT GGA GTT CAG ACG TGT GCT CTT CCG ATCT GGG AAC AGT GGT ATG CTG GT (SEQ ID NO: 353) |
| CLTA1-3-2 rev | GTG ACT GGA GTT CAG ACG TGT GCT CTT CCG ATCT AGT GTG GAC ACT GAC AAG AAA (SEQ ID NO: 354) |
| CLTA1-4-1 rev | GTG ACT GGA GTT CAG ACG TGT GCT CTT CCG ATCT TCA CTG CCT GGG TGC TTT AG (SEQ ID NO: 355) |
| CLTA1-4-2 rev | GTG ACT GGA GTT CAG ACG TGT GCT CTT CCG ATCT TAC CCC AGC CTC CAG CTT TA (SEQ ID NO: 356) |
| CLTA1-4-3 rev | GTG ACT GGA GTT CAG ACG TGT GCT CTT CCG ATCT TGA CTA CTG GGG AGC GAT GA (SEQ ID NO: 357) |
| CLTA1-4-4 rev | GTG ACT GGA GTT CAG ACG TGT GCT CTT CCG ATCT AGG CTG TTA TGC AGG AAA GGA A (SEQ ID NO: 358) |
| CLTA1-4-5 rev | GTG ACT GGA GTT CAG ACG TGT GCT CTT CCG ATCT GCG GTT GAG GTG GAT GGA AG (SEQ ID NO: 359) |
| CLTA1-4-6 rev | GTG ACT GGA GTT CAG ACG TGT GCT CTT CCG ATCT GGC AGC ATC CCT TAC ATC CT (SEQ ID NO: 360) |
| CLTA1-4-7 rev | GTG ACT GGA GTT CAG ACG TGT GCT CTT CCG ATCT AGA AAA AGC TTC CCC AGA AAG GA (SEQ ID NO: 361) |
| CLTA1-4-8 rev | GTG ACT GGA GTT CAG ACG TGT GCT CTT CCG ATCT CTG CAC CAA CCT CTA CGT CC (SEQ ID NO: 362) |
| CLTA1-5-1 rev | GTG ACT GGA GTT CAG ACG TGT GCT CTT CCG ATCT CTG GAG AGG GCA TAG TTG GC (SEQ ID NO: 363) |
| CLTA1-5-2 rev | GTG ACT GGA GTT CAG ACG TGT GCT CTT CCG ATCT TGG AAG GCT CTT TGT GGG TT (SEQ ID NO: 364) |
| CLTA1-5-3 rev | GTG ACT GGA GTT CAG ACG TGT GCT CTT CCG ATCT TTC CTA GCG GGA ACT GGA AA (SEQ ID NO: 365) |

TABLE 9-continued

| oligonucleotide name | oligonucleotide sequence(5'->3') |
|---|---|
| CLTA1-5-4 rev | GTG ACT GGA GTT CAG ACG TGT GCT CTT CCG ATCT AGG CTA ATG GGG TAG GGG AT (SEQ ID NO: 366) |
| CLTA1-5-5 rev | GTG ACT GGA GTT CAG ACG TGT GCT CTT CCG ATCT TGT CCA TGT TGG CTG AGG TG (SEQ ID NO: 367) |
| CLTA1-6-1 rev | GTG ACT GGA GTT CAG ACG TGT GCT CTT CCG ATCT CAG GCC AAC CTT GAC AAC TT (SEQ ID NO: 368) |
| CLTA4-0-1 rev | GTG ACT GGA GTT CAG ACG TGT GCT CTT CCG ATCT AGC AGG CCA AAG ATG TCT CC (SEQ ID NO: 369) |
| CLTA4-3-1 rev | GTG ACT GGA GTT CAG ACG TGT GCT CTT CCG ATCT TCT GCT CTT GAG GTT ATT TGT CC (SEQ ID NO: 370) |
| CLTA4-3-2 rev | GTG ACT GGA GTT CAG ACG TGT GCT CTT CCG ATCT GGG ACC AAT TTG CTA CTC ATG G (SEQ ID NO: 371) |
| CLTA4-3-3 rev | GTG ACT GGA GTT CAG ACG TGT GCT CTT CCG ATCT TGG AGG CTG TAA ACG TCC TG (SEQ ID NO: 372) |
| CLTA4-3-4 rev | GTG ACT GGA GTT CAG ACG TGT GCT CTT CCG ATCT TGC TAT GAT TTG CTG AAT TAC TCC T (SEQ ID NO: 373) |
| CLTA4-3-5 rev | GTG ACT GGA GTT CAG ACG TGT GCT CTT CCG ATCT GCA ATT TGC AGA CCA CCA TC (SEQ ID NO: 374) |
| CLTA4-3-6 rev | GTG ACT GGA GTT CAG ACG TGT GCT CTT CCG ATCT GGC AGC TTG CAA CCT TCT TG (SEQ ID NO: 375) |
| CLTA4-3-7 rev | GTG ACT GGA GTT CAG ACG TGT GCT CTT CCG ATCT TCA TGA GAG TTT CCC CAA CA (SEQ ID NO: 376) |
| CLTA4-4-1 rev | GTG ACT GGA GTT CAG ACG TGT GCT CTT CCG ATCT ACT TGA GGG GGA AAA AGT TTC TTA (SEQ ID NO: 377) |
| CLTA4-4-2 rev | GTG ACT GGA GTT CAG ACG TGT GCT CTT CCG ATCT TGG TCC CTG TCT GTC ATT GG (SEQ ID NO: 378) |
| CLTA4-4-3 rev | GTG ACT GGA GTT CAG ACG TGT GCT CTT CCG ATCT AAG CGA GTG ACT GTC TGG GA (SEQ ID NO: 379) |
| CLTA4-4-4 rev | GTG ACT GGA GTT CAG ACG TGT GCT CTT CCG ATCT CAT GGG TGG GAC ACG TAG TT (SEQ ID NO: 380) |
| CLTA4-4-5 rev | GTG ACT GGA GTT CAG ACG TGT GCT CTT CCG ATCT GGC TTT CCT GGA CAC CCT ATC (SEQ ID NO: 381) |
| CLTA4-4-6 rev | GTG ACT GGA GTT CAG ACG TGT GCT CTT CCG ATCT AGA GCG AGG GAG CGA TGT A (SEQ ID NO: 382) |
| CLTA4-4-7 rev | GTG ACT GGA GTT CAG ACG TGT GCT CTT CCG ATCT TTG TGG ACC ACT GCT TAG TGC (SEQ ID NO: 383) |
| CLTA4-4-8 rev | GTG ACT GGA GTT CAG ACG TGT GCT CTT CCG ATCT CAA CTA CCC TGA GGC CAC C (SEQ ID NO: 384) |
| CLTA4-4-9 rev | GTG ACT GGA GTT CAG ACG TGT GCT CTT CCG ATCT GGT CAG CAC TCC TCA GCT TT (SEQ ID NO: 385) |
| CLTA4-4-10 rev | GTG ACT GGA GTT CAG ACG TGT GCT CTT CCG ATCT TGG AGG ATG CAT GCC ACA TT (SEQ ID NO: 386) |
| CLTA4-4-11 rev | GTG ACT GGA GTT CAG ACG TGT GCT CTT CCG ATCT CCC AGC CTC TTT GAC CCT TC (SEQ ID NO: 387) |
| CLTA4-4-12 rev | GTG ACT GGA GTT CAG ACG TGT GCT CTT CCG ATCT CCC ACA CCA GGC TGT AAG G (SEQ ID NO: 388) |
| CLTA4-4-13 rev | GTG ACT GGA GTT CAG ACG TGT GCT CTT CCG ATCT TAG ATA TAT GGG TGT GTC TGT ACG (SEQ ID NO: 389) |
| CLTA4-4-14 rev | GTG ACT GGA GTT CAG ACG TGT GCT CTT CCG ATCT TTC CAA AGT GGC TGA ACC AT (SEQ ID NO: 390) |
| CLTA4-5-1 rev | GTG ACT GGA GTT CAG ACG TGT GCT CTT CCG ATCT CCC ACA GGG CTG ATG TTT CA (SEQ ID NO: 391) |

TABLE 9 -continued

| oligonucleotide name | oligonucleotide sequence(5'->3') |
|---|---|
| CLTA4-5-2 rev | GTG ACT GGA GTT CAG ACG TGT GCT CTT CCG ATCT TTG TAA TGC AAC CTC TGT CAT GC (SEQ ID NO: 392) |
| CLTA4-5-3 rev | GTG ACT GGA GTT CAG ACG TGT GCT CTT CCG ATCT CCA GCT CCA GCA ATC CAT GA (SEQ ID NO: 393) |
| CLTA4-5-4 rev | GTG ACT GGA GTT CAG ACG TGT GCT CTT CCG ATCT TTT GGG AAA GAT AGC CCT GGA (SEQ ID NO: 394) |
| CLTA4-5-5 rev | GTG ACT GGA GTT CAG ACG TGT GCT CTT CCG ATCT CAA TGA AAC AGC GGG GAG GT (SEQ ID NO: 395) |
| CLTA4-5-6 rev | GTG ACT GGA GTT CAG ACG TGT GCT CTT CCG ATCT ACA ATC ACG TGT CCT TCA CT (SEQ ID NO: 396) |
| CLTA4-6-1 rev | GTG ACT GGA GTT CAG ACG TGT GCT CTT CCG ATCT CAG ATC CCT CCT GGG CAA TG (SEQ ID NO: 397) |
| CLTA4-6-2 rev | GTG ACT GGA GTT CAG ACG TGT GCT CTT CCG ATCT GTC AGG AGG CAA GGA GGA AC (SEQ ID NO: 398) |
| CLTA4-6-3 rev | GTG ACT GGA GTT CAG ACG TGT GCT CTT CCG ATCT ACT TCC TTC CTT TTG AGA CCA AGT (SEQ ID NO: 399) |
| CLTA4-7-1 rev | GTG ACT GGA GTT CAG ACG TGT GCT CTT CCG ATCT GCG GCA GAT TCC TGG TGA TT (SEQ ID NO: 400) |
| CLTA4-7-2 rev | GTG ACT GGA GTT CAG ACG TGT GCT CTT CCG ATCT GGT CAC CAT CAG CAC AGT CA (SEQ ID NO: 401) |
| PE1-barcode1 | CAA GCA GAA GAC GGC ATA CGA GAT ATA TCA GTG TGA CTG GAG TTC AGA CGT GTG CT (SEQ ID NO: 402) |
| PE1-barcode2 | CAA GCA GAA GAC GGC ATA CGA GAT TTT CAC CGG TGA CTG GAG TTC AGA CGT GTG CT (SEQ ID NO: 403) |
| PE1-barcode3 | CAA GCA GAA GAC GGC ATA CGA GAT CCA CTC ATG TGA CTG GAG TTC AGA CGT GTG CT (SEQ ID NO: 404) |
| PE1-barcode4 | CAA GCA GAA GAC GGC ATA CGA GAT TAC GTA CGG TGA CTG GAG TTC AGA CGT GTG CT (SEQ ID NO: 405) |
| PE1-barcode5 | CAA GCA GAA GAC GGC ATA CGA GAT CGA AAC TCG TGA CTG GAG TTC AGA CGT GTG CT (SEQ ID NO: 406) |
| PE1-barcode6 | CAA GCA GAA GAC GGC ATA CGA GAT ATC AGT ATG TGA CTG GAG TTC AGA CGT GTG CT (SEQ ID NO: 407) |
| PE2-barcode1 | AAT GAT ACG GCG ACC ACC GAG ATC TAC ACA TTA CTC GAC ACT CTT TCC CTA CAC GAC (SEQ ID NO: 408) |
| PE2-barcode2 | AAT GAT ACG GCG ACC ACC GAG ATC TAC ACT CCG GAG AAC ACT CTT TCC CTA CAC GAC (SEQ ID NO: 409) |
| PE2-barcode3 | AAT GAT ACG GCG ACC ACC GAG ATC TAC ACC GCT CAT TAC ACT CTT TCC CTA CAC GAC (SEQ ID NO: 410) |

REFERENCES

1. Hockemeyer, D. et al. Genetic engineering of human pluripotent cells using TALE nucleases. Nature biotechnology 29, 731-734 (2011).
2. Zou, J. et al. Gene targeting of a disease-related gene in human induced pluripotent stem and embryonic stem cells. Cell stem cell 5, 97-110 (2009).
3. Hockemeyer, D. et al. Efficient targeting of expressed and silent genes in human ESCs and iPSCs using zinc-finger nucleases. Nature biotechnology 27, 851-857 (2009).
4. Doyon, Y. et al. Heritable targeted gene disruption in zebrafish using designed zinc-finger nucleases. Nature biotechnology 26, 702-708 (2008).
5. Meng, X., Noyes, M. B., Zhu, L. J., Lawson, N. D. & Wolfe, S. A. Targeted gene inactivation in zebrafish using engineered zinc-finger nucleases. Nature biotechnology 26, 695-701 (2008).
6. Sander, J. D. et al. Targeted gene disruption in somatic zebrafish cells using engineered TALENs. Nature biotechnology 29, 697-698 (2011).
7. Tesson, L. et al. Knockout rats generated by embryo microinjection of TALENs. Nature biotechnology 29, 695-696 (2011).
8. Cui, X. et al. Targeted integration in rat and mouse embryos with zinc-finger nucleases. Nature biotechnology 29, 64-67 (2011).
9. Perez, E. E. et al. Establishment of HIV-1 resistance in CD4+ T cells by genome editing using zinc-finger nucleases. Nature biotechnology 26, 808-816 (2008).

10. NCT00842634, NCT01044654, NCT01252641, NCT01082926.
11. Jinek, M. et al. A programmable dual-RNA-guided DNA endonuclease in adaptive bacterial immunity. Science 337, 816-821 (2012).
12. Cong, L. et al. Multiplex genome engineering using CRISPR/Cas systems. Science 339, 819-823 (2013).
13. Mali, P. et al. RNA-guided human genome engineering via Cas9. Science 339, 823-826 (2013).
14. Hwang, W. Y. et al. Efficient genome editing in zebrafish using a CRISPR-Cas system. Nature biotechnology 31, 227-229 (2013).
15. Jinek, M. et al. RNA-programmed genome editing in human cells. eLife 2, e00471 (2013).
16. Dicarlo, J. E. et al. Genome engineering in *Saccharomyces cerevisiae* using CRISPR-Cas systems. Nucleic acids research (2013).
17. Jiang, W., Bikard, D., Cox, D., Zhang, F. & Marraffini, L. A. RNA-guided editing of bacterial genomes using CRISPR-Cas systems. Nature biotechnology 31, 233-239 (2013).
18. Sapranauskas, R. et al. The *Streptococcus thermophilus* CRISPR/Cas system provides immunity in *Escherichia coli*. Nucleic acids research 39, 9275-9282 (2011).
19. Semenova, E. et al. Interference by clustered regularly interspaced short palindromic repeat (CRISPR) RNA is governed by a seed sequence. Proceedings of the National Academy of Sciences of the United States of America 108, 10098-10103 (2011).
20. Qi, L. S. et al. Repurposing CRISPR as an RNA-Guided Platform for Sequence-Specific Control of Gene Expression. Cell 152, 1173-1183 (2013).
21. Pattanayak, V., Ramirez, C. L., Joung, J. K. & Liu, D. R. Revealing off-target cleavage specificities of zinc-finger nucleases by in vitro selection. Nature methods 8, 765-770 (2011).
22. Doyon, J. B., Pattanayak, V., Meyer, C. B. & Liu, D. R. Directed evolution and substrate specificity profile of homing endonuclease I-SceI. Journal of the American Chemical Society 128, 2477-2484 (2006).
23. Jiang, W., Bikard, D., Cox, D., Zhang, F. & Marraffini, L. A. RNA-guided editing of bacterial genomes using CRISPR-Cas systems. Nature biotechnology 31, 233-239 (2013).
24. Pattanayak, V., Ramirez, C. L., Joung, J. K. & Liu, D. R. Revealing off-target cleavage specificities of zinc-finger nucleases by in vitro selection. Nature methods 8, 765-770 (2011).
25. Schneider, T. D. & Stephens, R. M. Sequence logos: a new way to display consensus sequences. Nucleic acids research 18, 6097-6100 (1990).

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:

1. A method for identifying a target site of a nuclease, the method comprising:
   (a) providing a nuclease that cuts a double-stranded nucleic acid target site, wherein cutting of the target site results in cut nucleic acid strands comprising a 5' phosphate moiety;
   (b) contacting the nuclease of step (a) with a library of candidate nucleic acid molecules, wherein each nucleic acid molecule comprises a concatemer of a sequence comprising a candidate nuclease target site and a constant insert sequence, under conditions suitable for the nuclease to cut a candidate nucleic acid molecule comprising a target site of the nuclease; and
   (c) identifying nuclease target sites cut by the nuclease in step (b) by determining the sequence of an uncut nuclease target site on the nucleic acid strand that was cut by the nuclease in step (b), wherein the determining of step (c) comprises (i) ligating a first nucleic acid adapter to the 5' end of a nucleic acid strand that was cut by the nuclease in step (b) via 5'-phosphate-dependent ligation, and (ii) amplifying a fragment of the concatemer cut by the nuclease that comprises an uncut target site via a PCR reaction using a PCR primer that hybridizes with the adapter and a PCR primer that hybridizes with the constant insert sequence.

2. The method of claim 1, wherein the nucleic acid adapter is provided in double-stranded form.

3. The method of claim 1, wherein the 5'-phosphate-dependent ligation is a blunt end ligation.

4. The method of claim 1, wherein the method comprises filling in the 5'-overhang before ligating the first nucleic acid adapter to the nucleic acid strand that was cut by the nuclease.

5. The method of claim 1, wherein the determining of step (c) further comprises sequencing the fragment obtained via PCR.

6. The method of claim 1, wherein the library of candidate nucleic acid molecules comprises at least $10^8$, at least $10^9$, at least $10^{10}$, at least $10^{11}$, or at least $10^{12}$ different candidate nuclease cleavage sites.

7. The method of claim 1 further comprising determining a maximum concentration of the nuclease at which the nuclease cuts the specific nuclease target site, and does not cut more than 10, more than 5, more than 4, more than 3, more than 2, more than 1, or no additional nuclease target sites.

8. The method of claim 7 further comprising administering the nuclease to a subject in an amount effective to generate a final concentration equal or lower than the maximum concentration.

9. The method of claim 1, wherein the nuclease is an RNA-programmable nuclease that forms a complex with an RNA molecule, and wherein the nuclease:RNA complex specifically binds a nucleic acid sequence complementary to the sequence of the RNA molecule.

10. The method of claim 9, wherein the RNA molecule is a single-guide RNA (sgRNA).

11. The method of claim 1, wherein the nuclease is a Cas9 nuclease.

12. A method of selecting a nuclease that specifically cuts a consensus target site from a plurality of nucleases, the method comprising:
   (a) providing a plurality of candidate nucleases that cut the same consensus sequence;
   (b) for each of the candidate nucleases of step (a), identifying a nuclease target site cleaved by the candidate nuclease that differ from the consensus target site using the method of claim 1; and
   (c) selecting a nuclease based on the nuclease target site(s) identified in step (b).

13. The method of claim 12, wherein the nuclease selected from step (c) is the nuclease that cleaves the consensus target site with the highest specificity.

14. The method of claim 12, wherein the nuclease target site comprises a [sgRNA-complementary sequence]-[protospacer adjacent motif (PAM)] structure, and the nuclease cuts the target site within the sgRNA-complementary sequence.

15. The method of claim 13, wherein the nuclease that cleaves the consensus target site with the highest specificity is the candidate nuclease that cleaves the lowest number of target sites that differ from the consensus site.

16. The method of claim 13, wherein the nuclease that cleaves the consensus target site with the highest specificity is the candidate nuclease that cleaves the lowest number of target sites that are different from the consensus site in the context of a target genome.

17. The method of claim 12, wherein the nuclease selected in step (c) is a nuclease that does not cleave any target site other than the consensus target site.

18. The method of claim 12, wherein the nuclease selected in step (c) is a nuclease that does not cleave any target site other than the consensus target site within the genome of a subject at a therapeutically effective concentration of the nuclease.

19. The method of claim 12 further comprising contacting a genome with the nuclease selected in step (c).

20. The method of claim 19, wherein the genome is a vertebrate or invertebrate genome.

21. The method of claim 19, wherein the genome is within a living cell.

22. The method of claim 19, wherein the genome is within a subject.

23. The method of claim 12, wherein the consensus target site is within an allele that is associated with a disease or disorder.

24. The method of claim 23, wherein cleavage of the consensus target results in treatment or prevention of the disease or disorder.

25. The method of claim 24, wherein cleavage of the consensus target site results in alleviation of a symptom of the disease or disorder.

26. The method of claim 23, wherein the disease is HIV/AIDS.

27. The method of claim 26, wherein the allele is a CCR5 allele.

28. The method of claim 23, wherein the disease is a proliferative disease.

29. The method of claim 28, wherein the allele is a VEGFA allele.

30. The method of claim 20, wherein the vertebrate genome is a human, non-human primate, rodent, mouse, rat, hamster, goat, sheep, cattle, dog, cat, reptile, amphibian, or fish genome.

31. The method of claim 20, wherein the invertebrate genome is a nematode or insect genome.

* * * * *